United States Patent
Pabst et al.

(10) Patent No.: US 11,548,933 B2
(45) Date of Patent: Jan. 10, 2023

(54) METHOD OF PURIFYING ALBUMIN-FUSION PROTEINS

(71) Applicant: MedImmune, LLC, Gaithersburg, MD (US)

(72) Inventors: Timothy Pabst, Gaithersburg, MD (US); Mariko Fonseca, Gaithersburg, MD (US); Christopher Thompson, Gaithersburg, MD (US); Alan Hunter, Gaithersburg, MD (US); Xiangyang Wang, Gaithersburg, MD (US); Liu Tie, Gaithersburg, MD (US); Yiming Li, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 16/901,812

(22) Filed: Jun. 15, 2020

(65) Prior Publication Data

US 2020/0407423 A1 Dec. 31, 2020

Related U.S. Application Data

(63) Continuation of application No. 15/557,358, filed as application No. PCT/US2016/022003 on Mar. 11, 2016, now Pat. No. 10,683,340.

(60) Provisional application No. 62/132,198, filed on Mar. 12, 2015.

(51) Int. Cl.
| | |
|---|---|
| *C07K 14/00* | (2006.01) |
| *C07K 14/765* | (2006.01) |
| *A61K 47/64* | (2017.01) |
| *C07K 1/18* | (2006.01) |
| *C07K 1/22* | (2006.01) |
| *C07K 14/78* | (2006.01) |
| *A61K 38/00* | (2006.01) |

(52) U.S. Cl.
CPC ........ *C07K 14/765* (2013.01); *A61K 47/643* (2017.08); *C07K 1/18* (2013.01); *C07K 1/22* (2013.01); *C07K 14/78* (2013.01); *A61K 38/00* (2013.01); *C07K 2319/00* (2013.01)

(58) Field of Classification Search
CPC ........... C07K 14/70521; C07K 14/765; A61K 47/06; A61P 35/00
See application file for complete search history.

(56) References Cited

U.S. PATENT DOCUMENTS

| | | | |
|---|---|---|---|
| 2003/0022308 A1 | 1/2003 | Fleer et al. | |
| 2012/0149873 A1* | 6/2012 | Blackwell | C07K 16/18 530/364 |
| 2015/0098955 A1* | 4/2015 | Coyle | A61P 29/00 424/185.1 |

FOREIGN PATENT DOCUMENTS

| | | |
|---|---|---|
| EP | 0570916 A2 | 11/1993 |
| WO | 2005/054289 A1 | 6/2005 |
| WO | 2007071068 A1 | 6/2007 |
| WO | 2010/128142 A1 | 11/2010 |
| WO | 2013055745 A2 | 4/2013 |
| WO | 2014/072481 A1 | 5/2014 |

OTHER PUBLICATIONS

Brody et al. HIC resolution of an IgG1 with an oxidized Trp in a complementarity determining region. J. Chromatag. B Apr. 15, 2011, vol. 879, p. 955-960.*
Boyd, et al., "HIC resolution of an IgG1 with an oxidized Trp in a complementarity determining region", Journal of Chromatography B, vol. 879 (2011) pp. 955-960.
Bornhorst, et al., "Purification of proteins using polyhistidine affinity tags", Methods In Enzymology, vol. 326, (2000) pp. 245-254.
Haverick, et al., "Separation of mAbs molecular variants by analytical hydrophobic interaction chromatography HPLC: overview and applications" mAbs; vol. 6(4); pp. 852-858; Apr. 1, 2014.

* cited by examiner

*Primary Examiner* — Jeanette M Lieb

(57) ABSTRACT

The present invention relates to a method of purifying albumin-fusion proteins to reduce the level of oxidation of susceptible amino acid residues. The method comprises an affinity matrix chromatography step and an anion exchange chromatography step. The purified albumin-fusion proteins have low levels of oxidation and retain their enhanced half-life in vivo and its bioactivity. In some embodiments, the albumin-fusion protein comprises a scaffold, such as human Tenascin C scaffold. Compositions comprising the albumin-fusion protein are further disclosed.

19 Claims, 14 Drawing Sheets

Specification includes a Sequence Listing.

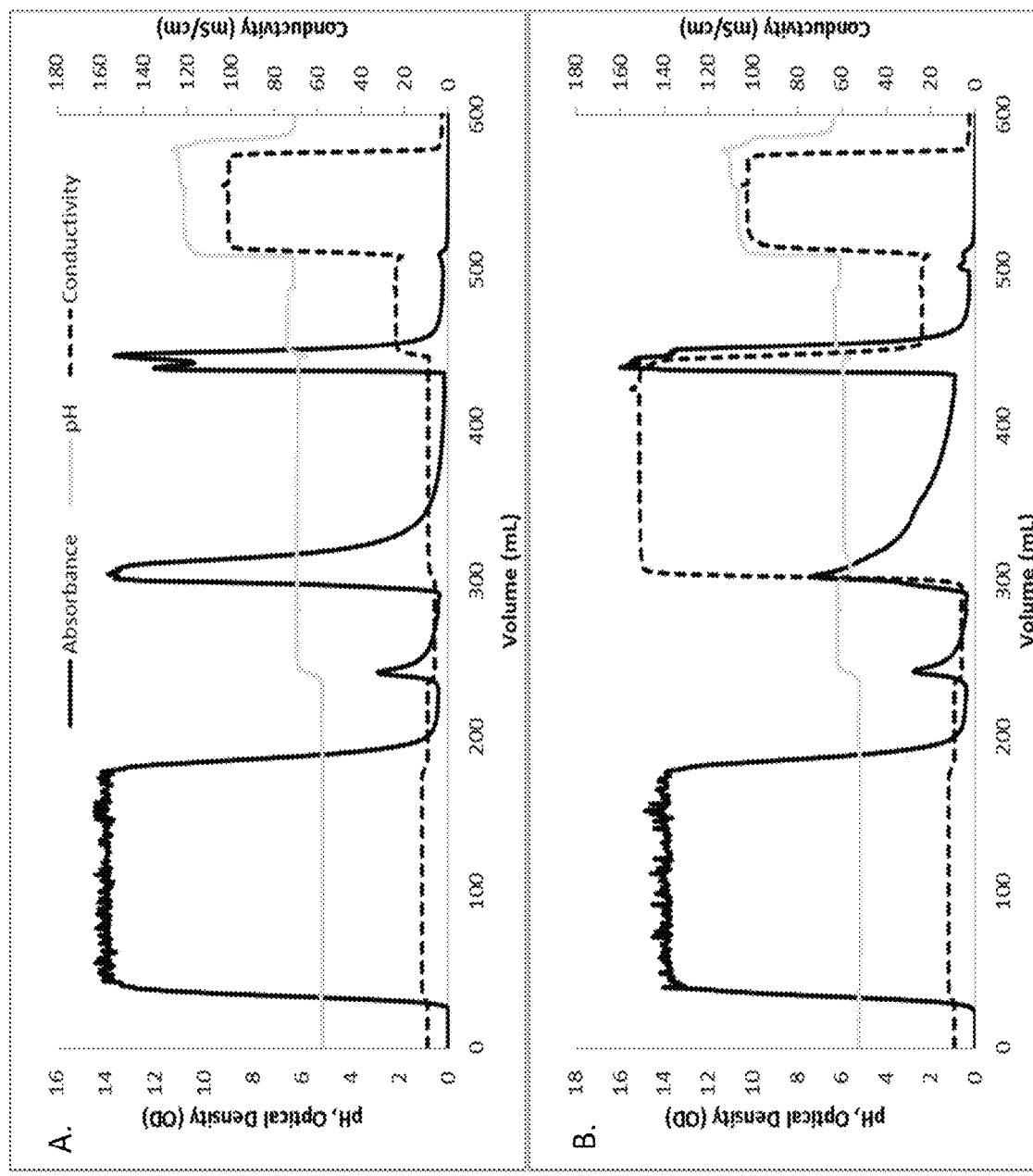
FIG. 8A-B

FIG. 9A-B
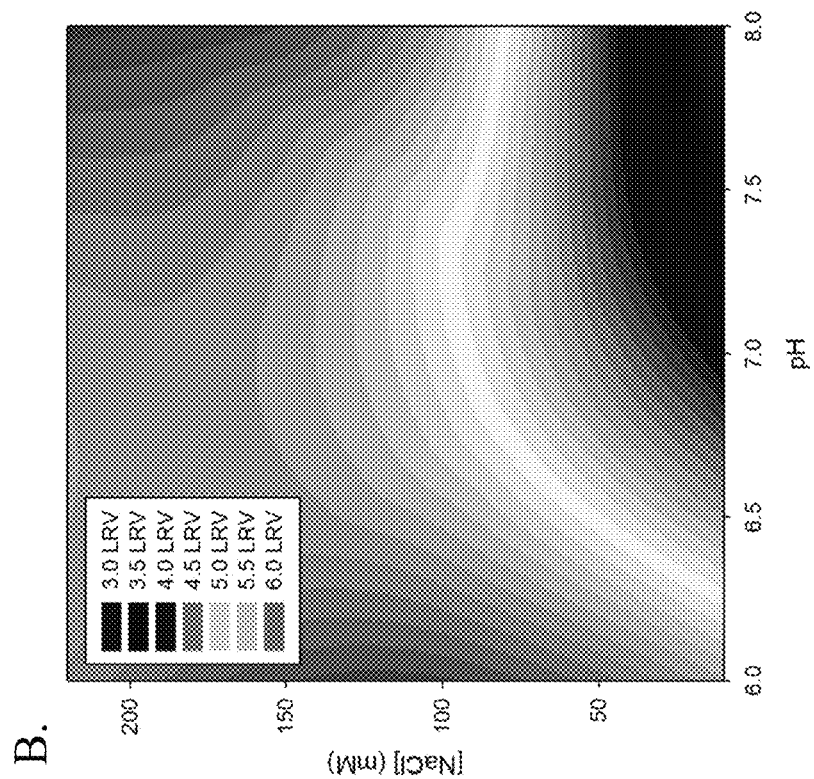
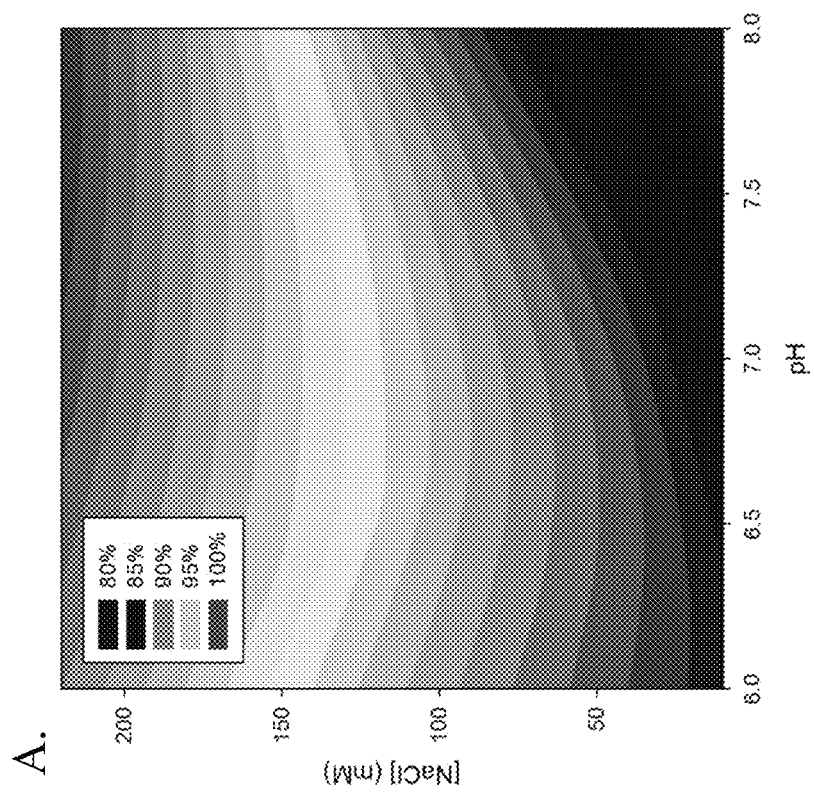

METHOD OF PURIFYING ALBUMIN-FUSION PROTEINS

CROSS-REFERENCE TO RELATED APPLICATIONS

This application is a continuation of U.S. patent application Ser. No. 15/557,358, filed on Sep. 11, 2017, which is a U.S. National Stage application of International Application No. PCT/US2016/022003, filed on Mar. 11, 2016. International Application No. PCT/US2016/022003 claims benefit under 35 U.S.C. § 119(e) of the U.S. Provisional Application No. 62/132,198, filed Mar. 12, 2015. Each of the above listed applications is incorporated by reference herein in its entirety for all purposes.

REFERENCE TO SEQUENCE LISTING

This application incorporates by reference a Sequence Listing submitted with the application via EFS-Web as a text file entitled "CD40L-300-US-CNT-SequenceListing.txt" created on Jun. 15, 2020 and having a size of 234,514 bytes.

BACKGROUND OF THE INVENTION

Field of the Invention

The present invention relates in general to a method of purifying albumin-fusion proteins having low levels of oxidation of the tryptophan and/or methionine residues of the protein. The low levels of oxidation of these residues allow the purified albumin-fusion protein to retain its relative potency and bioactivity. The albumin-fusion protein may include scaffolds, such as those derived from the third fibronectin type III domain of human Tenascin C useful, for example. The invention relates to the methods of purifying the albumin-fusion proteins, the purified proteins obtained from the method, and compositions comprising the purified albumin-fusion protein.

Background

The use of proteins as potential therapeutic drugs has seen increased interest in recent years. One disadvantage of protein drugs is they tend to have a short half-life in vivo. To overcome this challenge, proteins and peptides can be conjugated or fused with other molecules. One option to extended half-life is through PEGylation, a process by which poly(ethylene glycol), or PEG, is covalently attached to a protein through a number of available chemistries. In additional to half-life extension, PEGylation may also reduce immunogenicity, likely due to shielding of the protein surface by the inert PEG chains(s). The disadvantage of PEGylation is that it requires a conjugation reaction step and often an additional purification step to remove unreacted PEG chains. Despite these challenges, PEGylation technology has been successfully employed in several commercial biopharmaceutical drugs.

A second option for extending half-life is fusion protein technology. In this case, the therapeutic protein is genetically fused to a second protein designed to extend half-life in vivo. This option provides half-life extension similar to PEGylation; however, it does not require the additional manufacturing steps (conjugation reaction and associated purification) since the fusion protein is expressed and purified as a single entity. Examples of fusion proteins include Fc-fusions, transferrin-fusions, and albumin-fusions. All of the proteins are found in human plasma at high levels, mitigating the impact of increased levels due to the drug.

In addition to the benefits of half-life extension and ease of manufacturing, fusion proteins may also be able to take advantage of platform approaches to purification. This is because in many cases the carrier protein makes up a large portion of the fusion protein, and thus there similar physiochemical characteristics between various fusion proteins. For a platform approach to be successful, purification operations must be selective for the carrier protein.

The present invention relates to a method of purifying albumin-fusion proteins.

Citation or discussion of a reference herein shall not be construed as an admission that such is prior art to the present invention.

SUMMARY OF THE INVENTION

In certain aspects, the disclosure herein relates to a method of reducing oxidation of tryptophan and/or methionine during purification in an albumin-fusion protein, the method comprising subjecting a composition comprising the albumin-fusion protein to the following purification processes: (a) an affinity matrix; (b) an anion exchange matrix, wherein the albumin-fusion protein is eluted from the affinity matrix by applying an elution buffer comprising octanoate.

In further aspects the disclosure herein relates to a method of reducing oxidation of tryptophan and/or methionine during purification in an albumin-fusion protein, the method comprising subjecting a composition comprising the albumin-fusion protein to the following purification processes: (a) an affinity matrix; (b) an anion exchange matrix, wherein the affinity matrix is washed with a wash buffer comprising: (1) about 2% to about 20% polyol, wherein the polyol is selected from the group consisting of 1,2-propanediol, 1,3-propanediol, 1,2-butanediol, 1,3-butanediol, 1,4-butanediol, 1,6-hexanediol, and 2-Methyl-2,4-pentanediol; (2) 0.05 M to 2.0 M salt, wherein the salt is selected from sodium chloride, potassium chloride, calcium chloride, lithium chloride, sodium bromide, potassium bromide and lithium bromide; (3) about 0.02 M to about 0.2 M sodium sulfate; (4) about 0.01% to about 1% nonionic surfactant; (5) about 0.05 M to about 1.0 M urea; or (6) about 0.02 M to about 0.5 M nicotinamide.

In additional aspects the disclosure herein relates to a method of obtaining a composition comprising albumin-fusion protein essentially free of oxidized tryptophan residues, the method comprising subjecting a composition comprising oxidized tryptophan albumin-fusion proteins and non-oxidized tryptophan albumin-fusion proteins to a hydrophobic interaction matrix, wherein oxidized tryptophan albumin-fusion protein and non-oxidized tryptophan albumin-fusion protein are eluted from the hydrophobic interaction matrix at different times, thereby separating the oxidized tryptophan albumin-fusion protein from the non-oxidized tryptophan albumin-fusion protein.

In certain aspects the disclosure herein relates to a method of isolating an albumin-fusion protein essentially free from oxidation of tryptophan/methionine residues, the process comprising subjecting a composition comprising an albumin-fusion protein to the following purification processes: (a) an affinity matrix chromatography process; (b) an anion exchange chromatography process; and (c) a hydrophobic interaction matrix chromatography process, wherein an elution buffer comprising octanoate is applied to the affinity matrix, and wherein oxidized tryptophan albumin-fusion protein and non-oxidized tryptophan albumin-fusion protein are eluted from the hydrophobic interaction matrix at different times, thereby separating the oxidized tryptophan albumin-fusion protein from the non-oxidized tryptophan albumin-fusion protein.

In further aspects the disclosure herein relates to a method of purifying an albumin-fusion protein, the method comprising subjecting a composition comprising an albumin-fusion protein to a hydrophobic interaction matrix, and one or more of the following purification processes: (a) an affinity matrix, wherein an elution buffer comprising octanoate is applied to the affinity matrix; and/or (b) an anion exchange matrix; wherein affinity matrix is washed with a wash buffer comprising: (1) about 2% to about 20% polyol, wherein the polyol is selected from the group consisting of 1,2-propanediol, 1,3-propanediol, 1,2-butanediol, 1,3-butanediol, 1,4-butanediol, 1,6 hexanediol, and 2-methyl-2,4-pentanediol; (2) 0.05 M to 2.0 salt, wherein the salt is selected from sodium chloride, potassium chloride, calcium chloride, lithium chloride, sodium bromide, potassium bromide and lithium bromide; (3) about 0.02 M to about 0.2 M sodium sulfate; (4) about 0.01% to about 1% nonionic surfactant; (5) about 0.05 M to about 1.0 M urea; or (6) about 0.02 M to about 0.5 M nicotinamide, wherein the resulting purified albumin-fusion protein is essentially free of oxidized tryptophan residues.

In additional aspects the disclosure herein relates to a method of purifying an albumin-fusion protein, the method comprising: (a) applying a composition comprising the albumin-fusion protein to an affinity matrix; (b) eluting the albumin-fusion protein from the affinity matrix of (a) to obtain a first eluant; (c) applying the first eluant to an anion exchange matrix; (d) eluting the albumin-fusion protein from the anion exchange matrix to obtain a second eluant; (e) applying the second eluant to an anion exchange membrane; passing the albumin-fusion protein through an anion exchange membrane to obtain a flow through; (f) applying the flow through to a hydrophobic interaction matrix; eluting the albumin-fusion protein from the hydrophobic interaction matrix to obtain a third eluant, wherein the third eluant comprises the purified albumin-fusion protein.

The disclosure herein also relates to an albumin-fusion protein composition obtained by any of the methods disclosed herein.

The disclosure herein further relates to a composition comprising an albumin-fusion protein, wherein the composition has less than 20 ng/mg host cell protein, and wherein less than 15% of the tryptophan residues are oxidized.

The disclosure herein additionally relates to a composition comprising an albumin-fusion protein, wherein the composition has less than $5\times10^{-3}$ ng/mg DNA, and wherein the less than 15% of the tryptophan residues are oxidized.

The disclosure herein further relates to a composition comprising an albumin-fusion protein, wherein the composition has less than 20 ng/mg host cell protein, and wherein the albumin-fusion protein has a relative activity of >90%.

The disclosure herein also relates to a composition comprising an albumin-fusion protein, wherein the composition has less than $5\times10^{-3}$ ng/mg DNA and wherein the albumin-fusion protein has a relative activity of >90%.

The disclosure herein further relates to a composition comprising an albumin-fusion protein of SEQ ID NO: 134, 135, 201, 202, 203, 204, 205, 206, 207 or 208, wherein the composition has less than 20 ng/mg host cell protein, and wherein the tryptophan at position 46, 151 or both is not oxidized.

The disclosure herein also relates to a pharmaceutically acceptable formulation comprising: (a) any composition disclosed herein; (b) a buffer (c) a sugar; and (d) an emulsifier.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 8A-B depict a Cibacron blue dye chromatography of an albumin-fusion protein with (A) 25 mM octanoate and (B) 2M NaCl elution buffer.

FIG. 9A-B depict the step yield (A) and DNA log reduction values (LRV) (B) as a function of pH and NaCl concentration for Mustang Q membrane chromatography.

DETAILED DESCRIPTION OF THE INVENTION

Definitions

Figure 1:
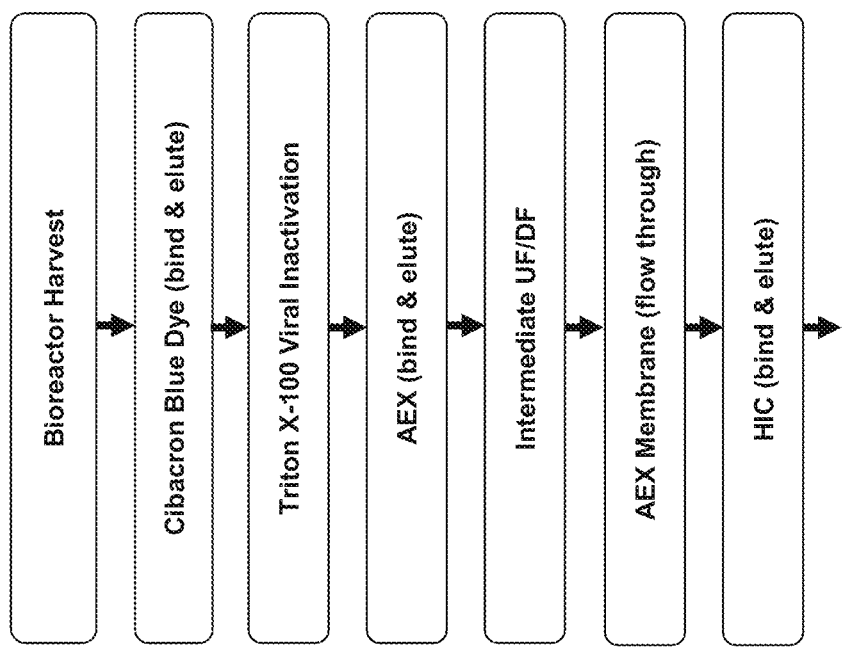
FIG. 1 depicts a flow chart of one embodiment of the rHSA purification process.

Before describing the present invention in detail, it is to be understood that this invention is not limited to specific compositions or process steps, as such can vary. It must be noted that, as used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A," (alone) and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this invention.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

It is understood that wherever embodiments are described herein with the language "comprising," otherwise analogous embodiments described in terms of "consisting of" and/or "consisting essentially of" are also provided.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The term "epitope" as used herein refers to a protein determinant capable of binding to a scaffold of the invention. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The terms "fibronectin type III (FnIII) domain," "FnIII domain" and "FnIII scaffold" refer to polypeptides homologous to the human fibronectin type III domain having at least 7 beta strands which are distributed between two beta sheets, which themselves pack against each other to form the core of the protein, and further containing solvent exposed loops which connect the beta strands to each other. There are at least three such loops at each edge of the beta sheet sandwich, where the edge is the boundary of the protein perpendicular to the direction of the beta strands. In certain embodiments, an FnIII domain comprises 7 beta strands designated A, B, C, D, E, F, and G linked to six loop regions designated AB, BC, CD, DE, EF, and FG, wherein a loop region connects each beta strand.

The term "Tn3 scaffold" used herein, refers to molecules comprising at least one FnIII scaffold wherein the A beta strand comprises SEQ ID NO: 11, the B beta strand comprises SEQ ID NO: 12, the C beta strand SEQ ID NO: 13 or 14, the D beta strand comprises SEQ ID NO: 15, the E beta strand comprises SEQ ID NO: 16, the F beta strand comprises SEQ ID NO: 17, and the beta strand G comprises SEQ ID NO: 18, wherein at least one loop is a non-naturally occurring variant of the loops in the "parent Tn3 scaffold." In certain embodiments, one or more of the beta strands of a Tn3 module comprise at least one amino acid substitution except that the cysteine residues in the C beta strand (e.g., the cysteine in SEQ ID NOs: 13 or 14) and F beta strands (SEQ ID NO: 17) are not substituted.

The term "parent Tn3" as used herein refers to an FnIII scaffold comprising SEQ ID NO: 3, i.e., a thermally stabilized cysteine-engineered FnIII scaffold derived from the 3rd FnIII domain of human tenascin C.

The terms "multimer" or "multimeric scaffold" refer to a molecule that comprises at least two FnIII scaffolds in association. The scaffolds forming a multimeric scaffold can be linked through a linker that permits each scaffold to function independently.

The terms "monomer," "monomer subunit" or "monomer scaffold" refer to a molecule that comprises only one FnIII scaffold.

The term "CD40L-specific monomer subunit" as used herein refers to a Tn3 monomer derived from a "parent Tn3" wherein the Tn3 monomer specifically binds to CD40L or a fragment thereof, e.g., a soluble form of CD40L.

The term "DNA" refers to a sequence of two or more covalently bonded, naturally occurring or modified deoxyribonucleotides.

The term "fusion protein" refers to a protein that includes (i) one or more therapeutic protein or fragment joined to (ii) a second, different protein (i.e., a "heterologous" protein). Within the scope of the present invention, albumin (HSA, a variant HSA, or fragment HSA) is joined with a therapeutic protein or fragment.

TABLE 1

Sequences and SEQ ID NOs of components of "parent Tn3"

| Name/Brief Description | Sequence | SEQ ID NO |
|---|---|---|
| Tn3 | IEVKDVTDTTALITWFKPLAEIDGCELT YGIKDVPGDRTTIDLTEDENQYSIGNLK PDTEYEVSLICRRGDMSSNPAKETFTT (cys residues of disulfide bond are underlined) | 3 |
| 3rd FnIII of tenascin C, AB loop (Tn3) | KDVTDTT | 4 |
| 3rd FnIII of tenascin C, BC loop (Tn3) | FKPLAEIDG | 5 |

TABLE 1-continued

Sequences and SEQ ID NOs of components of "parent Tn3"

| Name/Brief Description | Sequence | SEQ ID NO |
|---|---|---|
| 3$^{rd}$ FnIII of tenascin C, CD loop (Tn3) | KDVPGDR | 6 |
| 3$^{rd}$ FnIII of tenascin C, DE loop (Tn3) | TEDENQ | 7 |
| 3$^{rd}$ FnIII of tenascin C, EF loop (Tn3) | GNLKPDTE | 8 |
| 3$^{rd}$ FnIII of tenascin C, FG loop (Tn3) | RRGDMSSNPA | 9 |
| 3$^{rd}$ FnIII of tenascin C, beta strand A (Tn3) | RLDAPSQIEV | 10 |
| 3$^{rd}$ FnIII of tenascin C, beta strand A (Tn3) N-terminal truncation | IEV | 11 |
| 3$^{rd}$ FnIII of tenascin C, beta strand B (Tn3) | ALITW | 12 |
| 3$^{rd}$ FnIII of tenascin C, beta strand C (Tn3 variant) | CELAYGI | 13 |
| 3$^{rd}$ FnIII of tenascin C, beta strand C (Tn3) | CELTYGI | 14 |
| 3$^{rd}$ FnIII of tenascin C, beta strand D (Tn3) | TTIDL | 15 |
| 3$^{rd}$ FnIII of tenascin C, beta strand E (Tn3) | YSI | 16 |
| 3$^{rd}$ FnIII of tenascin C, beta strand F (Tn3) | YEVSLIC | 17 |
| 3$^{rd}$ FnIII of tenascin C, beta strand G (Tn3) | KETFTT | 18 |

The term "heterologous moiety" is used herein to indicate the addition of a composition to a Tn3 scaffold of the invention wherein the composition is not normally part of an FnIII domain. Exemplary heterologous moieties include proteins, peptides, protein domains, linkers, drugs, toxins, imaging agents, radioactive compounds, organic and inorganic polymers, and any other compositions which might provide an activity that is not inherent in the FnIII domain itself, including, but are not limited to, polyethylene glycol (PEG), a cytotoxic agent, a radionuclide, imaging agent, biotin, a dimerization domain (e.g. leucine zipper domain), human serum albumin (HSA) or an FcRn binding portion thereof, a domain or fragment of an antibody (e.g., antibody variable domain, a CH1 domain, a Ckappa domain, a Clambda domain, a CH2, or a CH3 domain), a single chain antibody, a domain antibody, an albumin binding domain, an IgG molecule, an enzyme, a ligand, a receptor, a binding peptide, a non-FnIII scaffold, an epitope tag, a recombinant polypeptide polymer, a cytokine, and the like.

The term "linker" as used herein refers to any molecular assembly that joins or connects two or more scaffolds. The linker can be a molecule whose function is to act as a "spacer" between modules in a scaffold, or it can also be a molecule with additional function (i.e., a "functional moiety"). A molecule included in the definition of "heterologous moiety" can also function as a linker.

The terms "linked", "conjugated" and "fused" are used interchangeably. These terms refer to the joining together of two or more scaffolds, heterologous moieties, or linkers by whatever means including chemical conjugation or recombinant means.

The terms "domain" or "protein domain" refer to a region of a protein that can fold into a stable three-dimensional structure, often independently of the rest of the protein, and which can be endowed with a particular function. This structure maintains a specific function associated with the domain's function within the original protein, e.g., enzymatic activity, creation of a recognition motif for another molecule, or to provide necessary structural components for a protein to exist in a particular environment of proteins. Both within a protein family and within related protein superfamilies, protein domains can be evolutionarily conserved regions. When describing the component of a multimeric scaffold, the terms "domain," "monomeric scaffold," "monomer subunit," and "module" can be used interchangeably. By "native FnIII domain" is meant any non-recombinant FnIII domain that is encoded by a living organism.

A "protein sequence" or "amino acid sequence" means a linear representation of the amino acid constituents in a polypeptide in an amino-terminal to carboxyl-terminal direction in which residues that neighbor each other in the representation are contiguous in the primary structure of the polypeptide.

The term "nucleic acid" refers to any two or more covalently bonded nucleotides or nucleotide analogs or derivatives. As used herein, this term includes, without limitation, DNA, RNA, and PNA. "Nucleic acid" and "polynucleotide" are used interchangeably herein.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). The term "isolated" nucleic acid or polynucleotide refers to a nucleic acid molecule, DNA or RNA that has been removed from its native environment. For example, a recombinant polynucleotide encoding, e.g., a scaffold of the invention contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid can be or can include a regulatory element such as a promoter, ribosome binding site, or a transcription terminator.

The term "pharmaceutically acceptable" refers to a compound or protein that can be administered to an animal (for example, a mammal) without significant adverse medical consequences.

The term "physiologically acceptable carrier" refers to a carrier which does not have a significant detrimental impact on the treated host and which retains the therapeutic properties of the compound with which it is administered. One exemplary physiologically acceptable carrier is physiological saline. Other physiologically acceptable carriers and their formulations are known to one skilled in the art and are described, for example, in Remington's Pharmaceutical Sciences, (18th edition), ed. A. Gennaro, 1990, Mack Publishing Company, Easton, Pa., incorporated herein by reference.

By a "polypeptide" is meant any sequence of two or more amino acids linearly linked by amide bonds (peptide bonds) regardless of length, post-translation modification, or function. "Polypeptide," "peptide," and "protein" are used interchangeably herein. Thus, peptides, dipeptides, tripeptides, or oligopeptides are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced by recombinant technology, but is not necessarily translated from a designated nucleic acid sequence. A polypeptide can be generated in any manner, including by chemical synthesis.

Also included as polypeptides of the present invention are fragments, derivatives, analogs, or variants of the foregoing polypeptides, and any combination thereof. Variants can occur naturally or be non-naturally occurring. Non-naturally occurring variants can be produced using art-known mutagenesis techniques. Variant polypeptides can comprise conservative or non-conservative amino acid substitutions, deletions, or additions. Also included as "derivatives" are those peptides that contain one or more naturally occurring amino acid derivatives of the twenty standard amino acids.

By "randomized" or "mutated" is meant including one or more amino acid alterations, including deletion, substitution or addition, relative to a template sequence. By "randomizing" or "mutating" is meant the process of introducing, into a sequence, such an amino acid alteration. Randomization or mutation can be accomplished through intentional, blind, or spontaneous sequence variation, generally of a nucleic acid coding sequence, and can occur by any technique, for example, PCR, error-prone PCR, or chemical DNA synthesis. The terms "randomizing", "randomized", "mutating", "mutated" and the like are used interchangeably herein.

By a "cognate" or "cognate, non-mutated protein" is meant a protein that is identical in sequence to a variant protein, except for the amino acid mutations introduced into the variant protein, wherein the variant protein is randomized or mutated.

By "RNA" is meant a sequence of two or more covalently bonded, naturally occurring or modified ribonucleotides. One example of a modified RNA included within this term is phosphorothioate RNA.

The terms "scaffold of the invention" or "scaffolds of the invention" as used herein, refers to multimeric Tn3 scaffolds as well as monomeric Tn3 scaffolds. The term "target" refers to a compound recognized by a specific scaffold of the invention. The terms "target" and "antigen" are used interchangeably herein. The term "specificity" as used herein, e.g., in the terms "specifically binds" or "specific binding," refers to the relative affinity by which a Tn3 scaffold of the invention binds to one or more antigens via one or more antigen binding domains, and that binding entails some complementarity between one or more antigen binding domains and one or more antigens. According to this definition, a Tn3 scaffold of the invention is said to "specifically bind" to an epitope when it binds to that epitope more readily than it would bind to a random, unrelated epitope.

An "affinity matured" scaffold is a scaffold with one or more alterations, generally in a loop, which result in an improvement in the affinity of the Tn3 scaffold for an epitope compared to a parent Tn3 scaffold which does not possess those alteration(s).

The term "affinity" as used herein refers to a measure of the strength of the binding of a certain Tn3 scaffold of the invention to an individual epitope.

The term "avidity" as used herein refers to the overall stability of the complex between a population of Tn3 scaffolds of the invention and a certain epitope, i.e., the functionally combined strength of the binding of a plurality of Tn3 scaffolds with the antigen. Avidity is related to both the affinity of individual antigen-binding domains with specific epitopes, and also the valency of the scaffold of the invention.

The term "action on the target" refers to the binding of a Tn3 scaffold of the invention to one or more targets and to the biological effects resulting from such binding. In this respect, multiple antigen binding units in a Tn3 scaffold can interact with a variety of targets and/or epitopes and, for example, bring two targets physically closer, trigger metabolic cascades through the interaction with distinct targets, etc. With reference to CD40L, "action on the target" refers to the effect achieved, for example, by the enhancement, stimulation or activation, of one or more biological activities of CD40L.

The term "valency" as used herein refers to the number of potential antigen-binding modules, e.g., the number of FnIII modules in a scaffold of the invention. When a Tn3 scaffold of the invention comprises more than one antigen-binding module, each binding module can specifically bind, e.g., the same epitope or a different epitope, in the same target or different targets.

The term "disulfide bond" as used herein includes the covalent bond formed between two sulfur atoms. The amino acid cysteine comprises a thiol group that can form a disulfide bond or bridge with a second thiol group.

The term "immunoglobulin" and "antibody" comprises various broad classes of polypeptides that can be distinguished biochemically. Those skilled in the art will appreciate that heavy chains are classified as gamma, mu, alpha, delta, or epsilon. It is the nature of this chain that determines the "class" of the antibody as IgG, IgM, IgA IgG, or IgE, respectively. Modified versions of each of these classes are readily discernible to the skilled artisan. As used herein, the term "antibody" includes but not limited to an intact antibody, a modified antibody, an antibody VL or VL domain, a CH1 domain, a Ckappa domain, a Clambda domain, an Fc domain (see below), a CH2, or a CH3 domain.

As used herein, the term "Fc domain" domain refers to a portion of an antibody constant region. Traditionally, the term Fc domain refers to a protease (e.g., papain) cleavage product encompassing the paired CH2, CH3 and hinge regions of an antibody. In the context of this disclosure, the term Fc domain or Fc refers to any polypeptide (or nucleic acid encoding such a polypeptide), regardless of the means of production, that includes all or a portion of the CH2, CH3 and hinge regions of an immunoglobulin polypeptide.

As used herein, the term "modified antibody" includes synthetic forms of antibodies which are altered such that they are not naturally occurring, e.g., antibodies that comprise at least two heavy chain portions but not two complete heavy chains (as, e.g., domain deleted antibodies or minibodies); multispecific forms of antibodies (e.g., bispecific, trispecific, etc.) altered to bind to two or more antigens or to different epitopes of a single antigen). In addition, the term "modified antibody" includes multivalent forms of antibodies (e.g., trivalent, tetravalent, etc., antibodies that to three or more copies of the same antigen). (See, e.g., Antibody Engineering, Kontermann & Dubel, eds., 2010, Springer Protocols, Springer).

The term "in vivo half-life" is used in its normal meaning, i.e., the time at which 50% of the biological activity of a polypeptide is still present in the body/target organ, or the time at which the activity of the polypeptide is 50% of its initial value. As an alternative to determining functional in vivo half-life, "serum half-life" may be determined, i.e., the time at which 50% of the polypeptide molecules circulate in the plasma or bloodstream prior to being cleared. Determination of serum-half-life is often more simple than determining functional in vivo half-life and the magnitude of serum-half-life is usually a good indication of the magnitude of functional in vivo half-life. Alternative terms to serum half-life include "plasma half-life," circulating half-life, circulatory half-life, serum clearance, plasma clearance, and clearance half-life. The functionality to be retained is normally selected from procoagulant, proteolytic, co-factor binding, receptor binding activity, or other type of biological activity associated with the particular protein.

The term "increased" with respect to the functional in vivo half-life or plasma half-life is used to indicate that the relevant half-life of the polypeptide is statistically significantly increased relative to that of a reference molecule (for example an unmodified polypeptide), as determined under comparable conditions.

The term "decreased" with respect to the functional in vivo half-life or plasma half-life is used to indicate that the relevant half-life of the polypeptide is statistically significantly decreased relative to that of a reference molecule (for example an unmodified polypeptide), as determined under comparable conditions.

The term "expression" as used herein refers to a process by which a gene produces a biochemical, for example, a scaffold of the invention or a fragment thereof. The process includes any manifestation of the functional presence of the gene within the cell including, without limitation, gene knockdown as well as both transient expression and stable expression. It includes without limitation transcription of the gene into one or more mRNAs, and the translation of such mRNAs into one or more polypeptides. If the final desired product is a biochemical, expression includes the creation of that biochemical and any precursors.

An "expression product" can be either a nucleic acid, e.g., a messenger RNA produced by transcription of a gene, or a polypeptide. Expression products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

The term "vector" or "expression vector" is used herein to mean vectors used in accordance with the present invention as a vehicle for introducing into and expressing a desired expression product in a host cell. As known to those skilled in the art, such vectors can easily be selected from the group consisting of plasmids, phages, viruses and retroviruses. In general, vectors compatible with the instant invention will comprise a selection marker, appropriate restriction sites to facilitate cloning of the desired nucleic acid and the ability to enter and/or replicate in eukaryotic or prokaryotic cells.

The term "host cells" refers to cells that harbor vectors constructed using recombinant DNA techniques and encoding at least one expression product. In descriptions of processes for the isolation of an expression product from recombinant hosts, the terms "cell" and "cell culture" are used interchangeably to denote the source of the expression product unless it is clearly specified otherwise, i.e., recovery of the expression product from the "cells" means either recovery from spun down whole cells, or recovery from the cell culture containing both the medium and the suspended cells.

The terms "treat" or "treatment" as used herein refer to both therapeutic treatment and prophylactic or preventative measures, wherein the object is to prevent or slow down (lessen) an undesired physiological change or disorder in a subject, such as the progression of an inflammatory disease or condition. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable.

The term "treatment" also means prolonging survival as compared to expected survival if not receiving treatment. Those in need of treatment include those already with the condition or disorder as well as those prone to have the condition or disorder or those in which the condition or disorder is to be prevented.

The terms "subject," "individual," "animal," "patient," or "mammal" refer to any individual, patient or animal, in particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

The term "CD40L" as used herein refers without limitations to CD40L expressed on the surface of T-cells, recombinantly expressed CD40L, CD40L expressed and purified form *E. coli* or other suitable recombinant protein expression systems, aglycosylated CD40L, and soluble fragments of CD40L. As used herein, "CD40L" also refers to MegaCD40L. MegaCD40L™ is a high activity construct in which two trimeric CD40 ligands are artificially linked via the collagen domain of ACRP30/adiponectin. This construct very effectively simulates the natural membrane-assisted aggregation of CD40L in vivo. It provides a simple and equally potent alternative to [CD40L+enhancer] combinations (Alexis biochemicals). The term "CD40L" refers to monomeric forms of CD40L as well as oligomeric forms, e.g., trimeric CD40L.

The term "CD40L" refers both to the full length CD40L and to soluble fragments, e.g., extracellular domain forms of CD40L resulting from proteolysis. Amino acid sequences of membrane-bound and soluble forms of human CD40L (Swissprot: P29965) are shown in SEQ ID NO: 1 and SEQ ID NO: 2, respectively.

The terms "CD40L antagonist" or "antagonist" are used in the broadest sense, and includes any molecule that partially or fully inhibits, decreases or inactivates one or more biological activities of CD40L, and biologically active variants thereof, in vitro, in situ, or in vivo. For instance, a CD40L antagonist may function to partially or fully inhibit, decrease or inactivate one or more biological activities of one or more CD40L molecules, or one or more CD40L molecules bound to CD40 or other targets, in vivo, in vitro or in situ, as a result of its binding to CD40L.

The term "CD40L agonist" or "agonist" is used in the broadest sense, and includes any molecule that partially or fully enhances, stimulates or activates one or more biological activities of CD40L, and biologically active variants thereof, in vitro, in situ, or in vivo. For instance, a CD40L agonist may function to partially or fully enhance, stimulate or activate one or more biological activities of one or more CD40L molecules, or one or more CD40L molecules bound to CD40R or other targets, in vivo, in vitro or in situ, as a result of its binding to CD40L.

The term "crystal" as used herein, refers to one form of solid state of matter in which atoms are arranged in a pattern that repeats periodically in three-dimensions, typically forming a lattice.

The term "space group symmetry," as used herein, refers to the whole symmetry of the crystal that combines the translational symmetry of a crystalline lattice with the point group symmetry. A "space group" is designated by a capital letter identifying the lattice group (P, A, F, etc.) followed by the point group symbol in which the rotation and reflection elements are extended to include screw axes and glide planes. Note that the point group symmetry for a given space group can be determined by removing the cell centering symbol of the space group and replacing all screw axes by similar rotation axes and replacing all glide planes with mirror planes. The point group symmetry for a space group describes the true symmetry of its reciprocal lattice.

The term "unit cell," as used herein, means the atoms in a crystal that are arranged in a regular repeated pattern, in which the smallest repeating unit is called the unit cell. The entire structure can be reconstructed from knowledge of the unit cell, which is characterized by three lengths (a, b, and c) and three angles ($\alpha$, $\beta$, and $\gamma$). The quantities a and b are the lengths of the sides of the base of the cell and $\gamma$ is the angle between these two sides. The quantity c is the height of the unit cell. The angles $\alpha$ and $\beta$ describe the angles between the base and the vertical sides of the unit cell.

The term "machine-readable data storage medium," as used herein, means a data storage material encoded with machine-readable data, wherein a machine is programmed with instructions for using such data and is capable of displaying data in the desired format, for example, a graphical three-dimensional representation of molecules or molecular complexes.

The term "X-ray diffraction pattern" means the pattern obtained from X-ray scattering of the periodic assembly of molecules or atoms in a crystal. X-ray crystallography is a technique that exploits the fact that X-rays are diffracted by crystals. X-rays have the proper wavelength (in the Angstrom range, approximately $10^{-8}$ cm) to be scattered by the electron cloud of an atom of comparable size. Based on the diffraction pattern obtained from X-ray scattering of the periodic assembly of molecules or atoms in the crystal, the electron density can be reconstructed. Additional phase information can be extracted either from the diffraction data or from supplementing diffraction experiments to complete the reconstruction (the phase problem in crystallography). A model is the progressively built into the experimental electron density, refined against the data to produce an accurate molecular structure. X-ray structure coordinates define a unique configuration of points in space. Those of skill in the art understand that a set of structure coordinates for a protein or a protein-ligand complex, or a portion thereof, define a relative set of points that, in turn, define a configuration in three dimensions. A similar or identical configuration can be defined by an entirely different set of coordinates, provided the distances and angles between coordinates remain essentially the same. In addition, a configuration of points can be defined by increasing or decreasing the distances between coordinates by a scalar factor, while keeping the angles essentially the same.

The term "crystal structure," as used herein, refers to the three-dimensional or lattice spacing arrangement of repeating atomic or molecular units in a crystalline material. The crystal structure of a crystalline material can be determined by X-ray crystallographic methods, see, for example, "Principles of Protein X-Ray Crystallography" by Jan Drenth, Springer Advanced Texts in Chemistry, Springer Verlag, 2nd ed., February 199, ISBN: 0387985875, and "Introduction to Macromolecular Crystallography" by Alexander McPherson, Wiley-Liss, Oct. 18, 2002, ISBN: 0471251224.

The term "effector function" refers to those biological activities of an antibody or antibody fragment attributable to the Fc region (a native Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; downregulation of cell surface receptors (e.g., B cell receptors); and B cell activation.

The term "antibody-dependent cell-mediate cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cells with cytotoxins.

The term "Fc receptor" or "FcR" describes a receptor that binds to the Fc region of an antibody. The FcR can be a native sequence human FcR. The FcR can bind to an IgG antibody (a gamma receptor) and includes receptors of the Fc$\gamma$RI, Fc$\gamma$RII and Fc$\gamma$RIII subclasses, including allelic variants and alternatively spliced forms of these receptors. The term also includes the neonatal receptor FcRn.

The term "consensus sequence" refers to a protein sequence showing the most common amino acids at a particular position after multiple sequences are aligned. A consensus sequence is a way of representing the results of a multiple sequence alignment, where related sequences are compared to each other. The consensus sequence shows which residues are most abundant in the alignment at each position, and the degree of variability at each position.

The term "essentially free" refers to a composition having less than 10% oxidized tryptophan residues relative to the total number of amino acid residues in the protein, less than 8% oxidized tryptophan residues relative to the total number of amino acid residues in the protein, less than 5% oxidized tryptophan residues relative to the total number of amino acid residues in the protein, less than 4% oxidized tryptophan residues relative to the total number of amino acid residues in the protein, less than 3% oxidized tryptophan residues relative to the total number of amino acid residues in the protein, less than 2% oxidized tryptophan residues relative to the total number of amino acid residues in the protein, less than 1% oxidized tryptophan residues relative to the total number of amino acid residues in the protein. In some embodiments, The term "essentially free" refers to a composition having less than 5% oxidized tryptophan residues relative to the total number of amino acid residues in the protein.

The term "bioactivity" or "activity" refers to the biological activity of the therapeutic protein, e.g., TN3 scaffold, and its ability to function in its intended manner in vivo, e.g., binding to CD40L. In some embodiments, activity refers to "relative activity," i.e., activity of the purified therapeutic protein relative to a non-oxidized therapeutic protein. In some embodiments, the relative activity of the purified therapeutic protein is greater than 80%, greater than 85%, greater than 90%, greater than 92%, greater than 94%, greater than 95%, greater than 98% or greater than 99%.

The fusion of albumin to therapeutic proteins has been found to increase or extend the in vivo or serum half-life of the fused therapeutic protein. However, it has been found that during the purification of such albumin-fusion proteins, certain amino acid residues may be susceptible to oxidation, thereby reducing or limiting the bioactivity of the albumin-fusion protein. The present invention is directed to a method of reducing the oxidation of susceptible amino acid residues in albumin-fusion proteins and the purification of such albumin-fusion proteins. In one embodiment, albumin-fusion proteins include a scaffold. In another embodiment, the scaffold comprises a Fn3 domain. In yet another embodiment, the scaffold comprises a human Tenascin C (Tn3) scaffold capable of binding to CD40L.

Process to Reduce Oxidation of Albumin-Fusion Proteins

During the purification process of albumin-fusion proteins, certain amino acid residues may become susceptible to oxidation, which can inhibit the bioactivity and relative potency of the albumin-fusion protein. For example, one or more tryptophan and/or methionine residues may become susceptible to oxidation. In accordance with the present invention, oxidation of susceptible amino acid residues of albumin-fusion proteins is decreased by subjecting a solution comprising albumin-fusion proteins to an affinity chromatography matrix and an anion exchange chromatography matrix under appropriate conditions.

Affinity Matrix Chromatography

The affinity chromatography step utilizes an affinity matrix that preferentially binds albumin. For example, suitable matrices include Cibacron blue dye, Reactive Blue 2, Procion Blue HB, Capto Blue, Capto Blue (high sub), Toyopearl, AF-Blue HC-650M, Blue Sepharose, Blue Tri-sacryl, Mimetic Blue 1, Mimetic Blue SA, Mimetic Blue SA HL and other anthraquinone-type compounds, nitrocellulose matrix, an antibody-based matrix such as Capture Select from Life Technologies, a fatty acid-based matrix, In one embodiment, Cibracon blue dye chromatography is an ideal choice for purification of albumin-fusion proteins from cell culture medium due to its affinity for albumin. Although many Cibacron blue dye chromatography resins are available commercially, many of them are less than ideal for large scale purification of albumin-fusion proteins. For large scale purification, the resin should be made of a material that minimizes non-specific interactions with host related impurities, have good pressure-flow characteristics, and be stable at pH extremes for sanitization purposes (preferable stable under caustic conditions). With these properties in mind, a few commercially available Cibacron blue dye chromatography resins stand out as potential resins for clinical and commercial scale purification: Capto Blue and Capto blue (high sub) from GE Healthcare, and Toyopearl AF-Blue HC-650M from Tosoh Biosciences. Of the two Capto Blue options, in some embodiments the high sub version is preferable for its higher ligand density and thus higher binding capacity.

In a typical purification process, the Cibacron blue dye column is equilibrated with a buffer (such as phosphate, tris, bis-tris, etc.) around neutral pH or slightly acidic pH, and then loaded with clarified cell culture broth or a process intermediate (if the Cibacron blue dye column is not the initial purification step) containing the albumin-fusion protein.

Various amounts of protein can be loaded on the column. In some embodiments, about 5 g protein/L resin to about 100 g protein/L resin, about 10 g protein/L to about 50 g protein/L resin, or about 25 g protein/L resin can be loaded on the affinity column.

After loading the sample, the affinity chromatography column containing the bound albumin-fusion protein is optionally re-equilibrated and then can be further washed with more aggressive buffers to further remove host cell impurities that are bound to the column (through non-specific interactions) or bound to the albumin-fusion protein (through protein-protein interactions). The wash buffer can be optimized to remove these impurities. In one embodiment, the wash buffer contains a polyol; a salt; a sodium sulfate; a nonionic surfactant; urea; and/or a nicotinamide.

In one embodiment, the wash buffer comprises about 2% to about 20% polyol. The polyol may be selected from the group consisting of 1,2-propanediol, 1,3-propanediol, 1,2-butanediol, 1,3-butanediol, 1,4-butanediol, 1,6-hexanediol, and 2-Methyl-2,4-pentanediol.

Various concentrations of salt can be present in the wash buffer. In some embodiments, the salt is present in a suitable amount, e.g., about 0.05 M to about 2.0 M salt, about 0.1 M to about 1.8 M salt, about 0.2 M to about 1.5 M salt, about 0.3 M to about 1.0 M salt, about 0.4 M to about 0.8 M salt, or about 0.5 M salt. The salt can be selected from those commonly used in the art, e.g., sodium chloride, potassium chloride, calcium chloride, lithium chloride, sodium bromide, potassium bromide, and lithium bromide.

Various concentrations of sodium sulfate can be used. The sodium sulfate may be present in an amount of about 0.01 M to about 0.5 M, 0.02 M to about 0.3 M, about 0.04 M to about 0.2 M, or about 0.05 M to about 0.1 M.

Various nonionic surfactants can be used. For example, in some embodiments, the nonionic surfactant can be selected from the group consisting of Triton X-100, Tween 80, polysorbate 20, polysorbate 80, nonoxynol-9, polyoxamer, stearyl alcohol, or sorbitan monostearate. Various concentrations of nonionic surfactant can be used. For example in some embodiments, the nonionic surfactants are present in the wash buffer at a concentration of about 0.01% to about 1%, about 0.02%, about 0.4%, about 0.05% to about 0.2%, or about 0.08% to about 0.01%.

Various chaotropic agents are known in the art. In the present invention, urea is a chaotropic agent to be used in the wash buffer. Urea may be present in an amount of about 0.02 M to about 1.5 M, about 0.05 M to about 1.0 M, or about 0.08 M to about 1.0 M of the wash buffer.

In some embodiments, nicotinamide is used in the wash buffer. Nicotinamide can be present in an amount of about 0.01 M to about 1.0 M, about 0.02 M to about 0.5 M, about 0.04 M to about 0.3 M, about 0.06 M to about 0.2 M, or about 0.1 M of the wash buffer.

The wash buffer can have various pH levels. In some embodiments, the pH of the wash buffer is greater than about 5.0, greater than about 5.5, or greater than about 6.0. In some embodiments, the pH of the wash buffer is less than about 8.0, less than about 7.5, less than about 7.0, or less than about 6.5. In some embodiments, the pH of the wash buffer is about 5.0 to about 8.0, about 5.5 to about 7.5, about 5.5 to about 7.0, about 6.0 to about 7.0 or about 6.5 to about 7.0.

In another embodiment of the invention, the wash buffer comprises about 5% to about 15% polyol, about 0.2 M to about 0.8 M salt, about 0.2 M to about 0.8 M sodium sulfate, about 0.02% to about 0.2% nonionic surfactant, and/or about 0.2 M to about 1.0 M urea. In one aspect of the invention, the wash buffer comprises the polyol, 1,2-propanediol, the salt, sodium chloride, and the nonionic surfactant, Triton X-100. In another aspect of the invention, the wash buffer comprises about 0.5 M sodium chloride; about 0.5 M sodium sulfate; or about 10% 1,3-propanediol. In accordance with one aspect of the invention, the wash buffer has a pH of about 5.5 to about 7.0.

In some embodiments, the wash buffer is suitable to reduce the DNA concentration to less than about $5\times10^2$ ng/mg DNA, less than about $2\times10^2$ ng/mg DNA, or less than about 50 ng/mg DNA. In some embodiments, the was buffer is suitable to reduce the Host Cell Proteins (HCP) to less than 50,000 ng/mg, less than 20,000 ng/mg, or less than 10,000 ng/mg.

In some embodiments, the purified product is eluted from the affinity matrix column by applying a high pH buffer to the column, or adding high concentrations of salts, mild organic solvents, or a combination to disrupt binding of the product. In one embodiment, the elution buffer comprises a base, such as bis-tris, tris, or phosphate base. In another aspect of the invention, the base of the elution buffer is 50 mM of bis-tris. In another embodiment, the elution buffer comprises an elution salt, such as octanoate, NaCl, or sodium and/or potassium salts of caprylate, heptanoate, hexanoate, or nonanoate. In some embodiments, the elution buffer comprises sodium caprylate. The salt may be present in the elution buffer in the amount of about 5 mM to about 500 mM, about 20 mM to about 250 mM, about 50 mM to about 200 mM or about 75 mM to about 150 mM. In another embodiment, the elution buffer comprises EDTA, or other chelating agents. In one embodiment, the affinity matrix elution buffer comprises EDTA, in a suitable amount, such as about 2 mM to about 20 mM EDTA. In an additional embodiment the affinity matrix elution buffer comprises ocatanoate.

In accordance with the present invention, the affinity chromatography has low levels of oxidized product. In one embodiment, the intermediate product containing the albumin-fusion protein following affinity chromatography has less than about 100%, less than about 90%, less than about 80%, less than about 70%, less than about 60%, less than about 50%, less than about 40%, less than about 30%, less than about 20%, less than about 10%, less than about 9%, less than about 8%, less than about 7%, less than about 6%, less than about 5%, or less than about 4% oxidized product relative to the whole protein. In another embodiment, the intermediate product containing the albumin-fusion protein following affinity chromatography has less than about 50%, less than about 40%, less than about 30%, less than about 20%, less than about 10%, less than about 9%, less than about 8%, less than about 7%, less than about 6%, less than about 5%, or less than about 4% oxidized tryptophan residues relative to the total number of tryptophan residues. In another embodiment, the affinity matrix step removes at least 1, 2, 3, 1-2, or 2-3 orders of magnitude of host cell proteins from the original sample. In an embodiment of the invention, the affinity matrix step removes at least 1, 2, 3, 4, 1-2, 2-3, 3-4 orders of magnitude of the DNA impurities from the original sample.

Viral Inactivation

In one embodiment of the invention, the albumin-fusion protein-containing fraction or sample may be treated to inactivate viruses that may be present. In this manner, the fraction/sample may be treated with a virus inactivation agent, e.g., Triton X-100, Tween 80, Tween 20, tri-n-butyl phosphate, or urea. In one embodiment, the viral inactivation step occurs between the affinity chromatography and anion exchange chromatography step(s). In this manner, the virus inactivation agent, e.g., Triton X-100, may be added in an amount of about 0.05% to about 3%, about 0.01% to about 1%, or about 0.1% to about 0.5% for a period of about 1 second to about 10 hours, about 30 seconds to about 5 hours, about 30 minutes to about 3 hours, or about 2 hours. In one embodiment, the virus inactivation agent is 0.5% Triton X-100 (w/w) is held for about 30 to about 240 minutes, e.g., 130 minutes.

Anion Exchange Chromatography

In another aspect of the invention, the albumin-fusion protein-containing fraction or sample is subjected to anion exchange chromatography. The anion exchange may be conducted via bind-and-elute system or a flow through system or both. Any suitable anion exchange matrix may be used. In one embodiment, the anion exchange matrix may be a resin, such as agarose or sepharose, for example, or synthetic microporous or macroporous membranes. Suitable bind-and-elute anion exchange matrices include, for example, Q-resin, Quaternary amines, DEAE. Commercially available matrices include, for example, Capto Q, Toyopearl SuperQ, ANX, DEAE, Q-Sepharose, Q-Sepharose FF, Q-Sepharose HP, and Q-Sepharose XL, Q-Hyper D, DEAE-cellulose, QAE-cellulose, TMAE, DMAE, or DEAE Fractogel, Mustang Q, Sartobind Q, or Sartobind STIC PA. Such matrices can comprise highly cross-linked agarose or be polymeric having, for example, a polyethersulfone polypropylene, methacrylate, or polypropylate base. The column load challenge is within a range of about 0.1 to about 50 g/L, about 0.5 to about 40 g/L, about 1 to about 30 g/L, or about 5 to about 25 g/L. The membrane load challenge is within a range of about 0.1 to about 10 g/mL, about 0.2 to about 5.0 g/mL, about 0.5 to about 2.5 g/mL, or about 1.0 to about 2.0 g/mL.

In another embodiment, the matrices are modified to enhance the purification of the albumin-fusion protein. For example, in one embodiment, the matrix is highly cross-linked agarose with dextran surface extenders. In another embodiment, a polyethersulfone base matrix is modified with quaternary amines. In another embodiment, a polypropylene base matrix is modified with quaternary amines.

When using the bind-and-elute system, the anion exchange chromatography step may involve an equilibration step with a buffer such as phosphate, tris, and bis-tris at neutral or slightly acidic pH. The sample is loaded and the matrix is optionally re-equilibrated. The loading buffer is optimized based on the pH and resin being used, as is known in the art, and to optimize separation of the target albumin-fusion protein. Suitable loading buffers include a base, such as tris or bis-tris, in a range of about 5 mM to about 200 mM, about 10 mM to about 150 mM, about 20 mM to about 100 mM, about 30 mM to about 80 mM, or about 50 mM, and salt, such as NaCl or octanoate, in an amount of about 5 mM to about 100 mM, about 10 mM to about 50 mM, or about 20 mM. In one embodiment, a suitable loading buffer for anion exchange comprises 50 mM bis-tris, 20 mM NaCl at pH 7.0.

In the bind-and-elute system, after equilibration of the anion exchange matrix, the sample containing the albumin-fusion protein is loaded and the desired protein is bound to the anion exchange matrix. The affinity chromatography column containing the bound albumin-fusion protein is washed with a wash buffer to remove materials present in the solution other than the albumin-fusion protein. In some embodiments, the wash buffer is the same as the loading buffer. In some embodiments, the wash buffer comprises 50 mM bis-tris, 20 mM NaCl at pH 7.0.

The bound albumin-fusion protein is eluted from the anion exchange matrix either by step elution or gradient elution. In one embodiment, the anion exchange matrix elution buffer employs salts, such as NaCl, $CaCl_2$, or KCl. The salt concentration of the buffer ranges from greater than above 10 mM, about 10 mM to about 150 mM, about 20 mM to about 400 mM, about 50 mM to about 300 mM, about 20 mM to about 140 mM, about 30 mM to about 130 M, about 40 mM to about 120 mM, or about 50 mM to about 110 mM. The pH range for elution varies between a pH of less than about 9, about 6 to about 8, about 6 to about 7.5, about 6 to about 7, or about 6.5 to about 7. In some embodiments, the bound albumin-fusion protein is eluted form the matrix using a linear gradient of about 10 mM to about 600 mM salt, e.g., NaCl, or about 20 mM to about 400 mM salt, e.g., NaCl.

In accordance with the present invention, the anion exchange bind-and-elute system results in an increased monomer content by reducing the aggregated product and removes the impurities that is responsible for oxidation of the albumin-fusion protein and having low levels of oxidized product. In one embodiment, the intermediate product from this step containing the albumin-fusion protein has less than about 100%, less than about 90%, less than about 80%, less than about 70%, less than about 60%, less than about 50%, less than about 40%, less than about 30%, less than about 20%, less than about 10%, less than about 9%, less than about 8%, less than about 7%, less than about 6%, less than about 5%, less than about 4%, less than about 3% or less than about 2% oxidized product relative to the whole protein. In one embodiment, the intermediate product from this step containing the albumin-fusion protein has less than about 50%, less than about 40%, less than about 30%, less than about 20%, less than about 10%, less than about 9%, less than about 8%, less than about 7%, less than about 6%, less than about 5%, less than about 4%, less than about 3% or less than about 2% oxidized tryptophan residues relative to the total number of tryptophan residues. In another embodiment, the bind-and-elute anion exchange step removes greater than 5, 10, 15, 20, or 30 or at least 5-30, 10-30, 10-40, 15-30, 15-40, 20-30, or 20-40 orders of magnitude of host cell proteins from the original sample. In an embodiment of the invention, the bind-and-elute anion exchange step removes at least 3, 4, 5, or 6 or between 1-2, 2-3, 3-4 orders of magnitude of the DNA impurities from the original sample.

In some embodiment, the anion exchange chromatography matrix is a flow through mode utilizing a membrane. In some embodiments, the albumin-fusion protein is subjected to both an anion exchange chromatography matrix and an anion exchange membrane. The membrane may be pre-conditioned and equilibrated prior to loading. Furthermore, the pH of the loading buffer may be adjusted so that the target albumin-fusion protein does not bind to the anion exchange matrix. In this manner, any contaminating materials, including DNA, host cell proteins (HCPs), viruses, and small molecule impurities, may be separated from the target albumin-fusion protein.

According to the present invention, in one embodiment, the membrane is operated at a pH of less than about 9, a range of about 6 to about 8, about 6.5 to about 7.5, about 6 to about 7.5, or about 7 to about 7.5 or a pH of about 6, 7, 8 or 9. In another embodiment, the salt concentration of the buffer will be greater than 10 mM or a range of about 10 mM to about 200 mM, about 40 mM to about 180 mM, about 50 mM to about 150 mM, about 60 mM to about 120 mM, about 60 mM to about 80 mM. In some embodiments, the salt concentration of the buffer is about 50 mM, about 60 mM, or about 70 mM. In other embodiments, the flow through buffer has a salt concentration of 10 mM to 150 mM and a pH of 6 to 8. In another embodiment, the flow through buffer has a salt concentration of greater than 10 mM and a pH of less than 8. Notably, it was observed that both yield and DNA clearance was optimal for albumin-fusion proteins at low pH, e.g., about 7 to about 7.5, and higher salt concentrations, e.g., greater than 60 mM salt.

In accordance with the present invention, the anion exchange flow through system results in an increased monomer content with low levels of oxidized product and removal of impurities, including HCPs and DNA. In one embodiment, the product from this step containing the albumin-fusion protein has less than about 10%, less than about 9%, less than about 8%, less than about 7%, less than about 6%, less than about 5%, less than about 4%, less than about 3% or less than about 2% oxidized product relative to the whole protein. In another embodiment, the product from this step containing the albumin-fusion protein has less than about 10%, less than about 9%, less than about 8%, less than about 7%, less than about 6%, less than about 5%, less than about 4%, less than about 3% or less than about 2% oxidized tryptophan residues relative to the total number of tryptophan residues. In another embodiment, the flow through anion exchange step removes greater than 1 or greater than 2 orders of magnitude of host cell proteins from the original sample. In an embodiment of the invention, the flow through anion exchange step removes at least 3, 4, 5, or 6 8, 9, or 10 or between 3-6, 4-6, or 5-6, 8-10 or 9-10 orders of magnitude of the DNA impurities from the original sample.

According to the present invention, the bind-to-elute mode of anion exchange may be performed in combination with the flow through mode of anion exchange. Additional optional purification steps may be performed before, in between, or after the anion exchange step(s). For example, sample comprising the albumin-fusion protein may be treated with Triton X-100 to inactivate enveloped viruses. Alternatively, the sample may undergo diafiltration or ultrafiltration. The salt may be added in a suitable concentration. In one embodiment, the eluent containing the albumin-fusion protein is diafiltered against 50 mM bis-tris, 20 mM NaCl at pH 7.0.

Additional Purification Steps

Additional purification steps may include subjecting the eluant/fraction comprising the albumin-fusion protein to a hydrophobic interaction or multimodal matrix. The hydrophobic interaction matrix may be any suitable matrix. In some instances the hydrophobic interaction matrix comprises a phenyl, octyl or butyl hydrophobic group. Hydrophobic interaction matrices are commercially available and are known to those in the art, e.g., Capto Butyl, Capto Phenyl, Capto Butyl, Butyl-S Fast Flow (GE Healthcare Life Sciences, Piscataway, N.J.), Toyopearl Hexyl, Toyopearl Butyl, Toyopearl Phenyl, Toyopearl PPG, Toyopearl Ether, Toyopearl PPG-600M, and Toyopearl Phenyl-650M, Toyopearl PPG-600M, TSKgel Phenyl, TSKgel Ether (TOSOH Corporations, Tokyo, Japan), Macro-Prep Methyl (Bio-Rad Laboratories, Hercules, Calif.). The multimodal matrix may be any suitable matrix. In some instances the multimodal matrix comprises a phenyl, octyl or butyl hydrophobic group along with a cation or anion exchange group. Multimodal matrices are commercially available and are known to those in the art, e.g., Capto MMC, Eshmuno HCX, Nuvia cPrime, or Toyopearl MX-Trp-650M. It has been found that the albumin-fusion protein is optionally equilibrated with a buffer containing a salt, such as, ammonium, lithium, potassium, magnesium, calcium, aluminum, or guanidinium salts as cations, and/or sulfate, phosphate, citrate, tartrate, chloride, bromide, iodide, nitrate, or chlorate salts as anions. For example, in some embodiments, the salt is sodium chloride, sodium sulfate, sodium citrate, or ammonium sulfate, in a suitable amount, e.g., about 100 mM to about 2 M, about 200 mM to about 1.5 M, about 300 mM to about 1 M, about 400 mM to about 800 mM salt, e.g., citrate salt. After equilibration, the sample/fraction containing the albumin-fusion protein is loaded onto the column. In one embodiment, the column is re-equilibrated and then eluted with a step or gradient to a buffer with a reduced salt concentration.

In another embodiment, the fractions may be further purified by subjecting the eluant/fraction comprising the albumin-fusion protein to nanofiltration. In some embodiments, nanofiltration can be used to remove potential virus particles and can be conducted in methods standard to those skilled in the art.

In other embodiments, the fractions may be subjected to size exclusion chromatography to further purify the albumin-fusion protein.

In another embodiment of the invention, a method of obtaining a composition comprising albumin-fusion protein essentially free of oxidized tryptophan residues is provided. According to this embodiment, the method comprises subjecting a composition comprising oxidized tryptophan albumin-fusion proteins and non-oxidized tryptophan albumin-fusion proteins to a hydrophobic interaction matrix, wherein the oxidized tryptophan albumin-fusion protein and non-oxidized tryptophan albumin-fusion protein are eluted from the hydrophobic interaction matrix at different times, thereby separating the oxidized tryptophan albumin-fusion protein from the non-oxidized tryptophan albumin-fusion protein.

Another embodiment of the invention is directed to a method of isolating an albumin-fusion protein essentially free from oxidation of tryptophan and/or methionine residues. According to this embodiment, the composition comprising an albumin-fusion protein is subjected to the following purification processes: (a) an affinity matrix chromatography process; (b) an anion exchange chromatography process; and (c) a hydrophobic interaction matrix chromatography process. The elution buffer for the affinity matrix chromatography process comprising caprylate/octanoate, and in some embodiments additionally EDTA, is applied to the affinity matrix. Moreover, the oxidized tryptophan albumin-fusion protein and non-oxidized tryptophan albumin-fusion protein are eluted from the hydrophobic interaction matrix at different times, thereby separating the oxidized tryptophan albumin-fusion protein from the non-oxidized tryptophan albumin-fusion protein.

Another aspect of the invention is a method of purifying an albumin-fusion protein comprising subjecting a composition comprising an albumin-fusion protein to a hydrophobic interaction matrix, and one or more of the following purification processes: (a) an affinity matrix, wherein an elution buffer comprising caprylate/octanoate, and in some embodiments additionally EDTA, is applied to the affinity matrix; and/or (b) an anion exchange matrix. According to this embodiment, the affinity matrix can be washed with a wash buffer comprising: (1) about 2% to about 20% polyol, wherein the polyol is selected from the group consisting of 1,2-propanediol, 1,3-propanediol, 1,2-butanediol, 1,3-butanediol, 1,4-butanediol, 1,6-hexanediol, and 2-Methyl-2,4-pentanediol; (2) 0.05 M to 2.0 salt, wherein the salt is selected from sodium chloride, potassium chloride, calcium chloride, lithium chloride, sodium bromide, potassium bromide and lithium bromide; (3) about 0.02 M to about 1 M sodium sulfate; (4) about 0.01% to about 1% nonionic surfactant; (5) about 0.05 M to about 1.0 M urea; and/or (6) about 0.02 M to about 0.5 M nicotinamide. The resulting purified albumin-fusion protein is essentially free of oxidized tryptophan residues.

A method of purifying an albumin-fusion protein, the method comprising: applying a composition comprising the albumin-fusion protein to an affinity matrix; eluting the albumin-fusion protein from the affinity matrix to obtain a first eluant; applying the first eluant to an anion exchange matrix; eluting the albumin-fusion protein from the anion exchange matrix to obtain a second eluant; applying the second eluant to an anion exchange membrane; passing the albumin-fusion protein through an anion exchange membrane to obtain a flow through; applying the flow through to a hydrophobic interaction matrix; eluting the albumin-fusion protein from the hydrophobic interaction matrix to obtain a third eluant, wherein the third eluant comprises the purified albumin-fusion protein. In accordance with this embodiment, the resulting purified albumin-fusion protein has 5% or less of tryptophan residues oxidized.

Compositions of Purified Albumin-Fusion Proteins

Compositions comprising the purified albumin-fusion proteins are within the scope of the present invention. These compositions are attributed with low levels of host cell proteins, DNA, and viral activity. Additionally, these compositions comprising the purified albumin-fusion proteins have low levels of oxidation and retained bioactivity.

The composition or fractions comprising the albumin-fusion protein purified according to the invention has less than about 1000 ng/mg, 200 ng/mg, 100 ng/mg, 50 ng/mg, 40 ng/mg, 30 ng/mg, 20 ng/mg or 10 ng/mg of host cell protein. In one embodiment, the albumin-fusion protein-containing composition has less than 20 ng/mg of host cell proteins. In some embodiments, the albumin-fusion protein composition has a level of host cell proteins acceptable to a governmental organization, e.g., the United States Food and Drug Administration, for administration to a human subject.

Moreover, the composition or fractions comprising the albumin-fusion protein purified according to the invention has less than about $5\times10^{-2}$, $1\times10^{-2}$, $5\times10^{-3}$, $1\times10^{-3}$, $5\times10^{-4}$, or $1\times10^{4}$ ng/mg. In one embodiment, the albumin-fusion protein purified according to the invention has less than $5\times10^{-3}$ ng/mg DNA. In some embodiments, the albumin-fusion protein composition has a level of DNA acceptable to a governmental organization, e.g., the United States Food and Drug Administration, for administration to a human subject.

It has been found that the oxidation of tryptophan/methionine residues on albumin-fusion proteins can affect the bioactivity and relative potency of the protein. The albumin-fusion proteins purified and obtained according to the methods of the present invention have low levels of oxidation. In an embodiment of the present invention, the relative potency of the albumin-fusion protein is at least 90%, at least 91%, at least 92%, at least 93%, at least 94% or at least 95%. In another embodiment, the albumin-fusion protein has less than 25%, less than 20%, less than 15%, less than 10%, or less than 5% of the tryptophan residues oxidized relative to the total amount of tryptophan residues in the protein. In one embodiment, the albumin-fusion protein has less than about 20% of the tryptophan residues oxidized relative to the total amount of protein. In another embodiment, the albumin-fusion protein has less than 10%, less than 9%, less than 8%, less than 7%, less than 6% or less than 5% of the tryptophan residues oxidized relative to the number of total tryptophan residues in the protein. In an embodiment of the invention, the albumin-fusion protein has less than about 5% of the tryptophan residues oxidized relative to the total number of tryptophan residues in the protein.

A composition within the scope of the invention comprises an albumin-fusion protein, wherein the composition has less than $5 \times 10^{-3}$ ng/mg DNA, and wherein the less than 15% of the tryptophan residues are oxidized. In one embodiment, the composition has less than $5 \times 10^{-3}$ ng/mg DNA and has albumin-fusion protein in which less than 5% of the tryptophan residues are oxidized.

Another composition of the invention comprises an albumin-fusion protein, wherein the composition has less than 20 ng/mg host cell protein, and wherein the albumin-fusion protein has a relative activity of >90%.

One embodiment of the invention is a composition comprising an albumin-fusion protein, wherein the composition has less than $5 \times 10^{-3}$ ng/mg DNA and wherein the albumin-fusion protein has a relative activity of >90%.

Albumin-Fusion Proteins

Albumin, such as human serum albumin (HSA), or fragments or variants thereof may be fused or conjugated to a therapeutic protein to increase or extend the protein's half-life in the bloodstream and/or its tissue penetration. In some embodiments, the property improved by conjugation with an HSA variant is plasma half-life. The improvement in plasma half-life of the albumin-fusion protein can be an alteration in that property such as an increase or decrease in plasma half-life, or changes in other pharmacokinetic parameters.

Fragments or variants of albumin or HSA that extend or increase the therapeutic protein's in vivo or serum half-life are within the scope of the present invention. HSA variants, i.e., a molecule derived from full length HSA (SEQ ID NO: 139) comprising at least an amino acid substitution, a deletion, or a sequence truncation, have been previously disclosed. For example, the following publications describe HSA variants that may be used: WO 2011/103076, WO2011/051489, and WO 2012/112188. In one embodiment, the albumin is HSA. In another embodiment, the albumin is a variant HSA.

In some embodiments, the HSA variant is a mutant derived from full length HSA (SEQ ID NO: 138). In a specific embodiment, the HSA variant comprises a substitution of cysteine at position 34 to serine (SEQ ID NO: 133). HSA variants that can be used to modify the plasma half-life of a Tn3 scaffold, for example, are described, e.g., in International Publications WO 2011/103076 and WO 2011/051489, both of which are incorporated by reference in their entireties. In some embodiments, the plasma half-life of a therapeutic protein of the invention is increased by fusing it with an HSA variant comprising at least one amino acid substitution in domain III of HSA. Another embodiment includes where the amino acid sequence of variant HSA is SEQ ID NO: 133.

In some embodiments, the albumin-fusion protein of the invention comprises an HSA variant comprising the sequence of full-length mature HSA (SEQ ID NO: 138) or a fragment thereof, except for at least one amino acid substitution, numbered relative to the position in full length mature HSA, at a position selected from the group consisting of 407, 415, 463, 500, 506, 508, 509, 511, 512, 515, 516, 521, 523, 524, 526, 535, 550, 557, 573, 574, and 580; wherein the at least one amino acid substitution does not comprise a lysine (K) to glutamic acid (E) at position 573, and wherein the therapeutic protein has a plasma half-life longer than the plasma half-life of a same therapeutic protein not conjugated to the HSA variant.

In some other embodiments, at least one amino acid substitution, numbered relative to the position in full length mature HSA, is at a position selected from the group consisting of 463, 508, 523, and 524, wherein the therapeutic protein has a plasma half-life longer than the plasma half-life of the therapeutic protein not conjugated to the HSA variant.

In other embodiments, an albumin-fusion protein of the invention comprises an HSA variant comprising the sequence of full-length mature HSA (SEQ ID NO: 133 or 138) or a fragment thereof, except for at least one amino acid substitution, numbered relative to the position in full length mature HSA, selected from the group consisting of:

(a) substitution of Leucine (L) at position 407 to Asparagine (N) or Tyrosine (Y);

(b) substitution of Valine (V) at position 415 to Threonine (T);

(c) substitution of Leucine (L) at position 463 to Asparagine (N);

(d) substitution of Lysine (K) at position 500 to Arginine (R);

(e) substitution of Threonine (T) at position 506 to Tyrosine (Y);

(f) substitution of Threonine (T) at position 508 to Arginine (R);

(g) substitution of Phenylalanine (F) at position 509 to Methionine (M) or Tryptophan (W);

(h) substitution of Alanine (A) at position 511 to Phenylalanine (F);

(i) substitution of Aspartic Acid (D) at position 512 to Tyrosine (Y);

(j) substitution of Threonine (T) at position 515 to Glutamine (Q);

(k) substitution of Leucine (L) at position 516 to Threonine (T) or Tryptophan (W);

(l) substitution of Arginine (R) at position 521 to Tryptophan (W);

(m) substitution of Isoleucine (I) at position 523 to Aspartic Acid (D), Glutamic Acid (E), Glycine (G), Lysine (K), or Arginine (R);

(n) substitution of Lysine (K) at position 524 to Leucine (L);

(o) substitution of Glutamine (Q) at position 526 to Methionine (M);

(p) substitution of Histidine (H) at position 535 to Proline (P);

(q) substitution of Aspartic Acid (D) at position 550 to Glutamic Acid (E);

(r) substitution of Lysine (K) at position 557 to Glycine (G);

(s) substitution of Lysine (K) at position 573 to Phenylalanine (F), Histidine (H), Proline (P), Tryptophan (W), or Tyrosine (Y);

(t) substitution of Lysine (K) at position 574 to Asparagine (N);

(u) substitution of Glutamine (Q) at position 580 to Lysine (K); and, (v) a combination of two or more of said substitutions, wherein the therapeutic protein has a plasma half-life longer than the plasma half-life of a same therapeutic protein not conjugated to said HSA variant.

In some embodiments, the albumin-fusion protein comprises a HSA variant which comprises the sequence of full-length mature HSA (SEQ ID NO: 133 or 138) or a fragment thereof, except for at least one amino acid substitution, numbered relative to the position in full length mature HSA, selected from the group consisting of:

(a) substitution of Leucine (L) at position 463 to Asparagine (N);

(b) substitution of Threonine (T) at position 508 to Arginine (R);

(c) substitution of Isoleucine (I) at position 523 to Aspartic Acid (D), Glutamic Acid (E), Glycine (G), Lysine (K), or Arginine (R);

(d) substitution of Lysine (K) at position 524 to Leucine (L); and, (e) a combination of two or more of said substitutions, wherein said therapeutic protein has a plasma half-life longer than the plasma half-life of a same therapeutic protein not conjugated to said HSA variant.

Albumin fusion proteins may be generated by standard techniques, for example, by expression of the fusion protein from a recombinant fusion gene constructed using publicly available gene sequences.

The therapeutic protein may be any protein that may be fused or conjugated to albumin to increase or extends its half-life. In one embodiment, the therapeutic protein comprises a scaffold moiety comprising a tryptophan residue, wherein oxidation of the tryptophan reduces the biological activity of the albumin-fusion protein. In another embodiment, the protein is capable of binding to CD40L. In another embodiment, the therapeutic protein is a scaffold moiety capable of binding to CD40L. Another embodiment provides that the scaffold moiety comprises a third fibronectin type III (FnIII) domain. Scaffolds comprising FnIII domains have been previously described, for example, in WO 98/56915, WO 2009/023184, WO 2009/05379, WO 2010/051274. WO 2010/093627). In some embodiments, the FnIII domain may be derived from human Tenascin C (Tn3 scaffolds). Such Tn3 scaffolds have been described, for example, in WO 2009/05379, WO 2010/051274, and WO2013/055745.

Albumin Fused to Scaffolds

In an embodiment of the invention, the albumin-fusion protein comprises a scaffold. For example, the scaffolds may comprise CD40L-specific monomer subunits derived from the third FnIII domain of human tenascin C (Tn3), in which at least one non-naturally occurring intramolecular disulfide bond has been engineered. The monomer subunits that make up the Tn3 scaffolds of the invention correctly fold independently of each other, retain their binding specificity and affinity, and each of the monomeric scaffolds retains its functional properties. When monomer subunits are assembled in high valency multimeric Tn3 scaffolds the monomer subunits correctly fold independently of each other, retain their binding specificity and affinity, and each one of the monomers retains its functional properties.

Scaffolds of the invention comprising more than one monomer subunit can bind to multiple epitopes, e.g., (i) bind to multiple epitopes in a single target, (ii) bind to a single epitope in multiple targets, (iii) bind to multiple epitopes located on different subunits of one target, or (iv) bind to multiple epitopes on multiple targets, thus increasing avidity.

In addition, due to the possibility of varying the distance between multiple monomers via linkers, multimeric Tn3 scaffolds are capable of binding to multiple target molecules on a surface (either on the same cell/surface or in different cells/surfaces). As a result of their ability to bind simultaneously to more than one target, a Tn3 multimeric scaffold of the invention can be used to modulate multiple pathways, cross-link receptors on a cell surface, bind cell surface receptors on separate cells, and/or bind target molecules or cells to a substrate.

In addition, the present invention provides affinity matured scaffolds wherein the affinity of a scaffold for a specific target is modulated via mutation. Also, the invention provides methods to produce the scaffolds of the invention as well as methods to engineer scaffolds with desirable physicochemical, pharmacological, or immunological properties. Furthermore, the present invention provides uses for such scaffolds and methods for therapeutic, prophylactic, and diagnostic use.

In one embodiment, the albumin-fusion protein has a Tn3 scaffold, such as that described in PCT Application Pub. No. WO 2013/055745, filed Oct. 10, 2012, and herein incorporated by reference. When purifying the albumin-Tn3 scaffold fusion protein, it has been found that tryptophan and methionine residues are susceptible to oxidation. For example, where the Tn3 scaffold is selected from an albumin-fusion protein of SEQ ID NOs: 134, 135, 201, 202, 203, 204, 205, 206, 207 or 208, it has been found that oxidation may occur at tryptophan amino acid residues, W46/151, on the binding loop of Tn3, and methionine amino acid residues, M74/179, M498, M529, on Tn3 and human serum albumin during the purification process. Impact studies revealed that oxidation at W46/151, M74/179, M498, and M529 of the albumin-Tn3 scaffold protein may impact bioactivity. In particular, it was found that oxidation at W46/151 on the binding loop of Tn3 negatively impacted the bioactivity and relative potency of MEDI4920. However, oxidation at M74/179, M498, and M529 had less of an impact of the fusion protein's bioactivity. Nevertheless, the goal of the present invention is to reduce the oxidation species of albumin-fusion proteins through a purification process intended to control oxidation of susceptible amino acids of albumin-fusion proteins.

The FnIII Structural Motif

Suitable scaffolds of the present invention include those based on the structure of a type III fibronectin module (FnIII), a domain found widely across all three domains of life and viruses, and in multitude of protein classes. In specific embodiments, the scaffolds of the invention are derived from the third FnIII domain of human tenascin C (see International Application No. International Application No. PCT/US2008/012398, published as WO 2009/058379; PCT/US2011/032184, published as WO 2011/130324; and International Application No. PCT/US2011/032188, published as WO2011130328).

In one specific embodiment, the Tn3 scaffolds of the invention comprise a CD40L-specific monomer subunit derived from a parent Tn3 scaffold. The overall tridimensional fold of the monomer is closely related to that of the smallest functional antibody fragment, the variable region of the heavy chain (VH), which in the single domain antibodies of camels and camelids (e.g., llamas) comprises the entire antigen recognition unit.

The Tn3 monomer subunits of the invention and the native FnIII domain from tenascin C are characterized by the same tridimensional structure, namely a beta-sandwich structure with three beta strands (A, B, and E) on one side and four beta strands (C, D, F, and G) on the other side, connected by six loop regions. These loop regions are designated according to the beta-strands connected to the N- and C-terminus of each loop. Accordingly, the AB loop is located between beta strands A and B, the BC loop is located between strands B and C, the CD loop is located between beta strands C and D, the DE loop is located between beta strands D and E, the EF loop is located between beta strands E and F, and the FG loop is located between beta strands F and G. FnIII domains possess solvent exposed loop s tolerant of randomization, which facilitates the generation of diverse pools of protein scaffolds capable of binding specific targets with high affinity.

In one aspect of the invention, Tn3 monomer subunits are subjected to directed evolution designed to randomize one or more of the loops which are analogous to the complementarity-determining regions (CDRs) of an antibody variable region. Such a directed evolution approach results in the production of antibody-like molecules with high affinities for targets of interest, e.g., CD40L.

In addition, in some embodiments the Tn3 scaffolds described herein can be used to display defined exposed loops (for example, loops previously randomized and selected on the basis of target binding) in order to direct the evolution of molecules that bind to such introduced loops. This type of selection can be carried out to identify recognition molecules for any individual CDR-like loop or, alternatively, for the recognition of two or all three CDR-like loops combined into a nonlinear epitope binding moiety. A set of three loops (designated BC, DE, and FG), which can confer specific target binding, run between the B and C strands; the D and E strands, and the F and G beta strands, respectively. The BC, DE, and FG loops of the third FnIII domain of human tenascin C are 9, 6, and 10 amino acid residues long, respectively. The length of these loops falls within the narrow range of the cognate antigen-recognition loops found in antibody heavy chains, that is, 7-10, 4-8, and 4-28 amino acids in length, respectively. Similarly, a second set of loops, the AB, CD, and EF loops (7, 7, and 8, amino acids in length respectively) run between the A and B beta strands; the C and D beta strands; and the E and F beta strands, respectively.

Once randomized and selected for high affinity binding to a target, the loops in the Tn3 monomer scaffold may make contacts with targets equivalent to the contacts of the cognate CDR loops in antibodies. Accordingly, in some embodiments the AB, CD, and EF loops are randomized and selected for high affinity binding to one or more targets, e.g., CD40L. In some embodiments, this randomization and selection process may be performed in parallel with the randomization of the BC, DE, and FG loops, whereas in other embodiments this randomization and selection process is performed in series.

CD40L-Specific Monomeric Subunits

The invention provides CD40L-specific recombinant, non-naturally occurring Tn3 scaffolds comprising, a plurality of beta strand domains linked to a plurality of loop regions, wherein one or more of said loop regions vary by deletion, substitution or addition of at least one amino acid from the cognate loops in wild type Tn3 (SEQ ID NO: 3) (see Table 1).

To generate improved CD40L-specific Tn3 monomer subunits with novel binding characteristics, parent Tn3 is subjected to amino acid additions, deletions or substitutions. It will be understood that, when comparing the sequence of a CD40L-specific Tn3 monomer subunit to the sequence of parent Tn3, the same definition of the beta strands and loops is utilized. In some embodiments, the CD40L-specific Tn3 monomer subunits of the invention comprise the amino acid sequence:

$$\text{IEV}(X_{AB})_n\text{ALITW}(X_{BC})_n\text{CELX}_1\text{YGI}(X_{CD})_n\text{TTIDL}(X_{DE})_n\text{YSI}$$
$$(X_{EF})_n\text{YEVSLIC}(X_{FG})_n\text{KETFTT}$$

wherein:

(a) $X_{AB}$, $X_{BC}$, $X_{CD}$, $X_{DE}$, $X_{EF}$, and $X_{FG}$ represent the amino acid residues present in the sequences of the AB, BC, CD, DE, EF, and FG loops, respectively;

(b) $X_1$ represents amino acid residue alanine (A) or threonine (T); and, (c) length of the loop n is an integer between 2 and 26.

TABLE 2

Loop Sequences of Tn3 Clones Used in These Studies

| Clone | AB Loop SEQ ID NO | BC Loop SEQ ID NO | CD Loop SEQ ID NO | DE Loop SEQ ID NO | EF Loop SEQ ID NO | FG Loop SEQ ID NO* |
|---|---|---|---|---|---|---|
| PARENT Tn3 | | | | | | |
| Tn3 | 4 | 5 | 6 | 7 | 8 | 9 |
| 309 FAMILY | | | | | | |
| 309FGwt | 4 | 83 | 6 | 94 | 8 | 9 |
| 309 | 4 | 83 | 6 | 94 | 8 | 99 |
| 340 | 4 | 84 | 6 | 95 | 8 | 9 |
| 341 | 4 | 85 | 6 | 94 | 8 | 9 |
| 342 | 4 | 86 | 6 | 96 | 8 | 9 |
| 343 | 4 | 87 | 6 | 97 | 8 | 9 |
| 344 | 4 | 88 | 6 | 95 | 8 | 9 |

TABLE 2-continued

Loop Sequences of Tn3 Clones Used in These Studies

| Clone | AB Loop SEQ ID NO | BC Loop SEQ ID NO | CD Loop SEQ ID NO | DE Loop SEQ ID NO | EF Loop SEQ ID NO | FG Loop SEQ ID NO* |
|---|---|---|---|---|---|---|
| 345 | 4 | 89 | 6 | 94 | 8 | 9 |
| 346 | 4 | 90 | 6 | 94 | 8 | 9 |
| 347 | 4 | 91 | 6 | 95 | 8 | 9 |
| 348 | 4 | 92 | 6 | 98 | 8 | 9 |
| 349 | 4 | 93 | 6 | 94 | 8 | 9 |
| 309FGwt consensus | 4 | 168 | 6 | 169 | 8 | 170 |
| 311 FAMILY** | | | | | | |
| 311 | 4 | 100 | 6 | 118 | 8 | 129 |
| 311K4E | 136 | 100 | 6 | 118 | 137 | 129 |
| 311K4E_1 | 136 | 101 | 6 | 119 | 8 | 129 |
| 311K4E_2 | 136 | 102 | 6 | 120 | 8 | 129 |
| 311K4E_3† | 136 | 103 | 6 | 121 | 8 | 129 |
| 311K4E_4† | 136 | 104 | 6 | 122 | 8 | 129 |
| 311K4E_5† | 136 | 105 | 6 | 121 | 8 | 129 |
| 311K4E_7 | 136 | 106 | 6 | 123 | 8 | 129 |
| 311K4E_8† | 136 | 107 | 6 | 123 | 8 | 129 |
| 311K4E_9 | 136 | 108 | 6 | 118 | 8 | 129 |
| 311K4E_10† | 136 | 109 | 6 | 123 | 8 | 129 |
| 311K4E_11 | 136 | 110 | 6 | 121 | 8 | 129 |
| 311K4E_12† | 136 | 111 | 6 | 123 | 8 | 130 |
| 311K4E_13 | 136 | 108 | 6 | 121 | 8 | 129 |
| 311K4E_14 | 136 | 112 | 6 | 124 | 8 | 129 |
| 311K4E_15 | 136 | 113 | 6 | 125 | 8 | 129 |
| 311K4E_16 | 136 | 114 | 6 | 118 | 8 | 129 |
| 311K4E_19 | 136 | 115 | 6 | 126 | 8 | 129 |
| 311K4E_20 | 136 | 116 | 6 | 127 | 8 | 129 |
| 311K4E_21 | 136 | 117 | 6 | 128 | 8 | 129 |
| 311 consensus | 173 | 174 | 6 | 175 | 176 | 177 |

†Clones comprising a C beta strand having the sequence CELAYGI (SEQ ID NO: 14), all other clones comprise a C beta strand having the sequence CELTYGI (SEQ ID NO: 13).
*In some variants in the 309 family, e.g., 342, the FG loop can be replaced with SEQ ID NO: 139.
**In some variants in the 311 family, the BC loop can be engineered to replace the tyrosine at position 21. It is specifically contemplated that the replacement amino acid residues can have a small side chain.

In some embodiments, the CD40L-specific Tn3 monomer subunits of the invention consist of the amino acid sequence:

$$IEV(X_{AB})_nALITW(X_{BC})_nCELX_1YGI(X_{CD})_nTTIDL(X_{DE})_nYSI(X_{EF})_nYEVSLIC(X_{FG})_nKETFTT$$

wherein:

(a) $X_{AB}$, $X_{BC}$, $X_{CD}$, $X_{DE}$, $X_{EF}$, and $X_{FG}$ represent the amino acid residues present in the sequences of the AB, BC, CD, DE, EF, and FG loops, respectively;

(b) $X_1$ represents amino acid residue alanine (A) or threonine (T); and, (c) length of the loop n is an integer between 2 and 26.

In one embodiment, the beta strands of the CD40L-specific Tn3 monomer scaffold have at least 90% sequence identity to the beta strands of the parent Tn3 scaffold (SEQ ID NO: 3). To calculate such percentage of sequence identify, amino acid sequences are aligned applying methods known in the art. The percentage of sequence identity is defined as the ratio between (a) the number of amino acids located in beta strands which are identical in the sequence alignment and (b) the total number of amino acids located in beta strands.

In one embodiment, the sequence of the AB loop comprises SEQ ID NO: 4 or SEQ ID NO: 136. In another embodiment, the sequence of the CD loop comprises SEQ ID NO: 6. In another embodiment, the sequence of the EF loop comprises SEQ ID NO: 8 or SEQ ID NO: 137. In one embodiment, the sequence of the AB loop consists of SEQ ID NO: 4 or SEQ ID NO: 136. In another embodiment, the sequence of the CD loop consists of SEQ ID NO: 6. In another embodiment, the sequence of the EF loop consists of SEQ ID NO: 8 or SEQ ID NO: 137.

In one embodiment, the sequence of the BC loop comprises a sequence selected from the group consisting of SEQ ID NOs: 83, 84, 85, 86, 87, 88, 89, 90, 91, 92 and 93. In another embodiment, the sequence of the BC loop consists of a sequence selected from the group consisting of SEQ ID NOs: 83, 84, 85, 86, 87, 88, 89, 90, 91, 92 and 93.

In one embodiment, the sequence of the DE loop comprises a sequence selected from the group consisting of SEQ ID NOs: 94, 95, 96, 97 and 98. In another embodiment, the sequence of the DE loop consists of a sequence selected from the group consisting of SEQ ID NOs: 94, 95, 96, 97 and 98.

In one embodiment, the sequence of the FG loop comprises a sequence selected from the group consisting of SEQ ID NOs: 9, 99, and 139. In another embodiment, the sequence of the FG loop consists of a sequence selected from the group consisting of SEQ ID NOs: 9, 99, and 139.

In one embodiment, the sequence of the BC loop comprises a sequence selected from the group consisting of SEQ ID NOs: 100, 101, 102, 103, 104, 105, 106, 107, 108, 109, 110, 111, 112, 113, 114, 115, 116 and 117. In another embodiment, the sequence of the BC loop consists of a sequence selected from the group consisting of SEQ ID NOs: 100, 101, 102, 103, 104, 105, 106, 107, 108, 109, 110, 111, 112, 113, 114, 115, 116 and 117.

In some embodiments, the sequence of the DE loop comprises a sequence selected from the group consisting of SEQ ID NOs: 118, 119, 120, 121, 122, 123, 124, 125, 126, 127 and 128. In other embodiments, the sequence of the DE loop consists of a sequence selected from the group consisting of SEQ ID NOs: 118, 119, 120, 121, 122, 123, 124, 125, 126, 127 and 128.

In some embodiments, the sequence of the FG loop comprises a sequence selected from the groups consisting of SEQ ID NOs: 129 and 130. In other embodiments, the sequence of the FG loop consists of a sequence selected from the groups consisting of SEQ ID NOs: 129 and 130.

In some embodiments, the sequence of the BC loop comprises SEQ ID NO: 83, the sequence of the DE loop comprises SEQ ID NO: 94, and the sequence of the FG loop comprises SEQ ID NO: 9 or 139. In some embodiments, the sequence of the BC loop consists of SEQ ID NO: 83, the sequence of the DE loop consists of SEQ ID NO: 94, and the sequence of the FG loop consists of SEQ ID NO: 9 or 139.

In some embodiments, the sequence of the BC loop comprises SEQ ID NO: 83, the sequence of the DE loop comprises SEQ ID NO: 94, and the sequence of the FG loop comprises SEQ ID NO: 99. In other embodiments, the sequence of the BC loop consists of SEQ ID NO: 83, the sequence of the DE loop consists of SEQ ID NO: 94, and the sequence of the FG loop consists of SEQ ID NO: 99.

In some embodiments, the sequence of the BC loop comprises SEQ ID NO: 84, the sequence of the DE loop comprises SEQ ID NO: 95, and the sequence of the FG loop comprises SEQ ID NO: 9 or 139. In other embodiments, the sequence of the BC loop consists of SEQ ID NO: 84, the sequence of the DE loop consists of SEQ ID NO: 95, and the sequence of the FG loop consists of SEQ ID NO: 9 or 139.

In some embodiments, the sequence of the BC loop comprises SEQ ID NO: 85, the sequence of the DE loop comprises SEQ ID NO: 94, and the sequence of the FG loop comprises SEQ ID NO: 9 or 139. In other embodiments, the sequence of the BC loop consists of SEQ ID NO: 85, the sequence of the DE loop consists of SEQ ID NO: 94, and the sequence of the FG loop consists of SEQ ID NO: 9 or 139.

In some embodiments, the sequence of the BC loop comprises SEQ ID NO: 86, the sequence of the DE loop comprises SEQ ID NO: 96, and the sequence of the FG loop comprises SEQ ID NO: 9 or 139. In other embodiments, the sequence of the BC loop consists of SEQ ID NO: 86, the sequence of the DE loop consists of SEQ ID NO: 96, and the sequence of the FG loop consists of SEQ ID NO: 9 or 139.

In some embodiments, the sequence of the BC loop comprises SEQ ID NO: 87, the sequence of the DE loop comprises SEQ ID NO: 97, and the sequence of the FG loop comprises SEQ ID NO: 9 or 139. In other embodiments, the sequence of the BC loop consists of SEQ ID NO: 87, the sequence of the DE loop consists of SEQ ID NO: 97, and the sequence of the FG loop consists of SEQ ID NO: 9 or 139.

In some embodiments, the sequence of the BC loop comprises SEQ ID NO: 88, the sequence of the DE loop comprises SEQ ID NO: 95, and the sequence of the FG loop comprises SEQ ID NO: 9 or 139. In other embodiments, the sequence of the BC loop consists of SEQ ID NO: 88, the sequence of the DE loop consists of SEQ ID NO: 95, and the sequence of the FG loop consists of SEQ ID NO: 9 or 139.

In some embodiments, the sequence of the BC loop comprises SEQ ID NO: 89, the sequence of the DE loop comprises SEQ ID NO: 94, and the sequence of the FG loop comprises SEQ ID NO: 9 or 139. In other embodiments, the sequence of the BC loop consists of SEQ ID NO: 89, the sequence of the DE loop consists of SEQ ID NO: 94, and the sequence of the FG loop consists of SEQ ID NO: 9 or 139.

In some embodiments, the sequence of the BC loop comprises SEQ ID NO: 90, the sequence of the DE loop comprises SEQ ID NO: 94, and the sequence of the FG loop comprises SEQ ID NO: 9 or 139. In other embodiments, the sequence of the BC loop consists of SEQ ID NO: 90, the sequence of the DE loop consists of SEQ ID NO: 94, and the sequence of the FG loop consists of SEQ ID NO: 9 or 139.

In some embodiments, the sequence of the BC loop comprises SEQ ID NO: 91, the sequence of the DE loop comprises SEQ ID NO: 95, and the sequence of the FG loop comprises SEQ ID NO: 9 or 139. In other embodiments, the sequence of the BC loop consists of SEQ ID NO: 91, the sequence of the DE loop consists of SEQ ID NO: 95, and the sequence of the FG loop consists of SEQ ID NO: 9 or 139.

In some embodiments, the sequence of the BC loop comprises SEQ ID NO: 92, the sequence of the DE loop comprises SEQ ID NO: 98, and the sequence of the FG loop comprises SEQ ID NO: 9 or 139. In other embodiments, the sequence of the BC loop consists of SEQ ID NO: 92, the sequence of the DE loop consists of SEQ ID NO: 98, and the sequence of the FG loop consists of SEQ ID NO: 9 or 139.

In some embodiments, the sequence of the BC loop comprises SEQ ID NO: 93, the sequence of the DE loop comprises SEQ ID NO: 94, and the sequence of the FG loop comprises SEQ ID NO: 9 or 139. In other embodiments, the sequence of the BC loop consists of SEQ ID NO: 93, the sequence of the DE loop consists of SEQ ID NO: 94, and the sequence of the FG loop consists of SEQ ID NO: 9 or 139.

In some embodiments, the sequence of the BC loop comprises SEQ ID NO: 168, the sequence of the DE loop comprises SEQ ID NO: 169, and the sequence of the FG loop comprises SEQ ID NO: 170. In other embodiments, the sequence of the BC loop consists of SEQ ID NO: 168, the sequence of the DE loop consists of SEQ ID NO: 169, and the sequence of the FG loop consists of SEQ ID NO: 170.

In some embodiments, the sequence of the BC loop comprises SEQ ID NO: 100, the sequence of the DE loop comprises SEQ ID NO: 118, and the sequence of the FG loop comprises SEQ ID NO: 129. In other embodiments, the sequence of the BC loop consists of SEQ ID NO: 100, the sequence of the DE loop consists of SEQ ID NO: 118, and the sequence of the FG loop consists of SEQ ID NO: 129.

In some embodiments, the sequence of the AB loop comprises SEQ ID NO: 136, the sequence of the BC loop comprises SEQ ID NO: 101, the sequence of the DE loop comprises SEQ ID NO: 119, and the sequence of the FG loop comprises SEQ ID NO: 129. In other embodiments, the sequence of the AB loop consists of SEQ ID NO: 136, the sequence of the BC loop consists of SEQ ID NO: 101, the sequence of the DE loop consists of SEQ ID NO: 119, and the sequence of the FG loop consists of SEQ ID NO: 129.

In some embodiments, the sequence of the AB loop comprises SEQ ID NO: 136, the sequence of the BC loop comprises SEQ ID NO: 102, the sequence of the DE loop comprises SEQ ID NO: 120, and the sequence of the FG loop comprises SEQ ID NO: 129. In other embodiments, the sequence of the AB loop consists of SEQ ID NO: 136, the sequence of the BC loop consists of SEQ ID NO: 102, the sequence of the DE loop consists of SEQ ID NO: 120, and the sequence of the FG loop consists of SEQ ID NO: 129.

In some embodiments, the sequence of the AB loop comprises SEQ ID NO: 136, the sequence of the BC loop comprises SEQ ID NO: 103, the sequence of the DE loop comprises SEQ ID NO: 121, and the sequence of the FG loop comprises SEQ ID NO: 129. In other embodiments, the sequence of the AB loop consists of SEQ ID NO: 136, the sequence of the BC loop consists of SEQ ID NO: 103, the sequence of the DE loop consists of SEQ ID NO: 121, and the sequence of the FG loop consists of SEQ ID NO: 129.

In some embodiments, the sequence of the AB loop comprises SEQ ID NO: 136, the sequence of the BC loop comprises SEQ ID NO: 104, the sequence of the DE loop comprises SEQ ID NO: 122, and the sequence of the FG loop comprises SEQ ID NO: 129. In other embodiments, the sequence of the AB loop consists of SEQ ID NO: 136, the sequence of the BC loop consists of SEQ ID NO: 104, the sequence of the DE loop consists of SEQ ID NO: 122, and the sequence of the FG loop consists of SEQ ID NO: 129.

In some embodiments, the sequence of the AB loop comprises SEQ ID NO: 136, the sequence of the BC loop comprises SEQ ID NO: 105, the sequence of the DE loop comprises SEQ ID NO: 121, and the sequence of the FG loop comprises SEQ ID NO: 129. In other embodiments, the sequence of the AB loop consists of SEQ ID NO: 136, the sequence of the BC loop consists of SEQ ID NO: 105, the sequence of the DE loop consists of SEQ ID NO: 121, and the sequence of the FG loop consists of SEQ ID NO: 129.

In some embodiments, the sequence of the AB loop comprises SEQ ID NO: 136, the sequence of the BC loop comprises SEQ ID NO: 106, the sequence of the DE loop comprises SEQ ID NO: 123, and the sequence of the FG loop comprises SEQ ID NO: 129. In other embodiments, the sequence of the AB loop consists of SEQ ID NO: 136, the sequence of the BC loop consists of SEQ ID NO: 106, the sequence of the DE loop consists of SEQ ID NO: 123, and the sequence of the FG loop consists of SEQ ID NO: 129.

In some embodiments, the sequence of the AB loop comprises SEQ ID NO: 136, the sequence of the BC loop comprises SEQ ID NO: 107, the sequence of the DE loop comprises SEQ ID NO: 123, and the sequence of the FG loop comprises SEQ ID NO: 129. In other embodiments, the sequence of the AB loop consists of SEQ ID NO: 136, the sequence of the BC loop consists of SEQ ID NO: 107, the sequence of the DE loop consists of SEQ ID NO: 123, and the sequence of the FG loop consists of SEQ ID NO: 129.

In some embodiments, the sequence of the AB loop comprises SEQ ID NO: 136, the sequence of the BC loop comprises SEQ ID NO: 108, the sequence of the DE loop comprises SEQ ID NO: 118, and the sequence of the FG loop comprises SEQ ID NO: 129. In other embodiments, the sequence of the AB loop consists of SEQ ID NO: 136, the sequence of the BC loop consists of SEQ ID NO: 108, the sequence of the DE loop consists of SEQ ID NO: 118, and the sequence of the FG loop consists of SEQ ID NO: 129.

In some embodiments, the sequence of the AB loop comprises SEQ ID NO: 136, the sequence of the BC loop comprises SEQ ID NO: 109, the sequence of the DE loop comprises SEQ ID NO: 123, and the sequence of the FG loop comprises SEQ ID NO: 129. In other embodiments, the sequence of the AB loop consists of SEQ ID NO: 136, the sequence of the BC loop consists of SEQ ID NO: 109, the sequence of the DE loop consists of SEQ ID NO: 123, and the sequence of the FG loop consists of SEQ ID NO: 129.

In some embodiments, the sequence of the AB loop comprises SEQ ID NO: 136, the sequence of the BC loop comprises SEQ ID NO: 110, the sequence of the DE loop comprises SEQ ID NO: 121, and the sequence of the FG loop comprises SEQ ID NO: 129. In other embodiments, the sequence of the AB loop consists of SEQ ID NO: 136, the sequence of the BC loop consists of SEQ ID NO: 110, the sequence of the DE loop consists of s SEQ ID NO: 121, and the sequence of the FG loop consists of SEQ ID NO: 129.

In some embodiments, the sequence of the AB loop comprises SEQ ID NO: 136, the sequence of the BC loop comprises SEQ ID NO: 111, the sequence of the DE loop comprises SEQ ID NO: 123, and the sequence of the FG loop comprises SEQ ID NO: 130. In other embodiments, the sequence of the AB loop consists of SEQ ID NO: 136, the sequence of the BC loop consists of SEQ ID NO: 111, the sequence of the DE loop consists of SEQ ID NO: 123, and the sequence of the FG loop consists of SEQ ID NO: 130.

In some embodiments, the sequence of the AB loop comprises SEQ ID NO: 136, the sequence of the BC loop comprises SEQ ID NO: 108, the sequence of the DE loop comprises SEQ ID NO: 121, and the sequence of the FG loop comprises SEQ ID NO: 129. In other embodiments, the sequence of the AB loop consists of SEQ ID NO: 136, the sequence of the BC loop consists of SEQ ID NO: 108, the sequence of the DE loop consists of SEQ ID NO: 121, and the sequence of the FG loop consists of SEQ ID NO: 129.

In some embodiments, the sequence of the AB loop comprises SEQ ID NO: 136, the sequence of the BC loop comprises SEQ ID NO: 112, the sequence of the DE loop comprises SEQ ID NO: 124, and the sequence of the FG loop comprises SEQ ID NO: 129. In other embodiments, the sequence of the AB loop consists of SEQ ID NO: 136, the sequence of the BC loop consists of SEQ ID NO: 112, the sequence of the DE loop consists of SEQ ID NO: 124, and the sequence of the FG loop consists of SEQ ID NO: 129.

In some embodiments, the sequence of the AB loop comprises SEQ ID NO: 136, the sequence of the BC loop comprises SEQ ID NO: 113, the sequence of the DE loop comprises SEQ ID NO: 125, and the sequence of the FG loop comprises SEQ ID NO: 129. In other embodiments, the sequence of the AB loop consists of SEQ ID NO: 136, the sequence of the BC loop consists of SEQ ID NO: 113, the sequence of the DE loop consists of SEQ ID NO: 125, and the sequence of the FG loop consists of SEQ ID NO: 129.

In some embodiments, the sequence of the AB loop comprises SEQ ID NO: 136, the sequence of the BC loop comprises SEQ ID NO: 114, the sequence of the DE loop comprises SEQ ID NO: 118, and the sequence of the FG loop comprises SEQ ID NO: 129. In other embodiments, the sequence of the AB loop consists of SEQ ID NO: 136, the sequence of the BC loop consists of SEQ ID NO: 114, the sequence of the DE loop consists of SEQ ID NO: 118, and the sequence of the FG loop consists of SEQ ID NO: 129.

In some embodiments, the sequence of the AB loop comprises SEQ ID NO: 136, the sequence of the BC loop comprises SEQ ID NO: 115, the sequence of the DE loop comprises SEQ ID NO: 126, and the sequence of the FG loop comprises SEQ ID NO: 129. In other embodiments, the sequence of the AB loop consists of SEQ ID NO: 136, the sequence of the BC loop consists of SEQ ID NO: 115, the sequence of the DE loop consists of SEQ ID NO: 126, and the sequence of the FG loop consists of SEQ ID NO: 129.

In some embodiments, the sequence of the AB loop comprises SEQ ID NO: 136, the sequence of the BC loop comprises SEQ ID NO: 116, the sequence of the DE loop comprises SEQ ID NO: 127, and the sequence of the FG loop comprises SEQ ID NO: 129. In other embodiments, the sequence of the AB loop consists of SEQ ID NO: 136, the sequence of the BC loop consists of SEQ ID NO: 116, the sequence of the DE loop consists of SEQ ID NO: 127, and the sequence of the FG loop consists of SEQ ID NO: 129.

In some embodiments, the sequence of the AB loop comprises SEQ ID NO: 136, the sequence of the BC loop comprises SEQ ID NO: 117, the sequence of the DE loop comprises SEQ ID NO: 128, and the sequence of the FG loop comprises SEQ ID NO: 129. In other embodiments, the sequence of the AB loop consists of SEQ ID NO: 136, the sequence of the BC loop consists of SEQ ID NO: 117, the sequence of the DE loop consists of SEQ ID NO: 128, and the sequence of the FG loop consists of SEQ ID NO: 129.

In some embodiments, the sequence of the BC loop comprises SEQ ID NO: 174, the sequence of the DE loop comprises SEQ ID NO: 175, and the sequence of the FG loop comprises SEQ ID NO: 177. In other embodiments, the sequence of the BC loop consists of SEQ ID NO: 174, the sequence of the DE loop consists of SEQ ID NO: 175, and the sequence of the FG loop consists of SEQ ID NO: 177.

In some embodiments, the CD40L-specific monomer subunit comprises a sequence selected from the group consisting of SEQ ID NO: 20, 22, 24, 26, 28, 30, 32, 34, 36, 38, 40, 42 and 146. In other embodiments, the CD40L-specific monomer subunit consists of a sequence selected from the group consisting of SEQ ID NO: 20, 22, 24, 26, 28, 30, 32, 34, 36, 38, 40, 42 and 146.

In some embodiments, the CD40L-specific monomer subunit comprises SEQ ID NO: 28 or 146. In other embodiments, the CD40L-specific monomer subunit consists of SEQ ID NO: 28 or 146.

In some embodiments, the CD40L-specific Tn3 monomer subunits of the invention comprise the amino acid sequence:

(SEQ ID NO: 167)
IEVKDVTDTTALITWX$_1$DX$_2$X$_3$X$_4$X$_5$X$_6$X$_7$X$_8$CELTYGIKDVPGDRTTIDL

WX$_9$HX$_{10}$AX$_{11}$YSIGNLKPDTEYEVSLICRX$_{12}$GDMSSNPAKETFTT wherein:

(a) $X_1$ represents amino acid residue serine (S) or leucine (L);

(b) $X_2$ represents amino acid residue aspartic acid (D) or glutamic acid (E);

(c) $X_3$ represents amino acid residue histidine (H), isoleucine (I), valine (V), phenylalanine (F) or tryptophan (W);

(d) $X_4$ represents amino acid residue alanine (A), glycine (G), glutamic acid (E) or aspartic acid (D);

(e) $X_5$ represents amino acid residue glutamic acid (E), leucine (L), glutamine (Q), serine (S), aspartic acid (D) or asparagine (N);

(f) $X_6$ represents amino acid residue phenylalanine (F) or tyrosine (Y);

(g) $X_7$ represents amino acid residue isoleucine (I), valine (V), histidine (H), glutamic acid (E) or aspartic acid (D);

(h) $X_8$ represents amino acid residue glycine (G), tryptophan (W) or valine (V);

(i) $X_9$ represents amino acid residue tryptophan (W), phenylalanine (F) or tyrosine (Y);

(j) $X_{10}$ represents amino acid residue serine (S), glutamine (Q), methionine (M) or histidine (H);

(k) $X_{11}$ represents amino acid residue tryptophan (W) or histidine (H); and, (l) $X_{12}$ represents amino acid residue arginine (R) or serine (S).

In some embodiments, the CD40L-specific Tn3 monomer subunits of the invention consist of the amino acid sequence:

(SEQ ID NO: 167)
IEVKDVTDTTALITWX$_1$DX$_2$X$_3$X$_4$X$_5$X$_6$X$_7$X$_8$CELTYGIKDVPGDRTTIDL

WX$_9$HX$_{10}$AX$_{11}$YSIGNLKPDTEYEVSLICRX$_{12}$GDMSSNPAKETFTT wherein:

(a) $X_1$ represents amino acid residue serine (S) or leucine (L);

(b) $X_2$ represents amino acid residue aspartic acid (D) or glutamic acid (E);

(c) $X_3$ represents amino acid residue histidine (H), isoleucine (I), valine (V), phenylalanine (F) or tryptophan (W);

(d) $X_4$ represents amino acid residue alanine (A), glycine (G), glutamic acid (E) or aspartic acid (D);

(e) $X_5$ represents amino acid residue glutamic acid (E), leucine (L), glutamine (Q), serine (S), aspartic acid (D) or asparagine (N);

(f) $X_6$ represents amino acid residue phenylalanine (F) or tyrosine (Y);

(g) $X_7$ represents amino acid residue isoleucine (I), valine (V), histidine (H), glutamic acid (E) or aspartic acid (D);

(h) $X_8$ represents amino acid residue glycine (G), tryptophan (W) or valine (V);

(i) $X_9$ represents amino acid residue tryptophan (W), phenylalanine (F) or tyrosine (Y);

(j) $X_{10}$ represents amino acid residue serine (S), glutamine (Q), methionine (M) or histidine (H);

(k) $X_{11}$ represents amino acid residue tryptophan (W) or histidine (H); and, (l) $X_{12}$ represents amino acid residue arginine (R) or serine (S).

In some embodiments, the CD40L-specific monomer subunit comprises a sequence selected from the group consisting of SEQ ID NO: 44, 46, 48, 50, 52, 54, 56, 58, 60, 62, 64, 66, 68, 70, 72, 74, 76, 78, 80, and 82. In some embodiments, the CD40L-specific monomer subunit consists of a sequence selected from the group consisting of SEQ ID NO: 44, 46, 48, 50, 52, 54, 56, 58, 60, 62, 64, 66, 68, 70, 72, 74, 76, 78, 80, and 82.

In some embodiments, the CD40L-specific Tn3 monomer subunits of the invention comprise the amino acid sequence:

(SEQ ID NO: 171)
IEVX$_1$DVTDTTALITWX$_2$X$_3$RSX$_4$X$_5$X$_6$X$_7$X$_8$X$_9$X$_{10}$CELX$_{11}$YGIKDVPG

DRTTIDLX$_{12}$X$_{13}$X$_{14}$X$_{15}$YVHYSIGNLKPDTX$_{16}$YEVSLICLTTDGTY

X$_{17}$NPAKETFTT wherein:
(a) $X_1$ represents amino acid residue lysine (K) or glutamic acid (E);
(b) $X_2$ represents amino acid residue threonine (T) or isoleucine (I);
(c) $X_3$ represents amino acid residue asparagine (N) or alanine (A);
(d) $X_4$ represents amino acid residue serine (S), leucine (L), alanine (A), phenylalanine (F) or tyrosine (Y);
(e) $X_5$ represents amino acid residue tyrosine (Y), alanine (A), glycine (G), valine (V), isoleucine (I) or serine (S);
(f) $X_6$ represents amino acid residue tyrosine (Y), serine (S), alanine (A) or histidine (H);
(g) $X_7$ represents amino acid residue asparagine (N), aspartic acid (D), histidine (H) or tyrosine (Y);
(h) $X_8$ represents amino acid residue leucine (L), phenylalanine (F), histidine (H) or tyrosine (Y);
(i) $X_9$ represents amino acid residue histidine (H), proline (P), serine (S), leucine (L) or aspartic acid (D);
(j) $X_{10}$ represents amino acid residue glycine (G), phenylalanine (F), histidine (H) or tyrosine (Y);
(k) $X_{11}$ represents amino acid residue alanine (A) or threonine (T);
(l) $X_{12}$ represents amino acid residue serine (S), asparagine (N), glutamic acid (E), asparagine (R) or aspartic acid (D);
(m) $X_{13}$ represents amino acid residue serine (S), glutamine (Q), threonine (T), asparagine (N) or alanine (A);
(n) $X_{14}$ represents amino acid residue proline (P), valine (V), isoleucine (I) or alanine (A) or no amino acid;
(o) $X_{15}$ represents amino acid residue isoleucine (I) or no amino acid;
(p) $X_{16}$ represents amino acid residue glutamic acid (E) or lysine (K); and,
(q) $X_{17}$ represents amino acid residue serine (S) or asparagine (N).

In some embodiments, the CD40L-specific Tn3 monomer subunits of the invention consist of the amino acid sequence:

(SEQ ID NO: 171)
IEVX$_1$DVTDTTALITWX$_2$X$_3$RSX$_4$X$_5$X$_6$X$_7$X$_8$X$_9$X$_{10}$CELX$_{11}$YGIKDVPG

DRTTIDLX$_{12}$X$_{13}$X$_{14}$X$_{15}$YVHYSIGNLKPDTX$_{16}$YEVSLICLTTDGTY

X$_{17}$NPAKETFTT wherein:
(a) $X_1$ represents amino acid residue lysine (K) or glutamic acid (E);
(b) $X_2$ represents amino acid residue threonine (T) or isoleucine (I);
(c) $X_3$ represents amino acid residue asparagine (N) or alanine (A);
(d) $X_4$ represents amino acid residue serine (S), leucine (L), alanine (A), phenylalanine (F) or tyrosine (Y);
(e) $X_5$ represents amino acid residue tyrosine (Y), alanine (A), glycine (G), valine (V), isoleucine (I) or serine (S);
(f) $X_6$ represents amino acid residue tyrosine (Y), serine (S), alanine (A) or histidine (H);
(g) $X_7$ represents amino acid residue asparagine (N), aspartic acid (D), histidine (H) or tyrosine (Y);
(h) $X_8$ represents amino acid residue leucine (L), phenylalanine (F), histidine (H) or tyrosine (Y);
(i) $X_9$ represents amino acid residue histidine (H), proline (P), serine (S), leucine (L) or aspartic acid (D);
(j) $X_{10}$ represents amino acid residue glycine (G), phenylalanine (F), histidine (H) or tyrosine (Y);
(k) $X_{11}$ represents amino acid residue alanine (A) or threonine (T);
(l) $X_{12}$ represents amino acid residue serine (S), asparagine (N), glutamic acid (E), asparagine (R) or aspartic acid (D);
(m) $X_{13}$ represents amino acid residue serine (S), glutamine (Q), threonine (T), asparagine (N) or alanine (A);
(n) $X_{14}$ represents amino acid residue proline (P), valine (V), isoleucine (I) or alanine (A) or no amino acid;
(o) $X_{15}$ represents amino acid residue isoleucine (I) or no amino acid;
(p) $X_{16}$ represents amino acid residue glutamic acid (E) or lysine (K); and,
(q) $X_{17}$ represents amino acid residue serine (S) or asparagine (N).

In some embodiments, a CD40L-specific monomer scaffold comprise a Tn3 module wherein one or more of the beta strands comprise at least one amino acid substitution except that the cysteine residues in the C and F beta strands (SEQ ID NOs: 13 or 14; and SEQ ID NO: 17, respectively) may not be substituted.

The loops connecting the various beta strands of a CD40L-specific monomer subunit can be randomized for length and/or sequence diversity. In one embodiment, a CD40L-specific monomer subunit has at least one loop that is randomized for length and/or sequence diversity. In one embodiment, at least one, at least two, at least three, at least four, at least five or at least six loops of a CD40L-specific monomer subunit are randomized for length and/or sequence diversity. In one embodiment, at least one loop of a CD40L-specific monomer subunit is kept constant while at least one additional loop is randomized for length and/or sequence diversity. In another embodiment, at least one, at least two, or all three of loops AB, CD, and EF are kept constant while at least one, at least two, or all three of loops BC, DE, and FG are randomized for length or sequence diversity. In another embodiment, at least one, at least two, or at least all three of loops AB, CD, and EF are randomized while at least one, at least two, or all three of loops BC, DE, and FG are randomized for length and/or sequence diversity. In still another embodiment, at least one, at least two, at least three of loops, at least 4, at least five, or all six of loops AB, CD, EF, BC, DE, and FG are randomized for length or sequence diversity.

In some embodiments, one or more residues within a loop are held constant while other residues are randomized for length and/or sequence diversity. In some embodiments, one or more residues within a loop are held to a predetermined and limited number of different amino acids while other residues are randomized for length and/or sequence diversity. Accordingly, a CD40L-specific monomer subunit of the invention can comprise one or more loops having a degenerate consensus sequence and/or one or more invariant amino acid residues.

In one embodiment, the CD40L-specific monomer subunit of the invention comprises an AB loop which is randomized. In another embodiment, the CD40L-specific monomer subunit of the invention comprises a BC loop which is randomized. In one embodiment, the CD40L-specific monomer subunit of the invention comprises a CD loop which is randomized. In one embodiment, the CD40L-specific monomer subunit of the invention comprises a DE loop which is randomized. In one embodiment, the CD40L-specific monomer subunit of the invention comprises an EF loop which is randomized.

In certain embodiments, the CD40L-specific monomer subunit of the invention comprises a FG loop which is held to be at least one amino acid residue shorter than the cognate FG loop of the third FnIII domain of human tenascin C and is further randomized at one or more positions.

In specific embodiments, at least one of loops BC, DE, and FG is randomized, wherein the A beta strand comprises SEQ ID NO:10 or 11, the B beta strand comprises SEQ ID NO:12, the C beta strand comprises SEQ ID NO:13 or 14, the D beta strand comprises SEQ ID NO:15, the E beta strand comprises SEQ ID NO:16, the F beta strand comprises SEQ ID NO:17, and the G beta strand comprises SEQ ID NO:18, the AB loop comprises SEQ ID NO:4 or 136, the CD loop comprises SEQ ID NO:6 and the EF loop comprises SEQ ID NO:8 or 137.

In other specific embodiments, at least one of loops AB, CD, and EF are randomized, wherein the A beta strand comprises SEQ ID NO:10 or 11, the B beta strand comprises SEQ ID NO:12, the C beta strand comprises SEQ ID NO:13 or 14, the D beta strand comprises SEQ ID NO:15, the E beta strand comprises SEQ ID NO:16, the F beta strand comprises SEQ ID NO:17, and the G beta strand comprises SEQ ID NO:18, the BC loop comprises SEQ ID NO:5, the DE loop comprises SEQ ID NO:7 and the FG loop comprises SEQ ID NO:9 or 139.

The stability of Tn3 scaffolds of the invention may be increased by many different approaches. In some embodiments, Tn3 scaffolds of the invention can be stabilized by elongating the N- and/or C-terminal regions. The N- and/or C-terminal regions can be elongated by 1, 2, 3, 4, 5, 6, 7, 8, 9, 10 or more than 10 amino acids. In other embodiments, the Tn3 scaffolds of the invention can be stabilized by introducing an alteration that increases serum half-life, as described herein. In yet another embodiment, the Tn3 scaffolds of the invention comprise an addition, deletion or substitution of at least one amino acid residue to stabilize the hydrophobic core of the scaffold.

Tn3 scaffolds of the invention can be effectively stabilized by engineering non-natural disulfide bonds as disclosed in International Patent Application No. PCT/US2011/032184. In some embodiments, scaffolds of the invention comprise non-naturally occurring disulfide bonds, as described in PCT Publication No: WO 2009/058379. A bioinformatics approach may be utilized to identify candidate positions suitable for engineering disulfide bonds.

In one embodiment, a Tn3 monomer subunit of the invention comprises at least one, at least two, at least three, at least four, or at least five non-naturally occurring intramolecular disulfide bonds. In one embodiment, a Tn3 monomer subunit of the invention comprises at least one non-naturally occurring intramolecular disulfide bond, wherein said at least one non-naturally occurring disulfide bond stabilizes the monomer. In yet another embodiment, Tn3 scaffolds of the invention comprise at least one non-naturally occurring disulfide bond, wherein the bond is located between two distinct monomer or multimer Tn3 scaffolds, i.e., the disulfide bond is an intermolecular disulfide bond. For example, a disulfide bond can link distinct scaffolds (for example, two CD40L-specific monomer scaffolds), a Tn3 scaffold and a linker, a Tn3 scaffold and an Fc domain, or a Tn3 scaffold and an antibody or fragment thereof.

In some embodiments, Tn3 scaffolds of the invention comprise at least one non-naturally occurring intermolecular disulfide bond that links a Tn3 monomer subunit and an isolated heterologous moiety, a Tn3 monomer subunit and a heterologous moiety fused or conjugated to the same Tn3 scaffold, or a Tn3 monomer subunit and a heterologous moiety fused or conjugated to a different Tn3 scaffold.

In some embodiments, Tn3 scaffolds of the invention comprise a disulfide bond that forms a Tn3 multimeric scaffold of at least 2, at least 3, at least 4 or more monomer subunits.

In another embodiment, Tn3 scaffolds of the invention may comprise an elongation of the N and/or C terminal regions. In one embodiment, the Tn3 scaffold of the invention comprises an alteration to increase serum half-life, as described herein. In yet another embodiment, the scaffolds of the invention comprise an addition, deletion or substitution of at least one amino acid residue to stabilize the hydrophobic core of the scaffold.

Multimeric Tn3 Scaffolds

One aspect of the present invention provides multimeric Tn3 scaffolds comprising at least two Tn3 monomer subunits of the invention joined in tandem, and wherein at least one of the monomers is a CD40L-specific monomer subunit. Such multimeric Tn3 scaffolds can be assembled in multiple formats. In a specific aspect, the invention provides multimeric Tn3 scaffolds, wherein at least two CD40L-specific monomer subunits are connected in tandem via a peptide linker. In some embodiments, the multimeric Tn3 scaffold exhibits an increase in the valency and/or avidity of target binding, or other action of the target(s). In some embodiments, the increase in valency and/or avidity of target binding is accomplished when multiple monomer subunits bind to the same target. In some embodiments, the increase in valency improves a specific action on the target, such as increasing the dimerization of a target protein.

In a specific embodiment, a multimeric Tn3 scaffold of the invention comprises at least two CD40L-specific monomer subunits connected in tandem, wherein each CD40L-specific monomer subunit binds at least one target, and wherein each CD40L-specific monomer subunit comprises a plurality of beta strands linked to a plurality of loop regions, wherein at least one loop is a non-naturally occurring variant of the cognate loop in the parent Tn3 scaffold (SEQ ID NO: 3).

In one embodiment, multimeric Tn3 scaffolds are generated through covalent binding between CD40L-specific monomer subunits, for example, by directly linking the CD40L-specific monomer subunits, or by the inclusion of a linker, e.g., a peptide linker. In particular examples, covalently bonded Tn3 scaffolds are generated by constructing fusion genes that encode the CD40L-specific monomer subunits or, alternatively, by engineering codons for cysteine residues into CD40L-specific monomer subunits and allowing disulfide bond formation to occur between the expression products.

In one embodiment, multimeric Tn3 scaffolds of the invention comprise at least two CD40L-specific monomer subunits that are connected directly to each other without any additional intervening amino acids. In another embodiment, multimeric Tn3 scaffolds of the invention comprise at least two CD40L-specific monomer subunits that are connected in tandem via a linker, e.g., a peptide linker.

In a specific embodiment, multimeric Tn3 scaffolds of the invention comprise at least two CD40L-specific monomer subunits that are connected in tandem via a peptide linker, wherein the peptide linker comprises 1 to about 1000, or 1 to about 500, or 1 to about 250, or 1 to about 100, or 1 to about 50, or 1 to about 25, amino acids. In a specific embodiment, the multimeric Tn3 scaffold comprises at least two CD40L-specific monomer subunits that are connected in tandem via a peptide linker, wherein the peptide linker comprises 1 to about 20, or 1 to about 15, or 1 to about 10, or 1 to about 5, amino acids.

In a specific embodiment, the multimeric Tn3 scaffold comprises at least two CD40L-specific monomer subunits that are connected in tandem via a linker, e.g., a peptide linker, wherein the linker is a functional moiety. The functional moiety will be selected based on the desired function and/or characteristics of the multimeric Tn3 scaffold. For example, a functional moiety useful for purification (e.g., a histidine tag) may be used as a linker. Functional moieties useful as linkers include, but are not limited to, polyethylene glycol (PEG), a cytotoxic agent, a radionuclide, imaging agent, biotin, a dimerization domain, human serum albumin (HSA) or an FcRn binding portion thereof, a domain or fragment of an antibody, a single chain antibody, a domain antibody, an albumin binding domain, an IgG molecule, an enzyme, a ligand, a receptor, a binding peptide, a non-Tn3 scaffold, an epitope tag, a recombinant polypeptide polymer, a cytokine, and the like. Specific peptide linkers and functional moieties which may be used as linkers are disclosed infra.

In specific embodiments, the functional moiety is an immunoglobulin or a fragment thereof. In some embodiments, the immunoglobulin or fragment thereof comprises an Fc domain. In some embodiments, the Fc domain fails to induce at least one FcγR-mediated effector function, such as ADCC (Antibody-dependent cell-mediated cytotoxicity). It is known in the art that the Fc domain may be altered to reduce or eliminate at least one FcγR-mediated effector function, see, for example, U.S. Pat. Nos. 5,624,821 and 6,737,056.

In some embodiments, the multimeric Tn3 scaffold comprises at least two CD40L-specific monomer subunits that are connected via one or more linkers, wherein the linkers interposed between each CD40L-specific monomer subunit can be the same linkers or different linkers. In some embodiments, a linker can comprise multiple linkers, which can be the same linker or different linkers. In some embodiments, when a plurality of linkers are concatenated, some or all the linkers can be functional moieties.

Scaffold Binding Stoichiometry

In some embodiments, a monomeric or multimeric Tn3 scaffold can comprise a CD40L-specific monomer subunit specific for different epitopes, which can be different epitopes on a single CD40L molecule or on different CD40L target molecules. In some embodiments, a multimeric Tn3 scaffold can comprise CD40L-specific monomer subunits wherein each subunit targets one or more different epitopes on one or more CD40L molecules.

In other embodiments, a monomeric or multimeric Tn3 scaffold can bind two or more different epitopes on the same CD40L molecule. In some embodiments, the different epitopes are non-overlapping epitopes. In other embodiments, the different epitopes are overlapping epitopes.

In yet another specific embodiment, a monomeric or multimeric Tn3 scaffold can bind one or more epitopes on a CD40L molecule and additionally bind one or more epitopes on a second CD40L molecule. In some embodiments, the different target molecules are part of an oligomeric complex, e.g., a trimeric CD40L complex.

In still another specific embodiment, a monomeric or multimeric Tn3 scaffold can bind to a single epitope on a CD40L trimer. In yet another embodiment, a monomeric or multimeric Tn3 scaffold can bind to the same epitope on at least two CD40L trimers.

In certain embodiments, a monomeric or multimeric Tn3 scaffold can bind the same epitope on two or more copies of a CD40L molecule on an adjacent cell surface. In certain embodiments, a monomeric or multimeric Tn3 scaffold can bind the same epitope on two or more copies of a CD40L molecule in solution. In some embodiments, a monomeric or multimeric Tn3 scaffold can bind to the same epitope or different epitopes on CD40L with the same or different binding affinities and/or avidities.

In another embodiment, a monomeric or multimeric Tn3 scaffolds can bind to epitopes on one or more copies of CD40L and achieve or enhance (e.g., synergistically) a desired action on the target, e.g., prevent binding to a receptor or prevent oligomerization.

In addition, when a monomeric or multimeric Tn3 scaffold of the invention comprises a plurality of CD40L-specific monomer subunits, e.g., different monomers wherein each monomer targets different epitopes on CD40L, such monomer subunits can be arranged according to a certain pattern or special orientation to achieve or enhance a certain biological effect. Such combinations of monomeric subunits can be assembled and subsequently evaluated using methods known in the art.

Moreover, the Tn3 scaffolds of the invention can be fused to marker sequences, such as a peptide to facilitate purification. In some embodiments, the marker amino acid sequence is a poly-histidine peptide (His-tag), e.g., a octa-histidine-tag (His-8-tag) or hexa-histidine-tag (His-6-tag) such as the tag provided in a pQE expression vector (QIAGEN, Inc., 9259 Eton Avenue, Chatsworth, Calif., 91311), among other vectors, many of which are commercially available. As described in Gentz et al., Proc. Natl. Acad. Sci. USA 86:821-824, 1989, for instance, poly-histidine provides for convenient purification of the fusion protein. Other peptide tags useful for purification include, but are not limited to, a hemagglutinin ("HA") tag, which corresponds to an epitope derived from the influenza hemagglutinin protein (see, e.g., Wilson et al., Cell 37:767, 1984), a FLAG tag, a Strep-tag, a myc-tag, a V5 tag, a GFP-tag, an AU1-tag, an AU5-tag, an ECS-tag, a GST-tag, or an OLLAS tag.

Additional fusion proteins comprising Tn3 scaffolds of the invention may be generated through the techniques of gene-shuffling, motif-shuffling, exon-shuffling, and/or codon-shuffling (collectively referred to as "DNA shuffling").

DNA shuffling may be employed to alter the action of Tn3 scaffolds on the target (e.g., generate scaffolds with higher affinities and lower dissociation rates). Tn3 scaffolds may be altered by random mutagenesis by error-prone PCR, random nucleotide insertion, or other methods prior to recombination. One or more portions of a polynucleotide encoding a scaffold, which bind to a specific target may be recombined with one or more components, motifs, sections, parts, domains, fragments, etc. of one or more heterologous molecules.

Antibody and Fc Domain Fusions

In some embodiments, the Tn3 scaffold of the invention comprises a CD40L-specific monomer subunit fused to a domain or fragment of an antibody (e.g., an IgG), including, but not limited to, an Fc domain.

In some embodiments, only one CD40L-specific monomer subunit is conjugated or fused to a domain or fragment of an antibody. For instance, a single a CD40L-specific monomer subunit can be fused to the N-terminus of a polypeptide of a domain or fragment of an antibody (e.g., a heavy chain or a light chain of an antibody). In other embodiments, Tn3 scaffolds are created by fusing or conjugating one or more CD40L-specific monomer subunits to the N-terminus and/or the C-terminus a polypeptide of a domain or fragment of an antibody (e.g., a heavy chain and/or a light chain of an antibody, or an Fc domain).

In some embodiments, some or all the a CD40L-specific monomer subunits fused to a domain or fragment of an antibody are identical. In some other embodiments, some or all the a CD40L-specific monomer subunit fused to a domain or fragment of an antibody are different.

In a specific embodiment, the Tn3 scaffold of the invention comprises one CD40L-specific monomer subunit fused to an Fc domain. In other embodiments, the Tn3 scaffold of the invention comprises at least two CD40L-specific monomer subunits fused to an Fc domain. In one specific embodiment, two of the CD40L-specific monomer subunits fused to an Fc domain are identical. In one specific embodiment, two of the CD40L-specific monomer subunits fused to an Fc domain are different. In one specific embodiment, two CD40L-specific monomer subunits fused to an Fc domain are connected to each other in tandem, and one of the CD40L-specific monomer subunits is fused to the Fc domain.

In some embodiments, different Tn3 scaffolds of the invention can be dimerized by the use of Fc domain mutations which favor the formation of heterodimers. It is known in the art that variants of the Fc region (e.g., amino acid substitutions and/or additions and/or deletions) enhance or diminish effector function of the antibody and can alter the pharmacokinetic properties (e.g. half-life) of the antibody. Thus, in certain embodiments, the Tn3 scaffolds of the invention comprise Fc domain(s) that comprise an altered Fc region in which one or more alterations have been made in the Fc region in order to change functional and/or pharmacokinetic properties of the Tn3 scaffold. In certain embodiments, the Tn3 scaffolds of the invention comprise Fc domain(s) that comprise an altered Fc region in which one or more alterations have been made in the Fc region in order reduce or eliminate at least one Fc□R-mediated effector function.

It is also known that the glycosylation of the Fc region can be modified to increase or decrease effector function and/or anti-inflammatory activity. Accordingly, in one embodiment a Tn3 scaffold of the invention comprise an Fc region with altered glycosylation of amino acid residues in order to change cytotoxic and/or anti-inflammatory properties of the Tn3 scaffolds.

Tn3 Scaffold Topologies

The Tn3 scaffolds of the invention can be fused to the C-terminus of the Fc domains, antibody light chains, and antibody heavy chains in any suitable spatial arrangement. See, e.g., International Publication PCT/US2011/032184 for a detailed description of contemplated scaffold topologies.

Generation of Scaffolds

The Tn3 scaffolds described herein may be used in any technique for evolving new or improved target binding proteins. In one particular example, the target is immobilized on a solid support, such as a column resin or microtiter plate well, and the target contacted with a library of candidate scaffold-based binding proteins. Such a library may consist of clones constructed from a Tn3 scaffold, through randomization of the sequence and/or the length of the CDR-like loops.

In this regard, bacteriophage (phage) display is one well known technique which allows one to screen large oligopeptide libraries to identify member(s) of those libraries which are capable of specifically binding to a target. Phage display is a technique by which variant polypeptides are displayed as fusion proteins to the coat protein on the surface of bacteriophage particles (Scott, J. K. and Smith, G. P. (1990) Science 249: 386). A bioinformatics approach may be employed to determine the loop length and diversity preferences of naturally occurring FnIII domains. Using this analysis, the preferences for loop length and sequence diversity may be employed to develop a "restricted randomization" approach. In this restricted randomization, the relative loop length and sequence preferences are incorporated into the development of a library strategy. Integrating the loop length and sequence diversity analysis into library development results in a restricted randomization (i.e. certain positions within the randomized loop are limited in which amino acid could reside in that position).

The invention also provides recombinant libraries comprising diverse populations of non-naturally occurring Tn3 scaffolds. In one embodiment, the libraries comprise non-naturally occurring Tn3 scaffolds comprising, a plurality of beta strand domains linked to a plurality of loop regions, wherein one or more of said loops vary by deletion, substitution or addition by at least one amino acid. In a specific embodiment, the libraries comprise Tn3 scaffolds derived from the wild type Tn3 scaffold.

As detailed above, the loops connecting the various beta strands of the scaffolds may be randomized for length and/or sequence diversity. In one embodiment, the libraries of the invention comprise Tn3 scaffolds having at least one loop that is randomized for length and/or sequence diversity. In one embodiment, at least one, at least two, at least three, at least four, at least five or at least six loops of the Tn3 scaffolds are randomized for length and/or sequence diversity. In one embodiment, at least one loop is kept constant while at least one additional loop is randomized for length and/or sequence diversity. In another embodiment, at least one, at least two, or all three of loops AB, CD, and EF are kept constant while at least one, at least two, or all three of loops BC, DE, and FG are randomized for length or sequence diversity. In another embodiment, at least one, at least two, or all three of loops AB, CD, and EF are randomized while at least one, at least two, or all three of loops BC, DE, and FG are randomized for length and/or sequence diversity.

In a specific embodiment, the libraries of the invention comprise FnIII scaffolds, wherein the A beta strand comprises SEQ ID NO: 10 or 11, the B beta strand comprises SEQ ID NO: 12, the C beta strand comprises SEQ ID NO: 13 or 14, the D beta strand comprises SEQ ID NO: 15, the E beta strand comprises SEQ ID NO: 16, the F beta strand comprises SEQ ID NO: 17, and the G beta strand comprises SEQ ID NO: 18.

In a specific embodiment, the libraries of the invention comprise FnIII scaffolds, wherein the A beta strand consists of SEQ ID NO: 10 or 11, the B beta strand consists of SEQ ID NO: 12, the C beta strand consists of SEQ ID NO: 13 or 14, the D beta strand consists of SEQ ID NO: 15, the E beta strand consists of SEQ ID NO: 16, the F beta strand consists of SEQ ID NO: 17, and the G beta strand consists of SEQ ID NO: 18.

In a specific embodiment, the libraries of the invention comprise FnIII scaffolds, wherein the A beta strand consists essentially of SEQ ID NO: 10 or 11, the B beta strand consists essentially of SEQ ID NO: 12, the C beta strand consists essentially of SEQ ID NO: 13 or 14, the D beta strand consists essentially of SEQ ID NO: 15, the E beta strand consists essentially of SEQ ID NO: 16, the F beta strand consists essentially of SEQ ID NO: 17, and the G beta strand consists essentially of SEQ ID NO: 18.

As detailed above, one or more residues within a loop may be held constant while other residues are randomized for length and/or sequence diversity. Optionally or alternatively, one or more residues within a loop may be held to a predetermined and limited number of different amino acids while other residues are randomized for length and/or sequence diversity. Accordingly, libraries of the invention comprise Tn3 scaffolds that may comprise one or more loops having a degenerate consensus sequence and/or one or more invariant amino acid residues. In another embodiment, the libraries of the invention comprise Tn3 scaffolds having BC loops which are randomized. In another embodiment, the libraries of the invention comprise Tn3 scaffolds having BC loops which are randomized. In still another embodiment, the libraries of the invention comprise Tn3 scaffolds having BC loops which are randomized.

In one embodiment the libraries of the invention comprise Tn3 scaffolds having DE loops which are randomized. In one embodiment, the libraries of the invention comprise Tn3 scaffolds having FG loops which are randomized. In another embodiment, the libraries of the invention comprise FnIII scaffolds having FG loops which are randomized.

In a specific embodiment, the libraries of the invention comprise scaffolds, wherein the scaffolds comprise the amino acid sequence:

IEV$(X_{AB})_n$ALITW$(X_{BC})_n$CEL$X_1$YGI$(X_{CD})_n$TTIDL$(X_{DE})_n$YSI $(X_{EF})_n$YEVSLIC$(X_{FG})_n$KETFTT wherein:

(a) $X_{AB}$, $X_{BC}$, $X_{CD}$, $X_{DE}$, $X_{EF}$, and $X_{FG}$ represent the amino acid residues present in the sequences of the AB, BC, CD, DE, EF, and FG loops, respectively;

(b) $X_1$ represents amino acid residue A or T; and, (c) length of the loop n is an integer between 2 and 26.

In some embodiments, the libraries of the invention comprise CD40L-specific Tn3 monomer subunits of the invention comprising the amino acid sequence:

(SEQ ID NO: 167)

IEVKDVTDTTALITW$X_1$D$X_2X_3X_4X_5X_6X_7X_8$CELTYGIKDVPGDRTTIDL

W$X_9$H$X_{10}$A$X_{11}$YSIGNLKPDTEYEVSLICR$X_{12}$GDMSSNPAKETFTT wherein:

(a) $X_1$ represents amino acid residue serine (S) or leucine (L);
(b) $X_2$ represents amino acid residue aspartic acid (D) or glutamic acid (E);

(c) $X_3$ represents amino acid residue histidine (H), isoleucine (I), valine (V), phenylalanine (F) or tryptophan (W);

(d) $X_4$ represents amino acid residue alanine (A), glycine (G), glutamic acid (E) or aspartic acid (D);

(e) $X_5$ represents amino acid residue glutamic acid (E), leucine (L), glutamine (Q), serine (S), aspartic acid (D) or asparagine (N);

(f) $X_6$ represents amino acid residue phenylalanine (F) or tyrosine (Y);

(g) $X_7$ represents amino acid residue isoleucine (I), valine (V), histidine (H), glutamic acid (E) or aspartic acid (D);

(h) $X_8$ represents amino acid residue glycine (G), tryptophan (W) or valine (V);

(i) $X_9$ represents amino acid residue tryptophan (W), phenylalanine (F) or tyrosine (Y);

(j) $X_{10}$ represents amino acid residue serine (S), glutamine (Q), methionine (M) or histidine (H);

(k) $X_{11}$ represents amino acid residue tryptophan (W) or histidine (H); and, (l) $X_{12}$ represents amino acid residue arginine (R) or serine (S).

In some embodiments, the libraries of the invention comprise CD40L-specific Tn3 monomer subunits of the invention comprising the amino acid sequence:

(SEQ ID NO: 171)

IEV$X_1$DVTDTTALITW$X_2X_3$RS$X_4X_5X_6X_7X_8X_9X_{10}$CEL$X_{11}$YGIKDVPG

DRTTIDL$X_{12}X_{13}X_{14}X_{15}$YVHYSIGNLKPDT$X_{16}$YEVSLICLTTDGTY $X_{17}$NPAKETFTT wherein:

(a) $X_1$ represents amino acid residue lysine (K) or glutamic acid (E);

(b) $X_2$ represents amino acid residue threonine (T) or isoleucine (I);

(c) $X_3$ represents amino acid residue asparagine (N) or alanine (A);

(d) $X_4$ represents amino acid residue serine (S), leucine (L), alanine (A), phenylalanine (F) or tyrosine (Y);

(e) $X_5$ represents amino acid residue tyrosine (Y), alanine (A), glycine (G), valine (V), isoleucine (I) or serine (S);

(f) $X_6$ represents amino acid residue tyrosine (Y), serine (S), alanine (A) or histidine (H);

(g) $X_7$ represents amino acid residue asparagine (N), aspartic acid (D), histidine (H) or tyrosine (Y);

(h) $X_8$ represents amino acid residue leucine (L), phenylalanine (F), histidine (H) or tyrosine (Y);

(i) $X_9$ represents amino acid residue histidine (H), proline (P), serine (S), leucine (L) or aspartic acid (D);

(j) $X_{10}$ represents amino acid residue glycine (G), phenylalanine (F), histidine (H) or tyrosine (Y);

(k) $X_{11}$ represents amino acid residue alanine (A) or threonine (T);

(l) $X_{12}$ represents amino acid residue serine (S), asparagine (N), glutamic acid (E), asparagine (R) or aspartic acid (D);

(m) $X_{13}$ represents amino acid residue serine (S), glutamine (Q), threonine (T), asparagine (N) or alanine (A);

(n) $X_{14}$ represents amino acid residue proline (P), valine (V), isoleucine (I) or alanine (A) or no amino acid;

(o) $X_{15}$ represents amino acid residue isoleucine (I) or no amino acid;

(p) $X_{16}$ represents amino acid residue glutamic acid (E) or lysine (K); and, (q) $X_{17}$ represents amino acid residue serine (S) or asparagine (N).

The invention further provides methods for identifying a recombinant Tn3 scaffold that binds a target, e.g., CD40L, and has increased stability or improved action on the target, e.g., CD40L, as compared to a parent Tn3 scaffold by screening the libraries of the invention.

In certain embodiments, the method for identifying a recombinant Tn3 scaffold having increased protein stability as compared to a parent Tn3 scaffold, and which specifically binds a target, comprises:

contacting the target ligand with a library of the invention under conditions suitable for forming a scaffold:target ligand complex;

obtaining from the complex, the scaffold that binds the target ligand;

determining if the stability of the scaffold obtained in step (b) is greater than that of the wild type Tn3 scaffold.

The same method can be used to identify a recombinant Tn3 scaffold with improved binding affinity, avidity, etc. to the target. In one embodiment, in step (a) the scaffold library of the invention is incubated with immobilized target. In one embodiment, in step (b) the scaffold:target ligand complex is washed to remove non-specific binders, and the tightest binders are eluted under very stringent conditions and subjected to PCR to recover the sequence information. It is specifically contemplated that the binders and/or sequence information obtained in step (b) can be used to create a new library using the methods disclosed herein or known to one of skill in the art, which may be used to repeat the selection process, with or without further mutagenesis of the sequence. In some embodiments, a number of rounds of selection may be performed until binders of sufficient affinity for the antigen are obtained.

A further embodiment of the invention is a collection of isolated nucleic acid molecules encoding a library comprising the scaffolds of the invention and as described above.

The scaffolds of the invention may be subjected to affinity maturation. In this art-accepted process, a specific binding protein is subject to a scheme that selects for increased affinity for a specific target (see Wu et al., Proc. Natl. Acad. Sci. USA. 95(11):6037-42). The resultant scaffolds of the invention may exhibit binding characteristics at least as high as compared to the scaffolds prior to affinity maturation.

The invention also provides methods of identifying the amino acid sequence of a protein scaffold capable of binding to target so as to form a scaffold:target complex. In one embodiment, the method comprises: (a) contacting a library of the invention with an immobilized or separable target; (b) separating the scaffold:target complexes from the free scaffolds; (c) causing the replication of the separated scaffolds of (b) so as to result in a new polypeptide display library distinguished from that in (a) by having a lowered diversity and by being enriched in displayed scaffolds capable of binding the target; d) optionally repeating steps (a), and (b) with the new library of (c); and e) determining the nucleic acid sequence of the region encoding the displayed scaffold of a species from (d) and hence deducing the peptide sequence capable of binding to the target.

In another embodiment, the Tn3 scaffolds of the invention may be further randomized after identification from a library screen. In one embodiment, methods of the invention comprise further randomizing at least one, at least two, at least three, at least four, at least five or at least six loops of a scaffold identified from a library using a method described herein. In another embodiment, the further randomized scaffold is subjected to a subsequent method of identifying a scaffold capable of binding a target. This method comprises (a) contacting said further randomized scaffold with an immobilized or separable target, (b) separating the further randomized scaffold:target complexes from the free scaffolds, (c) causing the replication of the separated scaffolds of (b), optionally repeating steps (a)-(c), and (d) determining the nucleic acid sequence of the region encoding said further randomized scaffold and hence, deducing the peptide sequence capable of binding to the target.

In a further embodiment, the further randomized scaffolds comprise at least one, at least two, at least three, at least four, at least five, or at least six randomized loops which were previously randomized in the first library. In an alternate further embodiment, the further randomized scaffolds comprise at least one, at least two, at least three, at least four, at least five, or at least six randomized loops which were not previously randomized in the first library.

The invention also provides a method for obtaining at least two Tn3 scaffolds that bind to at least one or more targets. This method allows for the screening of agents that act cooperatively to elicit a particular response. It may be advantageous to use such a screen when an agonistic activity requiring the cooperation of more than one scaffold is required. This method allows for the screening of cooperative agents without the reformatting of the library to form multimeric complexes. In one embodiment, the method of the invention comprises contacting a target ligand with a library of the invention under conditions that allow a scaffold:target ligand complex to form, engaging said scaffolds with a crosslinking agent (defined as an agent that brings together, in close proximity, at least two identical or distinct scaffolds) wherein the crosslinking of the scaffolds elicits a detectable response and obtaining from the complex, said scaffolds that bind the target. In a further embodiment, the crosslinking agent is a scaffold specific antibody, or fragment thereof, an epitope tag specific antibody of a fragment thereof, a dimerization domain, such as Fc region, a coiled coil motif (for example, but not limited to, a leucine zipper), a chemical crosslinker, or another dimerization domain known in the art.

Affinity Maturation

The development of Tn3 scaffolds of the invention may involve one or more in vitro or in vivo affinity maturation steps. In some embodiments, Tn3 monomer subunits can undergo a single step of affinity maturation. In other embodiments, Tn3 monomer subunits can under two or more steps of affinity maturation. Any affinity maturation approach can be employed that results, in general, in amino acid changes in a parent Tn3 scaffold, or specifically amino acid changes in a parent Tn3 scaffold's loops that improve the binding of the affinity matured Tn3 scaffold to the desired antigen.

These amino acid changes can, for example, be achieved via random mutagenesis, "walk though" mutagenesis, and "look through" mutagenesis. Such mutagenesis can be achieved by using, for example, error-prone PCR, "mutator" strains of yeast or bacteria, incorporation of random or defined nucleic acid changes during ab initio synthesis of all or part of a FnIII-based binding molecule. Methods for performing affinity maturation and/or mutagenesis are described, for example, in U.S. Pat. Nos. 7,195,880; 6,951,725; 7,078,197; 7,022,479; 5,922,545; 5,830,721; 5,605,793, 5,830,650; 6,194,550; 6,699,658; 7,063,943; 5,866,344 and PCT Publication WO06023144.

Such affinity maturation methods may further require that the stringency of the antigen-binding screening assay is increased to select for Tn3 scaffolds with improved affinity for an antigen. Art recognized methods for increasing the stringency of a protein-protein interaction assay can be used here. In one embodiment, one or more of the assay conditions are varied (for example, the salt concentration of the assay buffer) to reduce the affinity of the Tn3 scaffold for the desired antigen. In another embodiment, the length of time permitted for the Tn3 scaffold to bind to the desired antigen is reduced.

In another embodiment, a competitive binding step can be added to the protein-protein interaction assay. For example, the Tn3 scaffold can be first allowed to bind to a desired immobilized antigen. A specific concentration of non-immobilized antigen is then added which serves to compete for binding with the immobilized antigen such that the Tn3 scaffolds with the lowest affinity for antigen are eluted from the immobilized antigen resulting in selection of Tn3 scaffolds with improved antigen binding affinity. The stringency of the assay conditions can be further increased by increasing the concentration of non-immobilized antigen is added to the assay.

Screening methods may also require multiple rounds of selection to enrich for one or more Tn3 scaffolds with improved antigen binding. In one embodiment, at each round of selection further amino acid mutations are introduce into the Tn3 scaffold. In another embodiment, at each round of selection the stringency of binding to the desired antigen is increased to select for Tn3 scaffolds with increased affinity for antigen.

In some embodiments, affinity maturation is performed by saturation mutagenesis of portions of the BC, DE, and FG loops of Tn3. In some embodiments, saturation mutagenesis is performed using Kunkel mutagenesis. In other embodiments, saturation mutagenesis is performed by using PCR.

In some embodiments, at least one, at least two, at least three, at least four, at least five, or more than five rounds of affinity maturation are applied. In some embodiments, saturation mutagenesis is applied to only one loop, whereas in some other embodiments, only one loop or a portion of a loop is mutated during one round of affinity maturation. In some embodiments, more than one loop or portions of one or more than loop are mutated during the same round of affinity maturation.

In other embodiments, the BC, DE, and FG loops mutated simultaneously during the same round of affinity maturation.

In the case of the monomers to assemble into multimeric Tn3 scaffolds binding to different epitopes of the same target, each binding specificity can be screened independently.

In some embodiments, the loops are randomized using a phage display library. In some embodiments, the binding of a Tn3 scaffold to a desired target can be determined using methods recognized in the art. Also, the amino acid sequences of the Tn3 scaffolds identified in the screens can be determined using art recognized methods.

In some embodiments, the monomeric affinity matured scaffolds of the invention exhibit an increased in affinity for CD40L of at least 5-fold, at least 10-fold, at least 20-fold, at least 40-fold, at least 60-fold, at least 80-fold, or at least 100-fold or more compared to the same Tn3 scaffold prior to affinity maturation, as measured by Surface Plasmon Resonance or by other assays known in the art. In some embodiments, the monomeric affinity matured scaffolds of the invention have a dissociation constant ($K_d$) of less than 5 µM, less than 1 µM, less than 500 µM, less than 250 µM, less than 100 µM, or less than 50 µM, as measured by Surface Plasmon Resonance or by other assays known in the art.

These affinity maturation methods can be applied to develop Tn3 scaffolds with desirable improved binding properties such as increased affinity or other desirable characteristics, such as favorable pharmacokinetic properties, high potency, low immunogenicity, increased or decreased cross-reactivity, etc.

Generation of Tandem Repeats

Linking of tandem constructs, a dimer formed by linking two CD40L-specific monomer subunits, may be generated by ligation of oligonucleotides at restriction sites using restriction enzymes known in the art, including but not limited to type II and type IIS restriction enzymes.

The multimeric Tn3 scaffolds of the invention may comprise a linker at the C-terminus and/or the N-terminus and/or between domains as described herein. Further, scaffolds of the invention comprising at least 1, at least 2, at least 3, at least 4, at least 5, at least 6, at least 7, at least 8 or polypeptide scaffolds may be fused or conjugated to a dimerization domain, including but not limited to an antibody moiety selected from:
(i) a Fab fragment, having VL, CL, VH and CH1 domains;
(ii) a Fab' fragment, which is a Fab fragment having one or more cysteine residues at the C-terminus of the CH1 domain;
(iii) a Fd fragment having VH and CH1 domains;
(iv) a Fd' fragment having VH and CH1 domains and one or more cysteine residues at the C-terminus of the CH1 domain;
(v) a Fv fragment having the VL and VH domains of a single arm of an antibody;
(vi) a dAb fragment which consists of a VH domain;
(vii) isolated CDR regions;
(viii) F(ab')2 fragments, a bivalent fragment including two Fab' fragments linked by a disulphide bridge at the hinge region;
(ix) single chain antibody molecules (e.g., single chain Fv; scFv);
(x) a "diabody" with two antigen binding sites, comprising a heavy chain variable domain (VH) connected to a light chain variable domain (VL) in the same polypeptide chain;
(xi) a "linear antibody" comprising a pair of tandem Fd segments (VH-CH1-VH-CH1) which, together with complementary light chain polypeptides, form a pair of antigen binding regions;
(xii) a full length antibody; and
(xiii) an Fc region comprising CH2-CH3, which may further comprise all or a portion of a hinge region and/or a CH1 region.

Tn3 Scaffold Production

Recombinant expression of a Tn3 scaffold of the invention requires construction of an expression vector containing a polynucleotide that encodes the Tn3 scaffold. Once a polynucleotide encoding a Tn3 scaffold has been obtained, the vector for the production of the Tn3 scaffold may be produced by recombinant DNA technology using techniques well known in the art. Thus, methods for preparing a protein by expressing a polynucleotide containing a Tn3 scaffold encoding nucleotide sequence are described herein. Methods that are well known to those skilled in the art can be used to construct expression vectors containing scaffold polypeptide coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding a Tn3 scaffold of the invention, operably linked to a promoter.

The expression vector is transferred to a host cell by conventional techniques and the transfected cells are then cultured by conventional techniques to produce a Tn3 scaffold of the invention. Thus, the invention includes host cells containing a polynucleotide encoding a scaffold of the invention, operably linked to a heterologous promoter. Suitable host cells include, but are not limited to, microorganisms such as bacteria (e.g., *E. coli* and *B. subtilis*).

A variety of host-expression vector systems may be utilized to express the Tn3 scaffolds of the invention. Such host-expression systems represent vehicles by which the coding sequences of interest may be produced and subsequently purified, but also represent cells which may, when transformed or transfected with the appropriate nucleotide coding sequences, express a scaffold of the invention in situ. These include but are not limited to microorganisms such as bacteria (e.g., *E. coli* and *B. subtilis*) transformed with recombinant bacteriophage DNA, plasmid DNA or cosmid DNA expression vectors containing scaffold coding sequences or mammalian cell systems (e.g., COS, CHO, BHK, 293, NSO, and 3T3 cells).

Methods useful for the production of the Tn3 scaffolds of the invention are disclosed, for example, in International Patent Application Publication No WO 2009/058379. Once a scaffold of the invention has been produced by recombinant expression, it may be purified by any method known in the art for purification of a protein.

In some embodiments, scaffolds of the invention can be produced in an aglycosylated form by replacing amino acid residues that can be glycosylated during recombinant expression. In one specific embodiment, serine amino acids in a glycine-serine linker (e.g., SEQ ID NO: 131 or SEQ ID NO: 132) can be replaced by other amino acids residues such as alanine, glycine, leucine, isoleucine or valine (see, e.g., SEQ ID NOs: 140, 141, 142 and 143) in order to prevent glycosylation during recombinant expression. In some specific embodiments, an N-glycosylation site is removed from a Tn3 scaffolds of the invention. In other embodiments, a scaffold of the invention can be deglycosylated after recombinant expression. Methods of in vitro deglycosylation after recombinant expression using, e.g., enzymatic cocktails are known in the art (for example, the PFGase F, Enodo F Multi, Orela O-linked Glycan Release, Enzymatic CarboRelease, and Enzymatic DeGlycoMx deglycosylation kits marketed by QA-bio, Palm Desert, Calif.).

Production of the Tn3 scaffolds of the invention in the research laboratory can be scaled up to produce scaffolds in analytical scale reactors or production scale reactors, as described in U.S. Patent Publication No. US 2010-0298541 A1.

Scalable Production of Secreted Tn3 Scaffolds

The Tn3 scaffolds of the invention can be produced intracellularly or as a secreted form. In some embodiments, the secreted scaffolds are properly folded and fully functional. Tn3 scaffolds of the invention can be produced by a scalable process. In some embodiments, scaffolds can be produced by a scalable process of the invention in the research laboratory that can be scaled up to produce the scaffolds of the invention in analytical scale bioreactors (for example, but not limited to 5 L, 10 L, 15 L, 30 L, or 50 L bioreactors). In other embodiments, the Tn3 scaffolds can be produced by a scalable process of the invention in the research laboratory that can be scaled up to produce the Tn3 scaffolds of the invention in production scale bioreactors (for example, but not limited to 75 L, 100 L, 150 L, 300 L, or 500 L). In some embodiments, the scalable process of the invention results in little or no reduction in production efficiency as compared to the production process performed in the research laboratory.

Linkers

The monomer subunits in a multimeric Tn3 scaffold can be connected by protein and/or nonprotein linkers, wherein each linker is fused to at least two monomer subunits. A suitable linker can consist of a protein linker, a nonprotein linker, and combinations thereof. Combinations of linkers can be homomeric or heteromeric. In some embodiments, a multimeric Tn3 scaffold of the invention comprises a plurality of monomer subunits wherein are all the linkers are identical. In other embodiments, a multimeric Tn3 scaffold comprises a plurality of monomer subunits wherein at least one of the linkers is functionally or structurally different from the rest of the linkers. In some embodiments, linkers can themselves contribute to the activity of a multimeric Tn3 scaffold by participating directly or indirectly in the binding to a target.

In some embodiments, the protein linker is a polypeptide. The linker polypeptide should have a length, which is adequate to link two or more monomer subunits in such a way that they assume the correct conformation relative to one another so that they retain the desired activity.

In one embodiment, the polypeptide linker comprises 1 to about 1000 amino acids residues, 1 to about 50 amino acid residues, 1-25 amino acid residues, 1-20 amino acid residues, 1-15 amino acid residues, 1-10 amino acid residues, 1-5 amino acid residues, 1-3 amino acid residues. The invention further provides nucleic acids, such as DNA, RNA, or combinations of both, encoding the polypeptide linker sequence. The amino acid residues selected for inclusion in the polypeptide linker should exhibit properties that do not interfere significantly with the activity or function of the multimeric Tn3 scaffold of the invention. Thus, a polypeptide linker should on the whole not exhibit a charge which would be inconsistent with the activity or function of the Tn3 multimeric scaffold of the invention, or interfere with internal folding, or form bonds or other interactions with amino acid residues in one or more of the monomer subunits which would seriously impede the binding of the multimeric Tn3 scaffold of the invention to CD40L.

The use of naturally occurring as well as artificial peptide linkers to connect polypeptides into novel linked fusion polypeptides is well known in the literature. Accordingly, the linkers fusing two or more monomer subunits are natural linkers, artificial linkers, or combinations thereof. In some embodiments, the amino acid sequences of all peptide linkers present in a Tn3 multimeric scaffold of the invention are identical. In other embodiments, the amino acid sequences of at least two of the peptide linkers present in a multimeric Tn3 scaffold of the invention are different.

In some embodiments, a polypeptide linker possesses conformational flexibility. In some embodiments, a polypeptide linker sequence comprises a $(G-G-G-G-X)_m$ amino acid sequence where X is Alanine (A), Serine (S), Glycine (G), Isoleucine (I), Leucine (L) or Valine (V) and m is a positive integer (see, e.g., SEQ ID NO: 209). In a specific embodiment, a polypeptide linker sequence comprises a $(G-G-G-G-S)_m$ amino acid sequence where m is a positive integer (see, e.g., SEQ ID NO: 147). In another specific embodiment, a polypeptide linker sequence comprises a $(G-G-G-G-G)_m$ amino acid sequence where m is a positive integer (see, e.g., SEQ ID NO: 148). In still another specific embodiment, a polypeptide linker sequence comprises a $(G-G-G-G-A)_m$ amino acid sequence where m is a positive integer (see, e.g., SEQ ID NO: 149). In some embodiments, a polypeptide linker is an inherently unstructured natural or artificial polypeptide (see, e.g., Schellenberger et al., Nature Biotechnol. 27:1186-1190, 2009; see also, Sickmeier et al., Nucleic Acids Res. 35:D786-93, 2007).

The peptide linker can be modified in such a way that an amino acid residue comprising an attachment group for a non-polypeptide moiety is introduced. Examples of such amino acid residues may be a cysteine residue (to which the non-polypeptide moiety is then subsequently attached) or the amino acid sequence may include an in vivo N-glycosylation site (thereby attaching a sugar moiety (in vivo) to the peptide linker).

In some embodiments, the amino acid sequences of all peptide linkers present in the polypeptide multimer are identical. Alternatively, the amino acid sequences of all peptide linkers present in the polypeptide multimer may be different.

The present invention further encompasses uses of Tn3 scaffolds conjugated to a therapeutic moiety. A Tn3 scaffold may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

CD40L-Specific Tn3 Scaffolds

The invention provides Tn3 scaffolds that specifically bind to CD40L. In specific embodiments, scaffolds of the invention specifically bind to human CD40L. In other specific embodiments, Tn3 scaffolds of the invention bind to CD40L homologs from mouse, chicken, Rhesus, cynomolgus, rat, or rabbit. In some embodiments, Tn3 scaffolds of the invention bind to an exposed epitope of CD40L. Such embodiments include CD40L endogenously expressed on cells and/or cells transfected to ectopically express the receptor.

In some embodiments, Tn3 scaffolds of the invention recognize epitopes displayed on a monomeric CD40L. In other embodiments, Tn3 scaffolds of the invention recognize epitopes displayed on a trimeric form of CD40L. In other embodiments, Tn3 scaffolds of the invention recognize epitopes displayed on a membrane bound CD40L. In other embodiments, Tn3 scaffolds of the invention recognize epitopes displayed on soluble CD40L.

In yet other embodiments, Tn3 scaffolds of the invention bind monomeric CD40L and prevent or interfere with oligomerization of CD40L molecules. In yet other embodiments, scaffolds of the invention reduce or inhibit interaction of CD40L with CD40. In other embodiments, Tn3 scaffolds of the invention agonize cellular signaling mediated by CD40L. In yet other embodiments, Tn3 scaffolds of the invention antagonize cellular signaling mediated by CD40L.

The invention also provides methods of modulating CD40L activity using the Tn3 scaffolds described herein. In some embodiments, methods of the invention comprise contacting a CD40L with CD40L-specific scaffolds and blocking the interaction between CD40 and CD40L. In other embodiments, methods of the invention comprise contacting a cell expressing CD40L with a CD40L-specific Tn3 scaffold and preventing proteolytic cleavage of CD40L from the cell surface. In other embodiments, methods of the invention comprise contacting a CD40L monomer with a CD40L-specific Tn3 scaffold and preventing CD40L oligomerization. In other embodiments, dimerization or oligomerization of CD40L may be achieved through the use of multimeric Tn3 scaffolds.

In some embodiments, methods of the invention comprise the administration of a CD40L specific scaffold that reduces a CD40-mediated immune response (see, e.g., Elqueta et al. 229: 152-172, 2009), or a downstream signaling pathway initiated by CD40 binding to CD40L, as measured by routine assays known in the art.

Without wishing to be bound by any particular theory, CD40L scaffolds of the present invention could function by preventing binding of CD40L to CD40, by binding and sequestering soluble CD40L, by altering the interaction of CD40L with CD40 but not preventing binding, by preventing or enhancing metalloprotease-mediated enzymatic cleavage of CD40L from the cell surface to yield soluble CD40L, by preventing or enhancing cell surface CD40L endocytosis, etc.

Specific CD40L Binding Sequences

In some embodiments, the Tn3 scaffold of the invention comprise CD40L-specific monomer subunits comprising at least one, at least two, at least three, at least four, at least five, or at least six loop sequences that bind to CD40L.

In some embodiments, CD40L-specific monomer subunits comprise at least one, at least two, at least three, at least four, at least five, or at least six loop sequences of CD40L-binding monomer clones selected from: 309 (parental 309 family clone isolated from naive Tn3 library; SEQ ID NO: 20), 309FGwt (parental 309 clone with humanized FG loop; SEQ ID NO: 22), 340 (affinity matured 309 clone; SEQ ID NO: 24), 341 (affinity matured 309 clone; SEQ ID NO: 26), 342 (affinity matured 309 clone; SEQ ID NO: 28 or SEQ ID NO: 146), 343 (affinity matured 309 clone; SEQ ID NO: 30), 344 (affinity matured 309 clone; SEQ ID NO: 32), 345 (affinity matured 309 clone; SEQ ID NO: 34), 346 (affinity matured 309 clone; SEQ ID NO: 36), 347 (affinity matured 309 clone; SEQ ID NO: 38), 348 (affinity matured 309 clone; SEQ ID NO: 40), 349 (affinity matured 309 clone; SEQ ID NO: 42), 311 (parental 311 family clone isolated from naive Tn3 library; SEQ ID NO: 44), 311K4E (variant 311 family clone from first round of affinity maturation; SEQ ID NO: 46); 311K4E_1 (variant 311 family clone from second round of affinity maturation; SEQ ID NO: 48), 311K4E_2 (variant 311 family clone from second round of affinity maturation; SEQ ID NO: 50), 311K4E_3 (variant 311 family clone from second round of affinity maturation; SEQ ID NO: 52), 311K4E_4 (variant 311 family clone from second round of affinity maturation; SEQ ID NO: 54), 311K4E_5 (variant 311 family clone from second round of affinity maturation; SEQ ID NO: 56), 311K4E_7 (variant 311 family clone from second round of affinity maturation; SEQ ID NO: 58), 311K4E_8 (variant 311 family clone from second round of affinity maturation; SEQ ID NO: 60), 311K4E_9 (variant 311 family clone from second round of affinity maturation; SEQ ID NO: 62), 311K4E_10 (variant 311 family clone from second round of affinity maturation; SEQ ID NO: 64), 311K4E_11 (variant 311 family clone from second round of affinity maturation; SEQ ID NO: 66), 311K4E_12 (variant 311 family clone from second round of affinity maturation; SEQ ID NO: 68), 311K4E_13 (variant 311 family clone from second round of affinity maturation; SEQ ID NO: 70), 311K4E_14 (variant 311 family clone from second round of affinity maturation; SEQ ID NO: 72), 311K4E_15 (variant 311 family clone from second round of affinity maturation; SEQ ID NO: 74), 311K4E_16 (variant 311 family clone from second round of affinity maturation; SEQ ID NO: 76), 311K4E_19 (variant 311 family clone from second round of affinity maturation; SEQ ID NO: 78), 311K4E_20 (variant 311 family clone from second round of affinity maturation; SEQ ID NO: 80), and 311K4E_21 (variant 311 family clone from second round of affinity maturation; SEQ ID NO: 82).

In some embodiments, CD40L-specific monomer subunits comprise at least one loop sequence selected from the loop sequences listed in Table 2. In other embodiments, CD40L-specific monomer subunits comprise at least one BC loop sequence selected from the BC loop sequences listed in Table 2. In other embodiments, CD40L-specific monomer subunits comprise at least one DE loop sequence selected from the DE loop sequences listed in Table 2. In other embodiments, CD40L-specific monomer subunits comprise at least one FG loop sequence selected from the FG loop sequences listed in Table 2.

In some embodiments, CD40L-specific monomer subunits comprise a BC loop sequence selected from the BC loop sequences listed in Table 2; and a DE loop sequence selected from the DE loop sequences listed in Table 2. In other embodiments, CD40L-specific monomer subunits comprise a BC loop sequence selected from the BC loop sequences listed in Table 2; and an FG loop sequence selected from the FG loop sequences listed in Table 2. In other embodiments, CD40L-specific monomer subunits comprise a DE loop sequence selected from the DE loop sequences listed in Table 2; and an FG loop sequence selected from the FG loop sequences listed in Table 2. In some embodiments, a CD40L-specific monomer subunits comprises loop sequences corresponding to loop sequences from one, two or three different Tn3 clones.

In certain embodiments, where the CD40L-specific monomer scaffold sequence contains a linker and/or a Histidine tag (e.g., a His-8 tag) at the C-terminus of the sequence, or additional N-terminal amino acids, these C-terminal linker and/or Histidine tag and additional N-terminal amino acids can be removed, the corresponding amino acid sequence thus containing a deletion of the C-terminal linker and His tag sequences and the N-terminal additional amino acid or amino acids.

In some embodiments, the CD40L-specific Tn3 scaffold comprises a single monomer subunit, e.g., the 342 clone sequence (affinity matured 309 clone; SEQ ID NO: 28 and/or SEQ ID NO: 146). In other embodiments, the CD40L-specific scaffold comprises more than one monomer subunits, e.g., two 342 clone monomer subunits (SEQ ID NO: 28 and/or SEQ ID NO: 146) in tandem (see, e.g., SEQ ID NO: 135). In specific embodiments, Tn3 scaffolds of the invention are conjugated to a variant HSA (see, e.g., SEQ ID NO: 134 and SEQ ID NO: 135). In further embodiments, the HSA can be conjugated at either the N-terminus or the C-terminus of the multimeric Tn3 scaffold.

In a specific embodiment, the CD40L-specific Tn3 scaffold comprises a single 311K4E_12 monomer subunit, a GS linker, and a C34S HSA variant (see, e.g., SEQ ID NO: 201). In another specific embodiment, the CD40L-specific Tn3 scaffold comprises a single 311K4E_12 monomer subunit with a beta strand C CELTYG variant, an all glycine linker, and a C34S HSA variant (see, e.g., SEQ ID NO: 202). In another specific embodiment, the CD40L-specific Tn3 scaffold comprises two 311K4E_12 subunits in tandem, and two GS linkers, wherein one GS linker connects the subunits to each other and a second GS linker connects one subunit to a C34S HSA variant (see, e.g., SEQ ID NO: 203). In yet another specific embodiment, the CD40L-specific Tn3 scaffold comprises two 311K4E_12 subunits in tandem, and two all glycine linkers, wherein one all glycine linker connects the subunits to each other and a second all glycine linker connects one subunit to a C34S HSA variant (see, e.g., SEQ ID NO: 204).

In one specific embodiment, the CD40L-specific Tn3 scaffold comprises two 309 subunits connected in tandem via a GS linker (see, e.g., SEQ ID NO: 205). In another specific embodiment, the CD40L-specific Tn3 scaffold comprises a single 309 subunit connected to a C34S HSA variant (see, e.g., SEQ ID NO: 206). In another specific embodiment, the CD40L-specific Tn3 scaffold comprises two 309 subunits in tandem, and two GS linkers, wherein one GS linker connects the subunits to each other and a second GS linker connects one subunit to a C34S HSA variant (see, e.g., SEQ ID NO: 207).

In a specific embodiment, the CD40L-specific Tn3 scaffold comprises a single 342 monomer subunit, a GS linker, and a C34S HSA variant (see, e.g., SEQ ID NO: 134). In another specific embodiment, the CD40L-specific Tn3 scaffold comprises a single 342 monomer subunit, an all glycine linker, and a C34S HSA variant (see, e.g., SEQ ID NO: 144). In another specific embodiment, the CD40L-specific Tn3 scaffold comprises two 342 subunits in tandem, and two GS linkers, wherein one GS linker connects the subunits to each other and a second GS linker connects one subunit to a C34S HSA variant (see, e.g., SEQ ID NO: 135). In yet another specific embodiment, the CD40L-specific Tn3 scaffold comprises two 342 subunits in tandem, and two all glycine linkers, wherein one all glycine linker connects the subunits to each other and a second all glycine linker connects one subunit to a C34S HSA variant (see, e.g., SEQ ID NO: 145). In yet another specific embodiment, the CD40L-specific Tn3 scaffold comprises two 342 subunits connected in tandem by a GS linker (see, e.g., SEQ ID NO: 208).

In a specific embodiment, the CD40L-specific Tn3 scaffold comprises In another specific embodiment, the CD40L-specific Tn3 scaffold comprises a 311 subunit, or a subunit derived from 311 (e.g., 311K4E_12) and a 309 subunit, or a subunit derived from 309 (e.g., 342) in tandem and two GS linkers, wherein one GS linker connects the subunits to each other and a second GS linker connects one subunit to a C34S HSA variant (see, e.g., SEQ ID NO: 135). In yet another specific embodiment, the CD40L-specific Tn3 scaffold comprises a 311 subunit, or a subunit derived from 311 (e.g., 311K4E_12) and a 309 subunit, or a subunit derived from 309 (e.g., 342) in tandem, and two all glycine linkers, wherein one all glycine linker connects the subunits to each other and a second all glycine linker connects one subunit to a C34S HSA variant (see, e.g., SEQ ID NO: 145).

Examples of CD40L-specific tandem bivalent Tn3 scaffolds and Serum Albumin (SA) fusions are shown in FIG. 2A (also see FIG. 9A). Although specific linkers are provided in FIG. 2A, other linkers are contemplated as provided herein. Although wild type mature SA may be used, e.g., murine serum albumin (MSA) or human serum albumin (HSA), it is contemplated that one or more Cysteine (C) amino acid residues in the mature SA may be substituted, for example with Serine (S), Alanine (A), Glycine (G), etc.

Representative constructs are shown below. The sequence of the SA is underlined. Linkers are boxed. It will be understood that numerous variations are within the scope of the invention. For example, the linkers may be altered (several non-limited examples are provided herein), the first one or two N-terminal amino acid residues (SQ) may be absent and/or substituted with alternative amino acid residues, a tag (e.g., 6×His tag) may be incorporated, alternative CD40L-specific scaffolds (e.g., those based on the 10th Fn3 domain of fibronectin) may be utilized in a similar construct, etc.

```
342 Monovalent HSA construct 1 (SEQ ID NO: 134)
[342 monomer]-(G4S)2 linker-HSA_C34S
SQIEVKDVTDTTALITWSDDFGEYVWCELTYGIKDVPGDRTTIDLWYHHAHYSIGNLKPD

TEYEVSLICRSGDMSSNPAKETFTT GGGGSGGGGS DAHKSEVAHRFKDLGEENFKALVLI

AFAQYLQQSPFEDHVKLVNEVTEFAKTCVADESAENCDKSLHTLFGDKLCTVATLRETYG
```

EMADCCAKQEPERNECFLQHKDDNPNLPRLVRPEVDVMCTAFHDNEETFLKKYLYEIARR

HPYFYAPELLFFAKRYKAAFTECCQAADKAACLLPKLDELRDEGKASSAKQRLKCASLQK

FGERAFKAWAVARLSQRFPKAEFAEVSKLVTDLTKVHTECCHGDLLECADDRADLAKYIC

ENQDSISSKLKECCEKPLLEKSHCIAEVENDEMPADLPSLAADFVESKDVCKNYAEAKDV

FLGMFLYEYARRHPDYSVVLLLRLAKTYETTLEKCCAAADPHECYAKVFDEFKPLVEEPQ

NLIKQNCELFEQLGEYKFQNALLVRYTKKVPQVSTPTLVEVSRNLGKVGSKCCKHPEAKR

MPCAEDYLSVVLNQLCVLHEKTPVSDRVTKCCTESLVNRRPCFSALEVDETYVPKEFNAE

TFTFHADICTLSEKERQIKKQTALVELVKHKPKATKEQLKAVMDDFAAFVEKCCKADDKE

TCFAEEGKKLVAASQAALGL

342 Monovalent HSA construct 2 (SEQ ID NO: 144)
[342 monomer]-G₁₀ linker-HSA<sub>C34S</sub>:
SQIEVKDVTDTTALITWSDDFGEYVWCELTYGIKDVPGDRTTIDLWYHHAHYSIGNLKPD

TEYEVSLICRSGDMSSNPAKETFTTGGGGGGGGGGDAHKSEVAHRFKDLGEENFKALVLI

AFAQYLQQSPFEDHVKLVNEVTEFAKTCVADESAENCDKSLHTLFGDKLCTVATLRETYG

EMADCCAKQEPERNECFLQHKDDNPNLPRLVRPEVDVMCTAFHDNEETFLKKYLYEIARR

HPYFYAPELLFFAKRYKAAFTECCQAADKAACLLPKLDELRDEGKASSAKQRLKCASLQK

FGERAFKAWAVARLSQRFPKAEFAEVSKLVTDLTKVHTECCHGDLLECADDRADLAKYIC

ENQDSISSKLKECCEKPLLEKSHCIAEVENDEMPADLPSLAADFVESKDVCKNYAEAKDV

FLGMFLYEYARRHPDYSVVLLLRLAKTYETTLEKCCAAADPHECYAKVFDEFKPLVEEPQ

NLIKQNCELFEQLGEYKFQNALLVRYTKKVPQVSTPTLVEVSRNLGKVGSKCCKHPEAKR

MPCAEDYLSVVLNQLCVLHEKTPVSDRVTKCCTESLVNRRPCFSALEVDETYVPKEFNAE

TFTFHADICTLSEKERQIKKQTALVELVKHKPKATKEQLKAVMDDFAAFVEKCCKADDKE

TCFAEEGKKLVAASQAALGL

342 Bivalent HSA Construct 1 (SEQ ID NO: 135)
[342 monomer]-(G₄S)₃ linker-[342 monomer]-(G₄S)₂ linker-HSA<sub>C34S</sub>:
SQIEVKDVTDTTALITWSDDFGEYVWCELTYGIKDVPGDRTTIDLWYHHAHYSIGNLKPD

TEYEVSLICRSGDMSSNPAKETFTTGGGGSGGGGSGGGGSRLDAPSQIEVKDVTDTTALI

TWSDDFGEYVWCELTYGIKDVPGDRTTIDLWYHHAHYSIGNLKPDTEYEVSLICRSGDMS

SNPAKETFTTGGGGSGGGGSDAHKSEVAHRFKDLGEENFKALVLIAFAQYLQQSPFEDHV

KLVNEVTEFAKTCVADESAENCDKSLHTLFGDKLCTVATLRETYGEMADCCAKQEPERNE

CFLQHKDDNPNLPRLVRPEVDVMCTAFHDNEETFLKKYLYEIARRHPYFYAPELLFFAKR

YKAAFTECCQAADKAACLLPKLDELRDEGKASSAKQRLKCASLQKFGERAFKAWAVARLS

QRFPKAEFAEVSKLVTDLTKVHTECCHGDLLECADDRADLAKYICENQDSISSKLKECCE

KPLLEKSHCIAEVENDEMPADLPSLAADFVESKDVCKNYAEAKDVFLGMFLYEYARRHPD

YSVVLLLRLAKTYETTLEKCCAAADPHECYAKVFDEFKPLVEEPQNLIKQNCELFEQLGE

YKFQNALLVRYTKKVPQVSTPTLVEVSRNLGKVGSKCCKHPEAKRMPCAEDYLSVVLNQL

CVLHEKTPVSDRVTKCCTESLVNRRPCFSALEVDETYVPKEFNAETFTFHADICTLSEKE

RQIKKQTALVELVKHKPKATKEQLKAVMDDFAAFVEKCCKADDKETCFAEEGKKLVAASQ

AALGL

342 Bivalent HSA Construct 2 (SEQ ID NO: 145)
[342 monomer]-G<sub>15</sub> linker-[342 monomer]-G<sub>10</sub> linker-HSA<sub>C34S</sub>:
SQIEVKDVTDTTALITWSDDFGEYVWCELTYGIKDVPGDRTTIDLWYHHAHYSIGNLKPD

TEYEVSLICRSGDMSSNPAKETFTTGGGGGGGGGGGGGGGRLDAPSQIEVKDVTDTTALI

TWSDDFGEYVWCELTYGIKDVPGDRTTIDLWYHHAHYSIGNLKPDTEYEVSLICRSGDMS

SNPAKETFTTGGGGGGGGGGDAHKSEVAHRFKDLGEENFKALVLIAFAQYLQQSPFEDHV

KLVNEVTEFAKTCVADESAENCDKSLHTLFGDKLCTVATLRETYGEMADCCAKQEPERNE

CFLQHKDDNPNLPRLVRPEVDVMCTAFHDNEETFLKKYLYEIARRHPFYAPELLFFAKR

YKAAFTECCQAADKAACLLPKLDELRDEGKASSAKQRLKCASLQKFGERAFKAWAVARLS

QRFPKAEFAEVSKLVTDLTKVHTECCHGDLLECADDRADLAKYICENQDSISSKLKECCE

KPLLEKSHCIAEVENDEMPADLPSLAADFVESKDVCKNYAEAKDVFLGMFLYEYARRHPD

YSVVLLLRLAKTYETTLEKCCAAADPHECYAKVFDEFKPLVEEPQNLIKQNCELFEQLGE

YKFQNALLVRYTKKVPQVSTPTLVEVSRNLGKVGSKCCKHPEAKRMPCAEDYLSVVLNQL

CVLHEKTPVSDRVTKCCTESLVNRRPCFSALEVDETYVPKEFNAETFTFHADICTLSEKE

RQIKKQTALVELVKHKPKATKEQLKAVMDDFAAFVEKCCKADDKETCFAEEGKKLVAASQ

AALGL

311K4E_12 Monovalent HSA Construct 1 (SEQ ID NO: 201)
[311K4E_12 monomer]-(G<sub>4</sub>S)<sub>2</sub> linker-HSA<sub>C34S</sub>:
SQIEVEDVTDTTALITWTNRSSYSNLHGCELAYGIKDVPGDRTTIDLNQPYVHYSIGNLK

PDTEYEVSLICLTTDGTYNNPAKETFTTGGGGSGGGGSDAHKSEVAHRFKDLGEENFKAL

VLIAFAQYLQQSPFEDHVKLVNEVTEFAKTCVADESAENCDKSLHTLFGDKLCTVATLRE

TYGEMADCCAKQEPERNECFLQHKDDNPNLPRLVRPEVDVMCTAFHDNEETFLKKYLYEI

ARRHPYFYAPELLFFAKRYKAAFTECCQAADKAACLLPKLDELRDEGKASSAKQRLKCAS

LQKFGERAFKAWAVARLSQRFPKAEFAEVSKLVTDLTKVHTECCHGDLLECADDRADLAK

YICENQDSISSKLKECCEKPLLEKSHCIAEVENDEMPADLPSLAADFVESKDVCKNYAEA

KDVFLGMFLYEYARRHPDYSVVLLLRLAKTYETTLEKCCAAADPHECYAKVFDEFKPLVE

EPQNLIKQNCELFEQLGEYKFQNALLVRYTKKVPQVSTPTLVEVSRNLGKVGSKCCKHPE

AKRMPCAEDYLSVVLNQLCVLHEKTPVSDRVTKCCTESLVNRRPCFSALEVDETYVPKEF

NAETFTFHADICTLSEKERQIKKQTALVELVKHKPKATKEQLKAVMDDFAAFVEKCCKAD

DKETCFAEEGKKLVAASQAALGL

311K4E_12 Monovalent HSA Construct 2 (SEQ ID NO: 202)
[311K4E_12 monomer]-G<sub>10</sub> linker-HSA<sub>C34S</sub>:
SQIEVEDVTDTTALITWTNRSSYSNLHGCELTYGIKDVPGDRTTIDLNQPYVHYSIGNLK

PDTEYEVSLICLTTDGTYNNPAKETFTTGGGGGGGGGGDAHKSEVAHRFKDLGEENFKAL

VLIAFAQYLQQSPFEDHVKLVNEVTEFAKTCVADESAENCDKSLHTLFGDKLCTVATLRE

TYGEMADCCAKQEPERNECFLQHKDDNPNLPRLVRPEVDVMCTAFHDNEETFLKKYLYEI

ARRHPYFYAPELLFFAKRYKAAFTECCQAADKAACLLPKLDELRDEGKASSAKQRLKCAS

LQKFGERAFKAWAVARLSQRFPKAEFAEVSKLVTDLTKVHTECCHGDLLECADDRADLAK

YICENQDSISSKLKECCEKPLLEKSHCIAEVENDEMPADLPSLAADFVESKDVCKNYAEA

KDVFLGMFLYEYARRHPDYSVVLLLRLAKTYETTLEKCCAAADPHECYAKVFDEFKPLVE

EPQNLIKQNCELFEQLGEYKFQNALLVRYTKKVPQVSTPTLVEVSRNLGKVGSKCCKHPE

-continued

AKRMPCAEDYLSVVLNQLCVLHEKTPVSDRVTKCCTESLVNRRPCFSALEVDETYVPKEF

NAETFTFHADICTLSEKERQIKKQTALVELVKHKPKATKEQLKAVMDDFAAFVEKCCKAD

DKETCFAEEGKKLVAASQAALGL

311K4E_12 Bivalent HSA Construct 1 (SEQ ID NO: 203)
[311K4E_12 monomer]-G$_4$S$_3$ linker-[311K4E_12 monomer]-(G$_4$S)$_2$ linker-HSA$_{C34S}$:
SQIEVEDVTDTTALITWTNRSSYSNLHGCELAYGIKDVPGDRTTIDLNQPYVHYSIGNLK

PDTEYEVSLICLTTDGTYNNPAKETFTTGGGGSGGGGSGGGGSRLDAPSQIEVEDVTDTT

ALITWTNRSSYSNLHGCELAYGIKDVPGDRTTIDLNQPYVHYSIGNLKPDTEYEVSLICL

TTDGTYNNPAKETFTTGGGGSGGGGSDAHKSEVAHRFKDLGEENFKALVLIAFAQYLQQS

PFEDHVKLVNEVTEFAKTCVADESAENCDKSLHTLFGDKLCTVATLRETYGEMADCCAKQ

EPERNECFLQHKDDNPNLPRLVRPEVDVMCTAFHDNEETFLKKYLYEIARRHPYFYAPEL

LFFAKRYKAAFTECCQAADKAACLLPKLDELRDEGKASSAKQRLKCASLQKFGERAFKAW

AVARLSQRFPKAEFAEVSKLVTDLTKVHTECCHGDLLECADDRADLAKYICENQDSISSK

LKECCEKPLLEKSHCIAEVENDEMPADLPSLAADFVESKDVCKNYAEAKDVFLGMFLYEY

ARRHPDYSVVLLLRLAKTYETTLEKCCAAADPHECYAKVFDEFKPLVEEPQNLIKQNCEL

FEQLGEYKFQNALLVRYTKKVPQVSTPTLVEVSRNLGKVGSKCCKHPEAKRMPCAEDYLS

VVLNQLCVLHEKTPVSDRVTKCCTESLVNRRPCFSALEVDETYVPKEFNAETFTFHADIC

TLSEKERQIKKQTALVELVKHKPKATKEQLKAVMDDFAAFVEKCCKADDKETCFAEEGKK

LVAASQAALGL

311K4E_12 Bivalent HSA Construct 2 (SEQ ID NO: 204)
[311K4E_12 monomer]-G$_{15}$ linker-[311K4E_12 monomer]-G$_{10}$ linker-HSA$_{C34S}$:
SQIEVEDVTDTTALITWTNRSSYSNLHGCELTYGIKDVPGDRTTIDLNQPYVHYSIGNLK

PDTEYEVSLICLTTDGTYNNPAKETFTTGGGGGGGGGGGGGGGRLDAPSQIEVEDVTDTT

ALITWTNRSSYSNLHGCELAYGIKDVPGDRTTIDLNQPYVHYSIGNLKPDTEYEVSLICL

TTDGTYNNPAKETFTTGGGGGGGGGGDAHKSEVAHRFKDLGEENFKALVLIAFAQYLQQS

PFEDHVKLVNEVTEFAKTCVADESAENCDKSLHTLFGDKLCTVATLRETYGEMADCCAKQ

EPERNECFLQHKDDNPNLPRLVRPEVDVMCTAFHDNEETFLKKYLYEIARRHPYFYAPEL

LFFAKRYKAAFTECCQAADKAACLLPKLDELRDEGKASSAKQRLKCASLQKFGERAFKAW

AVARLSQRFPKAEFAEVSKLVTDLTKVHTECCHGDLLECADDRADLAKYICENQDSISSK

LKECCEKPLLEKSHCIAEVENDEMPADLPSLAADFVESKDVCKNYAEAKDVFLGMFLYEY

ARRHPDYSVVLLLRLAKTYETTLEKCCAAADPHECYAKVFDEFKPLVEEPQNLIKQNCEL

FEQLGEYKFQNALLVRYTKKVPQVSTPTLVEVSRNLGKVGSKCCKHPEAKRMPCAEDYLS

VVLNQLCVLHEKTPVSDRVTKCCTESLVNRRPCFSALEVDETYVPKEFNAETFTFHADIC

TLSEKERQIKKQTALVELVKHKPKATKEQLKAVMDDFAAFVEKCCKADDKETCFAEEGKK

LVAASQAALGL

Pharmaceutical Compositions

In another aspect, the present invention provides a composition, for example, but not limited to, a pharmaceutical composition, containing one or a combination of albumin-fusion proteins of the present invention, formulated together with a pharmaceutically acceptable carrier. In some embodiments, the pharmaceutical composition comprises an albumin-fusion protein having a scaffold, such as Tn3 scaffold. In another embodiment, the pharmaceutical composition comprises an albumin-fusion protein of SEQ ID NO: 134, 135, 201, 202, 203, 204, 205, 206, 207 or 208, wherein the composition has less than 20 ng/mg host cell protein, and wherein the tryptophan at position 46, 151 or both is not oxidized. Other embodiments relate to pharmaceutically acceptable formulation comprising an albumin-fusion protein purified according to the invention. The formulation may suitably include a buffer, a sugar, and an emulsifier. In an embodiment, the buffer is a sodium phosphate buffer, the sugar is sucrose, and the emulsifier is polysorbate 80. The pharmaceutical formulation of claim 100 or claim 101, wherein the formulation is lyophilized.

EQUIVALENTS

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

EXAMPLES

The invention is now described with reference to the following examples. These examples are illustrative only and the invention should in no way be construed as being limited to these examples but rather should be construed to encompass any and all variations which become evident as a result of the teachings provided herein.

Example 1

Chemicals

Propylene glycol was obtained from Alfa Aesar (Ward Hill, Mass., USA). Sucrose was obtained from Pfanstiehl (Waukegan, Ill., USA). Triton X-100 and sodium sulfate were obtained from EMD Millipore (Billerica, Mass., USA). Bis-tris, bis-tris HCl, and nicotinamide were obtained from Sigma-Aldrich (St. Louis, Mo., USA). Glacial acetic acid, arginine, glycine, sodium acetate, sodium caprylate, sodium chloride, sodium citrate, sodium hydroxide, sodium phosphate, tris, and urea were obtained from JT Baker (Center Valley, Pa., USA).

Proteins

The protein used in this work, albumin-fusion protein #1 (AFP-1) (SEQ ID NO: 145), is a CD40L antagonist comprised of two identical Tenascin C (TnC) domains, derived from a human fibronectin type III protein domain, fused to a human serum albumin. Each Tn3 (derived from the third fibronectin type III protein domain of human TnC) domain binds to human CD40L and inhibits its interaction with human CD40. Human serum albumin fusion ensures suitable pharmacokinetic properties of the molecule. The protein is expressed in Chinese hamster ovary (CHO) cells using techniques familiar to those trained in the art. Recombinant human albumin (rHSA; expressed in rice) was purchased as a lyophilized powder from Sigma-Aldrich (cat. No. A9731). Table 3 summarizes the properties of rHSA and AFP-1.

TABLE 3

Summary of protein properties

| molecule | Lab code | PI | Molecular weight (kDa) |
|---|---|---|---|
| Recombinant human albumin | rHSA | 5.3 [a] | 67.0 [a] |
| Anti-CD40L-albumin-fusion | AFP-1 | 5.4-5.5 [b] | 87.7 |

[a] Manufacturer's data
[a] As measured by cIEF.

Total Protein Concentration Measurements

Protein concentrations in all process intermediates (except clarified media and in some cases Cibacron Blue dye chromatography pools) were measured by absorbance at 280 nm using standard spectrophotometric procedures common in the industry. An extinction coefficient of 0.98 $(mg/mL)^{-1}cm^{-1}$ was used for AFP-1 and 0.531 $(mg/mL)^{-1}cm^{-1}$ was used for rHSA.

HSA Affinity High Performance Liquid Chromatography

Analytical high performance HSA affinity chromatography (HSA-HPLC) was performed using a Poros Capture-Select HSA column obtained from Life Technologies (Grand Island, N.Y., USA) with an Agilent 1200 HPLC system (Palo Alto, Calif., USA). The equilibration buffer phase was $10^{-50}$ mM sodium phosphate, pH 7.2 at 3.5 mL/min and product was eluted with 100 mM glycine, pH 2.0 buffer. Samples of $10^{-100}$ ug were injected neat and the elution profile was monitored using a spectrophotometer at 280 nm. Data was collected and analyzed using ChemStation software from Agilent and product-specific concentrations were determined from standard curves generated with purified protein.

Dye Affinity Chromatography

Cibacron blue Dye affinity chromatography was carried out under typical bind and elute conditions in small scale chromatography columns with 20 cm bed heights. All runs were conducted using an AKTA Explorer liquid chromatography system from GE Healthcare (Piscataway, N.J., USA) and the column was operated at 300 cm/h. Under baseline conditions, the column was equilibrated with 50 mM bis-tris (or phosphate), 50 mM NaCl, pH 6.0 and then loaded up to 25 g of protein/L of resin (based on HSA-HPLC titers in the clarified cell culture broth). After loading, the column was re-equilibrated, washed with 50 mM bis-tris (or phosphate), pH 7.0, and then eluted with 50 mM bis-tris (or phosphate), 25 mM sodium octanoate, 10 mM EDTA, pH 7.0. The product peak was collected based on absorbance criteria of 100 mAU on the leading and tailing side of the product peak. During optimization (see Example 2), additional washes were applied to the column between the re-equilibration and 50 mM phosphate, pH 7 wash. Capto Blue (high sub) resin was obtained from GE Healthcare (Piscataway, N.J., USA). Toyopearl AF-Blue HC-650M resin was obtained from Tosho Biosciences (King of Prussia, Pa., USA).

Anion Exchange Chromatography

Anion exchange chromatography (AEX) was carried out under typical bind and elute conditions in small chromatography columns packed to 20 cm bed height. All runs were conducted using an AKTA Explorer liquid chromatography system from GE Healthcare and the column was operated at 300 cm/h. Under baseline conditions, the column was equilibrated with 50 mM bis-tris, 20 mM sodium chloride, pH 7.0, loaded with protein, and then washed with equilibration buffer. The column was eluted using a step-wise or 10 column volume (CV) linear gradient of 20-400 mM sodium chloride in bis-tris buffer at pH 7.0. The product peak was collected based on absorbance criteria of 100 mAU on the leading and tailing side of the product peak. Capto Q resin was obtained from GE Healthcare (Piscataway, N.J., USA).

Anion Exchange Membrane Chromatography

Anion exchange membrane chromatography (AEMC) was carried out under typical flow through conditions. All runs were conducted using an AKTA Explorer liquid chromatography system from GE Healthcare and the column was operated at 10 MV/min. Under baseline conditions, the membrane was equilibrated with 50 mM bis-tris, 50 mM sodium chloride, pH 7.0 and then load material was passed through the membrane. The flow through product peak was collected based on absorbance criteria of 100 mAU on the leading and tailing side of the product peak. During optimization (see Example 2), buffer conditions between 10-220 mM NaCl and pH 6 to 8 were used. Mustang Q membranes were obtained from Pall Life Sciences (Port Washington, N.Y., USA).

Hydrophobic Interaction Chromatography

Hydrophobic interaction chromatography (HIC) was carried out under typical bind and elute conditions in small scale chromatography columns with 20 cm bench heights. All runs were conducted using an AKTA Explorer liquid chromatography system from GE Healthcare (Piscataway, N.J. USA) and the column was operated at 130-300 cm/h. Under baseline conditions, the column was equilibrated with 50 mM bis-tris, 1 M sodium citrate, pH 7.0. Load was prepared by diluting 1 part (by weight) protein solution with 2 parts 50 mM bis-tris, 2 M sodium citrate, pH 7.0 and then the column was loaded up to 25 g of protein/L of resin. After loading, the column was re-equilibrated with equilibration buffer and then eluted in a linear gradient of sodium citrate from 1 M to 0 mM sodium citrate over 20 column volumes. The product peak was collected in fractions, with early eluting material being enriched in oxidized product. Toyopearl PPG 600M and Toyopearl Phenyl 650M resins were from Tosoh Bioscience (King of Prussia, Pa., USA); Capto MMC and Butyl-S Fast Flow resins were from GE Healthcare (Piscataway, N.J., USA).

Analytical Size Exclusion Chromatography

Analytical high performance size exclusion chromatography (SEC-HPLC) was performed using a TSK-GEL G3000SWXL column (7.8 mm×30 cm) obtained from Tosoh Biosciences (King of Prussia, Pa. USA) with an Agilent 1200 HPLC system (Palo Alto, Calif., USA). The mobile phase was 0.1 M sodium phosphate, 0.1 M sodium sulfate, 10% isopropanol, pH 6.8 at 0.8 mL/min for 22 minutes at 30° C. Samples of 250 ug were injected neat and the column was calibrated using molecular weight standards from Bio-Rad (Hercules, Calif. USA). The elution profile was monitored using a spectrophotometer at 280 nm and data was collected and analyzed using ChemStation software from Agilent. The results are reported as the area percent of the product monomer peak compared to all other peaks excluding the buffer-related peak observed at approximately 12 minutes. When the SEC-HPLC method is run without 10% isopropanol in the mobile phase, a front shoulder (not completely resolved) on the monomer peak is observed that was identified as tryptophan oxidized monomer. Thus, depending on how the SEC-HPLC assay is operated, it can be used to measure monomer and aggregates, or estimate tryptophan oxidation.

Example 2

Purification of an Albumin-Fusion Protein (500 L Scale)

Recombinant human albumin (rHSA) was purified with a process that includes three bind-and-elute chromatography columns, a flow through chromatography membrane, a Triton viral inactivation step, and an ultrafiltration/diafiltration step. To make starting material for the rHSA process, cell culture supernatant from a monoclonal antibody (mAb) process was depleted of antibodies by collecting the non-bound material during a Protein A chromatography run, and then lyophilized rHSA powder was dissolved in the antibody-free supernatant. This starting material includes host cell proteins, DNA, and small molecule impurities that would typically be present in the cell culture supernatant of an albumin-fusion protein expressed in a CHO cell culture.

Figure 2:
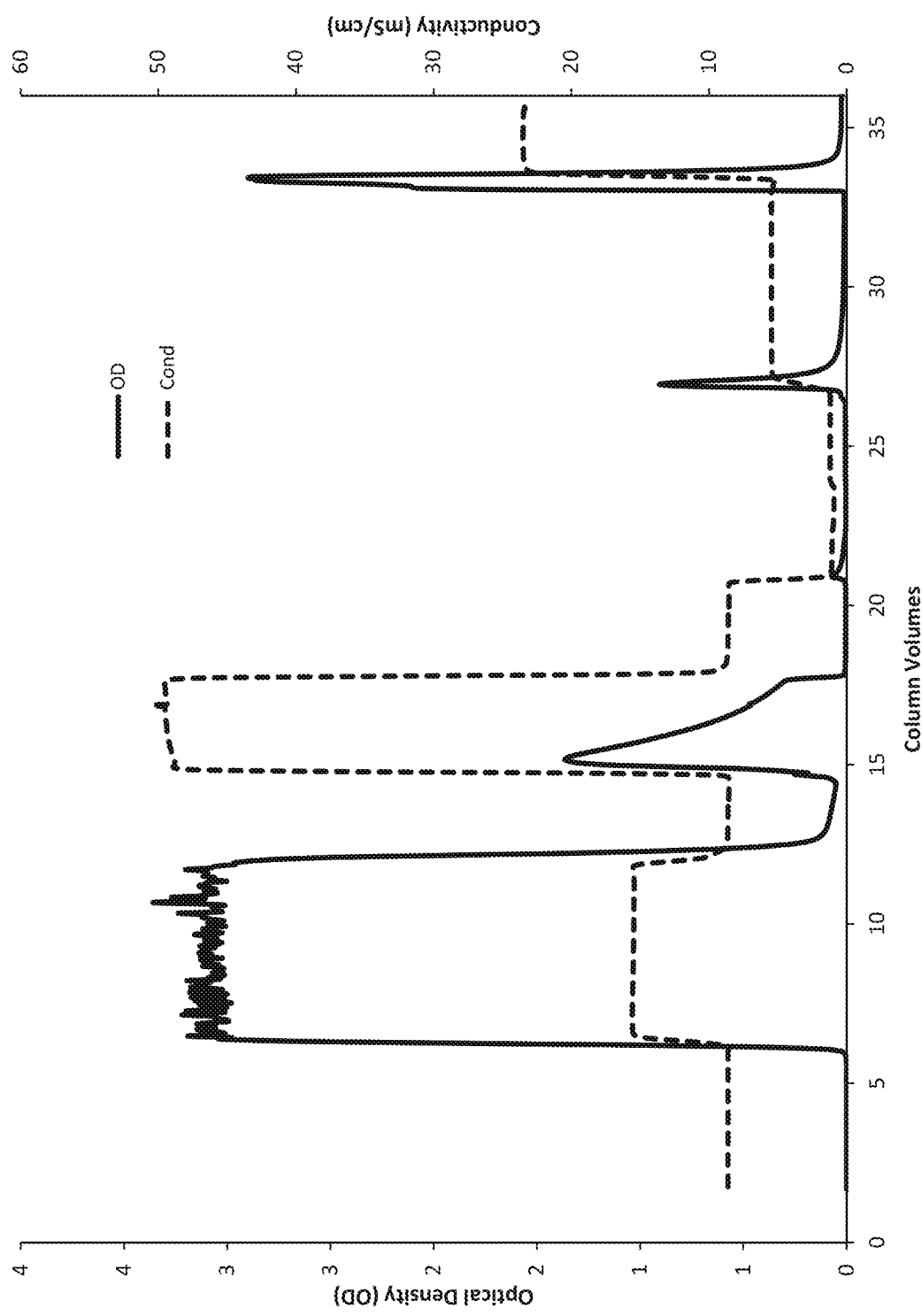
FIG. 2 depicts a representative chromatogram of the Cibacron blue due chromatography for rHSA operated at 300 cm/h.

The rHSA purification shown in FIG. 1 was used to purify ~700 mL of supernatant. Table 4 shows the performance parameters from the 1 L scale purifications. As can be seen in the table, step yields for the chromatography unit operations were generally high, with the exception of Capto Blue (high sub). FIG. 2 shows a Cibacron Blue (high sub) dye affinity chromatogram of rHSA. As can be seen in the figure, a large absorbance peak is observed during loading and during the 0.5 M NaCl wash. From this run alone it is unknown whether the low yield was due to the column being overloaded (i.e. the column was saturated with rHSA and not all of the rHSA was captured from the supernatant), or because of the 0.5 M NaCl wash. In either case, it is likely that the yield losses could be minimized by optimization of the column loading and wash step conditions.

TABLE 4

Summary of rHSA purification performance parameters

| Process Step | CV or MV [a] (mL) | Load challenge (g/L) | Step yield [b] (%) |
|---|---|---|---|
| Capto Blue (high sub) | 41.8 | 20 | 40 |
| Capto Q | 41.8 | 15 | 88 |
| Mustang Q | 0.86 | 1000 | 98 |
| PPG-600M | 19.7 | 20 | 94 |

[a] CV = column volume; MV = membrane volume.
[b] Capto Blue step yields are calculated based on HSA-HPLC product concentration in the load and A280 absorbance concentrations in the pool. All other step yields are calculated using A280 absorbance concentrations for both load and pool.

A summary of the product quality attributes of the rHSA process intermediates is shown in Table 5. As can be seen in the table, HCP and DNA are well controlled to low levels with the purification process, with HCP being measured at <10 ng/mg and DNA being measured at $1.7 \times 10^{-4}$ ng/mg in the fully purified material. HCP is reduced by greater than 2 logs over the Capto Blue column, and an additional 1 log (or more) from the CaptoQ and PPG-600M columns. Greater than 5 logs of DNA are removed by the CaptoQ column and an additional 1 log (or greater) is removed by the Capto Blue and MustangQ steps. In additional aggregate removal was observed over multiple steps in the purification process. Overall, the process was very successful at purifying rHSA and could be used as a starting point for purification of albumin-fusion proteins.

TABLE 5

Summary of product quality of rHSA

| Process Intermediate | HCP | | DNA | | Monomer |
|---|---|---|---|---|---|
| | ng/mg | LRV [a] | ng/mg | LRV [a] | % |
| Conditioned media | 514,028 | — | $3.0 \times 10^3$ | — | — |
| Capto Blue (high sub) | 1838 | 2.8 | $3.8 \times 10^2$ | 1.3 | 8.5 |
| Capto Q | <80 | >1.4 | $1.3 \times 10^{-3}$ | 5.6 | 5.8 |
| Mustang Q | 100 | 0 | $6.2 \times 10^{-5}$ | 1.4 | 4.7 |
| PPG-600M | <10 | >1.4 | $1.7 \times 10^{-4}$ | 0 | 4.0 |

[a] LRV = log reduction value. Calculated as $Log_{10}$ (ng of impurity in the load/ng of impurity in the pool)

Example 3

Purification of an Albumin-Fusion Protein (500 L Scale)

AFP-1, a recombinant human serum albumin-fusion protein (HSA-fusion or albumin-fusion) is expressed in CHO cells and purified with a process that includes three bind-and-elute chromatography columns, a flow through chromatography membrane, a Triton viral inactivation step, a nanofilter, and two intermediate ultrafiltration/diafiltration steps.

Figure 3:
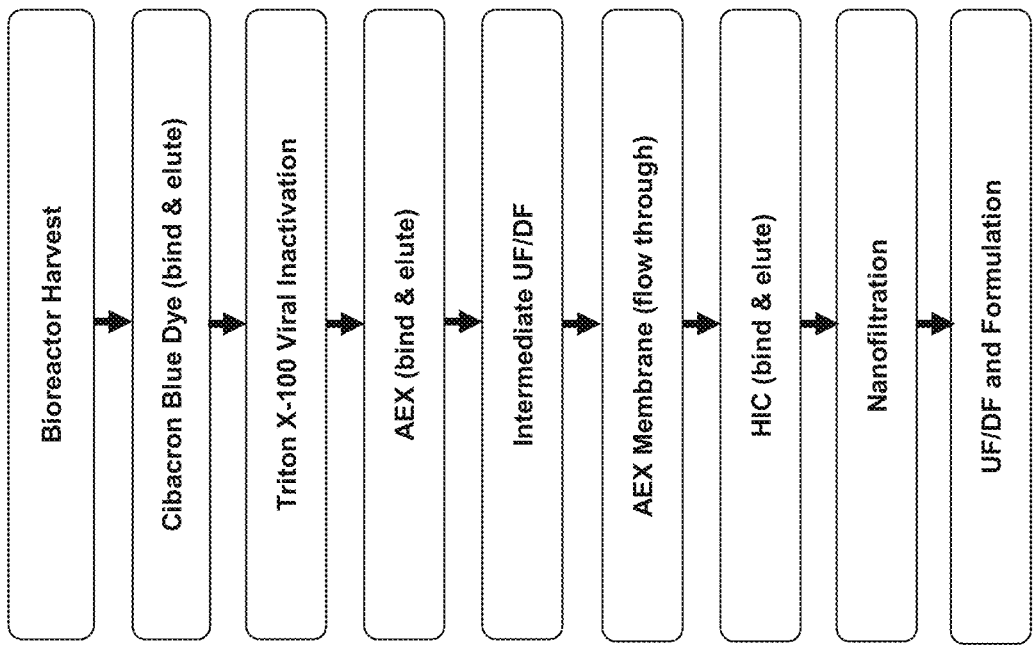
FIG. 3 depicts a flow chart of one embodiment of the albumin-fusion purification process.

The albumin-fusion purification process in shown in FIG. 3. The purification process shown in FIG. 3 was scaled up to purify two 500 L bioreactors. Table 6 shows the performance parameters from two 500 L bioreactor scale purifications. As can been seen in the table, step yields and pool volumes for the chromatography unit operations are consistent from lot to lot. The overall process yield (including UF/DF and nanofiltration) was 48% and 53% for Lot 1 and Lot 2, respectively. A summary of the product quality attributes of the process intermediates is shown in Table 7. The overall performance (i.e process yields) and product quality (absolute levels and LRV) is very comparable to the purification process used to purify rHSA. This is especially true for the step responsible for a majority of the HCP removal (Capto Blue (high sub) and Capto Q) and DNA clearance (Capto Q and Mustang Q).

TABLE 6

Summary of AFP-1 purification performance parameters.

| Process Step | CV or MV $^a$ (mL) | Load challenge (g/L) | Step yield $^b$ (%) |
|---|---|---|---|
| Lot 1 | | | |
| Capto Blue (high sub) | 33.9 | 19.8-22 | 68 |
| Capto Q | 35.0 | 12.1-12.8 | 92 |
| Mustang Q | 0.78 | 997.1 | 92 |
| PPG-600M | 13.6 | 14.4-18.2 | 106 |
| Lot 2 | | | |
| Capto Blue (high sub) | 33.9 | 20-22 | 78 |
| Capto Q | 35.0 | 10.5-19.9 | 93 |
| Mustang Q | 0.78 | 1221 | 99 |
| PPG-600M | 13.6 | 21.2-21.9 | 104 |

$^a$ CV = column volume; MV = membrane volume.
$^b$ Capto Blue step yields are calculated based on HSA-HPLC product concentration in the load and A280 absorbance concentrations in the pool. All other step yields are calculated using A280 absorbance concentrations for both load and pool.

TABLE 7

Summary of product quality of AFP-1.

| Process Intermediate | HCP ng/mg | HCP LRV $^a$ | DNA ng/mg | DNA LRV $^a$ | Monomer % | Oxidized % |
|---|---|---|---|---|---|---|
| Lot 1 | | | | | | |
| Conditioned media | 257,496 $^b$ | — | 4.3 × 10$^3$ $^b$ | — | — | — |
| Capto Blue (high sub) | 505 | 2.9 | 1.3 × 10$^3$ | 0.7 | 98.0 | 3.4 |
| Capto Q | 17 | 1.5 | 2.5 × 10$^{-4}$ | 6.7 | 99.5 | 3.3 |
| Mustang Q | <11 | >0.2 | <6.5 × 10$^{-5}$ | >0.6 | 99.9 | 3.5 |
| PPG-600M | <9 | >0.5 | <6.6 × 10$^{-5}$ | — | 99.6 | 3.1 |
| Lot 2 | | | | | | |
| Conditioned media | 264,097 $^b$ | — | 7.6 × 10$^2$ $^b$ | — | — | — |
| Capto Blue (high sub) | 661 $^c$ | 2.7 | 2.4 × 10$^2$ $^c$ | 0.6 | 99.5 | 4.6 |
| Capto Q | 34 $^c$ | 1.3 | 2.5 × 10$^{-4}$ $^c$ | 6.0 | 99.6 | 6.0 |
| Mustang Q | 12 | 0 | <2.3 × 10$^{-5}$ | >1.0 | 99.8 | 6.1 |
| PPG-600M | <8 | >0.6 | — | — | 99.6 | 6.4 |

$^a$ LRV = log reduction value. Calculated as Log$_{10}$ (ng of impurity in the load/ng of impurity in the pool).
$^b$ Values given are the weighted average of multiple product collection bags.
$^c$ Values given are the weighted average of multiple column cycles.

Figure 4:
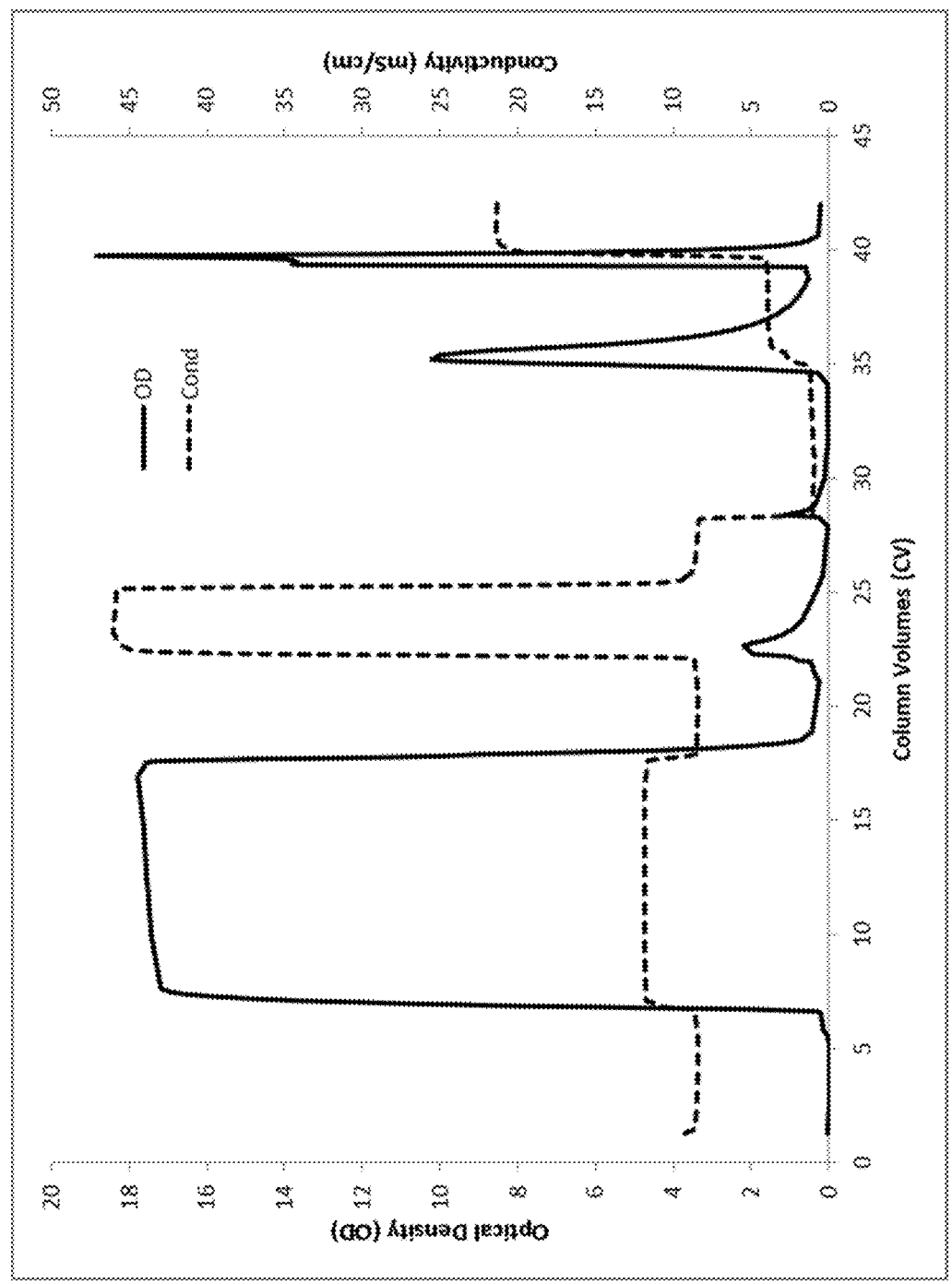
FIG. 4 depicts a representative chromatogram of the Cibacron blue due chromatography for albumin-fusion protein #1 (AFP-1) operated at 300 cm/h.

Cibacron blue dye affinity chromatography, using Capto Blue (high sub) resin is used as the capture column for the AFP-1 purification process. FIG. 4 shows a representative chromatogram of the Cibacron blue dye chromatography for AFP-1 operated at 300 cm/h. As can be seen in FIG. 4, a large flowthrough peak is seen during loading, as indicated by a large OD signal starting around 6 column volumes (CVs). This flowthrough peak contains a majority of the process-related impurities that are present in the conditioned media, including host cell proteins (HCPs) and DNA. After loading, the column is re-equilibrated and then washed with different buffers; the first containing 0.5 M NaCl at pH 6.0 followed by a re-equilibration and then with 10% propylene glycol at pH 7.0. The washes reduce HCP and DNA levels in the product pool by dissociating these impurities from the Cibacron blue dye ligand and/or the albumin-fusion protein. The column is then eluted with a buffer containing sodium octanoate and EDTA. As can be seen in Table 7, after Capto Blue (high sub) chromatography, the product intermediate has lower DNA (0.6-0.7 logs of clearance) compared to the conditioned media and lower HCP (2.7-2.9 logs of clearance). Moreover, the Capto Blue (high sub) product has high monomer (≥98.0%) and low levels of oxidized product.

After initial capture with Cibacron blue dye chromatography, the product is treated with Triton X-100 to inactivate potential enveloped viruses. In this example the Capto Blue (high sub) pool is spiked with 10% Triton X-100 to a final concentration of 0.5% Triton X-100 (w/w) and held for 130 minutes at room temperature. Under these conditions efficient virus inactivation is achieved (see Example 5 for details).

Figure 5:
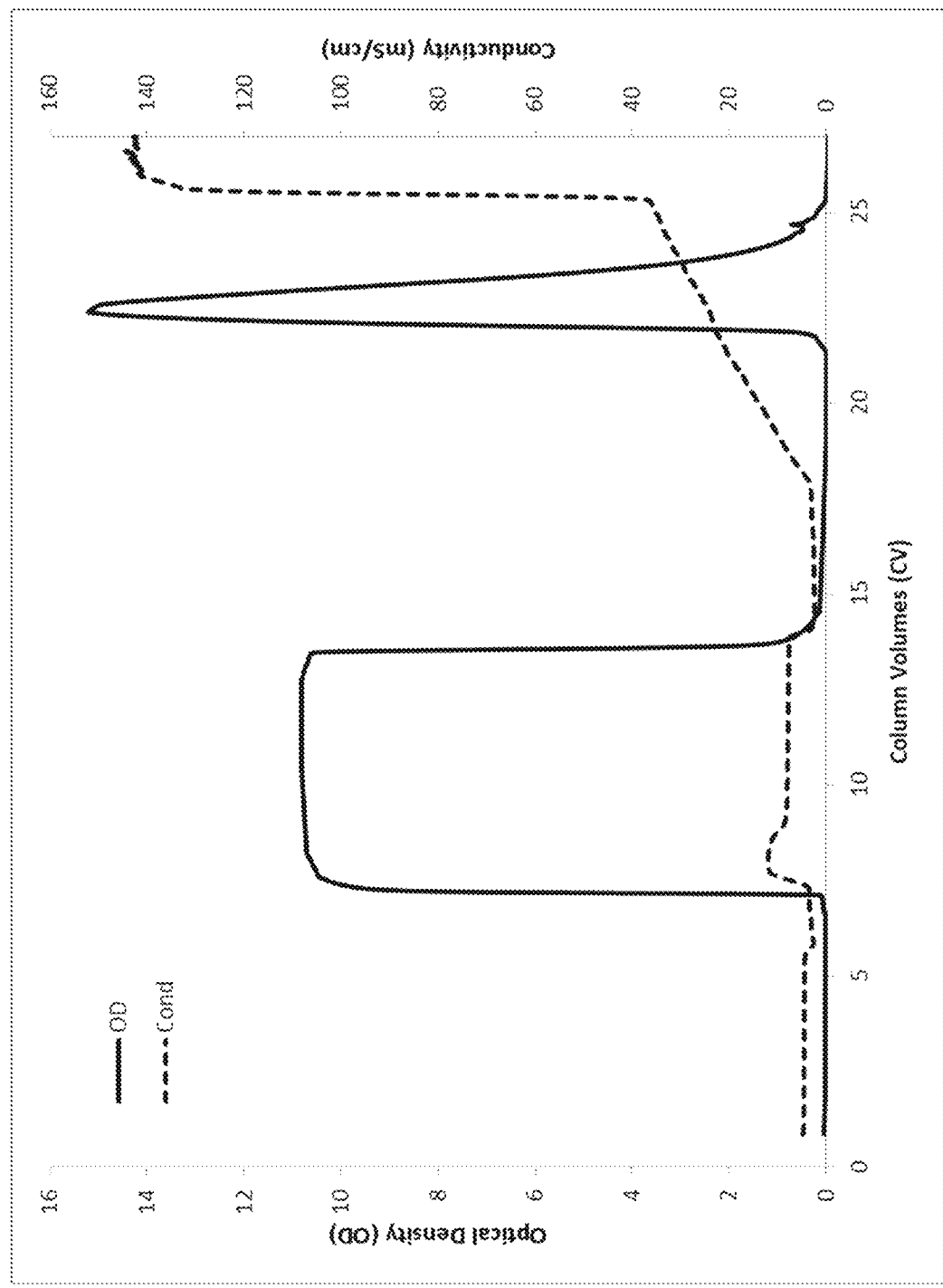
FIG. 5 depicts a representative Capto Q chromatogram for AFP-1 operated at 300 cm/hr.

After Triton X-100 treatment, the albumin-fusion protein is purified with anion exchange chromatography using a Capto Q column in bind-and-elute mode. FIG. 5 shows a representative Capto Q chromatogram for AFP-1 operated at 300 cm/h. As can be seen in FIG. 5, a large flowthrough peak is seen during loading, as indicated by a large OD signal starting around 7 CVs. This flowthrough peak contains Triton X-100 from the previous step. After loading, the column is re-equilibrated and then eluted with a linear NaCl gradient to 0.4 M NaCl over 10 CVs (at pH 7.0). As can be seen in Table 7, the Capto Q intermediate has lower HCP (1.3-1.5 logs of clearance) and much lower DNA (6-6.7 logs of clearance) than the Capto Blue (high sub) pool. It can also be seen that Capto Q has the ability to increase monomer content (by reducing aggregated product) and also removes the impurity that is responsible for oxidation of AFP-1 (see Example 7 for details).

Figure 6:
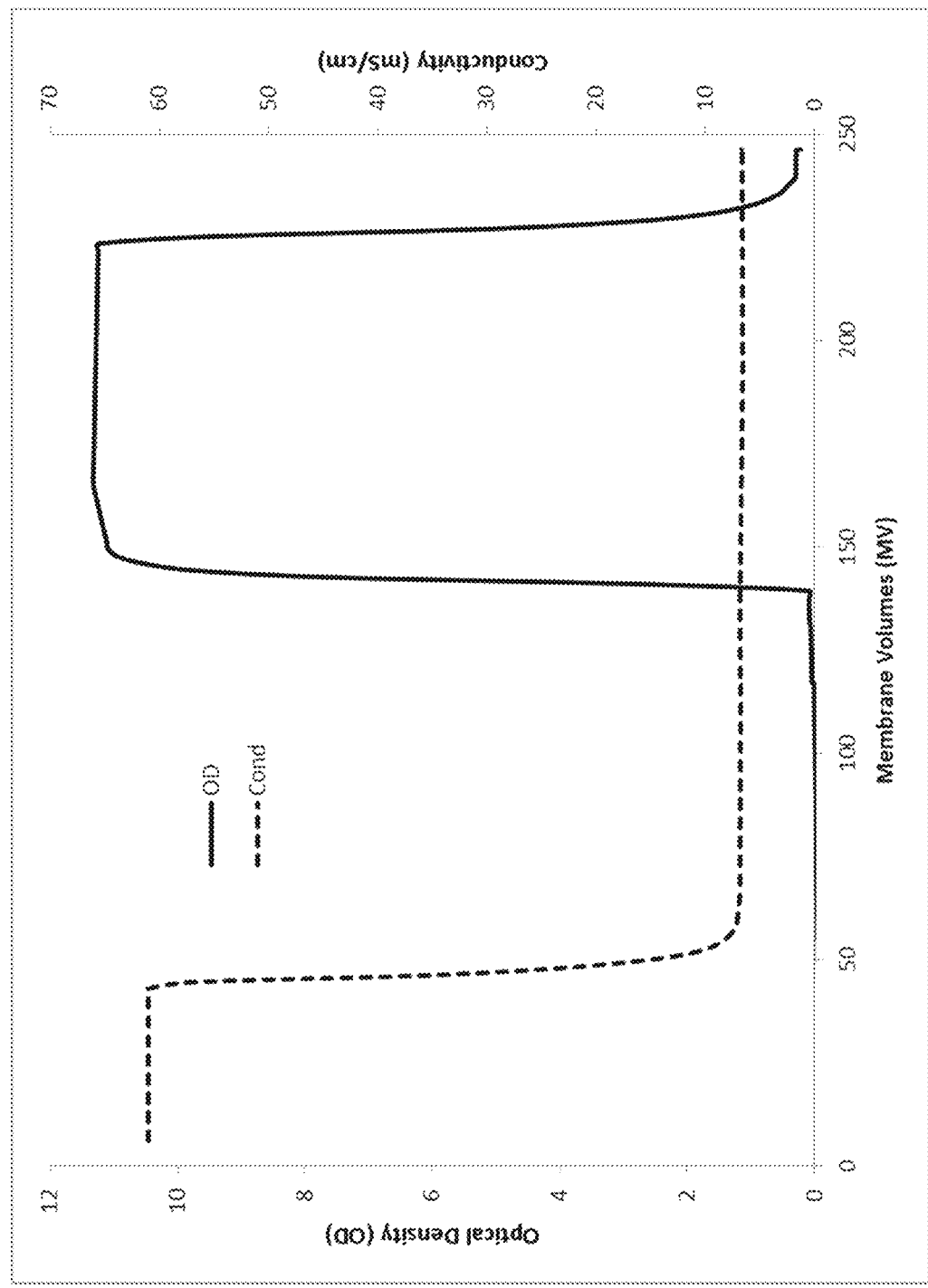
FIG. 6 depicts a representative Mustang Q membrane chromatogram operated at 10 MV/hr.

The Capto Q product is diafiltered against 50 mM bis-tris, 50 mM NaCl, pH 7.0 to prepare for purification using a Mustang Q membrane chromatography step. FIG. 6 shows a representative Mustang Q membrane chromatogram operated at 10 MV/hr. After conditioning and equilibrating the membrane, product is applied to the membrane and collected in the flowthrough while impurities are bound to the membrane. When stripped with 2 M NaCl, a large peak containing both impurities and some product is observed (strip peak is not included in the chromatogram in FIG. 6). As can be seen in Table 7, DNA is further reduced by the Mustang Q membrane (0.6-1 logs of clearance).

Figure 7:
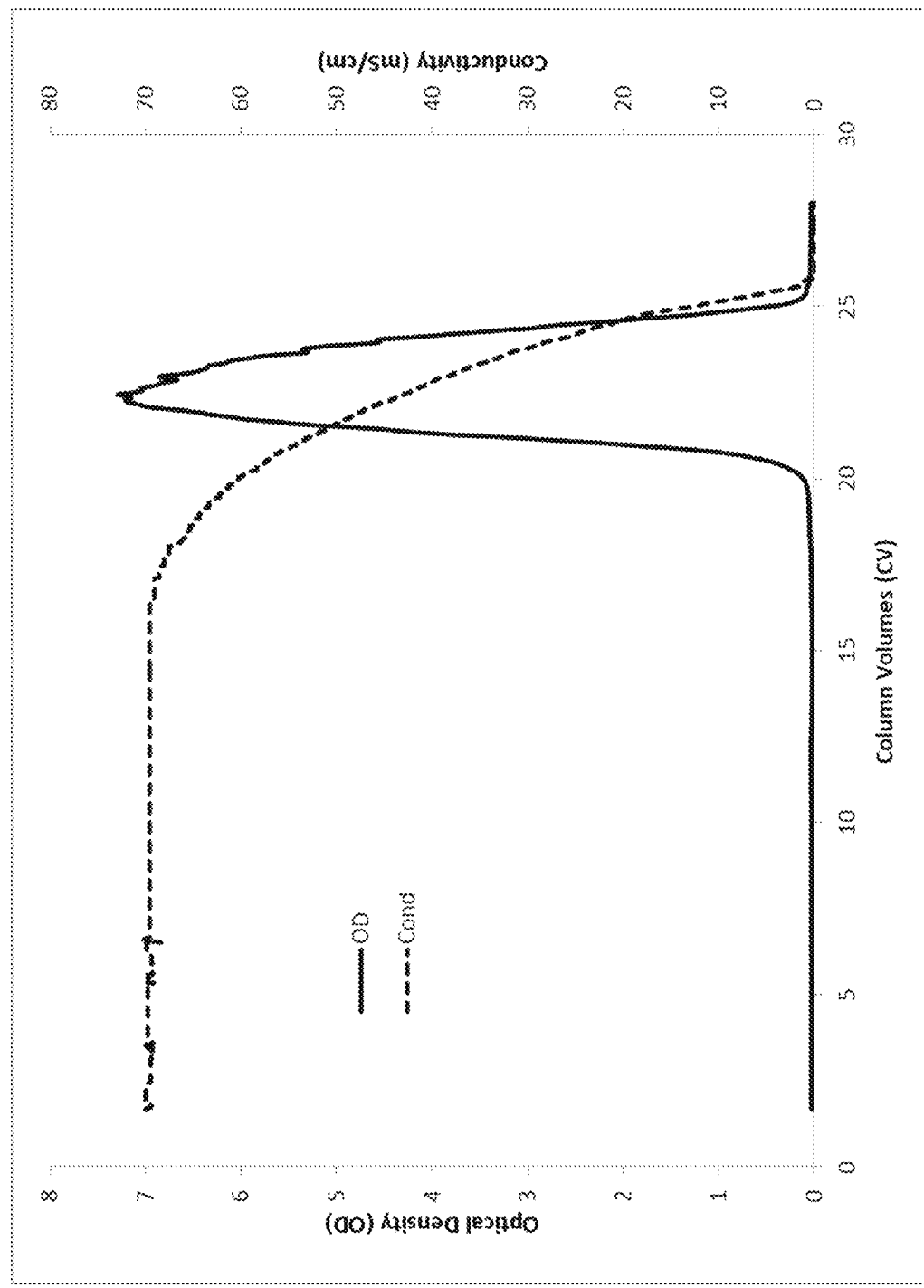
FIG. 7 depicts a representative Toyopearl PPG-600M chromatogram operated in band-and-elute mode at 130 cm/hr.

The final chromatography step is a hydrophobic interaction column using Toyopearl PPG-600M. FIG. 7 shows a representative Toyopearl PPG-600M chromatogram for AFP-1 operated at 130 cm/h. After equilibration in a buffer containing 1 M citrate, the product is loaded on to the column. Since the product is so pure by this stage in the purification process, no flowthrough peak is observed. After loading, the column is re-equilibrated and then eluted with a gradient to a buffer containing no citrate. The product is eluted in a sharp peak, which is collected in fractions that are assayed for oxidized product content by HIC-HPLC. All fractions containing less than 15% oxidized species by HIC-HPLC are pooled and carried forward for nanofiltration.

Nanofiltration using Viresolve Vpro+ is carried out using techniques standard to those skilled in the art of protein purification. The goal of nanofiltration is to remove potential virus particles. After nanofiltration, the product is concentrated, diafiltered, and formulated in 10 mM phosphate, 250 mM sucrose, 0.02% polysorbate 80. Upon completion of nanofiltration (or formulation), the product pool is tested for additional impurities that are introduced to the product during the purification process. Table 8 summarizes the process-related impurity testing. As seen in Table 8, the buffer components and Cibacron blue dye ligand that are introduced to the process in the early process steps (blue dye chromatography and viral inactivation steps) are reduced to very low levels by the subsequent purification steps.

TABLE 8

Summary of process-related impurities

| Impurity | Step where impurity is introduced to process | Measured value after purification (µg/mL) | |
|---|---|---|---|
| | | Lot 1 | Lot 2 |
| Propylene glycol | Capto Blue (high sub) wash | <2.5 | <2.5 |
| EDTA | Capto Blue (high sub) elution | <0.25 | <0.25 |
| Cibacron blue dye ligand | Capto Blue (high sub) | — | <0.05 |
| Triton X-100 | Triton viral inactivation | <0.1 | <0.1 |

Example 4

Cibacron Blue Dye Affinity Chromatography

Capto Blue (high sub) and Toyopearl AF-Blue HC-650M were compared in terms of binding capacity and impurity removal from clarified cell culture broth. Table 9 summarizes dynamic binding capacities of AFP-1 in clarified cell culture broth. For Capto Blue (high sub), dynamic binding capacity showed an indirect correlation with pH, where pH 5 had the highest binding capacity (37.4 g AFP-1 per L resin) and pH 8 had the lowest binding capacity (12.3 g/L). While high binding capacity is desirable, operation at pH 5 is less desirable due to increased aggregation rates for the molecule at pH 6 and below (data not shown). Thus, pH 6 was chosen as the optimal pH to balance high binding capacity and product stability. Comparison of dynamic binding capacities for Capto Blue (high sub) and Toyopearl AF-Blue HC-650M revealed nearly double the dynamic binding capacity for Capto Blue (high sub) at pH 6.

TABLE 9

Comparison of dynamic binding capacities on Cibacron blue dye resins.

| Resin | pH | DBC at 10% breakthrough (g/L) |
|---|---|---|
| Capto Blue (high sub) | 5 | 37.4 |
| | 6 | 22.0 |
| | 7 | 15.6 |
| | 8 | 12.3 |
| Toyopearl AF-Blue HC-650M | 6 | 13.3 |

To compare these two resins for impurity clearance from clarified cell culture broth, each column was operated under baseline conditions with the column loaded to 75-80% of its dynamic binding capacity (17.5 g/L for Capto Blue (high sub) and 10.0 g/L for Toyopearl AF-Blue HC-650M) and eluted from the column using 25 mM sodium octanoate. Table 10 shows a comparison of two Cibacron blue dye resins used for the capture and purification of AFP-1 from clarified cell culture broth. As can been seen in Table 10, yields for both resins are similar (for elution with 25 mM octanoate), with typical yields >90%. Moreover, both resins reduce HCP and DNA levels effectively from clarified cell culture broth; however, Toyopearl AF-Blue HC-650M chromatography showed slightly better HCP and DNA clearance compared to Capto Blue (high sub).

TABLE 10

Optimization of albumin-fusion purification using Cibacron blue dye chromatography.

| Column Loading (g/L) | Elution Salt | Yield$^a$ (%) | HCP (ng/mg) | DNA (ng/mg) | HPSEC (% Monomer) |
|---|---|---|---|---|---|
| Clarified cell culture broth | | | | | |
| N/A | N/A | N/A | 241,210 | $2.26 \times 10^3$ | N/A |
| Capto Blue (high sub) | | | | | |
| 10.0 | 25 mM octanoate | 95 | 6,166 | $2.79 \times 10^2$ | 99.2 |
| 17.5 | 25 mM octanoate | 94 | 9,306 | $2.81 \times 10^2$ | 98.9 |
| 25.0 | 25 mM octanoate | 93 | 6,722 | $2.55 \times 10^2$ | 99.0 |
| 17.5 | 2M NaCl | 60 | 119,419 | $1.11 \times 10^3$ | 82.2 |
| Toyopearl AF-Blue HC-650M | | | | | |
| 10.0 | 25 mM octanoate | 103 | 5,660 | $1.48 \times 10^1$ | 99.0 |

$^a$ Yield is based on HSA-HPLC concentration measurements in the load and pool.

For AFP-1, Capto Blue (high sub) resin was selected for the manufacturing process due to its higher binding capacity. To optimize the capture step with Capto blue (high sub), several factors were considered, including column loading and wash and elution buffer composition. As can be seen in Table 10, column loading had no effect on DNA, but showed a slight effect on HCP clearance. At extremes in column loading tested (10 g/L or 25 g/L loading) HCP clearance is more effective than at an intermediate loading (17.5 g/L loading). Thus it is beneficial to operate the column at or near the dynamic binding capacity to both increase throughput and also to increase HCP removal.

Elution buffer composition was optimized for the Cibacron blue dye chromatography capture step. FIG. 8 shows a comparison of elution buffers for Cibacron blue dye chromatography. As can be seen in FIG. 8 and in Table 10, octanoate is a much more effective choice for elution from the Cibacron blue dye column compared to 2 M NaCl. For this example, 2 M NaCl gave incomplete elution of AFP-1 from the column based on a 60% yield and broad elution profile seen in the chromatogram. Product quality of the 2 M NaCl run showed HCP levels were much higher and monomer levels were much lower compared to elution using 25 mM octanoate. Moreover, the use of 2 M NaCl (alone or in combination with solvents) would be less desirable from a manufacturing standpoint as these elution buffers would be costly and the process may require a buffer exchange step to facilitate binding to the next chromatography column in the process.

The final step in the development of a Cibacron blue dye capture step was wash optimization. It is well known that albumin can bind many types of molecules, and the same is true for albumin-fusion proteins. Therefore it is expected that impurities (such as HCP and DNA) may interact with the albumin-fusion protein and co-purify with the desired product. Taking advantage for the strong binding of the albumin-fusion protein on the Cibacron blue dye chromatography resin, several washes were tested in an effort to improve impurity clearance by breaking interactions between the impurities and the Cibacron blue dye ligand or between the impurities and the albumin-fusion protein that is bound to the ligand. Various types of washes were employed, including ionic, chaotropic, kosmotropic, surfactants and mild solvents. Moreover, each wash was tested at pH 6 and pH 7 to determine the effect, if any, of pH.

Table 11 summarizes the washes tested on Cibacron blue dye chromatography. As can be seen in the Table 11, pH of the wash is very important for HCP removal. At pH 7, all of the washes tested were more effective at reducing HCP, with most washes decreasing HCP by two-fold or higher compared to identical washes at pH 6. Of the washes tested, 0.5 M NaCl at pH 7 was the most effective at reducing HCP, showing a greater than seven-fold decrease in HCP compared to the control run. Unlike HCP clearance, DNA clearance was not impacted by pH between pH 6 and 7. Of all of the washes tested, only the ionic washes (NaCl and $Na_2SO_4$) showed improved DNA clearance compared to the control run. In these cases, 4-5 fold reduction in DNA was observed compared to the control run. It should also be noted that higher monomer levels were observed with runs containing 10% propylene glycol; however, marginal increases in the monomer level were observed with a number of the washes tested. No impact was observed in monomer purity with pH.

Based on the data in Table 11, 0.5 M NaCl is a very effective wash in terms of HCP and DNA clearance and 10% propylene glycol is an effective wash for increasing monomer purity. It should be noted here that the 10% propylene glycol wash was also effective at reducing oxidation potential of the product in the Capto Blue pool (see Example 7 for additional details). Yield was most negatively impacted by 0.5 M NaCl washes, with a yield loss of 5% and 14% at pH 6 and 7, respectively. Interestingly, no yield loss was observed with the other washes tested. Based on these results, a wash containing 0.5 M NaCl at pH 6 and a wash containing 1000 propylene glycol at pH 7 were incorporated in to the manufacturing process in Example 3.

TABLE 11

Summary of Cibacron blue dye chromatography wash optimization.

| Wash species | Wash pH | Yield [a] (%) | HCP (ng/mg) | DNA (ng/mg) | HPSEC (% Monomer) |
|---|---|---|---|---|---|
| Clarified cell culture broth | | | | | |
| N/A | N/A | N/A | 241,210 | $2.26 \times 10^3$ | N/A |
| Control | | | | | |
| 0.05M NaCl | 6 | 95 | 7,332 | $2.25 \times 10^2$ | 99.1 |
| Wash development runs | | | | | |
| 0.5M NaCl | 6 | 90 | 2,125 | $6.35 \times 10^1$ | 98.8 |
| | 7 | 81 | 1,004 | $5.07 \times 10^1$ | 98.9 |
| 0.5M $Na_2SO_4$ | 6 | 96 | 5,629 | $5.29 \times 10^1$ | 98.8 |
| | 7 | 95 | 2,939 | $3.97 \times 10^1$ | 98.9 |
| 10% propylene glycol | 6 | 98.4 | 8,665 | $1.70 \times 10^2$ | 99.4 |
| | 7 | 95 | 5,311 | $2.09 \times 10^2$ | 99.4 |
| 0.1% Triton X-100 | 6 | 100 | 5,540 | $1.70 \times 10^2$ | 99.6 |
| | 7 | 101 | 2,878 | $2.04 \times 10^2$ | 99.3 |
| 0.5M urea | 6 | 100 | 7,133 | $1.02 \times 10^2$ | 99.3 |
| | 7 | 99 | 4,321 | $1.84 \times 10^2$ | 99.1 |
| 0.1M nicotinamide | 6 | 100 | 9,407 | $1.69 \times 10^2$ | 99.2 |
| | 7 | 97 | 3,567 | $1.49 \times 10^2$ | 99.4 |

[a] Yield is based on HSA-HPLC concentration measurements in the load and pool.

Example 5

Triton X-100 Viral Inactivation

For AFP-1, an albumin-fusion molecule with an isoelectric point in the range of 5.4-5.5, low pH treatment was determined to be detrimental (observed aggregation and precipitation) to the product quality of the molecule. Thus, Triton X-100 treatment was chosen for viral inactivation. Similar to low pH treatment, the addition of Triton X-100 will disrupt the envelope around the virus rendering it inactive. Unlike low pH treatment, Triton X-100 has no measurable impact on the product quality of AFP-1.

Virus inactivation with Triton X-100 was tested using Xenotropic Murine Leukemia Virus (XMuLV) as a model enveloped virus. Briefly, material purified by Cibacron blue dye chromatography was spiked with 10% (w/w) Triton X-100 to a final concentration of 0.5% (w/w) Triton X-100, incubated for a given time, and then tested for infectivity using plate-based methods common to those skilled in the art. Log reduction values (LRV) were calculated based on XMuLV titers from infectivity assays run on samples before and after Triton X-100 treatment.

Table 12 summarizes the LRV obtained for XMuLV viral inactivation. As can be seen in the table, treatment with 0.5% (w/w) Triton X-100 is an effective method for XMuLV inactivation. For samples measured immediately after Triton X-100 treatment, LRV values of 4.73 and >5.15 were obtained for duplicate experiments. By the end of a 120 minute incubation, both studies showed inactivation of >5.15 logs of XMuLV. These LRV are in the same range as values obtained with low pH treatment for monoclonal antibodies.

TABLE 12

Summary of XMuLV LRV for Triton X-100 treatment of an albumin-fusion protein

| | LRV after incubation with 0.5% (w/w) Triton X-100 | | | | |
|---|---|---|---|---|---|
| Study | 0 min | 30 min | 60 min | 90 min | 120 min |
| 1 | 4.73 | 4.43 | 5.21 | 4.73 | >5.21 |
| 2 | >5.15 | 5.15 | 4.03 | 5.15 | >5.15 |

After Triton X-100 treatment the product is purified with an anion exchange chromatography (see FIG. 3 for purification process). During anion exchange chromatography, the albumin-fusion is strongly bound to the stationary phase while some impurities flow though the column. Triton X-100 is unretained by the anion exchange column and can be seen in the flowthrough of the anion exchange column due to its absorbance at 280 nm. FIG. 5 shows a representative anion exchange chromatogram with a strong 280 nm absorbance signal during the column loading. Additional clearance of Triton X-100 may be achieved during hydrophobic interaction chromatography; however, Triton X-100 is expected to bind to the hydrophobic column along with the product. Thus, removal of Triton X-100 from the product is less robust and dependent on selectivity between the Triton X-100 and the albumin-fusion protein. After purification by the process shown in FIG. 3, Triton X-100 levels were measured below 0.1 µg/mL (see Table 5).

Example 6

Anion Exchange Membrane Chromatography

Anion exchange (AEX) membranes operated in flow through mode can offer excellent removal of host cell impurities such as host cell proteins (HCPs), DNA, and viruses. For a monoclonal antibody (mAb), where the pI is typically in the range of 7.5 to 9.5, product binding is of minimal concern when a flow-through AEX membrane is operated around neutral pH and yield is often >95% (regardless of salt concentration or conductivity). As operating pH approaches the pI of the mAb, binding can occur and yield may be lost. For mAbs, host cell impurity clearance is achieved under conditions of high pH and low salt (or conductivity). Thus for a typical mAb, operation conditions are optimized such that conductivity is minimized and the pH is as high as possible while remaining below the pI.

For albumin fusion proteins with a low pI, the development and optimization of a flow through AEX membrane chromatography step is more complex and cannot be predicted a priori. Unlike a typical mAb there is likely to be some binding of the target molecule to the AEX membrane at all pH values around neutral, and less binding is expected at lower pH (due to the lower protein charge) and higher salt concentrations (that would shield interactions between the albumin fusion protein and the chromatography ligand). Thus, higher yields would be expected at lower pH and higher salt concentrations. On the other hand, trends in impurity clearance with respect to salt and pH are expected to mirror trends seen with mAbs, where higher pH and lower salt concentrations result in greater impurity clearance. Thus, a balance must be struck between high yield (low pH and high salt) and high purity (hi pH and low salt), and pH, salt concentration, and membrane loading must be optimized for a given product.

To optimize the AEX membrane chromatography step for AFP-1, pH (pH 6.0 to 8.0), NaCl concentration (10-220 mM), and membrane load challenge (0.5-2.5 g/mL of membrane) were investigated in a multivariate design of experiments (DoE). For this study, a screening design was used where the corners of the design space were tested, along with two center point conditions and two additional points along the edges to determine the effect on step yield and impurity clearance. Table 13 summarizes AEX membrane optimization experiments for AFP-1. As can be seen in Table 13, yield was impacted by all three factors, and generally followed the trends expected with higher yields obtained at low pH, low salt, and higher loading. On the other hand, DNA clearance did not follow the expected trend of better clearance at higher pH and lower salt. Instead, DNA clearance was observed to be worst at pH 8 at 10 mM NaCl. Interestingly the effect was not caused by a single factor. For example, increased impurity clearance was observed under weak (pH 6, 220 mM NaCl) and intermediate (pH 6, 10 mM NaCl or pH 8, 110 mM NaCl) binding conditions when compared to strong binding conditions (pH 8.0, 10 mM NaCl). Only under the strongest binding conditions tested was impurity clearance negatively impacted. One explanation for this result may be competitive binding between the albumin-fusion protein and the impurities. Under strong binding conditions, the albumin-fusion protein may out compete for the binding sites which would result in lower binding capacities for DNA and lower yield for the product. It should also be noted that no HCP clearance was observed and aggregate levels remained relatively unchanged for all condition tested.

Prior to completing the above optimization study for the Mustang Q step, it was expected that a balance would need to be struck between yield and impurity clearance. But actually the opposite was observed in the study. FIG. 9 shows step yield and DNA log reduction values (LRV) as a function of pH and NaCl concentration. As can be seen in the figure, both yield and DNA clearance were shown to be optimal at low pH and higher NaCl concentrations (shown by the red contours). This was an unexpected finding for DNA, and a similar effect may be observed with viral clearance.

TABLE 13

Summary of process and analytical data for Mustang Q membrane chromatography.

| pH | [NaCl] (mM) | Membrane Loading (g/mL) | Yield (%) | HCP (ng/mg) | DNA (LRV) | Monomer (%) |
|---|---|---|---|---|---|---|
| — | — | — | — | 2,241 | — | 99.6 |
| 6 | 10 | 0.5 | 83 | 2,764 | 5.5 | 99.5 |
| 6 | 10 | 2.5 | 90 | 2,802 | 5.7 | 99.2 |
| 6 | 110 | 0.5 | 90 | 2,898 | 6.0 | 99.2 |
| 6 | 110 | 2.5 | 92 | 2,720 | 6.4 | 99.1 |
| 6 | 220 | 1.5 | 98 | 2,210 | 5.8 | — |
| 7 | 60 | 1.5 | 89 | 2,520 | 4.6 | 99.6 |
| 7 | 60 | 1.5 | 89 | 2,294 | 4.8 | 99.5 |
| 8 | 10 | 0.5 | 73 | 2,672 | 2.9 | 99.5 |
| 8 | 10 | 2.5 | 85 | 2,432 | 2.6 | 99.4 |
| 8 | 110 | 0.5 | 87 | 2,438 | 5.7 | 99.8 |
| 8 | 110 | 2.5 | 91 | 2,328 | 5.9 | 99.5 |
| 8 | 190 | 1.5 | 98 | 2,535 | 6.3 | — |

Example 7

Control of an Oxidation Variant Using Hydrophobic Interaction Chromatography

Figure 10:
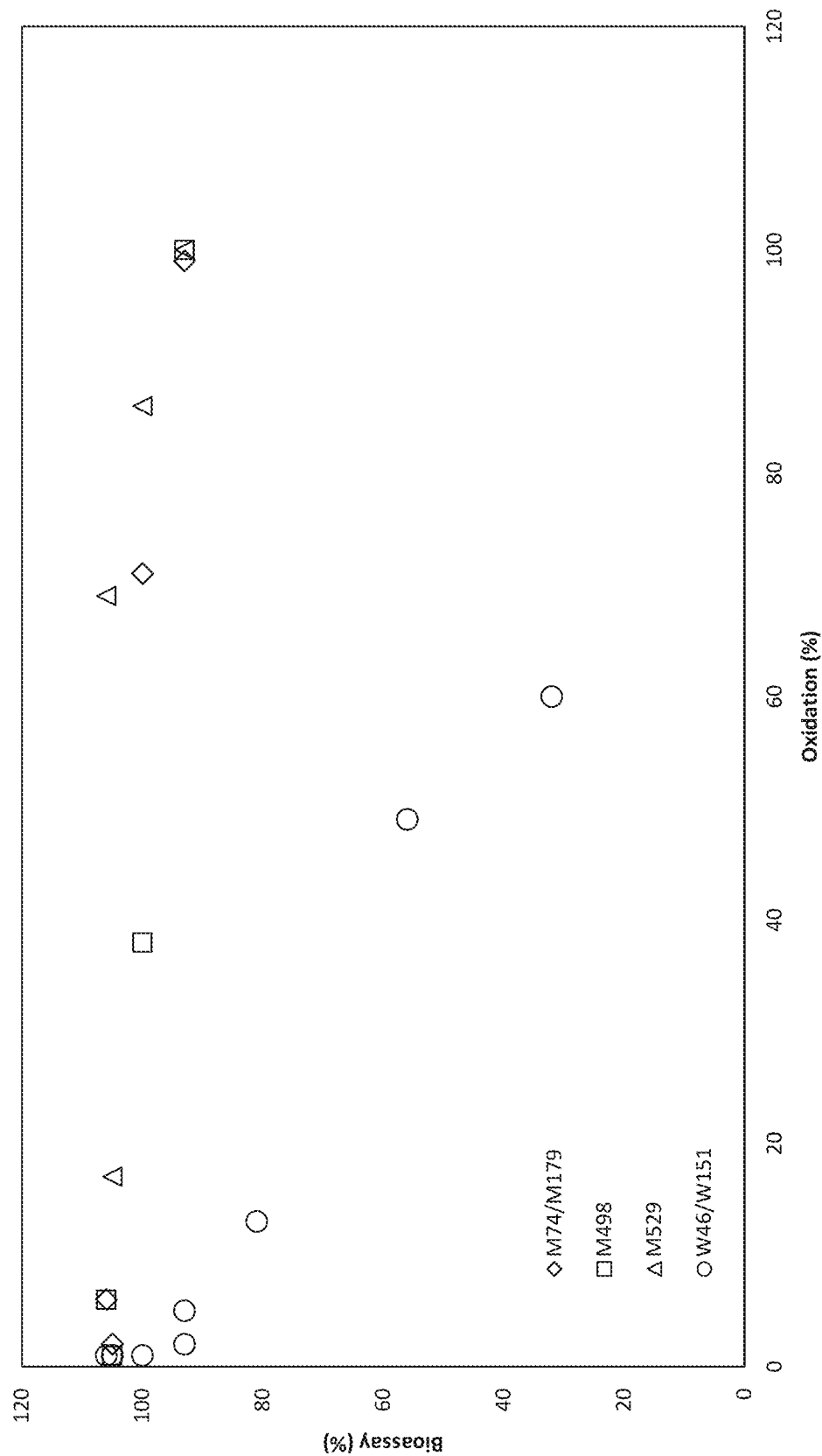
FIG. 10 depicts the relative potency of an albumin-fusion protein as a function of oxidation. The □ represents methionine M498 of AFP-1; ○ represents tryptophan W46/W151 of AFP-1; ◇ represents methionine residues M74/M179 of AFP-1; and Δ represents methionine M529 of AFP-1.

The protein used in this work is an albumin-fusion protein that contains two Tn3 scaffolds linked to the recombinant human serum albumin. Each Tn3 scaffold contains an active site capable of binding to the CD40L ligand. The albumin-fusion protein contains eight methionine residues (six on the albumin portion of the molecule, and one on each Tn3 scaffold) and seven tryptophan residues (five on the albumin portion of the molecule, and one on each Tn3 scaffold). The methionine and tryptophan residues that are close to the surface area can be oxidized during the cell culture and/or purification process. FIG. 10 shows the relative potency as a function of oxidation determined by peptide mapping mass spectrometry. As can be seen, methionine oxidation on the albumin (M498 and M529) or Tn3 (M74 and M17) portion of the molecule does not contribute to a loss of potency. On the other hand, the tryptophan oxidation (W46 and W151), which occurs on the Tn3 scaffold near the active sites (on the BC loops) of the molecule, results in a loss of potency for the molecule. Thus, tryptophan oxidation must be well controlled throughout the manufacturing process.

In order to monitor tryptophan oxidation during the development and manufacturing of AFP-1, peptide mapping mass spectrometry, SEC-HPLC, and HIC-HPLC were utilized at various stages of development. While mass spectrometry can be used to determine levels of methionine and tryptophan levels quite precisely, it is low-throughput and involves more time and resources and so it is typically used for characterization of important samples. On the other hand, the faster HPLC methods can be used for in-process testing; however, both HPLC assays have disadvantages. For example, SEC-HPLC can measure tryptophan oxidation, but is only an estimate since the tryptophan shoulder is not fully resolved form the native molecule, while HIC-HPLC can accurately measure oxidation levels, but cannot distinguish between methionine and tryptophan oxidation. All three methods were employed during development and manufacturing to gain a better understanding of AFP-1 oxidation. To improve the specificity of AFP-oxidation quantitation, a RP-HPLC method was developed to focus the detection of peptides that contain TN3 tryptophan (W46 and W151) oxidation. The method can be used for future in-process testing and quality control of AFP-1.

Figure 11:
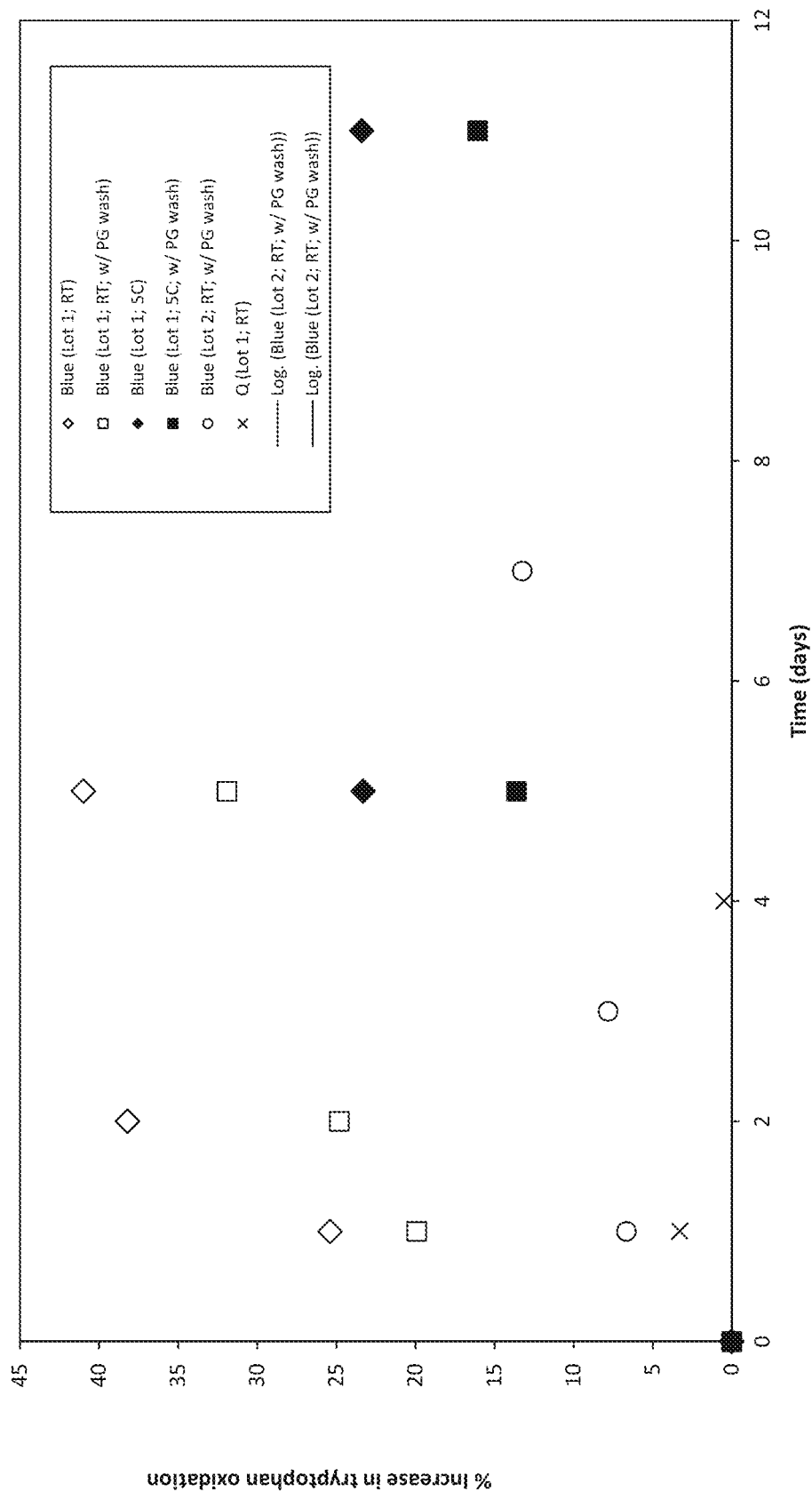
FIG. 11 depicts a summary of tryptophan oxidation over time (days) for process intermediates from Capto Blue ("Blue") and Capto Q ("Q") processes as measured by SEC-HPLC.

A successful oxidation control strategy incorporates both inhibition of oxidation as well as removal of oxidized species that form during manufacturing process. FIG. 11 shows tryptophan oxidation as a function of time for Capto Blue and Capto Q pool. For these runs, pools were nominally pH 7 to pH 8, which is typical of the operating pH for the purification process. As can be seen in FIG. 11, tryptophan oxidation (measured by SEC-HPLC) in Capto Blue pools varied with bioreactor and was reduced when a 10% propylene glycol wash was employed and also when the pool was stored at lower temperatures. Moreover, the addition of 10 mM EDTA to the Capto Blue pool also slowed the tryptophan oxidation (data not shown). As can be seen in FIG. 9, tryptophan oxidation in the Capto Q pool seems to be negligible and the Capto Q pool is quite stable even at room temperature.

Figure 12:
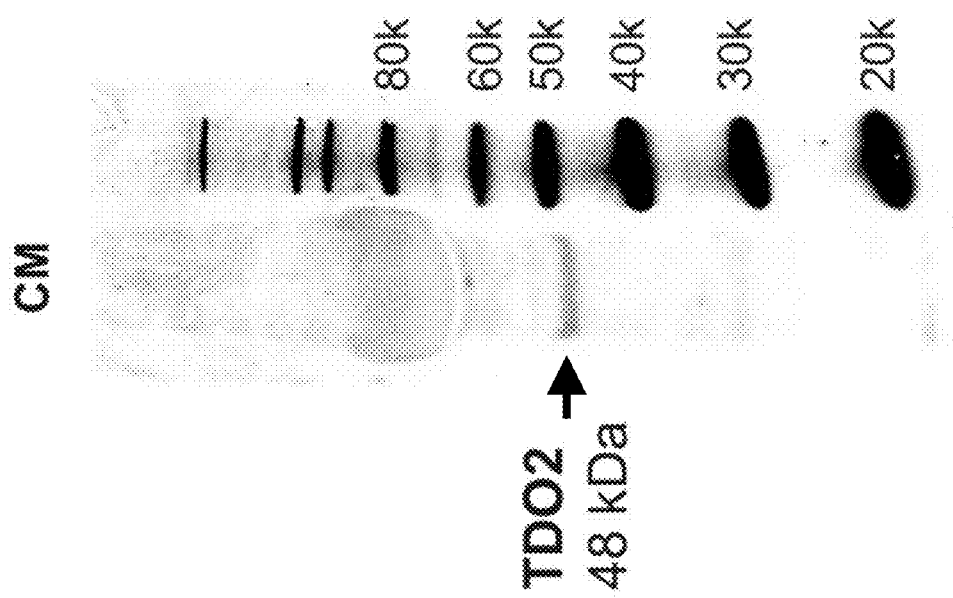
FIG. 12 shows representative HIC chromatograms for AFP-1, including Capto MMC, Butyl-S Fast Flow, Toyopearl PPG-600M, and Toyopearl Phenyl-650M.

To further study the root cause of AFP-1 tryptophan oxidation, experiments were conducted to reveal that the presence of Cibcron Blue dye and/or high salt concentrations will not cause oxidation. It was observed that AFP-1 tryptophan oxidation requires a unique combination of components found in the early process samples (condition medium or Capto Blue pool) and light exposure. One potential source of tryptophan oxidation is an enzyme, such as Tryptophan 2,3-dioxygenase (TDO2), or Tryptophan hydroxylase (TPH), both of which can oxidize tryptophan specifically. It should be noted that TDO2 has been positively identified in the CM using anti-TDO2 western blot (see FIG. 12) and may cause tryptophan oxidation of AFP-1.

Figure 13:
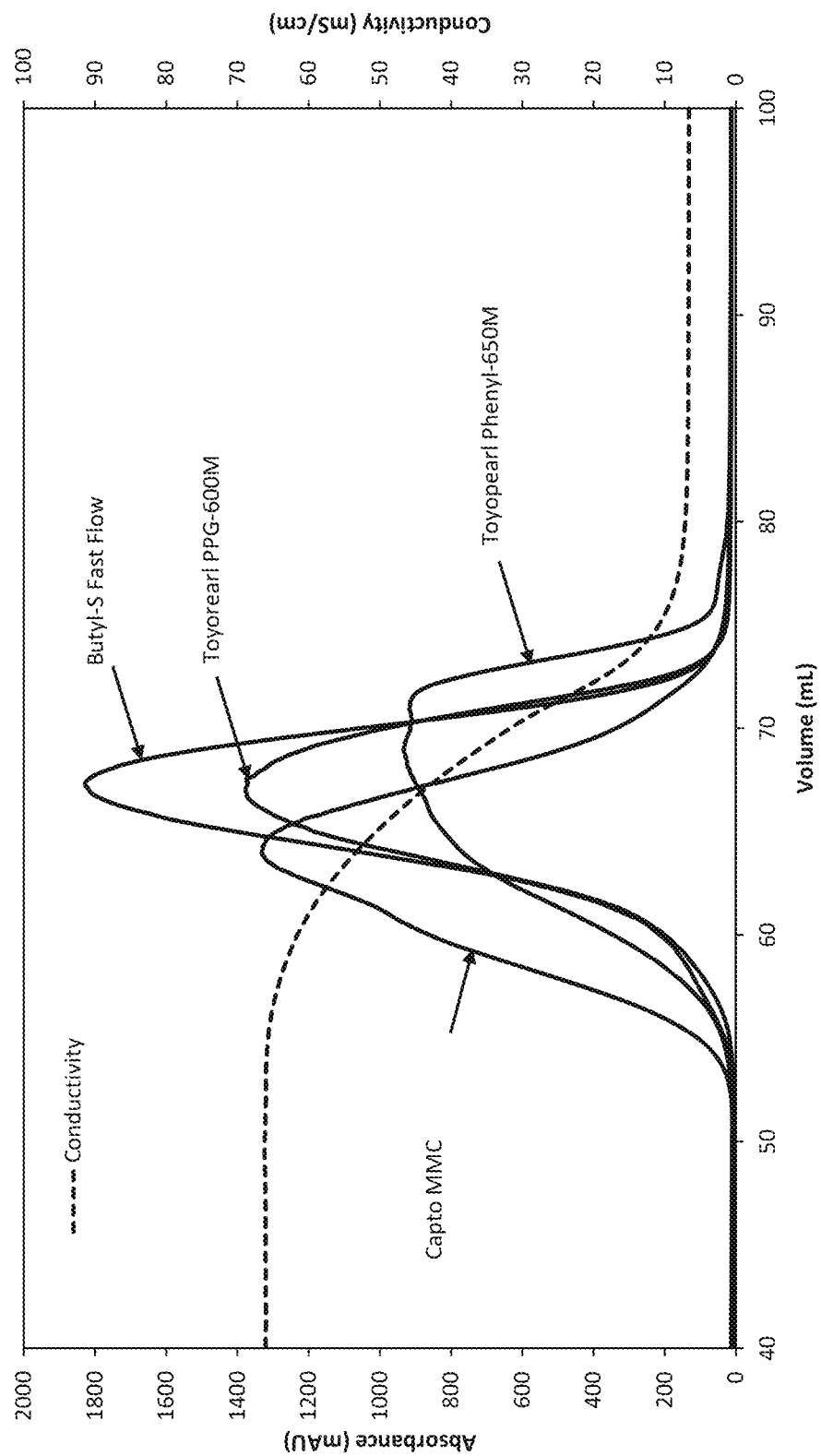
FIG. 13 shows representative HIC chromatograms for AFP-1.

Once oxidation occurs during the early process steps, the level of oxidized variant may need to be controlled later in the downstream process. For AFP-1, a hydrophobic interaction chromatography step was employed to remove excessive amounts of oxidation, including tryptophan oxidation. FIG. 13 shows representative HIC chromatograms for AFP-1. As can be seen in the figure, multiple HIC resins and a multi-modal (cation exchange/HIC) resin were investigated for the purification of AFP-1. For all resins tested, AFP-1 eluted near the center of the gradient, and was suitable for removal of tryptophan oxidation. When HIC is employed in a gradient elution for AFP-1, the oxidized product (including methionine and tryptophan oxidation) eluted earlier than native product, and is concentrated in the front of the peak. Under preparative-scale conditions the oxidized species are concentrated in the front of the peak; however, there is not enough resolution to see a distinct oxidized product peak.

Figure 14:
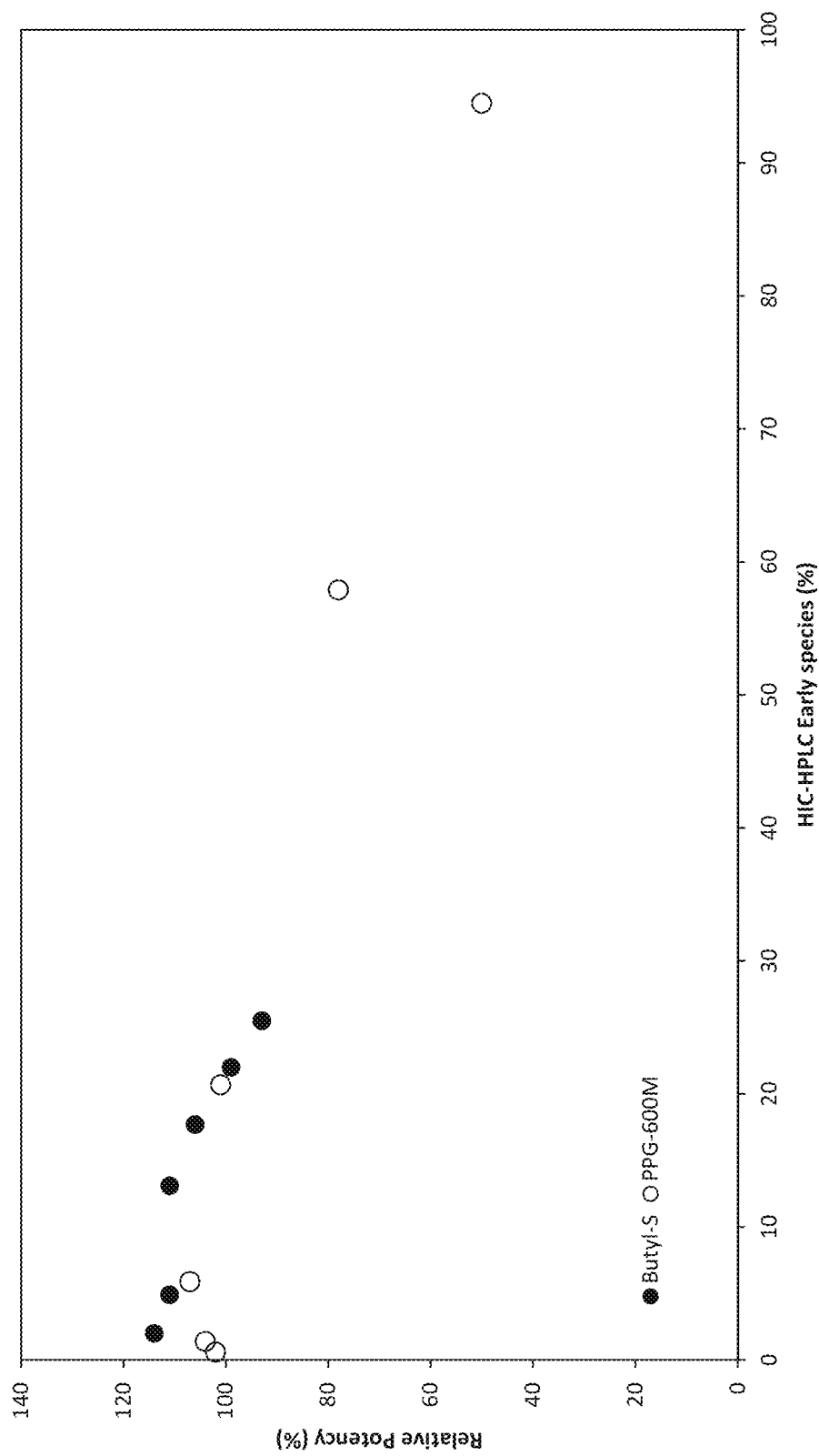
FIG. 14 shows the relative potency of purified albumin-fusion protein as a function of HIC-HPLC early species content in HIC fractions taken during Butyl-S Fast Flow (●) or PPG-600M (○) chromatography runs.

During development, both Butyl-S Fast Flow (Butyl-S) and Toyopearl PPG-600M (PPG-600M) were scaled up and operated in linear gradient mode to see if each column could be used to remove oxidized product. In each case, the elution pool was fractionated with 0.5 column volume fraction until the peak max, and then the remaining product peak was collected in a single, final fraction. In both runs, the fractions were tested for oxidized content (by HIC-HPLC) and potency. FIG. 14 shows the relative potency vs. HIC-HPLC early species content for fractions taken during Butyl-S or PPG-600M chromatography runs. In both cases, early eluting fractions (starting from the right side of the figure) contained more oxidized product (as measured by HIC-HPLC) and had lower potency than later eluting fractions (left side of the figure). Under these conditions, preparative HIC can be used to control the oxidation level, and as a result, control the potency of the product.

CONCLUSIONS

The description above outlines various approaches to purify recombinant human albumin (rHSA) and albumin-fusions proteins using scalable techniques that may be suitable for clinical or commercial manufacturing. The initial steps in the process were optimized to reduce host related impurities, such as HCP, DNA, and viruses. The Cibacron blue dye chromatography capture step included aggressive washes to reduce HCP and utilized selective elution with octanoate. Triton X-100 viral inactivation was shown to be a robust method for inactivation of enveloped viruses without impacting product quality. The AEX column and membrane chromatography steps were optimized to reduce DNA to very low levels. Interestingly, the membrane chromatography step was shown to be optimal at low pH and high salt, which was not expected prior to this work. Finally, the purification process was designed to control the level of an oxidized variant which was shown to be less potent. The control strategy included a propylene glycol wash during the Cibacron blue chromatography step as well as addition of EDTA to the elution buffer to help limit tryptophan oxidation. In addition, hydrophobic interaction chromatography was used as an effective option for removal of the oxidized product. The purification process was scaled up to purify 500 L bioreactors and was shown to be consistent in terms of yield and product quality from batch to batch.

The examples shown above illustrate various aspects of the invention and practice of the methods of the invention. These examples are not intended to provide an exhaustive description of the many different embodiments of the invention. Thus, although the invention has been described in some detail by way of illustration and example for purposes of clarity of understanding, those of ordinary skill in the art will realize readily that many changes and modifications can be made without departing from the spirit or scope of the appended claims.

All publications, patents and patent applications mentioned in this specification are herein incorporated by reference into the specification to the same extent as if each individual publication, patent or patent application was specifically and individually indicated to be incorporated herein by reference.

What is claimed is:

1. A method of isolating an albumin-fusion protein essentially free from oxidation of tryptophan residues, the process comprising subjecting a composition comprising an albumin-fusion protein to the following purification processes:
   (a) an affinity matrix chromatography process;
   (b) an anion exchange chromatography process; and
   (c) a hydrophobic interaction matrix chromatography process, wherein an elution buffer comprising octanoate is applied to the affinity matrix, and wherein oxidized tryptophan albumin-fusion protein and non-oxidized tryptophan albumin-fusion protein are eluted from the hydrophobic interaction matrix at different times, thereby separating the oxidized tryptophan albumin-fusion protein from the non-oxidized tryptophan albumin-fusion protein.

2. The method of claim 1, wherein the albumin in the albumin-fusion protein is a human serum albumin (HSA).

3. The method of claim 2, wherein the HSA is a variant HSA.

4. The method of claim 3, wherein the amino acid sequence of the variant HSA is SEQ ID NO: 133.

5. The method of claim 1, wherein the albumin-fusion protein comprises a scaffold moiety comprising a third fibronectin type III (FnIII) domain.

6. The method of claim 5, wherein the FnIII domain is derived from human Tenascin C (Tn3 scaffold).

7. The method of claim 1, wherein the albumin-fusion protein comprises a scaffold.

8. The method of claim 7, wherein the scaffold comprises a tryptophan residue.

9. The method of claim 8, wherein oxidation of the tryptophan residue reduces the activity of the albumin-fusion protein.

10. The method of claim 7, wherein the scaffold specifically binds to CD40L.

11. The method of claim 10, wherein the scaffold comprises a single CD40L-specific monomer subunit.

12. The method of claim 10, wherein the scaffold comprises two CD40L-specific monomer subunits connected in tandem.

13. The method of claim 12, wherein the two CD40L-specific monomer subunits are directly connected.

14. The method of claim 12, wherein the two CD40L-specific monomer subunits are connected by a linker.

15. The method of claim 14, wherein the linker comprises a peptide linker.

16. The method of claim 15, wherein the peptide linker comprises a $(G_m X)_n$ sequence wherein:
   (a) X is Serine (S), Alanine (A), Glycine (G), Leu (L), Isoleucine (I), or Valine (V);
   (b) m and n are integers;
   (c) m is 1, 2, 3 or 4; and
   (d) n is 1, 2, 3, 4, 5, 6, or 7.

17. The method of claim 16, wherein the peptide linker comprises SEQ ID NO: 131, SEQ ID NO: 132, SEQ ID NO: 142 or SEQ ID NO: 143.

18. The method of claim 6, wherein the Tn3 scaffold comprises a beta strand, and wherein the beta strand comprises at least one CD40L-specific monomer subunit having at least 90% sequence identity to the beta strand of SEQ ID NO: 3.

19. An albumin-fusion protein composition obtained by the method of claim 1.

* * * * *

SEQUENCE LISTING

<160> NUMBER OF SEQ ID NOS: 210

<210> SEQ ID NO 1
<211> LENGTH: 261
<212> TYPE: PRT
<213> ORGANISM: Homo sapiens

<400> SEQUENCE: 1

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260
```

<210> SEQ ID NO 2
<211> LENGTH: 149
<212> TYPE: PRT
<213> ORGANISM: Homo sapiens

<400> SEQUENCE: 2

```
Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly
            20                  25                  30

Tyr Tyr Thr Met Ser Asn Asn Leu Val Thr Leu Glu Asn Gly Lys Gln
        35                  40                  45

Leu Thr Val Lys Arg Gln Gly Leu Tyr Tyr Ile Tyr Ala Gln Val Thr
```

```
Phe Cys Ser Asn Arg Glu Ala Ser Ser Gln Ala Pro Phe Ile Ala Ser
 65                  70                  75                  80

Leu Cys Leu Lys Ser Pro Gly Arg Phe Glu Arg Ile Leu Leu Arg Ala
                 85                  90                  95

Ala Asn Thr His Ser Ser Ala Lys Pro Cys Gly Gln Gln Ser Ile His
            100                 105                 110

Leu Gly Gly Val Phe Glu Leu Gln Pro Gly Ala Ser Val Phe Val Asn
        115                 120                 125

Val Thr Asp Pro Ser Gln Val Ser His Gly Thr Gly Phe Thr Ser Phe
130                 135                 140

Gly Leu Leu Lys Leu
145
```

<210> SEQ ID NO 3
<211> LENGTH: 83
<212> TYPE: PRT
<213> ORGANISM: Artificial Sequence
<220> FEATURE:
<223> OTHER INFORMATION: synthetic construct

<400> SEQUENCE: 3

```
Ile Glu Val Lys Asp Val Thr Asp Thr Thr Ala Leu Ile Thr Trp Phe
 1               5                  10                  15

Lys Pro Leu Ala Glu Ile Asp Gly Cys Glu Leu Thr Tyr Gly Ile Lys
                 20                  25                  30

Asp Val Pro Gly Asp Arg Thr Thr Ile Asp Leu Thr Glu Asp Glu Asn
             35                  40                  45

Gln Tyr Ser Ile Gly Asn Leu Lys Pro Asp Thr Glu Tyr Glu Val Ser
     50                  55                  60

Leu Ile Cys Arg Arg Gly Asp Met Ser Ser Asn Pro Ala Lys Glu Thr
 65                  70                  75                  80

Phe Thr Thr
```

<210> SEQ ID NO 4
<211> LENGTH: 7
<212> TYPE: PRT
<213> ORGANISM: Artificial Sequence
<220> FEATURE:
<223> OTHER INFORMATION: synthetic construct

<400> SEQUENCE: 4

```
Lys Asp Val Thr Asp Thr Thr
 1               5
```

<210> SEQ ID NO 5
<211> LENGTH: 9
<212> TYPE: PRT
<213> ORGANISM: Artificial Sequence
<220> FEATURE:
<223> OTHER INFORMATION: synthetic construct

<400> SEQUENCE: 5

```
Phe Lys Pro Leu Ala Glu Ile Asp Gly
 1               5
```

<210> SEQ ID NO 6
<211> LENGTH: 7
<212> TYPE: PRT
<213> ORGANISM: Artificial Sequence
<220> FEATURE:

```
<223> OTHER INFORMATION: synthetic construct

<400> SEQUENCE: 6

Lys Asp Val Pro Gly Asp Arg
1               5

<210> SEQ ID NO 7
<211> LENGTH: 6
<212> TYPE: PRT
<213> ORGANISM: Artificial Sequence
<220> FEATURE:
<223> OTHER INFORMATION: synthetic construct

<400> SEQUENCE: 7

Thr Glu Asp Glu Asn Gln
1               5

<210> SEQ ID NO 8
<211> LENGTH: 8
<212> TYPE: PRT
<213> ORGANISM: Artificial Sequence
<220> FEATURE:
<223> OTHER INFORMATION: synthetic construct

<400> SEQUENCE: 8

Gly Asn Leu Lys Pro Asp Thr Glu
1               5

<210> SEQ ID NO 9
<211> LENGTH: 10
<212> TYPE: PRT
<213> ORGANISM: Artificial Sequence
<220> FEATURE:
<223> OTHER INFORMATION: synthetic construct

<400> SEQUENCE: 9

Arg Arg Gly Asp Met Ser Ser Asn Pro Ala
1               5                   10

<210> SEQ ID NO 10
<211> LENGTH: 10
<212> TYPE: PRT
<213> ORGANISM: Artificial Sequence
<220> FEATURE:
<223> OTHER INFORMATION: synthetic construct

<400> SEQUENCE: 10

Arg Leu Asp Ala Pro Ser Gln Ile Glu Val
1               5                   10

<210> SEQ ID NO 11
<211> LENGTH: 3
<212> TYPE: PRT
<213> ORGANISM: Artificial Sequence
<220> FEATURE:
<223> OTHER INFORMATION: synthetic construct

<400> SEQUENCE: 11

Ile Glu Val
1

<210> SEQ ID NO 12
<211> LENGTH: 5
<212> TYPE: PRT
<213> ORGANISM: Artificial Sequence
<220> FEATURE:
<223> OTHER INFORMATION: synthetic construct
```

<400> SEQUENCE: 12

Ala Leu Ile Thr Trp
1               5

<210> SEQ ID NO 13
<211> LENGTH: 7
<212> TYPE: PRT
<213> ORGANISM: Artificial Sequence
<220> FEATURE:
<223> OTHER INFORMATION: synthetic construct

<400> SEQUENCE: 13

Cys Glu Leu Ala Tyr Gly Ile
1               5

<210> SEQ ID NO 14
<211> LENGTH: 7
<212> TYPE: PRT
<213> ORGANISM: Artificial Sequence
<220> FEATURE:
<223> OTHER INFORMATION: synthetic construct

<400> SEQUENCE: 14

Cys Glu Leu Thr Tyr Gly Ile
1               5

<210> SEQ ID NO 15
<211> LENGTH: 5
<212> TYPE: PRT
<213> ORGANISM: Artificial Sequence
<220> FEATURE:
<223> OTHER INFORMATION: synthetic construct

<400> SEQUENCE: 15

Thr Thr Ile Asp Leu
1               5

<210> SEQ ID NO 16
<211> LENGTH: 3
<212> TYPE: PRT
<213> ORGANISM: Artificial Sequence
<220> FEATURE:
<223> OTHER INFORMATION: synthetic construct

<400> SEQUENCE: 16

Tyr Ser Ile
1

<210> SEQ ID NO 17
<211> LENGTH: 7
<212> TYPE: PRT
<213> ORGANISM: Artificial Sequence
<220> FEATURE:
<223> OTHER INFORMATION: synthetic construct

<400> SEQUENCE: 17

Tyr Glu Val Ser Leu Ile Cys
1               5

<210> SEQ ID NO 18
<211> LENGTH: 6
<212> TYPE: PRT
<213> ORGANISM: Artificial Sequence
<220> FEATURE:
<223> OTHER INFORMATION: synthetic construct

```
<400> SEQUENCE: 18

Lys Glu Thr Phe Thr Thr
1               5

<210> SEQ ID NO 19
<211> LENGTH: 98
<212> TYPE: PRT
<213> ORGANISM: Artificial Sequence
<220> FEATURE:
<223> OTHER INFORMATION: synthetic construct

<400> SEQUENCE: 19

Ala Ile Glu Val Lys Asp Val Thr Asp Thr Thr Ala Leu Ile Thr Trp
1               5                   10                  15

Ser Asp Glu Phe Gly His Tyr Asp Gly Cys Glu Leu Thr Tyr Gly Ile
                20                  25                  30

Lys Asp Val Pro Gly Asp Arg Thr Thr Ile Asp Leu Trp Trp His Ser
            35                  40                  45

Ala Trp Tyr Ser Ile Gly Asn Leu Lys Pro Asp Thr Glu Tyr Glu Val
    50                  55                  60

Ser Leu Ile Cys Tyr Thr Asp Gln Glu Ala Gly Asn Pro Ala Lys Glu
65                  70                  75                  80

Thr Phe Thr Thr Gly Gly Gly Thr Leu Gly His His His His His
                85                  90                  95

His His

<210> SEQ ID NO 20
<211> LENGTH: 83
<212> TYPE: PRT
<213> ORGANISM: Artificial Sequence
<220> FEATURE:
<223> OTHER INFORMATION: synthetic construct

<400> SEQUENCE: 20

Ile Glu Val Lys Asp Val Thr Asp Thr Thr Ala Leu Ile Thr Trp Ser
1               5                   10                  15

Asp Glu Phe Gly His Tyr Asp Gly Cys Glu Leu Thr Tyr Gly Ile Lys
                20                  25                  30

Asp Val Pro Gly Asp Arg Thr Thr Ile Asp Leu Trp Trp His Ser Ala
            35                  40                  45

Trp Tyr Ser Ile Gly Asn Leu Lys Pro Asp Thr Glu Tyr Glu Val Ser
    50                  55                  60

Leu Ile Cys Tyr Thr Asp Gln Glu Ala Gly Asn Pro Ala Lys Glu Thr
65                  70                  75                  80

Phe Thr Thr

<210> SEQ ID NO 21
<211> LENGTH: 98
<212> TYPE: PRT
<213> ORGANISM: Artificial Sequence
<220> FEATURE:
<223> OTHER INFORMATION: synthetic construct

<400> SEQUENCE: 21

Ala Ile Glu Val Lys Asp Val Thr Asp Thr Thr Ala Leu Ile Thr Trp
1               5                   10                  15

Ser Asp Glu Phe Gly His Tyr Asp Gly Cys Glu Leu Thr Tyr Gly Ile
                20                  25                  30

Lys Asp Val Pro Gly Asp Arg Thr Thr Ile Asp Leu Trp Trp His Ser
```

```
                    35                  40                  45
Ala Trp Tyr Ser Ile Gly Asn Leu Lys Pro Asp Thr Glu Tyr Glu Val
 50                  55                  60

Ser Leu Ile Cys Arg Arg Gly Asp Met Ser Ser Asn Pro Ala Lys Glu
 65                  70                  75                  80

Thr Phe Thr Thr Gly Gly Gly Thr Leu Gly His His His His His His
                 85                  90                  95

His His
```

```
<210> SEQ ID NO 22
<211> LENGTH: 83
<212> TYPE: PRT
<213> ORGANISM: Artificial Sequence
<220> FEATURE:
<223> OTHER INFORMATION: synthetic construct

<400> SEQUENCE: 22

Ile Glu Val Lys Asp Val Thr Asp Thr Thr Ala Leu Ile Thr Trp Ser
 1               5                  10                  15

Asp Glu Phe Gly His Tyr Asp Gly Cys Glu Leu Thr Tyr Gly Ile Lys
                20                  25                  30

Asp Val Pro Gly Asp Arg Thr Thr Ile Asp Leu Trp Trp His Ser Ala
             35                  40                  45

Trp Tyr Ser Ile Gly Asn Leu Lys Pro Asp Thr Glu Tyr Glu Val Ser
 50                  55                  60

Leu Ile Cys Arg Arg Gly Asp Met Ser Ser Asn Pro Ala Lys Glu Thr
 65                  70                  75                  80

Phe Thr Thr
```

```
<210> SEQ ID NO 23
<211> LENGTH: 98
<212> TYPE: PRT
<213> ORGANISM: Artificial Sequence
<220> FEATURE:
<223> OTHER INFORMATION: synthetic construct

<400> SEQUENCE: 23

Ala Ile Glu Val Lys Asp Val Thr Asp Thr Thr Ala Leu Ile Thr Trp
 1               5                  10                  15

Ser Asp Asp Phe Asp Asn Tyr Glu Trp Cys Glu Leu Thr Tyr Gly Ile
                20                  25                  30

Lys Asp Val Pro Gly Asp Arg Thr Thr Ile Asp Leu Trp Tyr His Met
             35                  40                  45

Ala Trp Tyr Ser Ile Gly Asn Leu Lys Pro Asp Thr Glu Tyr Glu Val
 50                  55                  60

Ser Leu Ile Cys Arg Arg Gly Asp Met Ser Ser Asn Pro Ala Lys Glu
 65                  70                  75                  80

Thr Phe Thr Thr Gly Gly Gly Thr Leu Gly His His His His His His
                 85                  90                  95

His His
```

```
<210> SEQ ID NO 24
<211> LENGTH: 83
<212> TYPE: PRT
<213> ORGANISM: Artificial Sequence
<220> FEATURE:
<223> OTHER INFORMATION: synthetic construct

<400> SEQUENCE: 24
```

```
Ile Glu Val Lys Asp Val Thr Asp Thr Thr Ala Leu Ile Thr Trp Ser
1               5                   10                  15

Asp Asp Phe Asp Asn Tyr Glu Trp Cys Glu Leu Thr Tyr Gly Ile Lys
                20                  25                  30

Asp Val Pro Gly Asp Arg Thr Thr Ile Asp Leu Trp Tyr His Met Ala
            35                  40                  45

Trp Tyr Ser Ile Gly Asn Leu Lys Pro Asp Thr Glu Tyr Glu Val Ser
        50                  55                  60

Leu Ile Cys Arg Arg Gly Asp Met Ser Ser Asn Pro Ala Lys Glu Thr
65                  70                  75                  80

Phe Thr Thr
```

<210> SEQ ID NO 25
<211> LENGTH: 98
<212> TYPE: PRT
<213> ORGANISM: Artificial Sequence
<220> FEATURE:
<223> OTHER INFORMATION: synthetic construct

<400> SEQUENCE: 25

```
Ala Ile Glu Val Lys Asp Val Thr Asp Thr Thr Ala Leu Ile Thr Trp
1               5                   10                  15

Ser Asp Asp Phe Ala Asp Tyr Val Trp Cys Glu Leu Thr Tyr Gly Ile
                20                  25                  30

Lys Asp Val Pro Gly Asp Arg Thr Thr Ile Asp Leu Trp Trp His Ser
            35                  40                  45

Ala Trp Tyr Ser Ile Gly Asn Leu Lys Pro Asp Thr Glu Tyr Glu Val
        50                  55                  60

Ser Leu Ile Cys Arg Arg Gly Asp Met Ser Ser Asn Pro Ala Lys Glu
65                  70                  75                  80

Thr Phe Thr Thr Gly Gly Gly Thr Leu Gly His His His His His
                85                  90                  95

His His
```

<210> SEQ ID NO 26
<211> LENGTH: 83
<212> TYPE: PRT
<213> ORGANISM: Artificial Sequence
<220> FEATURE:
<223> OTHER INFORMATION: synthetic construct

<400> SEQUENCE: 26

```
Ile Glu Val Lys Asp Val Thr Asp Thr Thr Ala Leu Ile Thr Trp Ser
1               5                   10                  15

Asp Asp Phe Ala Asp Tyr Val Trp Cys Glu Leu Thr Tyr Gly Ile Lys
                20                  25                  30

Asp Val Pro Gly Asp Arg Thr Thr Ile Asp Leu Trp Trp His Ser Ala
            35                  40                  45

Trp Tyr Ser Ile Gly Asn Leu Lys Pro Asp Thr Glu Tyr Glu Val Ser
        50                  55                  60

Leu Ile Cys Arg Arg Gly Asp Met Ser Ser Asn Pro Ala Lys Glu Thr
65                  70                  75                  80

Phe Thr Thr
```

<210> SEQ ID NO 27
<211> LENGTH: 98
<212> TYPE: PRT

<213> ORGANISM: Artificial Sequence
<220> FEATURE:
<223> OTHER INFORMATION: synthetic construct

<400> SEQUENCE: 27

Ala Ile Glu Val Lys Asp Val Thr Asp Thr Thr Ala Leu Ile Thr Trp
1               5                   10                  15

Ser Asp Asp Phe Gly Glu Tyr Val Trp Cys Glu Leu Thr Tyr Gly Ile
                20                  25                  30

Lys Asp Val Pro Gly Asp Arg Thr Thr Ile Asp Leu Trp Tyr His His
            35                  40                  45

Ala His Tyr Ser Ile Gly Asn Leu Lys Pro Asp Thr Glu Tyr Glu Val
        50                  55                  60

Ser Leu Ile Cys Arg Arg Gly Asp Met Ser Ser Asn Pro Ala Lys Glu
65                  70                  75                  80

Thr Phe Thr Thr Gly Gly Gly Thr Leu Gly His His His His His
                85                  90                  95

His His

<210> SEQ ID NO 28
<211> LENGTH: 83
<212> TYPE: PRT
<213> ORGANISM: Artificial Sequence
<220> FEATURE:
<223> OTHER INFORMATION: synthetic construct

<400> SEQUENCE: 28

Ile Glu Val Lys Asp Val Thr Asp Thr Thr Ala Leu Ile Thr Trp Ser
1               5                   10                  15

Asp Asp Phe Gly Glu Tyr Val Trp Cys Glu Leu Thr Tyr Gly Ile Lys
                20                  25                  30

Asp Val Pro Gly Asp Arg Thr Thr Ile Asp Leu Trp Tyr His His Ala
            35                  40                  45

His Tyr Ser Ile Gly Asn Leu Lys Pro Asp Thr Glu Tyr Glu Val Ser
        50                  55                  60

Leu Ile Cys Arg Arg Gly Asp Met Ser Ser Asn Pro Ala Lys Glu Thr
65                  70                  75                  80

Phe Thr Thr

<210> SEQ ID NO 29
<211> LENGTH: 98
<212> TYPE: PRT
<213> ORGANISM: Artificial Sequence
<220> FEATURE:
<223> OTHER INFORMATION: synthetic construct

<400> SEQUENCE: 29

Ala Ile Glu Val Lys Asp Val Thr Asp Thr Thr Ala Leu Ile Thr Trp
1               5                   10                  15

Leu Asp Asp Trp Gly Ser Tyr His Val Cys Glu Leu Thr Tyr Gly Ile
                20                  25                  30

Lys Asp Val Pro Gly Asp Arg Thr Thr Ile Asp Leu Trp Tyr His Gln
            35                  40                  45

Ala Trp Tyr Ser Ile Gly Asn Leu Lys Pro Asp Thr Glu Tyr Glu Val
        50                  55                  60

Ser Leu Ile Cys Arg Arg Gly Asp Met Ser Ser Asn Pro Ala Lys Glu
65                  70                  75                  80

Thr Phe Thr Thr Gly Gly Gly Thr Leu Gly His His His His His His

```
                85                  90                  95

His His

<210> SEQ ID NO 30
<211> LENGTH: 83
<212> TYPE: PRT
<213> ORGANISM: Artificial Sequence
<220> FEATURE:
<223> OTHER INFORMATION: synthetic construct

<400> SEQUENCE: 30

Ile Glu Val Lys Asp Val Thr Asp Thr Thr Ala Leu Ile Thr Trp Leu
1               5                   10                  15

Asp Asp Trp Gly Ser Tyr His Val Cys Glu Leu Thr Tyr Gly Ile Lys
            20                  25                  30

Asp Val Pro Gly Asp Arg Thr Thr Ile Asp Leu Trp Tyr His Gln Ala
        35                  40                  45

Trp Tyr Ser Ile Gly Asn Leu Lys Pro Asp Thr Glu Tyr Glu Val Ser
    50                  55                  60

Leu Ile Cys Arg Arg Gly Asp Met Ser Ser Asn Pro Ala Lys Glu Thr
65                  70                  75                  80

Phe Thr Thr

<210> SEQ ID NO 31
<211> LENGTH: 98
<212> TYPE: PRT
<213> ORGANISM: Artificial Sequence
<220> FEATURE:
<223> OTHER INFORMATION: synthetic construct

<400> SEQUENCE: 31

Ala Ile Glu Val Lys Asp Val Thr Asp Thr Thr Ala Leu Ile Thr Trp
1               5                   10                  15

Ser Asp Glu Val Gly Asp Tyr Val Val Cys Glu Leu Thr Tyr Gly Ile
            20                  25                  30

Lys Asp Val Pro Gly Asp Arg Thr Thr Ile Asp Leu Trp Tyr His Met
        35                  40                  45

Ala Trp Tyr Ser Ile Gly Asn Leu Lys Pro Asp Thr Glu Tyr Glu Val
    50                  55                  60

Ser Leu Ile Cys Arg Arg Gly Asp Met Ser Ser Asn Pro Ala Lys Glu
65                  70                  75                  80

Thr Phe Thr Thr Gly Gly Gly Thr Leu Gly His His His His His His
                85                  90                  95

His His

<210> SEQ ID NO 32
<211> LENGTH: 83
<212> TYPE: PRT
<213> ORGANISM: Artificial Sequence
<220> FEATURE:
<223> OTHER INFORMATION: synthetic construct

<400> SEQUENCE: 32

Ile Glu Val Lys Asp Val Thr Asp Thr Thr Ala Leu Ile Thr Trp Ser
1               5                   10                  15

Asp Glu Val Gly Asp Tyr Val Val Cys Glu Leu Thr Tyr Gly Ile Lys
            20                  25                  30

Asp Val Pro Gly Asp Arg Thr Thr Ile Asp Leu Trp Tyr His Met Ala
        35                  40                  45
```

```
Trp Tyr Ser Ile Gly Asn Leu Lys Pro Asp Thr Glu Tyr Glu Val Ser
         50                  55                  60

Leu Ile Cys Arg Arg Gly Asp Met Ser Ser Asn Pro Ala Lys Glu Thr
 65                  70                  75                  80

Phe Thr Thr

<210> SEQ ID NO 33
<211> LENGTH: 98
<212> TYPE: PRT
<213> ORGANISM: Artificial Sequence
<220> FEATURE:
<223> OTHER INFORMATION: synthetic construct

<400> SEQUENCE: 33

Ala Ile Glu Val Lys Asp Val Thr Asp Thr Thr Ala Leu Ile Thr Trp
 1               5                  10                  15

Ser Asp Asp Phe Ala Glu Tyr Val Gly Cys Glu Leu Thr Tyr Gly Ile
                 20                  25                  30

Lys Asp Val Pro Gly Asp Arg Thr Thr Ile Asp Leu Trp Trp His Ser
             35                  40                  45

Ala Trp Tyr Ser Ile Gly Asn Leu Lys Pro Asp Thr Glu Tyr Glu Val
         50                  55                  60

Ser Leu Ile Cys Arg Arg Gly Asp Met Ser Ser Asn Pro Ala Lys Glu
 65                  70                  75                  80

Thr Phe Thr Thr Gly Gly Gly Thr Leu Gly His His His His His His
                 85                  90                  95

His His

<210> SEQ ID NO 34
<211> LENGTH: 83
<212> TYPE: PRT
<213> ORGANISM: Artificial Sequence
<220> FEATURE:
<223> OTHER INFORMATION: synthetic construct

<400> SEQUENCE: 34

Ile Glu Val Lys Asp Val Thr Asp Thr Thr Ala Leu Ile Thr Trp Ser
 1               5                  10                  15

Asp Asp Phe Ala Glu Tyr Val Gly Cys Glu Leu Thr Tyr Gly Ile Lys
                 20                  25                  30

Asp Val Pro Gly Asp Arg Thr Thr Ile Asp Leu Trp Trp His Ser Ala
             35                  40                  45

Trp Tyr Ser Ile Gly Asn Leu Lys Pro Asp Thr Glu Tyr Glu Val Ser
         50                  55                  60

Leu Ile Cys Arg Arg Gly Asp Met Ser Ser Asn Pro Ala Lys Glu Thr
 65                  70                  75                  80

Phe Thr Thr

<210> SEQ ID NO 35
<211> LENGTH: 98
<212> TYPE: PRT
<213> ORGANISM: Artificial Sequence
<220> FEATURE:
<223> OTHER INFORMATION: synthetic construct

<400> SEQUENCE: 35

Ala Ile Glu Val Lys Asp Val Thr Asp Thr Thr Ala Leu Ile Thr Trp
 1               5                  10                  15
```

Ser Asp Asp Phe Glu Glu Tyr Val Val Cys Glu Leu Thr Tyr Gly Ile
            20                  25                  30

Lys Asp Val Pro Gly Asp Arg Thr Thr Ile Asp Leu Trp Trp His Ser
            35                  40                  45

Ala Trp Tyr Ser Ile Gly Asn Leu Lys Pro Asp Thr Glu Tyr Glu Val
50                  55                  60

Ser Leu Ile Cys Arg Arg Gly Asp Met Ser Ser Asn Pro Ala Lys Glu
65                  70                  75                  80

Thr Phe Thr Thr Gly Gly Gly Thr Leu Gly His His His His His
            85                  90                  95

His His

<210> SEQ ID NO 36
<211> LENGTH: 83
<212> TYPE: PRT
<213> ORGANISM: Artificial Sequence
<220> FEATURE:
<223> OTHER INFORMATION: synthetic construct

<400> SEQUENCE: 36

Ile Glu Val Lys Asp Val Thr Asp Thr Thr Ala Leu Ile Thr Trp Ser
1               5                   10                  15

Asp Asp Phe Glu Glu Tyr Val Val Cys Glu Leu Thr Tyr Gly Ile Lys
            20                  25                  30

Asp Val Pro Gly Asp Arg Thr Thr Ile Asp Leu Trp Trp His Ser Ala
            35                  40                  45

Trp Tyr Ser Ile Gly Asn Leu Lys Pro Asp Thr Glu Tyr Glu Val Ser
    50                  55                  60

Leu Ile Cys Arg Arg Gly Asp Met Ser Ser Asn Pro Ala Lys Glu Thr
65                  70                  75                  80

Phe Thr Thr

<210> SEQ ID NO 37
<211> LENGTH: 98
<212> TYPE: PRT
<213> ORGANISM: Artificial Sequence
<220> FEATURE:
<223> OTHER INFORMATION: synthetic construct

<400> SEQUENCE: 37

Ala Ile Glu Val Lys Asp Val Thr Asp Thr Thr Ala Leu Ile Thr Trp
1               5                   10                  15

Ser Asp Gly Val Gly Gln Tyr Val Gly Cys Glu Leu Thr Tyr Gly Ile
            20                  25                  30

Lys Asp Val Pro Gly Asp Arg Thr Thr Ile Asp Leu Trp Tyr His Met
            35                  40                  45

Ala Trp Tyr Ser Ile Gly Asn Leu Lys Pro Asp Thr Glu Tyr Glu Val
50                  55                  60

Ser Leu Ile Cys Arg Arg Gly Asp Met Ser Ser Asn Pro Ala Lys Glu
65                  70                  75                  80

Thr Phe Thr Thr Gly Gly Gly Thr Leu Gly His His His His His
            85                  90                  95

His His

<210> SEQ ID NO 38
<211> LENGTH: 83
<212> TYPE: PRT
<213> ORGANISM: Artificial Sequence

```
<220> FEATURE:
<223> OTHER INFORMATION: synthetic construct

<400> SEQUENCE: 38

Ile Glu Val Lys Asp Val Thr Asp Thr Thr Ala Leu Ile Thr Trp Ser
1               5                   10                  15

Asp Glu Val Gly Gln Tyr Val Gly Cys Glu Leu Thr Tyr Gly Ile Lys
            20                  25                  30

Asp Val Pro Gly Asp Arg Thr Thr Ile Asp Leu Trp Tyr His Met Ala
        35                  40                  45

Trp Tyr Ser Ile Gly Asn Leu Lys Pro Asp Thr Glu Tyr Glu Val Ser
    50                  55                  60

Leu Ile Cys Arg Arg Gly Asp Met Ser Ser Asn Pro Ala Lys Glu Thr
65                  70                  75                  80

Phe Thr Thr

<210> SEQ ID NO 39
<211> LENGTH: 98
<212> TYPE: PRT
<213> ORGANISM: Artificial Sequence
<220> FEATURE:
<223> OTHER INFORMATION: synthetic construct

<400> SEQUENCE: 39

Ala Ile Glu Val Lys Asp Val Thr Asp Thr Thr Ala Leu Ile Thr Trp
1               5                   10                  15

Ser Asp Asp Ile Gly Leu Tyr Val Trp Cys Glu Leu Thr Tyr Gly Ile
            20                  25                  30

Lys Asp Val Pro Gly Asp Arg Thr Thr Ile Asp Leu Trp Phe His Gln
        35                  40                  45

Ala Trp Tyr Ser Ile Gly Asn Leu Lys Pro Asp Thr Glu Tyr Glu Val
    50                  55                  60

Ser Leu Ile Cys Arg Arg Gly Asp Met Ser Ser Asn Pro Ala Lys Glu
65                  70                  75                  80

Thr Phe Thr Thr Gly Gly Gly Thr Leu Gly His His His His His
                85                  90                  95

His His

<210> SEQ ID NO 40
<211> LENGTH: 83
<212> TYPE: PRT
<213> ORGANISM: Artificial Sequence
<220> FEATURE:
<223> OTHER INFORMATION: synthetic construct

<400> SEQUENCE: 40

Ile Glu Val Lys Asp Val Thr Asp Thr Thr Ala Leu Ile Thr Trp Ser
1               5                   10                  15

Asp Asp Ile Gly Leu Tyr Val Trp Cys Glu Leu Thr Tyr Gly Ile Lys
            20                  25                  30

Asp Val Pro Gly Asp Arg Thr Thr Ile Asp Leu Trp Phe His Gln Ala
        35                  40                  45

Trp Tyr Ser Ile Gly Asn Leu Lys Pro Asp Thr Glu Tyr Glu Val Ser
    50                  55                  60

Leu Ile Cys Arg Arg Gly Asp Met Ser Ser Asn Pro Ala Lys Glu Thr
65                  70                  75                  80

Phe Thr Thr
```

<210> SEQ ID NO 41
<211> LENGTH: 98
<212> TYPE: PRT
<213> ORGANISM: Artificial Sequence
<220> FEATURE:
<223> OTHER INFORMATION: synthetic construct

<400> SEQUENCE: 41

```
Ala Ile Glu Val Lys Asp Val Thr Asp Thr Thr Ala Leu Ile Thr Trp
1               5                   10                  15

Ser Asp Glu His Ala Glu Phe Ile Gly Cys Glu Leu Thr Tyr Gly Ile
                20                  25                  30

Lys Asp Val Pro Gly Asp Arg Thr Thr Ile Asp Leu Trp Trp His Ser
            35                  40                  45

Ala Trp Tyr Ser Ile Gly Asn Leu Lys Pro Asp Thr Glu Tyr Glu Val
        50                  55                  60

Ser Leu Ile Cys Arg Arg Gly Asp Met Ser Ser Asn Pro Ala Lys Glu
65                  70                  75                  80

Thr Phe Thr Thr Gly Gly Gly Thr Leu Gly His His His His His His
                85                  90                  95

His His
```

<210> SEQ ID NO 42
<211> LENGTH: 83
<212> TYPE: PRT
<213> ORGANISM: Artificial Sequence
<220> FEATURE:
<223> OTHER INFORMATION: synthetic construct

<400> SEQUENCE: 42

```
Ile Glu Val Lys Asp Val Thr Asp Thr Thr Ala Leu Ile Thr Trp Ser
1               5                   10                  15

Asp Glu His Ala Glu Phe Ile Gly Cys Glu Leu Thr Tyr Gly Ile Lys
                20                  25                  30

Asp Val Pro Gly Asp Arg Thr Thr Ile Asp Leu Trp Trp His Ser Ala
            35                  40                  45

Trp Tyr Ser Ile Gly Asn Leu Lys Pro Asp Thr Glu Tyr Glu Val Ser
        50                  55                  60

Leu Ile Cys Arg Arg Gly Asp Met Ser Ser Asn Pro Ala Lys Glu Thr
65                  70                  75                  80

Phe Thr Thr
```

<210> SEQ ID NO 43
<211> LENGTH: 101
<212> TYPE: PRT
<213> ORGANISM: Artificial Sequence
<220> FEATURE:
<223> OTHER INFORMATION: synthetic construct

<400> SEQUENCE: 43

```
Ala Ile Glu Val Lys Asp Val Thr Asp Thr Thr Ala Leu Ile Thr Trp
1               5                   10                  15

Thr Asn Arg Ser Ser Tyr Tyr Asn Leu His Gly Cys Glu Leu Thr Tyr
                20                  25                  30

Gly Ile Lys Asp Val Pro Gly Asp Arg Thr Thr Ile Asp Leu Ser Ser
            35                  40                  45

Pro Tyr Val His Tyr Ser Ile Gly Asn Leu Lys Pro Asp Thr Glu Tyr
        50                  55                  60
```

```
Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                85                  90                  95

His His His His His
            100

<210> SEQ ID NO 44
<211> LENGTH: 86
<212> TYPE: PRT
<213> ORGANISM: Artificial Sequence
<220> FEATURE:
<223> OTHER INFORMATION: synthetic construct

<400> SEQUENCE: 44

Ile Glu Val Lys Asp Val Thr Asp Thr Thr Ala Leu Ile Thr Trp Thr
1               5                   10                  15

Asn Arg Ser Ser Tyr Tyr Asn Leu His Gly Cys Glu Leu Thr Tyr Gly
                20                  25                  30

Ile Lys Asp Val Pro Gly Asp Arg Thr Thr Ile Asp Leu Ser Ser Pro
            35                  40                  45

Tyr Val His Tyr Ser Ile Gly Asn Leu Lys Pro Asp Thr Glu Tyr Glu
        50                  55                  60

Val Ser Leu Ile Cys Leu Thr Thr Asp Gly Thr Tyr Ser Asn Pro Ala
65                  70                  75                  80

Lys Glu Thr Phe Thr Thr
                85

<210> SEQ ID NO 45
<211> LENGTH: 101
<212> TYPE: PRT
<213> ORGANISM: Artificial Sequence
<220> FEATURE:
<223> OTHER INFORMATION: synthetic construct

<400> SEQUENCE: 45

Ala Ile Glu Val Glu Asp Val Thr Asp Thr Thr Ala Leu Ile Thr Trp
1               5                   10                  15

Thr Asn Arg Ser Ser Tyr Tyr Asn Leu His Gly Cys Glu Leu Thr Tyr
                20                  25                  30

Gly Ile Lys Asp Val Pro Gly Asp Arg Thr Thr Ile Asp Leu Ser Ser
            35                  40                  45

Pro Tyr Val His Tyr Ser Ile Gly Asn Leu Lys Pro Asp Thr Glu Tyr
        50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                85                  90                  95

His His His His His
            100

<210> SEQ ID NO 46
<211> LENGTH: 86
<212> TYPE: PRT
<213> ORGANISM: Artificial Sequence
<220> FEATURE:
<223> OTHER INFORMATION: synthetic construct

<400> SEQUENCE: 46

Ile Glu Val Glu Asp Val Thr Asp Thr Thr Ala Leu Ile Thr Trp Thr
```

```
1               5                   10                  15
Asn Arg Ser Ser Tyr Tyr Asn Leu His Gly Cys Glu Leu Thr Tyr Gly
                20                  25                  30

Ile Lys Asp Val Pro Gly Asp Arg Thr Thr Ile Asp Leu Ser Ser Pro
                35                  40                  45

Tyr Val His Tyr Ser Ile Gly Asn Leu Lys Pro Asp Thr Glu Tyr Glu
                50                  55                  60

Val Ser Leu Ile Cys Leu Thr Thr Asp Gly Thr Tyr Ser Asn Pro Ala
65                  70                  75                  80

Lys Glu Thr Phe Thr Thr
                85

<210> SEQ ID NO 47
<211> LENGTH: 101
<212> TYPE: PRT
<213> ORGANISM: Artificial Sequence
<220> FEATURE:
<223> OTHER INFORMATION: synthetic construct

<400> SEQUENCE: 47

Ala Ile Glu Val Glu Asp Val Thr Asp Thr Thr Ala Leu Ile Thr Trp
1               5                   10                  15

Ile Asn Arg Ser Tyr Tyr Ala Asp Leu His Gly Cys Glu Leu Thr Tyr
                20                  25                  30

Gly Ile Lys Asp Val Pro Gly Asp Arg Thr Thr Ile Asp Leu Asp Gln
                35                  40                  45

Ile Tyr Val His Tyr Ser Ile Gly Asn Leu Lys Pro Asp Thr Lys Tyr
                50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                85                  90                  95

His His His His His
                100

<210> SEQ ID NO 48
<211> LENGTH: 86
<212> TYPE: PRT
<213> ORGANISM: Artificial Sequence
<220> FEATURE:
<223> OTHER INFORMATION: synthetic construct

<400> SEQUENCE: 48

Ile Glu Val Glu Asp Val Thr Asp Thr Thr Ala Leu Ile Thr Trp Ile
1               5                   10                  15

Asn Arg Ser Tyr Tyr Ala Asp Leu His Gly Cys Glu Leu Thr Tyr Gly
                20                  25                  30

Ile Lys Asp Val Pro Gly Asp Arg Thr Thr Ile Asp Leu Asp Gln Ile
                35                  40                  45

Tyr Val His Tyr Ser Ile Gly Asn Leu Lys Pro Asp Thr Lys Tyr Glu
                50                  55                  60

Val Ser Leu Ile Cys Leu Thr Thr Asp Gly Thr Tyr Ser Asn Pro Ala
65                  70                  75                  80

Lys Glu Thr Phe Thr Thr
                85

<210> SEQ ID NO 49
<211> LENGTH: 102
```

```
<212> TYPE: PRT
<213> ORGANISM: Artificial Sequence
<220> FEATURE:
<223> OTHER INFORMATION: synthetic construct

<400> SEQUENCE: 49

Ala Ile Glu Val Glu Asp Val Thr Asp Thr Thr Ala Leu Ile Thr Trp
1               5                   10                  15

Thr Asn Arg Ser Ser Tyr Ser His Leu Asp Gly Cys Glu Leu Thr Tyr
                20                  25                  30

Gly Ile Lys Asp Val Pro Gly Asp Arg Thr Thr Ile Asp Leu Ser Ala
            35                  40                  45

Ala Ile Tyr Val His Tyr Ser Ile Gly Asn Leu Lys Pro Asp Thr Glu
        50                  55                  60

Tyr Glu Val Ser Leu Ile Cys Leu Thr Thr Asp Gly Thr Tyr Ser Asn
65                  70                  75                  80

Pro Ala Lys Glu Thr Phe Thr Thr Gly Gly Gly Thr Leu Gly His His
                85                  90                  95

His His His His His His
            100

<210> SEQ ID NO 50
<211> LENGTH: 87
<212> TYPE: PRT
<213> ORGANISM: Artificial Sequence
<220> FEATURE:
<223> OTHER INFORMATION: synthetic construct

<400> SEQUENCE: 50

Ile Glu Val Glu Asp Val Thr Asp Thr Thr Ala Leu Ile Thr Trp Thr
1               5                   10                  15

Asn Arg Ser Ser Tyr Ser His Leu Asp Gly Cys Glu Leu Thr Tyr Gly
                20                  25                  30

Ile Lys Asp Val Pro Gly Asp Arg Thr Thr Ile Asp Leu Ser Ala Ala
            35                  40                  45

Ile Tyr Val His Tyr Ser Ile Gly Asn Leu Lys Pro Asp Thr Glu Tyr
        50                  55                  60

Glu Val Ser Leu Ile Cys Leu Thr Thr Asp Gly Thr Tyr Ser Asn Pro
65                  70                  75                  80

Ala Lys Glu Thr Phe Thr Thr
                85

<210> SEQ ID NO 51
<211> LENGTH: 101
<212> TYPE: PRT
<213> ORGANISM: Artificial Sequence
<220> FEATURE:
<223> OTHER INFORMATION: synthetic construct

<400> SEQUENCE: 51

Ala Ile Glu Val Glu Asp Val Thr Asp Thr Thr Ala Leu Ile Thr Trp
1               5                   10                  15

Ile Asn Arg Ser Ser Tyr His Asn Phe Pro His Cys Glu Leu Ala Tyr
                20                  25                  30

Gly Ile Lys Asp Val Pro Gly Asp Arg Thr Thr Ile Asp Leu Asn Ser
            35                  40                  45

Pro Tyr Val His Tyr Ser Ile Gly Asn Leu Lys Pro Asp Thr Glu Tyr
        50                  55                  60

Glu Val Ser Leu Ile Cys Leu Thr Thr Asp Gly Thr Tyr Ser Asn Pro
```

```
                65                  70                  75                  80
Ala Lys Glu Thr Phe Thr Thr Gly Gly Gly Thr Leu Gly His His His
                    85                  90                  95

His His His His His
            100

<210> SEQ ID NO 52
<211> LENGTH: 86
<212> TYPE: PRT
<213> ORGANISM: Artificial Sequence
<220> FEATURE:
<223> OTHER INFORMATION: synthetic construct

<400> SEQUENCE: 52

Ile Glu Val Glu Asp Val Thr Asp Thr Thr Ala Leu Ile Thr Trp Ile
1               5                   10                  15

Asn Arg Ser Ser Tyr His Asn Phe Pro His Cys Glu Leu Ala Tyr Gly
            20                  25                  30

Ile Lys Asp Val Pro Gly Asp Arg Thr Thr Ile Asp Leu Asn Ser Pro
        35                  40                  45

Tyr Val His Tyr Ser Ile Gly Asn Leu Lys Pro Asp Thr Glu Tyr Glu
    50                  55                  60

Val Ser Leu Ile Cys Leu Thr Thr Asp Gly Thr Tyr Ser Asn Pro Ala
65                  70                  75                  80

Lys Glu Thr Phe Thr Thr
                85

<210> SEQ ID NO 53
<211> LENGTH: 101
<212> TYPE: PRT
<213> ORGANISM: Artificial Sequence
<220> FEATURE:
<223> OTHER INFORMATION: synthetic construct

<400> SEQUENCE: 53

Ala Ile Glu Val Glu Asp Val Thr Asp Thr Thr Ala Leu Ile Thr Trp
1               5                   10                  15

Thr Asn Arg Ser Ser Tyr Ser Asn His Leu Gly Cys Glu Leu Ala Tyr
            20                  25                  30

Gly Ile Lys Asp Val Pro Gly Asp Arg Thr Thr Ile Asp Leu Asn Asn
        35                  40                  45

Ile Tyr Val His Tyr Ser Ile Gly Asn Leu Lys Pro Asp Thr Glu Tyr
    50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                    85                  90                  95

His His His His His
            100

<210> SEQ ID NO 54
<211> LENGTH: 86
<212> TYPE: PRT
<213> ORGANISM: Artificial Sequence
<220> FEATURE:
<223> OTHER INFORMATION: synthetic construct

<400> SEQUENCE: 54

Ile Glu Val Glu Asp Val Thr Asp Thr Thr Ala Leu Ile Thr Trp Thr
1               5                   10                  15
```

```
Asn Arg Ser Ser Tyr Ser Asn His Leu Gly Cys Glu Leu Ala Tyr Gly
                20                  25                  30

Ile Lys Asp Val Pro Gly Asp Arg Thr Thr Ile Asp Leu Asn Asn Ile
            35                  40                  45

Tyr Val His Tyr Ser Ile Gly Asn Leu Lys Pro Asp Thr Glu Tyr Glu
        50                  55                  60

Val Ser Leu Ile Cys Leu Thr Thr Asp Gly Tyr Ser Asn Pro Ala
 65                 70                  75                  80

Lys Glu Thr Phe Thr Thr
                    85
```

<210> SEQ ID NO 55
<211> LENGTH: 101
<212> TYPE: PRT
<213> ORGANISM: Artificial Sequence
<220> FEATURE:
<223> OTHER INFORMATION: synthetic construct

<400> SEQUENCE: 55

```
Ala Ile Glu Val Glu Asp Val Thr Asp Thr Thr Ala Leu Ile Thr Trp
 1               5                  10                  15

Thr Asn Arg Ser Ser Tyr Ser Asn Phe His Gly Cys Glu Leu Ala Tyr
                20                  25                  30

Gly Ile Lys Asp Val Pro Gly Asp Arg Thr Thr Ile Asp Leu Asn Ser
            35                  40                  45

Pro Tyr Val His Tyr Ser Ile Gly Asn Leu Lys Pro Asp Thr Glu Tyr
        50                  55                  60

Glu Val Ser Leu Ile Cys Leu Thr Thr Asp Gly Thr Tyr Ser Asn Pro
 65                 70                  75                  80

Ala Lys Glu Thr Phe Thr Thr Gly Gly Gly Thr Leu Gly His His His
                    85                  90                  95

His His His His His
                100
```

<210> SEQ ID NO 56
<211> LENGTH: 86
<212> TYPE: PRT
<213> ORGANISM: Artificial Sequence
<220> FEATURE:
<223> OTHER INFORMATION: synthetic construct

<400> SEQUENCE: 56

```
Ile Glu Val Glu Asp Val Thr Asp Thr Thr Ala Leu Ile Thr Trp Thr
 1               5                  10                  15

Asn Arg Ser Ser Tyr Ser Asn Phe His Gly Cys Glu Leu Ala Tyr Gly
                20                  25                  30

Ile Lys Asp Val Pro Gly Asp Arg Thr Thr Ile Asp Leu Asn Ser Pro
            35                  40                  45

Tyr Val His Tyr Ser Ile Gly Asn Leu Lys Pro Asp Thr Glu Tyr Glu
        50                  55                  60

Val Ser Leu Ile Cys Leu Thr Thr Asp Gly Thr Tyr Ser Asn Pro Ala
 65                 70                  75                  80

Lys Glu Thr Phe Thr Thr
                    85
```

<210> SEQ ID NO 57
<211> LENGTH: 101
<212> TYPE: PRT

<213> ORGANISM: Artificial Sequence
<220> FEATURE:
<223> OTHER INFORMATION: synthetic construct

<400> SEQUENCE: 57

Ala Ile Glu Val Glu Asp Val Thr Asp Thr Thr Ala Leu Ile Thr Trp
1               5                   10                  15

Thr Asn Arg Ser Phe Tyr Ser Asn Leu His Gly Cys Glu Leu Thr Tyr
            20                  25                  30

Gly Ile Lys Asp Val Pro Gly Asp Arg Thr Thr Ile Asp Leu Asn Gln
        35                  40                  45

Pro Tyr Val His Tyr Ser Ile Gly Asn Leu Lys Pro Asp Thr Glu Tyr
    50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                85                  90                  95

His His His His His
        100

<210> SEQ ID NO 58
<211> LENGTH: 86
<212> TYPE: PRT
<213> ORGANISM: Artificial Sequence
<220> FEATURE:
<223> OTHER INFORMATION: synthetic construct

<400> SEQUENCE: 58

Ile Glu Val Glu Asp Val Thr Asp Thr Thr Ala Leu Ile Thr Trp Thr
1               5                   10                  15

Asn Arg Ser Phe Tyr Ser Asn Leu His Gly Cys Glu Leu Thr Tyr Gly
            20                  25                  30

Ile Lys Asp Val Pro Gly Asp Arg Thr Thr Ile Asp Leu Asn Gln Pro
        35                  40                  45

Tyr Val His Tyr Ser Ile Gly Asn Leu Lys Pro Asp Thr Glu Tyr Glu
    50                  55                  60

Val Ser Leu Ile Cys Leu Thr Thr Asp Gly Thr Tyr Ser Asn Pro Ala
65                  70                  75                  80

Lys Glu Thr Phe Thr Thr
                85

<210> SEQ ID NO 59
<211> LENGTH: 101
<212> TYPE: PRT
<213> ORGANISM: Artificial Sequence
<220> FEATURE:
<223> OTHER INFORMATION: synthetic construct

<400> SEQUENCE: 59

Ala Ile Glu Val Glu Asp Val Thr Asp Thr Thr Ala Leu Ile Thr Trp
1               5                   10                  15

Thr Asn Arg Ser Ser Tyr Ala Tyr Leu His Gly Cys Glu Leu Ala Tyr
            20                  25                  30

Gly Ile Lys Asp Val Pro Gly Asp Arg Thr Thr Ile Asp Leu Asn Gln
        35                  40                  45

Pro Tyr Val His Tyr Ser Ile Gly Asn Leu Lys Pro Asp Thr Glu Tyr
    50                  55                  60

Glu Val Ser Leu Ile Cys Leu Thr Thr Asp Gly Thr Tyr Ser Asn Pro
65                  70                  75                  80

```
Ala Lys Glu Thr Phe Thr Thr Gly Gly Gly Thr Leu Gly His His His
                85                  90                  95

His His His His His
            100

<210> SEQ ID NO 60
<211> LENGTH: 86
<212> TYPE: PRT
<213> ORGANISM: Artificial Sequence
<220> FEATURE:
<223> OTHER INFORMATION: synthetic construct

<400> SEQUENCE: 60

Ile Glu Val Glu Asp Val Thr Asp Thr Thr Ala Leu Ile Thr Trp Thr
1               5                   10                  15

Asn Arg Ser Ser Tyr Ala Tyr Leu His Gly Cys Glu Leu Ala Tyr Gly
                20                  25                  30

Ile Lys Asp Val Pro Gly Asp Arg Thr Thr Ile Asp Leu Asn Gln Pro
            35                  40                  45

Tyr Val His Tyr Ser Ile Gly Asn Leu Lys Pro Asp Thr Glu Tyr Glu
        50                  55                  60

Val Ser Leu Ile Cys Leu Thr Thr Asp Gly Thr Tyr Ser Asn Pro Ala
65                  70                  75                  80

Lys Glu Thr Phe Thr Thr
                85

<210> SEQ ID NO 61
<211> LENGTH: 101
<212> TYPE: PRT
<213> ORGANISM: Artificial Sequence
<220> FEATURE:
<223> OTHER INFORMATION: synthetic construct

<400> SEQUENCE: 61

Ala Ile Glu Val Glu Asp Val Thr Asp Thr Thr Ala Leu Ile Thr Trp
1               5                   10                  15

Ile Asn Arg Ser Ser Tyr Ala Asn Leu His Gly Cys Glu Leu Thr Tyr
                20                  25                  30

Gly Ile Lys Asp Val Pro Gly Asp Arg Thr Thr Ile Asp Leu Ser Ser
            35                  40                  45

Pro Tyr Val His Tyr Ser Ile Gly Asn Leu Lys Pro Asp Thr Glu Tyr
        50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                85                  90                  95

His His His His His
            100

<210> SEQ ID NO 62
<211> LENGTH: 86
<212> TYPE: PRT
<213> ORGANISM: Artificial Sequence
<220> FEATURE:
<223> OTHER INFORMATION: synthetic construct

<400> SEQUENCE: 62

Ile Glu Val Glu Asp Val Thr Asp Thr Thr Ala Leu Ile Thr Trp Ile
1               5                   10                  15
```

Asn Arg Ser Ser Tyr Ala Asn Leu His Gly Cys Glu Leu Thr Tyr Gly
            20                  25                  30

Ile Lys Asp Val Pro Gly Asp Arg Thr Thr Ile Asp Leu Ser Ser Pro
                35                  40                  45

Tyr Val His Tyr Ser Ile Gly Asn Leu Lys Pro Asp Thr Glu Tyr Glu
    50                  55                  60

Val Ser Leu Ile Cys Leu Thr Thr Asp Gly Thr Tyr Ser Asn Pro Ala
65                  70                  75                  80

Lys Glu Thr Phe Thr Thr
                85

<210> SEQ ID NO 63
<211> LENGTH: 101
<212> TYPE: PRT
<213> ORGANISM: Artificial Sequence
<220> FEATURE:
<223> OTHER INFORMATION: synthetic construct

<400> SEQUENCE: 63

Ala Ile Glu Val Glu Asp Val Thr Asp Thr Thr Ala Leu Ile Thr Trp
1               5                   10                  15

Thr Asn Arg Ser Ser Tyr Ala Asn Tyr His Gly Cys Glu Leu Ala Tyr
            20                  25                  30

Gly Ile Lys Asp Val Pro Gly Asp Arg Thr Thr Ile Asp Leu Asn Gln
                35                  40                  45

Pro Tyr Val His Tyr Ser Ile Gly Asn Leu Lys Pro Asp Thr Glu Tyr
    50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                85                  90                  95

His His His His His
            100

<210> SEQ ID NO 64
<211> LENGTH: 86
<212> TYPE: PRT
<213> ORGANISM: Artificial Sequence
<220> FEATURE:
<223> OTHER INFORMATION: synthetic construct

<400> SEQUENCE: 64

Ile Glu Val Glu Asp Val Thr Asp Thr Thr Ala Leu Ile Thr Trp Thr
1               5                   10                  15

Asn Arg Ser Ser Tyr Ala Asn Tyr His Gly Cys Glu Leu Ala Tyr Gly
            20                  25                  30

Ile Lys Asp Val Pro Gly Asp Arg Thr Thr Ile Asp Leu Asn Gln Pro
                35                  40                  45

Tyr Val His Tyr Ser Ile Gly Asn Leu Lys Pro Asp Thr Glu Tyr Glu
    50                  55                  60

Val Ser Leu Ile Cys Leu Thr Thr Asp Gly Thr Tyr Ser Asn Pro Ala
65                  70                  75                  80

Lys Glu Thr Phe Thr Thr
                85

<210> SEQ ID NO 65
<211> LENGTH: 101
<212> TYPE: PRT
<213> ORGANISM: Artificial Sequence

```
<220> FEATURE:
<223> OTHER INFORMATION: synthetic construct

<400> SEQUENCE: 65

Ala Ile Glu Val Glu Asp Val Thr Asp Thr Thr Ala Leu Ile Thr Trp
1               5                   10                  15

Thr Asn Arg Ser Ser Tyr Ala Asn Leu Pro Gly Cys Glu Leu Thr Tyr
                20                  25                  30

Gly Ile Lys Asp Val Pro Gly Asp Arg Thr Thr Ile Asp Leu Asn Ser
            35                  40                  45

Pro Tyr Val His Tyr Ser Ile Gly Asn Leu Lys Pro Asp Thr Glu Tyr
        50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                85                  90                  95

His His His His His
            100

<210> SEQ ID NO 66
<211> LENGTH: 86
<212> TYPE: PRT
<213> ORGANISM: Artificial Sequence
<220> FEATURE:
<223> OTHER INFORMATION: synthetic construct

<400> SEQUENCE: 66

Ile Glu Val Glu Asp Val Thr Asp Thr Thr Ala Leu Ile Thr Trp Thr
1               5                   10                  15

Asn Arg Ser Ser Tyr Ala Asn Leu Pro Gly Cys Glu Leu Thr Tyr Gly
                20                  25                  30

Ile Lys Asp Val Pro Gly Asp Arg Thr Thr Ile Asp Leu Asn Ser Pro
            35                  40                  45

Tyr Val His Tyr Ser Ile Gly Asn Leu Lys Pro Asp Thr Glu Tyr Glu
        50                  55                  60

Val Ser Leu Ile Cys Leu Thr Thr Asp Gly Thr Tyr Ser Asn Pro Ala
65                  70                  75                  80

Lys Glu Thr Phe Thr Thr
                85

<210> SEQ ID NO 67
<211> LENGTH: 101
<212> TYPE: PRT
<213> ORGANISM: Artificial Sequence
<220> FEATURE:
<223> OTHER INFORMATION: synthetic construct

<400> SEQUENCE: 67

Ala Ile Glu Val Glu Asp Val Thr Asp Thr Thr Ala Leu Ile Thr Trp
1               5                   10                  15

Thr Asn Arg Ser Ser Tyr Ser Asn Leu His Gly Cys Glu Leu Ala Tyr
                20                  25                  30

Gly Ile Lys Asp Val Pro Gly Asp Arg Thr Thr Ile Asp Leu Asn Gln
            35                  40                  45

Pro Tyr Val His Tyr Ser Ile Gly Asn Leu Lys Pro Asp Thr Glu Tyr
        50                  55                  60

Glu Val Ser Leu Ile Cys Leu Thr Thr Asp Gly Thr Tyr Asn Asn Pro
65                  70                  75                  80
```

Ala Lys Glu Thr Phe Thr Thr Gly Gly Gly Thr Leu Gly His His His
                85                  90                  95

His His His His His
            100

<210> SEQ ID NO 68
<211> LENGTH: 86
<212> TYPE: PRT
<213> ORGANISM: Artificial Sequence
<220> FEATURE:
<223> OTHER INFORMATION: synthetic construct

<400> SEQUENCE: 68

Ile Glu Val Glu Asp Val Thr Asp Thr Thr Ala Leu Ile Thr Trp Thr
1               5                   10                  15

Asn Arg Ser Ser Tyr Ser Asn Leu His Gly Cys Glu Leu Ala Tyr Gly
            20                  25                  30

Ile Lys Asp Val Pro Gly Asp Arg Thr Thr Ile Asp Leu Asn Gln Pro
        35                  40                  45

Tyr Val His Tyr Ser Ile Gly Asn Leu Lys Pro Asp Thr Glu Tyr Glu
    50                  55                  60

Val Ser Leu Ile Cys Leu Thr Thr Asp Gly Thr Tyr Asn Asn Pro Ala
65                  70                  75                  80

Lys Glu Thr Phe Thr Thr
                85

<210> SEQ ID NO 69
<211> LENGTH: 101
<212> TYPE: PRT
<213> ORGANISM: Artificial Sequence
<220> FEATURE:
<223> OTHER INFORMATION: synthetic construct

<400> SEQUENCE: 69

Ala Ile Glu Val Glu Asp Val Thr Asp Thr Thr Ala Leu Ile Thr Trp
1               5                   10                  15

Ile Asn Arg Ser Ser Tyr Ala Asn Leu His Gly Cys Glu Leu Thr Tyr
            20                  25                  30

Gly Ile Lys Asp Val Pro Gly Asp Arg Thr Thr Ile Asp Leu Asn Ser
        35                  40                  45

Pro Tyr Val His Tyr Ser Ile Gly Asn Leu Lys Pro Asp Thr Glu Tyr
    50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                85                  90                  95

His His His His His
            100

<210> SEQ ID NO 70
<211> LENGTH: 86
<212> TYPE: PRT
<213> ORGANISM: Artificial Sequence
<220> FEATURE:
<223> OTHER INFORMATION: synthetic construct

<400> SEQUENCE: 70

Ile Glu Val Glu Asp Val Thr Asp Thr Thr Ala Leu Ile Thr Trp Ile
1               5                   10                  15

Asn Arg Ser Ser Tyr Ala Asn Leu His Gly Cys Glu Leu Thr Tyr Gly

```
                20                  25                  30
Ile Lys Asp Val Pro Gly Asp Arg Thr Thr Ile Asp Leu Asn Ser Pro
            35                  40                  45
Tyr Val His Tyr Ser Ile Gly Asn Leu Lys Pro Asp Thr Glu Tyr Glu
        50                  55                  60
Val Ser Leu Ile Cys Leu Thr Thr Asp Gly Thr Tyr Ser Asn Pro Ala
65                  70                  75                  80
Lys Glu Thr Phe Thr Thr
                85
```

<210> SEQ ID NO 71
<211> LENGTH: 101
<212> TYPE: PRT
<213> ORGANISM: Artificial Sequence
<220> FEATURE:
<223> OTHER INFORMATION: synthetic construct

<400> SEQUENCE: 71

```
Ala Ile Glu Val Glu Asp Val Thr Asp Thr Thr Ala Leu Ile Thr Trp
1               5                   10                  15
Thr Ala Arg Ser Ala Tyr Ser His His His Tyr Cys Glu Leu Thr Tyr
            20                  25                  30
Gly Ile Lys Asp Val Pro Gly Asp Arg Thr Thr Ile Asp Leu Arg Gln
        35                  40                  45
Pro Tyr Val His Tyr Ser Ile Gly Asn Leu Lys Pro Asp Thr Glu Tyr
    50                  55                  60
Glu Val Ser Leu Ile Cys Leu Thr Thr Asp Gly Thr Tyr Ser Asn Pro
65                  70                  75                  80
Ala Lys Glu Thr Phe Thr Thr Gly Gly Gly Thr Leu Gly His His His
                85                  90                  95
His His His His His
            100
```

<210> SEQ ID NO 72
<211> LENGTH: 86
<212> TYPE: PRT
<213> ORGANISM: Artificial Sequence
<220> FEATURE:
<223> OTHER INFORMATION: synthetic construct

<400> SEQUENCE: 72

```
Ile Glu Val Glu Asp Val Thr Asp Thr Thr Ala Leu Ile Thr Trp Thr
1               5                   10                  15
Ala Arg Ser Ala Tyr Ser His His His Tyr Cys Glu Leu Thr Tyr Gly
            20                  25                  30
Ile Lys Asp Val Pro Gly Asp Arg Thr Thr Ile Asp Leu Arg Gln Pro
        35                  40                  45
Tyr Val His Tyr Ser Ile Gly Asn Leu Lys Pro Asp Thr Glu Tyr Glu
    50                  55                  60
Val Ser Leu Ile Cys Leu Thr Thr Asp Gly Thr Tyr Ser Asn Pro Ala
65                  70                  75                  80
Lys Glu Thr Phe Thr Thr
                85
```

<210> SEQ ID NO 73
<211> LENGTH: 100
<212> TYPE: PRT
<213> ORGANISM: Artificial Sequence
<220> FEATURE:

<223> OTHER INFORMATION: synthetic construct

<400> SEQUENCE: 73

```
Ala Ile Glu Val Glu Asp Val Thr Asp Thr Thr Ala Leu Ile Thr Trp
1               5                   10                  15
Thr Asn Arg Ser Ser Tyr Ala Asn Tyr His His Cys Glu Leu Thr Tyr
            20                  25                  30
Gly Ile Lys Asp Val Pro Gly Asp Arg Thr Thr Ile Asp Leu Glu Leu
        35                  40                  45
Tyr Val His Tyr Ser Ile Gly Asn Leu Lys Pro Asp Thr Glu Tyr Glu
    50                  55                  60
Val Ser Leu Ile Cys Leu Thr Thr Asp Gly Thr Tyr Ser Asn Pro Ala
65                  70                  75                  80
Lys Glu Thr Phe Thr Thr Gly Gly Gly Thr Leu Gly His His His His
                85                  90                  95
His His His His
        100
```

<210> SEQ ID NO 74
<211> LENGTH: 85
<212> TYPE: PRT
<213> ORGANISM: Artificial Sequence
<220> FEATURE:
<223> OTHER INFORMATION: synthetic construct

<400> SEQUENCE: 74

```
Ile Glu Val Glu Asp Val Thr Asp Thr Thr Ala Leu Ile Thr Trp Thr
1               5                   10                  15
Asn Arg Ser Ser Tyr Ala Asn Tyr His His Cys Glu Leu Thr Tyr Gly
            20                  25                  30
Ile Lys Asp Val Pro Gly Asp Arg Thr Thr Ile Asp Leu Glu Leu Tyr
        35                  40                  45
Val His Tyr Ser Ile Gly Asn Leu Lys Pro Asp Thr Glu Tyr Glu Val
    50                  55                  60
Ser Leu Ile Cys Leu Thr Thr Asp Gly Thr Tyr Ser Asn Pro Ala Lys
65                  70                  75                  80
Glu Thr Phe Thr Thr
                85
```

<210> SEQ ID NO 75
<211> LENGTH: 101
<212> TYPE: PRT
<213> ORGANISM: Artificial Sequence
<220> FEATURE:
<223> OTHER INFORMATION: synthetic construct

<400> SEQUENCE: 75

```
Ala Ile Glu Val Glu Asp Val Thr Asp Thr Thr Ala Leu Ile Thr Trp
1               5                   10                  15
Thr Asn Arg Ser Ser Tyr Ser Asp Leu Pro Gly Cys Glu Leu Thr Tyr
            20                  25                  30
Gly Ile Lys Asp Val Pro Gly Asp Arg Thr Thr Ile Asp Leu Ser Ser
        35                  40                  45
Pro Tyr Val His Tyr Ser Ile Gly Asn Leu Lys Pro Asp Thr Glu Tyr
    50                  55                  60
Glu Val Ser Leu Ile Cys Leu Thr Thr Asp Gly Thr Tyr Ser Asn Pro
65                  70                  75                  80
Ala Lys Glu Thr Phe Thr Thr Gly Gly Gly Thr Leu Gly His His His
```

His His His His His
        100

<210> SEQ ID NO 76
<211> LENGTH: 86
<212> TYPE: PRT
<213> ORGANISM: Artificial Sequence
<220> FEATURE:
<223> OTHER INFORMATION: synthetic construct

<400> SEQUENCE: 76

Ile Glu Val Glu Asp Val Thr Asp Thr Thr Ala Leu Ile Thr Trp Thr
1               5                   10                  15

Asn Arg Ser Ser Tyr Ser Asp Leu Pro Gly Cys Glu Leu Thr Tyr Gly
            20                  25                  30

Ile Lys Asp Val Pro Gly Asp Arg Thr Thr Ile Asp Leu Ser Ser Pro
        35                  40                  45

Tyr Val His Tyr Ser Ile Gly Asn Leu Lys Pro Asp Thr Glu Tyr Glu
    50                  55                  60

Val Ser Leu Ile Cys Leu Thr Thr Asp Gly Thr Tyr Ser Asn Pro Ala
65                  70                  75                  80

Lys Glu Thr Phe Thr Thr
            85

<210> SEQ ID NO 77
<211> LENGTH: 101
<212> TYPE: PRT
<213> ORGANISM: Artificial Sequence
<220> FEATURE:
<223> OTHER INFORMATION: synthetic construct

<400> SEQUENCE: 77

Ala Ile Glu Val Glu Asp Val Thr Asp Thr Thr Ala Leu Ile Thr Trp
1               5                   10                  15

Thr His Arg Ser Ala Tyr Ser Asn His Ser Phe Cys Glu Leu Thr Tyr
            20                  25                  30

Gly Ile Lys Asp Val Pro Gly Asp Arg Thr Thr Ile Asp Leu Asn Thr
        35                  40                  45

Pro Tyr Val His Tyr Ser Ile Gly Asn Leu Lys Pro Asp Thr Glu Tyr
    50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
            85                  90                  95

His His His His His
        100

<210> SEQ ID NO 78
<211> LENGTH: 86
<212> TYPE: PRT
<213> ORGANISM: Artificial Sequence
<220> FEATURE:
<223> OTHER INFORMATION: synthetic construct

<400> SEQUENCE: 78

Ile Glu Val Glu Asp Val Thr Asp Thr Thr Ala Leu Ile Thr Trp Thr
1               5                   10                  15

His Arg Ser Ala Tyr Ser Asn His Ser Phe Cys Glu Leu Thr Tyr Gly
            20                  25                  30

```
Ile Lys Asp Val Pro Gly Asp Arg Thr Thr Ile Asp Leu Asn Thr Pro
            35                  40                  45
Tyr Val His Tyr Ser Ile Gly Asn Leu Lys Pro Asp Thr Glu Tyr Glu
 50                  55                  60
Val Ser Leu Ile Cys Leu Thr Thr Asp Gly Thr Tyr Ser Asn Pro Ala
 65                  70                  75                  80
Lys Glu Thr Phe Thr Thr
                 85
```

```
<210> SEQ ID NO 79
<211> LENGTH: 101
<212> TYPE: PRT
<213> ORGANISM: Artificial Sequence
<220> FEATURE:
<223> OTHER INFORMATION: synthetic construct

<400> SEQUENCE: 79

Ala Ile Glu Val Glu Asp Val Thr Asp Thr Thr Ala Leu Ile Thr Trp
 1               5                  10                  15
Thr Asn Arg Ser Leu Tyr Ala Asn Phe His Gly Cys Glu Leu Thr Tyr
            20                  25                  30
Gly Ile Lys Asp Val Pro Gly Asp Arg Thr Thr Ile Asp Leu Glu Gln
            35                  40                  45
Val Tyr Val His Tyr Ser Ile Gly Asn Leu Lys Pro Asp Thr Glu Tyr
 50                  55                  60
Glu Val Ser Leu Ile Cys Leu Thr Thr Asp Gly Thr Tyr Ser Asn Pro
 65                  70                  75                  80
Ala Lys Glu Thr Phe Thr Thr Gly Gly Gly Thr Leu Gly His His His
                 85                  90                  95
His His His His His
            100
```

```
<210> SEQ ID NO 80
<211> LENGTH: 86
<212> TYPE: PRT
<213> ORGANISM: Artificial Sequence
<220> FEATURE:
<223> OTHER INFORMATION: synthetic construct

<400> SEQUENCE: 80

Ile Glu Val Glu Asp Val Thr Asp Thr Thr Ala Leu Ile Thr Trp Thr
 1               5                  10                  15
Asn Arg Ser Leu Tyr Ala Asn Phe His Gly Cys Glu Leu Thr Tyr Gly
            20                  25                  30
Ile Lys Asp Val Pro Gly Asp Arg Thr Thr Ile Asp Leu Glu Gln Val
            35                  40                  45
Tyr Val His Tyr Ser Ile Gly Asn Leu Lys Pro Asp Thr Glu Tyr Glu
 50                  55                  60
Val Ser Leu Ile Cys Leu Thr Thr Asp Gly Thr Tyr Ser Asn Pro Ala
 65                  70                  75                  80
Lys Glu Thr Phe Thr Thr
                 85
```

```
<210> SEQ ID NO 81
<211> LENGTH: 101
<212> TYPE: PRT
<213> ORGANISM: Artificial Sequence
<220> FEATURE:
<223> OTHER INFORMATION: synthetic construct
```

<400> SEQUENCE: 81

Ala Ile Glu Val Glu Asp Val Thr Asp Thr Thr Ala Leu Ile Thr Trp
1               5                   10                  15

Thr Asn Arg Ser Ser Tyr Ser Asn Leu Pro Gly Cys Glu Leu Thr Tyr
            20                  25                  30

Gly Ile Lys Asp Val Pro Gly Asp Arg Thr Thr Ile Asp Leu Asn Gln
        35                  40                  45

Val Tyr Val His Tyr Ser Ile Gly Asn Leu Lys Pro Asp Thr Glu Tyr
    50                  55                  60

Glu Val Ser Leu Ile Cys Leu Thr Thr Asp Gly Thr Tyr Ser Asn Pro
65                  70                  75                  80

Ala Lys Glu Thr Phe Thr Thr Gly Gly Gly Thr Leu Gly His His His
                85                  90                  95

His His His His His
            100

<210> SEQ ID NO 82
<211> LENGTH: 86
<212> TYPE: PRT
<213> ORGANISM: Artificial Sequence
<220> FEATURE:
<223> OTHER INFORMATION: synthetic construct

<400> SEQUENCE: 82

Ile Glu Val Glu Asp Val Thr Asp Thr Thr Ala Leu Ile Thr Trp Thr
1               5                   10                  15

Asn Arg Ser Ser Tyr Ser Asn Leu Pro Gly Cys Glu Leu Thr Tyr Gly
            20                  25                  30

Ile Lys Asp Val Pro Gly Asp Arg Thr Thr Ile Asp Leu Asn Gln Val
        35                  40                  45

Tyr Val His Tyr Ser Ile Gly Asn Leu Lys Pro Asp Thr Glu Tyr Glu
    50                  55                  60

Val Ser Leu Ile Cys Leu Thr Thr Asp Gly Thr Tyr Ser Asn Pro Ala
65                  70                  75                  80

Lys Glu Thr Phe Thr Thr
                85

<210> SEQ ID NO 83
<211> LENGTH: 9
<212> TYPE: PRT
<213> ORGANISM: Artificial Sequence
<220> FEATURE:
<223> OTHER INFORMATION: synthetic construct

<400> SEQUENCE: 83

Ser Asp Glu Phe Gly His Tyr Asp Gly
1               5

<210> SEQ ID NO 84
<211> LENGTH: 9
<212> TYPE: PRT
<213> ORGANISM: Artificial Sequence
<220> FEATURE:
<223> OTHER INFORMATION: synthetic construct

<400> SEQUENCE: 84

Ser Asp Asp Phe Asp Asn Tyr Glu Trp
1               5

```
<210> SEQ ID NO 85
<211> LENGTH: 9
<212> TYPE: PRT
<213> ORGANISM: Artificial Sequence
<220> FEATURE:
<223> OTHER INFORMATION: synthetic construct

<400> SEQUENCE: 85

Ser Asp Asp Phe Ala Asp Tyr Val Trp
1               5

<210> SEQ ID NO 86
<211> LENGTH: 9
<212> TYPE: PRT
<213> ORGANISM: Artificial Sequence
<220> FEATURE:
<223> OTHER INFORMATION: synthetic construct

<400> SEQUENCE: 86

Ser Asp Asp Phe Gly Glu Tyr Val Trp
1               5

<210> SEQ ID NO 87
<211> LENGTH: 9
<212> TYPE: PRT
<213> ORGANISM: Artificial Sequence
<220> FEATURE:
<223> OTHER INFORMATION: synthetic construct

<400> SEQUENCE: 87

Leu Asp Asp Trp Gly Ser Tyr His Val
1               5

<210> SEQ ID NO 88
<211> LENGTH: 9
<212> TYPE: PRT
<213> ORGANISM: Artificial Sequence
<220> FEATURE:
<223> OTHER INFORMATION: synthetic construct

<400> SEQUENCE: 88

Ser Asp Glu Val Gly Asp Tyr Val Val
1               5

<210> SEQ ID NO 89
<211> LENGTH: 9
<212> TYPE: PRT
<213> ORGANISM: Artificial Sequence
<220> FEATURE:
<223> OTHER INFORMATION: synthetic construct

<400> SEQUENCE: 89

Ser Asp Asp Phe Ala Glu Tyr Val Gly
1               5

<210> SEQ ID NO 90
<211> LENGTH: 9
<212> TYPE: PRT
<213> ORGANISM: Artificial Sequence
<220> FEATURE:
<223> OTHER INFORMATION: synthetic construct

<400> SEQUENCE: 90

Ser Asp Asp Phe Glu Glu Tyr Val Val
1               5

<210> SEQ ID NO 91
```

```
<211> LENGTH: 9
<212> TYPE: PRT
<213> ORGANISM: Artificial Sequence
<220> FEATURE:
<223> OTHER INFORMATION: synthetic construct

<400> SEQUENCE: 91

Ser Asp Glu Val Gly Gln Tyr Val Gly
1               5

<210> SEQ ID NO 92
<211> LENGTH: 9
<212> TYPE: PRT
<213> ORGANISM: Artificial Sequence
<220> FEATURE:
<223> OTHER INFORMATION: synthetic construct

<400> SEQUENCE: 92

Ser Asp Asp Ile Gly Leu Tyr Val Trp
1               5

<210> SEQ ID NO 93
<211> LENGTH: 9
<212> TYPE: PRT
<213> ORGANISM: Artificial Sequence
<220> FEATURE:
<223> OTHER INFORMATION: synthetic construct

<400> SEQUENCE: 93

Ser Asp Glu His Ala Glu Phe Ile Gly
1               5

<210> SEQ ID NO 94
<211> LENGTH: 6
<212> TYPE: PRT
<213> ORGANISM: Artificial Sequence
<220> FEATURE:
<223> OTHER INFORMATION: synthetic construct

<400> SEQUENCE: 94

Trp Trp His Ser Ala Trp
1               5

<210> SEQ ID NO 95
<211> LENGTH: 6
<212> TYPE: PRT
<213> ORGANISM: Artificial Sequence
<220> FEATURE:
<223> OTHER INFORMATION: synthetic construct

<400> SEQUENCE: 95

Trp Tyr His Met Ala Trp
1               5

<210> SEQ ID NO 96
<211> LENGTH: 6
<212> TYPE: PRT
<213> ORGANISM: Artificial Sequence
<220> FEATURE:
<223> OTHER INFORMATION: synthetic construct

<400> SEQUENCE: 96

Trp Tyr His His Ala His
1               5

<210> SEQ ID NO 97
<211> LENGTH: 6
```

```
<212> TYPE: PRT
<213> ORGANISM: Artificial Sequence
<220> FEATURE:
<223> OTHER INFORMATION: synthetic construct

<400> SEQUENCE: 97

Trp Tyr His Gln Ala Trp
1               5

<210> SEQ ID NO 98
<211> LENGTH: 6
<212> TYPE: PRT
<213> ORGANISM: Artificial Sequence
<220> FEATURE:
<223> OTHER INFORMATION: synthetic construct

<400> SEQUENCE: 98

Trp Phe His Gln Ala Trp
1               5

<210> SEQ ID NO 99
<211> LENGTH: 10
<212> TYPE: PRT
<213> ORGANISM: Artificial Sequence
<220> FEATURE:
<223> OTHER INFORMATION: synthetic construct

<400> SEQUENCE: 99

Tyr Thr Asp Gln Glu Ala Gly Asn Pro Ala
1               5                   10

<210> SEQ ID NO 100
<211> LENGTH: 11
<212> TYPE: PRT
<213> ORGANISM: Artificial Sequence
<220> FEATURE:
<223> OTHER INFORMATION: synthetic construct

<400> SEQUENCE: 100

Thr Asn Arg Ser Ser Tyr Tyr Asn Leu His Gly
1               5                   10

<210> SEQ ID NO 101
<211> LENGTH: 11
<212> TYPE: PRT
<213> ORGANISM: Artificial Sequence
<220> FEATURE:
<223> OTHER INFORMATION: synthetic construct

<400> SEQUENCE: 101

Ile Asn Arg Ser Tyr Tyr Ala Asp Leu His Gly
1               5                   10

<210> SEQ ID NO 102
<211> LENGTH: 11
<212> TYPE: PRT
<213> ORGANISM: Artificial Sequence
<220> FEATURE:
<223> OTHER INFORMATION: synthetic construct

<400> SEQUENCE: 102

Thr Asn Arg Ser Ser Tyr Ser His Leu Asp Gly
1               5                   10

<210> SEQ ID NO 103
<211> LENGTH: 11
<212> TYPE: PRT
```

<213> ORGANISM: Artificial Sequence
<220> FEATURE:
<223> OTHER INFORMATION: synthetic construct

<400> SEQUENCE: 103

Ile Asn Arg Ser Ser Tyr His Asn Phe Pro His
1               5                   10

<210> SEQ ID NO 104
<211> LENGTH: 11
<212> TYPE: PRT
<213> ORGANISM: Artificial Sequence
<220> FEATURE:
<223> OTHER INFORMATION: synthetic construct

<400> SEQUENCE: 104

Thr Asn Arg Ser Ser Tyr Ser Asn His Leu Gly
1               5                   10

<210> SEQ ID NO 105
<211> LENGTH: 11
<212> TYPE: PRT
<213> ORGANISM: Artificial Sequence
<220> FEATURE:
<223> OTHER INFORMATION: synthetic construct

<400> SEQUENCE: 105

Thr Asn Arg Ser Ser Tyr Ser Asn Phe His Gly
1               5                   10

<210> SEQ ID NO 106
<211> LENGTH: 11
<212> TYPE: PRT
<213> ORGANISM: Artificial Sequence
<220> FEATURE:
<223> OTHER INFORMATION: synthetic construct

<400> SEQUENCE: 106

Thr Asn Arg Ser Phe Tyr Ser Asn Leu His Gly
1               5                   10

<210> SEQ ID NO 107
<211> LENGTH: 11
<212> TYPE: PRT
<213> ORGANISM: Artificial Sequence
<220> FEATURE:
<223> OTHER INFORMATION: synthetic construct

<400> SEQUENCE: 107

Thr Asn Arg Ser Ser Tyr Ala Tyr Leu His Gly
1               5                   10

<210> SEQ ID NO 108
<211> LENGTH: 11
<212> TYPE: PRT
<213> ORGANISM: Artificial Sequence
<220> FEATURE:
<223> OTHER INFORMATION: synthetic construct

<400> SEQUENCE: 108

Ile Asn Arg Ser Ser Tyr Ala Asn Leu His Gly
1               5                   10

<210> SEQ ID NO 109
<211> LENGTH: 11
<212> TYPE: PRT
<213> ORGANISM: Artificial Sequence

```
<220> FEATURE:
<223> OTHER INFORMATION: synthetic construct

<400> SEQUENCE: 109

Thr Asn Arg Ser Ser Tyr Ala Asn Tyr His Gly
1               5                   10

<210> SEQ ID NO 110
<211> LENGTH: 11
<212> TYPE: PRT
<213> ORGANISM: Artificial Sequence
<220> FEATURE:
<223> OTHER INFORMATION: synthetic construct

<400> SEQUENCE: 110

Thr Asn Arg Ser Ser Tyr Ala Asn Leu Pro Gly
1               5                   10

<210> SEQ ID NO 111
<211> LENGTH: 11
<212> TYPE: PRT
<213> ORGANISM: Artificial Sequence
<220> FEATURE:
<223> OTHER INFORMATION: synthetic construct

<400> SEQUENCE: 111

Thr Asn Arg Ser Ser Tyr Ser Asn Leu His Gly
1               5                   10

<210> SEQ ID NO 112
<211> LENGTH: 11
<212> TYPE: PRT
<213> ORGANISM: Artificial Sequence
<220> FEATURE:
<223> OTHER INFORMATION: synthetic construct

<400> SEQUENCE: 112

Thr Ala Arg Ser Ala Tyr Ser His His His Tyr
1               5                   10

<210> SEQ ID NO 113
<211> LENGTH: 11
<212> TYPE: PRT
<213> ORGANISM: Artificial Sequence
<220> FEATURE:
<223> OTHER INFORMATION: synthetic construct

<400> SEQUENCE: 113

Thr Asn Arg Ser Ser Tyr Ala Asn Tyr His His
1               5                   10

<210> SEQ ID NO 114
<211> LENGTH: 11
<212> TYPE: PRT
<213> ORGANISM: Artificial Sequence
<220> FEATURE:
<223> OTHER INFORMATION: synthetic construct

<400> SEQUENCE: 114

Thr Asn Arg Ser Ser Tyr Ser Asp Leu Pro Gly
1               5                   10

<210> SEQ ID NO 115
<211> LENGTH: 11
<212> TYPE: PRT
<213> ORGANISM: Artificial Sequence
<220> FEATURE:
```

```
<223> OTHER INFORMATION: synthetic construct

<400> SEQUENCE: 115

Thr His Arg Ser Ala Tyr Ser Asn His Ser Phe
1               5                   10

<210> SEQ ID NO 116
<211> LENGTH: 11
<212> TYPE: PRT
<213> ORGANISM: Artificial Sequence
<220> FEATURE:
<223> OTHER INFORMATION: synthetic construct

<400> SEQUENCE: 116

Thr Asn Arg Ser Leu Tyr Ala Asn Phe His Gly
1               5                   10

<210> SEQ ID NO 117
<211> LENGTH: 11
<212> TYPE: PRT
<213> ORGANISM: Artificial Sequence
<220> FEATURE:
<223> OTHER INFORMATION: synthetic construct

<400> SEQUENCE: 117

Thr Asn Arg Ser Ser Tyr Ser Asn Leu Pro Gly
1               5                   10

<210> SEQ ID NO 118
<211> LENGTH: 6
<212> TYPE: PRT
<213> ORGANISM: Artificial Sequence
<220> FEATURE:
<223> OTHER INFORMATION: synthetic construct

<400> SEQUENCE: 118

Ser Ser Pro Tyr Val His
1               5

<210> SEQ ID NO 119
<211> LENGTH: 6
<212> TYPE: PRT
<213> ORGANISM: Artificial Sequence
<220> FEATURE:
<223> OTHER INFORMATION: synthetic construct

<400> SEQUENCE: 119

Asp Gln Ile Tyr Val His
1               5

<210> SEQ ID NO 120
<211> LENGTH: 7
<212> TYPE: PRT
<213> ORGANISM: Artificial Sequence
<220> FEATURE:
<223> OTHER INFORMATION: synthetic construct

<400> SEQUENCE: 120

Ser Ala Ala Ile Tyr Val His
1               5

<210> SEQ ID NO 121
<211> LENGTH: 6
<212> TYPE: PRT
<213> ORGANISM: Artificial Sequence
<220> FEATURE:
<223> OTHER INFORMATION: synthetic construct
```

```
<400> SEQUENCE: 121

Asn Ser Pro Tyr Val His
1               5

<210> SEQ ID NO 122
<211> LENGTH: 6
<212> TYPE: PRT
<213> ORGANISM: Artificial Sequence
<220> FEATURE:
<223> OTHER INFORMATION: synthetic construct

<400> SEQUENCE: 122

Asn Asn Ile Tyr Val His
1               5

<210> SEQ ID NO 123
<211> LENGTH: 6
<212> TYPE: PRT
<213> ORGANISM: Artificial Sequence
<220> FEATURE:
<223> OTHER INFORMATION: synthetic construct

<400> SEQUENCE: 123

Asn Gln Pro Tyr Val His
1               5

<210> SEQ ID NO 124
<211> LENGTH: 6
<212> TYPE: PRT
<213> ORGANISM: Artificial Sequence
<220> FEATURE:
<223> OTHER INFORMATION: synthetic construct

<400> SEQUENCE: 124

Arg Gln Pro Tyr Val His
1               5

<210> SEQ ID NO 125
<211> LENGTH: 5
<212> TYPE: PRT
<213> ORGANISM: Artificial Sequence
<220> FEATURE:
<223> OTHER INFORMATION: synthetic construct

<400> SEQUENCE: 125

Glu Leu Tyr Val His
1               5

<210> SEQ ID NO 126
<211> LENGTH: 6
<212> TYPE: PRT
<213> ORGANISM: Artificial Sequence
<220> FEATURE:
<223> OTHER INFORMATION: synthetic construct

<400> SEQUENCE: 126

Asn Thr Pro Tyr Val His
1               5

<210> SEQ ID NO 127
<211> LENGTH: 6
<212> TYPE: PRT
<213> ORGANISM: Artificial Sequence
<220> FEATURE:
<223> OTHER INFORMATION: synthetic construct
```

```
<400> SEQUENCE: 127

Glu Gln Val Tyr Val His
1               5

<210> SEQ ID NO 128
<211> LENGTH: 6
<212> TYPE: PRT
<213> ORGANISM: Artificial Sequence
<220> FEATURE:
<223> OTHER INFORMATION: synthetic construct

<400> SEQUENCE: 128

Asn Gln Val Tyr Val His
1               5

<210> SEQ ID NO 129
<211> LENGTH: 11
<212> TYPE: PRT
<213> ORGANISM: Artificial Sequence
<220> FEATURE:
<223> OTHER INFORMATION: synthetic construct

<400> SEQUENCE: 129

Leu Thr Thr Asp Gly Thr Tyr Ser Asn Pro Ala
1               5                   10

<210> SEQ ID NO 130
<211> LENGTH: 11
<212> TYPE: PRT
<213> ORGANISM: Artificial Sequence
<220> FEATURE:
<223> OTHER INFORMATION: synthetic construct

<400> SEQUENCE: 130

Leu Thr Thr Asp Gly Thr Tyr Asn Asn Pro Ala
1               5                   10

<210> SEQ ID NO 131
<211> LENGTH: 10
<212> TYPE: PRT
<213> ORGANISM: Artificial Sequence
<220> FEATURE:
<223> OTHER INFORMATION: synthetic construct

<400> SEQUENCE: 131

Gly Gly Gly Gly Ser Gly Gly Gly Gly Ser
1               5                   10

<210> SEQ ID NO 132
<211> LENGTH: 15
<212> TYPE: PRT
<213> ORGANISM: Artificial Sequence
<220> FEATURE:
<223> OTHER INFORMATION: synthetic construct

<400> SEQUENCE: 132

Gly Gly Gly Gly Ser Gly Gly Gly Ser Gly Gly Gly Gly Ser
1               5                   10                  15

<210> SEQ ID NO 133
<211> LENGTH: 585
<212> TYPE: PRT
<213> ORGANISM: Artificial Sequence
<220> FEATURE:
<223> OTHER INFORMATION: synthetic construct

<400> SEQUENCE: 133
```

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415
```

```
Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 134
<211> LENGTH: 680
<212> TYPE: PRT
<213> ORGANISM: Artificial Sequence
<220> FEATURE:
<223> OTHER INFORMATION: synthetic construct

<400> SEQUENCE: 134

Ser Gln Ile Glu Val Lys Asp Val Thr Asp Thr Thr Ala Leu Ile Thr
1               5                   10                  15

Trp Ser Asp Asp Phe Gly Glu Tyr Val Trp Cys Glu Leu Thr Tyr Gly
            20                  25                  30

Ile Lys Asp Val Pro Gly Asp Arg Thr Thr Ile Asp Leu Trp Tyr His
        35                  40                  45

His Ala His Tyr Ser Ile Gly Asn Leu Lys Pro Asp Thr Glu Tyr Glu
    50                  55                  60

Val Ser Leu Ile Cys Arg Ser Gly Asp Met Ser Ser Asn Pro Ala Lys
65                  70                  75                  80

Glu Thr Phe Thr Thr Gly Gly Gly Gly Ser Gly Gly Gly Gly Ser Asp
                85                  90                  95

Ala His Lys Ser Glu Val Ala His Arg Phe Lys Asp Leu Gly Glu Glu
            100                 105                 110

Asn Phe Lys Ala Leu Val Leu Ile Ala Phe Ala Gln Tyr Leu Gln Gln
        115                 120                 125

Ser Pro Phe Glu Asp His Val Lys Leu Val Asn Glu Val Thr Glu Phe
    130                 135                 140

Ala Lys Thr Cys Val Ala Asp Glu Ser Ala Glu Asn Cys Asp Lys Ser
145                 150                 155                 160

Leu His Thr Leu Phe Gly Asp Lys Leu Cys Thr Val Ala Thr Leu Arg
                165                 170                 175

Glu Thr Tyr Gly Glu Met Ala Asp Cys Cys Ala Lys Gln Glu Pro Glu
            180                 185                 190
```

-continued

Arg Asn Glu Cys Phe Leu Gln His Lys Asp Asp Pro Asn Leu Pro
    195                 200                 205

Arg Leu Val Arg Pro Glu Val Asp Val Met Cys Thr Ala Phe His Asp
210                 215                 220

Asn Glu Glu Thr Phe Leu Lys Lys Tyr Leu Tyr Glu Ile Ala Arg Arg
225                 230                 235                 240

His Pro Tyr Phe Tyr Ala Pro Glu Leu Leu Phe Phe Ala Lys Arg Tyr
                245                 250                 255

Lys Ala Ala Phe Thr Glu Cys Cys Gln Ala Ala Asp Lys Ala Ala Cys
                260                 265                 270

Leu Leu Pro Lys Leu Asp Glu Leu Arg Asp Glu Gly Lys Ala Ser Ser
            275                 280                 285

Ala Lys Gln Arg Leu Lys Cys Ala Ser Leu Gln Lys Phe Gly Glu Arg
        290                 295                 300

Ala Phe Lys Ala Trp Ala Val Ala Arg Leu Ser Gln Arg Phe Pro Lys
305                 310                 315                 320

Ala Glu Phe Ala Glu Val Ser Lys Leu Val Thr Asp Leu Thr Lys Val
                325                 330                 335

His Thr Glu Cys Cys His Gly Asp Leu Leu Glu Cys Ala Asp Asp Arg
                340                 345                 350

Ala Asp Leu Ala Lys Tyr Ile Cys Glu Asn Gln Asp Ser Ile Ser Ser
            355                 360                 365

Lys Leu Lys Glu Cys Cys Glu Lys Pro Leu Leu Glu Lys Ser His Cys
        370                 375                 380

Ile Ala Glu Val Glu Asn Asp Glu Met Pro Ala Asp Leu Pro Ser Leu
385                 390                 395                 400

Ala Ala Asp Phe Val Glu Ser Lys Asp Val Cys Lys Asn Tyr Ala Glu
                405                 410                 415

Ala Lys Asp Val Phe Leu Gly Met Phe Leu Tyr Glu Tyr Ala Arg Arg
                420                 425                 430

His Pro Asp Tyr Ser Val Val Leu Leu Leu Arg Leu Ala Lys Thr Tyr
            435                 440                 445

Glu Thr Thr Leu Glu Lys Cys Cys Ala Ala Ala Asp Pro His Glu Cys
        450                 455                 460

Tyr Ala Lys Val Phe Asp Glu Phe Lys Pro Leu Val Glu Glu Pro Gln
465                 470                 475                 480

Asn Leu Ile Lys Gln Asn Cys Glu Leu Phe Glu Gln Leu Gly Glu Tyr
                485                 490                 495

Lys Phe Gln Asn Ala Leu Leu Val Arg Tyr Thr Lys Lys Val Pro Gln
            500                 505                 510

Val Ser Thr Pro Thr Leu Val Glu Val Ser Arg Asn Leu Gly Lys Val
        515                 520                 525

Gly Ser Lys Cys Cys Lys His Pro Glu Ala Lys Arg Met Pro Cys Ala
    530                 535                 540

Glu Asp Tyr Leu Ser Val Val Leu Asn Gln Leu Cys Val Leu His Glu
545                 550                 555                 560

Lys Thr Pro Val Ser Asp Arg Val Thr Lys Cys Cys Thr Glu Ser Leu
                565                 570                 575

Val Asn Arg Arg Pro Cys Phe Ser Ala Leu Glu Val Asp Glu Thr Tyr
                580                 585                 590

Val Pro Lys Glu Phe Asn Ala Glu Thr Phe Thr Phe His Ala Asp Ile
            595                 600                 605

Cys Thr Leu Ser Glu Lys Glu Arg Gln Ile Lys Lys Gln Thr Ala Leu

```
                610                 615                 620
Val Glu Leu Val Lys His Lys Pro Lys Ala Thr Lys Glu Gln Leu Lys
625                 630                 635                 640

Ala Val Met Asp Asp Phe Ala Ala Phe Val Glu Lys Cys Cys Lys Ala
                645                 650                 655

Asp Asp Lys Glu Thr Cys Phe Ala Glu Gly Lys Lys Leu Val Ala
            660                 665                 670

Ala Ser Gln Ala Ala Leu Gly Leu
        675                 680

<210> SEQ ID NO 135
<211> LENGTH: 785
<212> TYPE: PRT
<213> ORGANISM: Artificial Sequence
<220> FEATURE:
<223> OTHER INFORMATION: synthetic construct

<400> SEQUENCE: 135

Ser Gln Ile Glu Val Lys Asp Val Thr Asp Thr Thr Ala Leu Ile Thr
1               5                   10                  15

Trp Ser Asp Asp Phe Gly Glu Tyr Val Trp Cys Glu Leu Thr Tyr Gly
            20                  25                  30

Ile Lys Asp Val Pro Gly Asp Arg Thr Thr Ile Asp Leu Trp Tyr His
        35                  40                  45

His Ala His Tyr Ser Ile Gly Asn Leu Lys Pro Asp Thr Glu Tyr Glu
    50                  55                  60

Val Ser Leu Ile Cys Arg Ser Gly Asp Met Ser Ser Asn Pro Ala Lys
65                  70                  75                  80

Glu Thr Phe Thr Thr Gly Gly Gly Ser Gly Gly Gly Ser Gly
                85                  90                  95

Gly Gly Gly Ser Arg Leu Asp Ala Pro Ser Gln Ile Glu Val Lys Asp
            100                 105                 110

Val Thr Asp Thr Thr Ala Leu Ile Thr Trp Ser Asp Asp Phe Gly Glu
        115                 120                 125

Tyr Val Trp Cys Glu Leu Thr Tyr Gly Ile Lys Asp Val Pro Gly Asp
    130                 135                 140

Arg Thr Thr Ile Asp Leu Trp Tyr His His Ala His Tyr Ser Ile Gly
145                 150                 155                 160

Asn Leu Lys Pro Asp Thr Glu Tyr Glu Val Ser Leu Ile Cys Arg Ser
                165                 170                 175

Gly Asp Met Ser Ser Asn Pro Ala Lys Glu Thr Phe Thr Thr Gly Gly
            180                 185                 190

Gly Gly Ser Gly Gly Gly Gly Ser Asp Ala His Lys Ser Glu Val Ala
        195                 200                 205

His Arg Phe Lys Asp Leu Gly Glu Glu Asn Phe Lys Ala Leu Val Leu
    210                 215                 220

Ile Ala Phe Ala Gln Tyr Leu Gln Gln Ser Pro Phe Glu Asp His Val
225                 230                 235                 240

Lys Leu Val Asn Glu Val Thr Glu Phe Ala Lys Thr Cys Val Ala Asp
                245                 250                 255

Glu Ser Ala Glu Asn Cys Asp Lys Ser Leu His Thr Leu Phe Gly Asp
            260                 265                 270

Lys Leu Cys Thr Val Ala Thr Leu Arg Glu Thr Tyr Gly Glu Met Ala
        275                 280                 285

Asp Cys Cys Ala Lys Gln Glu Pro Glu Arg Asn Glu Cys Phe Leu Gln
```

```
            290                 295                 300
His Lys Asp Asp Asn Pro Asn Leu Pro Arg Leu Val Arg Pro Glu Val
305                 310                 315                 320

Asp Val Met Cys Thr Ala Phe His Asp Asn Glu Thr Phe Leu Lys
                325                 330                 335

Lys Tyr Leu Tyr Glu Ile Ala Arg Arg His Pro Tyr Phe Tyr Ala Pro
            340                 345                 350

Glu Leu Leu Phe Phe Ala Lys Arg Tyr Lys Ala Ala Phe Thr Glu Cys
                355                 360                 365

Cys Gln Ala Ala Asp Lys Ala Ala Cys Leu Leu Pro Lys Leu Asp Glu
            370                 375                 380

Leu Arg Asp Glu Gly Lys Ala Ser Ser Ala Lys Gln Arg Leu Lys Cys
385                 390                 395                 400

Ala Ser Leu Gln Lys Phe Gly Glu Arg Ala Phe Lys Ala Trp Ala Val
                405                 410                 415

Ala Arg Leu Ser Gln Arg Phe Pro Lys Ala Glu Phe Ala Glu Val Ser
            420                 425                 430

Lys Leu Val Thr Asp Leu Thr Lys Val His Thr Glu Cys Cys His Gly
                435                 440                 445

Asp Leu Leu Glu Cys Ala Asp Asp Arg Ala Asp Leu Ala Lys Tyr Ile
            450                 455                 460

Cys Glu Asn Gln Asp Ser Ile Ser Ser Lys Leu Lys Glu Cys Cys Glu
465                 470                 475                 480

Lys Pro Leu Leu Glu Lys Ser His Cys Ile Ala Glu Val Glu Asn Asp
                485                 490                 495

Glu Met Pro Ala Asp Leu Pro Ser Leu Ala Ala Asp Phe Val Glu Ser
            500                 505                 510

Lys Asp Val Cys Lys Asn Tyr Ala Glu Ala Lys Asp Val Phe Leu Gly
                515                 520                 525

Met Phe Leu Tyr Glu Tyr Ala Arg Arg His Pro Asp Tyr Ser Val Val
            530                 535                 540

Leu Leu Leu Arg Leu Ala Lys Thr Tyr Glu Thr Thr Leu Glu Lys Cys
545                 550                 555                 560

Cys Ala Ala Ala Asp Pro His Glu Cys Tyr Ala Lys Val Phe Asp Glu
                565                 570                 575

Phe Lys Pro Leu Val Glu Glu Pro Gln Asn Leu Ile Lys Gln Asn Cys
            580                 585                 590

Glu Leu Phe Glu Gln Leu Gly Glu Tyr Lys Phe Gln Asn Ala Leu Leu
                595                 600                 605

Val Arg Tyr Thr Lys Lys Val Pro Gln Val Ser Thr Pro Thr Leu Val
            610                 615                 620

Glu Val Ser Arg Asn Leu Gly Lys Val Gly Ser Lys Cys Cys Lys His
625                 630                 635                 640

Pro Glu Ala Lys Arg Met Pro Cys Ala Glu Asp Tyr Leu Ser Val Val
                645                 650                 655

Leu Asn Gln Leu Cys Val Leu His Glu Lys Thr Pro Val Ser Asp Arg
            660                 665                 670

Val Thr Lys Cys Cys Thr Glu Ser Leu Val Asn Arg Arg Pro Cys Phe
                675                 680                 685

Ser Ala Leu Glu Val Asp Glu Thr Tyr Val Pro Lys Glu Phe Asn Ala
            690                 695                 700

Glu Thr Phe Thr Phe His Ala Asp Ile Cys Thr Leu Ser Glu Lys Glu
705                 710                 715                 720
```

```
Arg Gln Ile Lys Lys Gln Thr Ala Leu Val Glu Leu Val Lys His Lys
            725                 730                 735

Pro Lys Ala Thr Lys Glu Gln Leu Lys Ala Val Met Asp Asp Phe Ala
            740                 745                 750

Ala Phe Val Glu Lys Cys Cys Lys Ala Asp Asp Lys Glu Thr Cys Phe
            755                 760                 765

Ala Glu Glu Gly Lys Lys Leu Val Ala Ala Ser Gln Ala Ala Leu Gly
            770                 775                 780

Leu
785

<210> SEQ ID NO 136
<211> LENGTH: 7
<212> TYPE: PRT
<213> ORGANISM: Artificial Sequence
<220> FEATURE:
<223> OTHER INFORMATION: synthetic construct

<400> SEQUENCE: 136

Glu Asp Val Thr Asp Thr Thr
1               5

<210> SEQ ID NO 137
<211> LENGTH: 8
<212> TYPE: PRT
<213> ORGANISM: Artificial Sequence
<220> FEATURE:
<223> OTHER INFORMATION: synthetic construct

<400> SEQUENCE: 137

Gly Asn Leu Lys Pro Asp Thr Lys
1               5

<210> SEQ ID NO 138
<211> LENGTH: 585
<212> TYPE: PRT
<213> ORGANISM: Homo sapiens

<400> SEQUENCE: 138

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160
```

-continued

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
                195                 200                 205

Arg Ala Phe Lys Ala Trp Ala Val Ala Arg Leu Ser Gln Arg Phe Pro
            210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
                275                 280                 285

Cys Ile Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

```
Ala Ala Ser Gln Ala Ala Leu Gly Leu
        580                 585

<210> SEQ ID NO 139
<211> LENGTH: 10
<212> TYPE: PRT
<213> ORGANISM: Artificial Sequence
<220> FEATURE:
<223> OTHER INFORMATION: synthetic construct

<400> SEQUENCE: 139

Arg Ser Gly Asp Met Ser Ser Asn Pro Ala
1               5                   10

<210> SEQ ID NO 140
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: Xaa  is any of Ala, Gly, Leu, Ile and Val
<220> FEATURE:
<221> NAME/KEY: MISC_FEATURE
<222> LOCATION: (10)..(10)
<223> OTHER INFORMATION: Xaa  is any of Ala, Gly, Leu, Ile and Val

<400> SEQUENCE: 140

Gly Gly Gly Gly Xaa Gly Gly Gly Gly Xaa
1               5                   10

<210> SEQ ID NO 141
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: Xaa is any of Ala, Gly, Leu, Ile and Val
<220> FEATURE:
<221> NAME/KEY: MISC_FEATURE
<222> LOCATION: (10)..(10)
<223> OTHER INFORMATION: Xaa is any of Ala, Gly, Leu, Ile and Val
<220> FEATURE:
<221> NAME/KEY: MISC_FEATURE
<222> LOCATION: (15)..(15)
<223> OTHER INFORMATION: Xaa is any of Ala, Gly, Leu, Ile and Val

<400> SEQUENCE: 141

Gly Gly Gly Gly Xaa Gly Gly Gly Gly Xaa Gly Gly Gly Gly Xaa
1               5                   10                  15

<210> SEQ ID NO 142
<211> LENGTH: 10
<212> TYPE: PRT
<213> ORGANISM: Artificial Sequence
<220> FEATURE:
<223> OTHER INFORMATION: synthetic construct

<400> SEQUENCE: 142

Gly Gly Gly Gly Gly Gly Gly Gly Gly Gly
1               5                   10

<210> SEQ ID NO 143
<211> LENGTH: 15
<212> TYPE: PRT
```

<213> ORGANISM: Artificial Sequence
<220> FEATURE:
<223> OTHER INFORMATION: synthetic construct

<400> SEQUENCE: 143

```
Gly Gly Gly Gly Gly Gly Gly Gly Gly Gly Gly Gly Gly Gly Gly
1               5                   10                  15
```

<210> SEQ ID NO 144
<211> LENGTH: 680
<212> TYPE: PRT
<213> ORGANISM: Artificial Sequence
<220> FEATURE:
<223> OTHER INFORMATION: synthetic construct

<400> SEQUENCE: 144

```
Ser Gln Ile Glu Val Lys Asp Val Thr Asp Thr Thr Ala Leu Ile Thr
1               5                   10                  15

Trp Ser Asp Asp Phe Gly Glu Tyr Val Trp Cys Glu Leu Thr Tyr Gly
                20                  25                  30

Ile Lys Asp Val Pro Gly Asp Arg Thr Thr Ile Asp Leu Trp Tyr His
            35                  40                  45

His Ala His Tyr Ser Ile Gly Asn Leu Lys Pro Asp Thr Glu Tyr Glu
    50                  55                  60

Val Ser Leu Ile Cys Arg Ser Gly Asp Met Ser Ser Asn Pro Ala Lys
65                  70                  75                  80

Glu Thr Phe Thr Thr Gly Gly Gly Gly Gly Gly Gly Gly Gly Gly Asp
                85                  90                  95

Ala His Lys Ser Glu Val Ala His Arg Phe Lys Asp Leu Gly Glu Glu
            100                 105                 110

Asn Phe Lys Ala Leu Val Leu Ile Ala Phe Ala Gln Tyr Leu Gln Gln
        115                 120                 125

Ser Pro Phe Glu Asp His Val Lys Leu Val Asn Glu Val Thr Glu Phe
    130                 135                 140

Ala Lys Thr Cys Val Ala Asp Glu Ser Ala Glu Asn Cys Asp Lys Ser
145                 150                 155                 160

Leu His Thr Leu Phe Gly Asp Lys Leu Cys Thr Val Ala Thr Leu Arg
                165                 170                 175

Glu Thr Tyr Gly Glu Met Ala Asp Cys Cys Ala Lys Gln Glu Pro Glu
            180                 185                 190

Arg Asn Glu Cys Phe Leu Gln His Lys Asp Asp Asn Pro Asn Leu Pro
        195                 200                 205

Arg Leu Val Arg Pro Glu Val Asp Val Met Cys Thr Ala Phe His Asp
    210                 215                 220

Asn Glu Glu Thr Phe Leu Lys Lys Tyr Leu Tyr Glu Ile Ala Arg Arg
225                 230                 235                 240

His Pro Tyr Phe Tyr Ala Pro Glu Leu Leu Phe Phe Ala Lys Arg Tyr
                245                 250                 255

Lys Ala Ala Phe Thr Glu Cys Cys Gln Ala Ala Asp Lys Ala Ala Cys
            260                 265                 270

Leu Leu Pro Lys Leu Asp Glu Leu Arg Asp Glu Gly Lys Ala Ser Ser
        275                 280                 285

Ala Lys Gln Arg Leu Lys Cys Ala Ser Leu Gln Lys Phe Gly Glu Arg
    290                 295                 300

Ala Phe Lys Ala Trp Ala Val Ala Arg Leu Ser Gln Arg Phe Pro Lys
305                 310                 315                 320
```

Ala Glu Phe Ala Glu Val Ser Lys Leu Val Thr Asp Leu Thr Lys Val
            325                 330                 335

His Thr Glu Cys Cys His Gly Asp Leu Leu Glu Cys Ala Asp Asp Arg
        340                 345                 350

Ala Asp Leu Ala Lys Tyr Ile Cys Glu Asn Gln Asp Ser Ile Ser Ser
    355                 360                 365

Lys Leu Lys Glu Cys Cys Glu Lys Pro Leu Leu Glu Lys Ser His Cys
370                 375                 380

Ile Ala Glu Val Glu Asn Asp Glu Met Pro Ala Asp Leu Pro Ser Leu
385                 390                 395                 400

Ala Ala Asp Phe Val Glu Ser Lys Asp Val Cys Lys Asn Tyr Ala Glu
            405                 410                 415

Ala Lys Asp Val Phe Leu Gly Met Phe Leu Tyr Glu Tyr Ala Arg Arg
        420                 425                 430

His Pro Asp Tyr Ser Val Val Leu Leu Leu Arg Leu Ala Lys Thr Tyr
    435                 440                 445

Glu Thr Thr Leu Glu Lys Cys Cys Ala Ala Ala Asp Pro His Glu Cys
450                 455                 460

Tyr Ala Lys Val Phe Asp Glu Phe Lys Pro Leu Val Glu Glu Pro Gln
465                 470                 475                 480

Asn Leu Ile Lys Gln Asn Cys Glu Leu Phe Glu Gln Leu Gly Glu Tyr
            485                 490                 495

Lys Phe Gln Asn Ala Leu Leu Val Arg Tyr Thr Lys Lys Val Pro Gln
        500                 505                 510

Val Ser Thr Pro Thr Leu Val Glu Val Ser Arg Asn Leu Gly Lys Val
    515                 520                 525

Gly Ser Lys Cys Cys Lys His Pro Glu Ala Lys Arg Met Pro Cys Ala
530                 535                 540

Glu Asp Tyr Leu Ser Val Val Leu Asn Gln Leu Cys Val Leu His Glu
545                 550                 555                 560

Lys Thr Pro Val Ser Asp Arg Val Thr Lys Cys Cys Thr Glu Ser Leu
            565                 570                 575

Val Asn Arg Arg Pro Cys Phe Ser Ala Leu Glu Val Asp Glu Thr Tyr
        580                 585                 590

Val Pro Lys Glu Phe Asn Ala Glu Thr Phe Thr Phe His Ala Asp Ile
    595                 600                 605

Cys Thr Leu Ser Glu Lys Glu Arg Gln Ile Lys Lys Gln Thr Ala Leu
610                 615                 620

Val Glu Leu Val Lys His Lys Pro Lys Ala Thr Lys Glu Gln Leu Lys
625                 630                 635                 640

Ala Val Met Asp Asp Phe Ala Ala Phe Val Glu Lys Cys Cys Lys Ala
            645                 650                 655

Asp Asp Lys Glu Thr Cys Phe Ala Glu Glu Gly Lys Lys Leu Val Ala
        660                 665                 670

Ala Ser Gln Ala Ala Leu Gly Leu
    675                 680

<210> SEQ ID NO 145
<211> LENGTH: 785
<212> TYPE: PRT
<213> ORGANISM: Artificial Sequence
<220> FEATURE:
<223> OTHER INFORMATION: synthetic construct

<400> SEQUENCE: 145

-continued

```
Ser Gln Ile Glu Val Lys Asp Val Thr Asp Thr Thr Ala Leu Ile Thr
1               5                   10                  15

Trp Ser Asp Asp Phe Gly Glu Tyr Val Trp Cys Glu Leu Thr Tyr Gly
            20                  25                  30

Ile Lys Asp Val Pro Gly Asp Arg Thr Thr Ile Asp Leu Trp Tyr His
            35                  40                  45

His Ala His Tyr Ser Ile Gly Asn Leu Lys Pro Asp Thr Glu Tyr Glu
        50                  55                  60

Val Ser Leu Ile Cys Arg Ser Gly Asp Met Ser Ser Asn Pro Ala Lys
65                  70                  75                  80

Glu Thr Phe Thr Thr Gly Gly Gly Gly Gly Gly Gly Gly Gly Gly Gly
                85                  90                  95

Gly Gly Gly Gly Arg Leu Asp Ala Pro Ser Gln Ile Glu Val Lys Asp
                100                 105                 110

Val Thr Asp Thr Thr Ala Leu Ile Thr Trp Ser Asp Asp Phe Gly Glu
            115                 120                 125

Tyr Val Trp Cys Glu Leu Thr Tyr Gly Ile Lys Asp Val Pro Gly Asp
            130                 135                 140

Arg Thr Thr Ile Asp Leu Trp Tyr His His Ala His Tyr Ser Ile Gly
145                 150                 155                 160

Asn Leu Lys Pro Asp Thr Glu Tyr Glu Val Ser Leu Ile Cys Arg Ser
                165                 170                 175

Gly Asp Met Ser Ser Asn Pro Ala Lys Glu Thr Phe Thr Thr Gly Gly
            180                 185                 190

Gly Gly Gly Gly Gly Gly Gly Asp Ala His Lys Ser Glu Val Ala
        195                 200                 205

His Arg Phe Lys Asp Leu Gly Glu Glu Asn Phe Lys Ala Leu Val Leu
210                 215                 220

Ile Ala Phe Ala Gln Tyr Leu Gln Gln Ser Pro Phe Glu Asp His Val
225                 230                 235                 240

Lys Leu Val Asn Glu Val Thr Glu Phe Ala Lys Thr Cys Val Ala Asp
                245                 250                 255

Glu Ser Ala Glu Asn Cys Asp Lys Ser Leu His Thr Leu Phe Gly Asp
            260                 265                 270

Lys Leu Cys Thr Val Ala Thr Leu Arg Glu Thr Tyr Gly Glu Met Ala
            275                 280                 285

Asp Cys Cys Ala Lys Gln Glu Pro Glu Arg Asn Glu Cys Phe Leu Gln
            290                 295                 300

His Lys Asp Asp Asn Pro Asn Leu Pro Arg Leu Val Arg Pro Glu Val
305                 310                 315                 320

Asp Val Met Cys Thr Ala Phe His Asp Asn Glu Glu Thr Phe Leu Lys
            325                 330                 335

Lys Tyr Leu Tyr Glu Ile Ala Arg Arg His Pro Tyr Phe Tyr Ala Pro
            340                 345                 350

Glu Leu Leu Phe Phe Ala Lys Arg Tyr Lys Ala Ala Phe Thr Glu Cys
            355                 360                 365

Cys Gln Ala Ala Asp Lys Ala Ala Cys Leu Leu Pro Lys Leu Asp Glu
        370                 375                 380

Leu Arg Asp Glu Gly Lys Ala Ser Ser Ala Lys Gln Arg Leu Lys Cys
385                 390                 395                 400

Ala Ser Leu Gln Lys Phe Gly Glu Arg Ala Phe Lys Ala Trp Ala Val
            405                 410                 415

Ala Arg Leu Ser Gln Arg Phe Pro Lys Ala Glu Phe Ala Glu Val Ser
```

```
                420                 425                 430
Lys Leu Val Thr Asp Leu Thr Lys Val His Thr Glu Cys Cys His Gly
            435                 440                 445

Asp Leu Leu Glu Cys Ala Asp Asp Arg Ala Asp Leu Ala Lys Tyr Ile
        450                 455                 460

Cys Glu Asn Gln Asp Ser Ile Ser Ser Lys Leu Lys Glu Cys Cys Glu
465                 470                 475                 480

Lys Pro Leu Leu Glu Lys Ser His Cys Ile Ala Glu Val Glu Asn Asp
                485                 490                 495

Glu Met Pro Ala Asp Leu Pro Ser Leu Ala Ala Asp Phe Val Glu Ser
            500                 505                 510

Lys Asp Val Cys Lys Asn Tyr Ala Glu Ala Lys Asp Val Phe Leu Gly
        515                 520                 525

Met Phe Leu Tyr Glu Tyr Ala Arg Arg His Pro Asp Tyr Ser Val Val
    530                 535                 540

Leu Leu Leu Arg Leu Ala Lys Thr Tyr Glu Thr Thr Leu Glu Lys Cys
545                 550                 555                 560

Cys Ala Ala Ala Asp Pro His Glu Cys Tyr Ala Lys Val Phe Asp Glu
                565                 570                 575

Phe Lys Pro Leu Val Glu Glu Pro Gln Asn Leu Ile Lys Gln Asn Cys
            580                 585                 590

Glu Leu Phe Glu Gln Leu Gly Glu Tyr Lys Phe Gln Asn Ala Leu Leu
        595                 600                 605

Val Arg Tyr Thr Lys Lys Val Pro Gln Val Ser Thr Pro Thr Leu Val
    610                 615                 620

Glu Val Ser Arg Asn Leu Gly Lys Val Gly Ser Lys Cys Cys Lys His
625                 630                 635                 640

Pro Glu Ala Lys Arg Met Pro Cys Ala Glu Asp Tyr Leu Ser Val Val
                645                 650                 655

Leu Asn Gln Leu Cys Val Leu His Glu Lys Thr Pro Val Ser Asp Arg
            660                 665                 670

Val Thr Lys Cys Cys Thr Glu Ser Leu Val Asn Arg Arg Pro Cys Phe
        675                 680                 685

Ser Ala Leu Glu Val Asp Glu Thr Tyr Val Pro Lys Glu Phe Asn Ala
    690                 695                 700

Glu Thr Phe Thr Phe His Ala Asp Ile Cys Thr Leu Ser Glu Lys Glu
705                 710                 715                 720

Arg Gln Ile Lys Lys Gln Thr Ala Leu Val Glu Leu Val Lys His Lys
                725                 730                 735

Pro Lys Ala Thr Lys Glu Gln Leu Lys Ala Val Met Asp Asp Phe Ala
            740                 745                 750

Ala Phe Val Glu Lys Cys Cys Lys Ala Asp Asp Lys Glu Thr Cys Phe
        755                 760                 765

Ala Glu Glu Gly Lys Lys Leu Val Ala Ala Ser Gln Ala Ala Leu Gly
    770                 775                 780

Leu
785

<210> SEQ ID NO 146
<211> LENGTH: 83
<212> TYPE: PRT
<213> ORGANISM: Artificial Sequence
<220> FEATURE:
<223> OTHER INFORMATION: synthetic construct
```

<400> SEQUENCE: 146

Ile Glu Val Lys Asp Val Thr Asp Thr Thr Ala Leu Ile Thr Trp Ser
1               5                   10                  15
Asp Asp Phe Gly Glu Tyr Val Trp Cys Glu Leu Thr Tyr Gly Ile Lys
                20                  25                  30
Asp Val Pro Gly Asp Arg Thr Thr Ile Asp Leu Trp Tyr His His Ala
            35                  40                  45
His Tyr Ser Ile Gly Asn Leu Lys Pro Asp Thr Glu Tyr Glu Val Ser
        50                  55                  60
Leu Ile Cys Arg Ser Gly Asp Met Ser Ser Asn Pro Ala Lys Glu Thr
65                  70                  75                  80
Phe Thr Thr

<210> SEQ ID NO 147
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: Xaa is any of Ser, Ala, Gly, Leu, Ile, and Val

<400> SEQUENCE: 147

Gly Gly Gly Gly Xaa
1               5

<210> SEQ ID NO 148
<211> LENGTH: 5
<212> TYPE: PRT
<213> ORGANISM: Artificial Sequence
<220> FEATURE:
<223> OTHER INFORMATION: synthetic construct

<400> SEQUENCE: 148

Gly Gly Gly Gly Ser
1               5

<210> SEQ ID NO 149
<211> LENGTH: 5
<212> TYPE: PRT
<213> ORGANISM: Artificial Sequence
<220> FEATURE:
<223> OTHER INFORMATION: synthetic construct

<400> SEQUENCE: 149

Gly Gly Gly Gly Gly
1               5

<210> SEQ ID NO 150
<211> LENGTH: 5
<212> TYPE: PRT
<213> ORGANISM: Artificial Sequence
<220> FEATURE:
<223> OTHER INFORMATION: synthetic construct

<400> SEQUENCE: 150

Gly Gly Gly Gly Ala
1               5

<210> SEQ ID NO 151
<211> LENGTH: 8
<212> TYPE: PRT

```
<213> ORGANISM: Artificial Sequence
<220> FEATURE:
<223> OTHER INFORMATION: synthetic construct

<400> SEQUENCE: 151

His His His His His His His His
1               5

<210> SEQ ID NO 152
<211> LENGTH: 13
<212> TYPE: PRT
<213> ORGANISM: Artificial Sequence
<220> FEATURE:
<223> OTHER INFORMATION: synthetic construct

<400> SEQUENCE: 152

Gly Gly Gly Gly Ser His His His His His His His
1               5                   10

<210> SEQ ID NO 153
<211> LENGTH: 584
<212> TYPE: PRT
<213> ORGANISM: mus muscus

<400> SEQUENCE: 153

Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
            20                  25                  30

Lys Cys Ser Tyr Asp Glu His Ala Lys Leu Val Gln Glu Val Thr Asp
        35                  40                  45

Phe Ala Lys Thr Cys Val Ala Asp Glu Ser Ala Ala Asn Cys Asp Lys
    50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
    130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
    210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
```

```
                260                 265                 270
Ser Lys Leu Gln Thr Cys Cys Asp Lys Pro Leu Leu Lys Lys Ala His
            275                 280                 285

Cys Leu Ser Glu Val Glu His Asp Thr Met Pro Ala Asp Leu Pro Ala
290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

Arg His Pro Asp Tyr Ser Val Ser Leu Leu Arg Leu Ala Lys Lys
                340                 345                 350

Tyr Glu Ala Thr Leu Glu Lys Cys Cys Ala Glu Ala Asn Pro Pro Ala
            355                 360                 365

Cys Tyr Gly Thr Val Leu Ala Glu Phe Gln Pro Leu Val Glu Glu Pro
        370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
                405                 410                 415

Gln Val Ser Thr Pro Thr Leu Val Glu Ala Ala Arg Asn Leu Gly Arg
            420                 425                 430

Val Gly Thr Lys Cys Cys Thr Leu Pro Glu Asp Gln Arg Leu Pro Cys
        435                 440                 445

Val Glu Asp Tyr Leu Ser Ala Ile Leu Asn Arg Val Cys Leu Leu His
450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
        515                 520                 525

Leu Ala Glu Leu Val Lys His Lys Pro Lys Ala Thr Ala Glu Gln Leu
    530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
                565                 570                 575

Thr Arg Cys Lys Asp Ala Leu Ala
            580

<210> SEQ ID NO 154
<211> LENGTH: 584
<212> TYPE: PRT
<213> ORGANISM: Artificial Sequence
<220> FEATURE:
<223> OTHER INFORMATION: synthetic construct

<400> SEQUENCE: 154

Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
                20                  25                  30

Lys Ser Ser Tyr Asp Glu His Ala Lys Leu Val Gln Glu Val Thr Asp
```

```
            35                  40                  45
Phe Ala Lys Thr Cys Val Ala Asp Glu Ser Ala Ala Asn Cys Asp Lys
 50                  55                  60
Ser Leu His Thr Leu Phe Gly Asp Lys Leu Cys Ala Ile Pro Asn Leu
 65                  70                  75                  80
Arg Glu Asn Tyr Gly Glu Leu Ala Asp Cys Cys Thr Lys Gln Pro
                     85                  90                  95
Glu Arg Asn Glu Cys Phe Leu Gln His Lys Asp Asp Asn Pro Ser Leu
                100                 105                 110
Pro Pro Phe Glu Arg Pro Glu Ala Glu Ala Met Cys Thr Ser Phe Lys
            115                 120                 125
Glu Asn Pro Thr Thr Phe Met Gly His Tyr Leu His Glu Val Ala Arg
            130                 135                 140
Arg His Pro Tyr Phe Tyr Ala Pro Glu Leu Leu Tyr Tyr Ala Glu Gln
145                 150                 155                 160
Tyr Asn Glu Ile Leu Thr Gln Cys Cys Ala Glu Ala Asp Lys Glu Ser
                165                 170                 175
Cys Leu Thr Pro Lys Leu Asp Gly Val Lys Glu Lys Ala Leu Val Ser
            180                 185                 190
Ser Val Arg Gln Arg Met Lys Cys Ser Ser Met Gln Lys Phe Gly Glu
            195                 200                 205
Arg Ala Phe Lys Ala Trp Ala Val Ala Arg Leu Ser Gln Thr Phe Pro
210                 215                 220
Asn Ala Asp Phe Ala Glu Ile Thr Lys Leu Ala Thr Asp Leu Thr Lys
225                 230                 235                 240
Val Asn Lys Glu Cys Cys His Gly Asp Leu Leu Glu Cys Ala Asp Asp
                245                 250                 255
Arg Ala Glu Leu Ala Lys Tyr Met Cys Glu Asn Gln Ala Thr Ile Ser
            260                 265                 270
Ser Lys Leu Gln Thr Cys Cys Asp Lys Pro Leu Leu Lys Lys Ala His
            275                 280                 285
Cys Leu Ser Glu Val Glu His Asp Thr Met Pro Ala Asp Leu Pro Ala
            290                 295                 300
Ile Ala Ala Asp Phe Val Glu Asp Gln Glu Val Cys Lys Asn Tyr Ala
305                 310                 315                 320
Glu Ala Lys Asp Val Phe Leu Gly Thr Phe Leu Tyr Glu Tyr Ser Arg
                325                 330                 335
Arg His Pro Asp Tyr Ser Val Ser Leu Leu Leu Arg Leu Ala Lys Lys
                340                 345                 350
Tyr Glu Ala Thr Leu Glu Lys Cys Cys Ala Glu Ala Asn Pro Pro Ala
            355                 360                 365
Cys Tyr Gly Thr Val Leu Ala Glu Phe Gln Pro Leu Val Glu Glu Pro
            370                 375                 380
Lys Asn Leu Val Lys Thr Asn Cys Asp Leu Tyr Glu Lys Leu Gly Glu
385                 390                 395                 400
Tyr Gly Phe Gln Asn Ala Ile Leu Val Arg Tyr Thr Gln Lys Ala Pro
                405                 410                 415
Gln Val Ser Thr Pro Thr Leu Val Glu Ala Ala Arg Asn Leu Gly Arg
            420                 425                 430
Val Gly Thr Lys Cys Cys Thr Leu Pro Glu Asp Gln Arg Leu Pro Cys
            435                 440                 445
Val Glu Asp Tyr Leu Ser Ala Ile Leu Asn Arg Val Cys Leu Leu His
450                 455                 460
```

```
Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
                515                 520                 525

Leu Ala Glu Leu Val Lys His Lys Pro Lys Ala Thr Ala Glu Gln Leu
            530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
                565                 570                 575

Thr Arg Ser Lys Asp Ala Leu Ala
            580
```

<210> SEQ ID NO 155
<211> LENGTH: 84
<212> TYPE: PRT
<213> ORGANISM: Artificial Sequence
<220> FEATURE:
<223> OTHER INFORMATION: synthetic construct

<400> SEQUENCE: 155

```
Ile Glu Val Lys Asp Val Thr Asp Thr Thr Ala Leu Ile Thr Trp His
1               5                   10                  15

Asp Ala Phe Gly Tyr Asp Phe Gly Cys Glu Leu Thr Tyr Gly Ile Lys
            20                  25                  30

Asp Val Pro Gly Asp Arg Thr Thr Ile Asp Leu Pro Asp His Phe His
        35                  40                  45

Asn Tyr Ser Ile Gly Asn Leu Lys Pro Asp Thr Glu Tyr Glu Val Ser
    50                  55                  60

Leu Ile Cys Ala Asn Asp His Gly Phe Asp Ser Asn Pro Ala Lys Glu
65                  70                  75                  80

Thr Phe Thr Thr
```

<210> SEQ ID NO 156
<211> LENGTH: 84
<212> TYPE: PRT
<213> ORGANISM: Artificial Sequence
<220> FEATURE:
<223> OTHER INFORMATION: synthetic construct

<400> SEQUENCE: 156

```
Ile Glu Val Lys Asp Val Thr Asp Thr Thr Ala Leu Ile Thr Trp His
1               5                   10                  15

Asp Ala Phe Gly Tyr Asp Phe Gly Cys Glu Leu Thr Tyr Gly Ile Lys
            20                  25                  30

Asp Val Pro Gly Asp Arg Thr Thr Ile Asp Leu Pro Asp His Phe His
        35                  40                  45

Gln Tyr Ser Ile Gly Asn Leu Lys Pro Asp Thr Glu Tyr Glu Val Ser
    50                  55                  60

Leu Ile Cys Ala Asn Asp His Gly Phe Asp Ser Asn Pro Ala Lys Glu
65                  70                  75                  80

Thr Phe Thr Thr
```

<210> SEQ ID NO 157
<211> LENGTH: 183
<212> TYPE: PRT
<213> ORGANISM: Artificial Sequence
<220> FEATURE:
<223> OTHER INFORMATION: synthetic construct

<400> SEQUENCE: 157

```
Ser Gln Ile Glu Val Lys Asp Val Thr Asp Thr Thr Ala Leu Ile Thr
1               5                   10                  15

Trp His Asp Ala Phe Gly Tyr Asp Phe Gly Cys Glu Leu Thr Tyr Gly
            20                  25                  30

Ile Lys Asp Val Pro Gly Asp Arg Thr Thr Ile Asp Leu Pro Asp His
        35                  40                  45

Phe His Gln Tyr Ser Ile Gly Asn Leu Lys Pro Asp Thr Glu Tyr Glu
    50                  55                  60

Val Ser Leu Ile Cys Ala Asn Asp His Gly Phe Asp Ser Asn Pro Ala
65                  70                  75                  80

Lys Glu Thr Phe Thr Thr Gly Gly Gly Ser Arg Leu Asp Ala
                85                  90                  95

Pro Ser Gln Ile Glu Val Lys Asp Val Thr Asp Thr Thr Ala Leu Ile
                100                 105                 110

Thr Trp His Asp Ala Phe Gly Tyr Asp Phe Gly Cys Glu Leu Thr Tyr
            115                 120                 125

Gly Ile Lys Asp Val Pro Gly Asp Arg Thr Thr Ile Asp Leu Pro Asp
        130                 135                 140

His Phe His Gln Tyr Ser Ile Gly Asn Leu Lys Pro Asp Thr Glu Tyr
145                 150                 155                 160

Glu Val Ser Leu Ile Cys Ala Asn Asp His Gly Phe Asp Ser Asn Pro
                165                 170                 175

Ala Lys Glu Thr Phe Thr Thr
            180
```

<210> SEQ ID NO 158
<211> LENGTH: 685
<212> TYPE: PRT
<213> ORGANISM: Artificial Sequence
<220> FEATURE:
<223> OTHER INFORMATION: synthetic construct

<400> SEQUENCE: 158

```
Ser Gln Ile Glu Val Lys Asp Val Thr Asp Thr Thr Ala Leu Ile Thr
1               5                   10                  15

Trp His Asp Ala Phe Gly Tyr Asp Phe Gly Cys Glu Leu Thr Tyr Gly
            20                  25                  30

Ile Lys Asp Val Pro Gly Asp Arg Thr Thr Ile Asp Leu Pro Asp His
        35                  40                  45

Phe His Gln Tyr Ser Ile Gly Asn Leu Lys Pro Asp Thr Glu Tyr Glu
    50                  55                  60

Val Ser Leu Ile Cys Ala Asn Asp His Gly Phe Asp Ser Asn Pro Ala
65                  70                  75                  80

Lys Glu Thr Phe Thr Thr Gly Gly Gly Ser Gly Gly Gly Ser
                85                  90                  95

Gly Gly Gly Gly Ser Glu Ala His Lys Ser Glu Ile Ala His Arg Tyr
                100                 105                 110

Asn Asp Leu Gly Glu Gln His Phe Lys Gly Leu Val Leu Ile Ala Phe
            115                 120                 125
```

```
Ser Gln Tyr Leu Gln Lys Ser Tyr Asp Glu His Ala Lys Leu Val
    130                 135                 140
Gln Glu Val Thr Asp Phe Ala Lys Thr Cys Val Ala Asp Glu Ser Ala
145                 150                 155                 160
Ala Asn Cys Asp Lys Ser Leu His Thr Leu Phe Gly Asp Lys Leu Cys
                165                 170                 175
Ala Ile Pro Asn Leu Arg Glu Asn Tyr Gly Glu Leu Ala Asp Cys Cys
            180                 185                 190
Thr Lys Gln Glu Pro Glu Arg Asn Glu Cys Phe Leu Gln His Lys Asp
        195                 200                 205
Asp Asn Pro Ser Leu Pro Pro Phe Glu Arg Pro Glu Ala Glu Ala Met
210                 215                 220
Cys Thr Ser Phe Lys Glu Asn Pro Thr Thr Phe Met Gly His Tyr Leu
225                 230                 235                 240
His Glu Val Ala Arg Arg His Pro Tyr Phe Tyr Ala Pro Glu Leu Leu
                245                 250                 255
Tyr Tyr Ala Glu Gln Tyr Asn Glu Ile Leu Thr Gln Cys Cys Ala Glu
            260                 265                 270
Ala Asp Lys Glu Ser Cys Leu Thr Pro Lys Leu Asp Gly Val Lys Glu
        275                 280                 285
Lys Ala Leu Val Ser Ser Val Arg Gln Arg Met Lys Cys Ser Ser Met
290                 295                 300
Gln Lys Phe Gly Glu Arg Ala Phe Lys Ala Trp Ala Val Ala Arg Leu
305                 310                 315                 320
Ser Gln Thr Phe Pro Asn Ala Asp Phe Ala Glu Ile Thr Lys Leu Ala
                325                 330                 335
Thr Asp Leu Thr Lys Val Asn Lys Glu Cys Cys His Gly Asp Leu Leu
            340                 345                 350
Glu Cys Ala Asp Asp Arg Ala Glu Leu Ala Lys Tyr Met Cys Glu Asn
        355                 360                 365
Gln Ala Thr Ile Ser Ser Lys Leu Gln Thr Cys Cys Asp Lys Pro Leu
370                 375                 380
Leu Lys Lys Ala His Cys Leu Ser Glu Val Glu His Asp Thr Met Pro
385                 390                 395                 400
Ala Asp Leu Pro Ala Ile Ala Ala Asp Phe Val Glu Asp Gln Glu Val
                405                 410                 415
Cys Lys Asn Tyr Ala Glu Ala Lys Asp Val Phe Leu Gly Thr Phe Leu
            420                 425                 430
Tyr Glu Tyr Ser Arg Arg His Pro Asp Tyr Ser Val Ser Leu Leu Leu
        435                 440                 445
Arg Leu Ala Lys Lys Tyr Glu Ala Thr Leu Glu Lys Cys Cys Ala Glu
450                 455                 460
Ala Asn Pro Pro Ala Cys Tyr Gly Thr Val Leu Ala Glu Phe Gln Pro
465                 470                 475                 480
Leu Val Glu Glu Pro Lys Asn Leu Val Lys Thr Asn Cys Asp Leu Tyr
                485                 490                 495
Glu Lys Leu Gly Glu Tyr Gly Phe Gln Asn Ala Ile Leu Val Arg Tyr
            500                 505                 510
Thr Gln Lys Ala Pro Gln Val Ser Thr Pro Thr Leu Val Glu Ala Ala
        515                 520                 525
Arg Asn Leu Gly Arg Val Gly Thr Lys Cys Cys Thr Leu Pro Glu Asp
530                 535                 540
```

```
Gln Arg Leu Pro Cys Val Glu Asp Tyr Leu Ser Ala Ile Leu Asn Arg
545                 550                 555                 560

Val Cys Leu Leu His Glu Lys Thr Pro Val Ser Glu His Val Thr Lys
                565                 570                 575

Cys Cys Ser Gly Ser Leu Val Glu Arg Arg Pro Cys Phe Ser Ala Leu
            580                 585                 590

Thr Val Asp Glu Thr Tyr Val Pro Lys Glu Phe Lys Ala Glu Thr Phe
        595                 600                 605

Thr Phe His Ser Asp Ile Cys Thr Leu Pro Glu Lys Glu Lys Gln Ile
    610                 615                 620

Lys Lys Gln Thr Ala Leu Ala Glu Leu Val Lys His Lys Pro Lys Ala
625                 630                 635                 640

Thr Ala Glu Gln Leu Lys Thr Val Met Asp Asp Phe Ala Gln Phe Leu
                645                 650                 655

Asp Thr Cys Cys Lys Ala Ala Asp Lys Asp Thr Cys Phe Ser Thr Glu
            660                 665                 670

Gly Pro Asn Leu Val Thr Arg Ser Lys Asp Ala Leu Ala
        675                 680                 685

<210> SEQ ID NO 159
<211> LENGTH: 782
<212> TYPE: PRT
<213> ORGANISM: Artificial Sequence
<220> FEATURE:
<223> OTHER INFORMATION: synthetic construct

<400> SEQUENCE: 159

Ser Gln Ile Glu Val Lys Asp Val Thr Asp Thr Ala Leu Ile Thr
1               5                   10                  15

Trp His Asp Ala Phe Gly Tyr Asp Phe Gly Cys Glu Leu Thr Tyr Gly
                20                  25                  30

Ile Lys Asp Val Pro Gly Asp Arg Thr Thr Ile Asp Leu Pro Asp His
            35                  40                  45

Phe His Gln Tyr Ser Ile Gly Asn Leu Lys Pro Asp Thr Glu Tyr Glu
    50                  55                  60

Val Ser Leu Ile Cys Ala Asn Asp His Gly Phe Asp Ser Asn Pro Ala
65                  70                  75                  80

Lys Glu Thr Phe Thr Thr Gly Gly Gly Ser Arg Leu Asp Ala
                85                  90                  95

Pro Ser Gln Ile Glu Val Lys Asp Val Thr Asp Thr Ala Leu Ile
            100                 105                 110

Thr Trp His Asp Ala Phe Gly Tyr Asp Phe Gly Cys Glu Leu Thr Tyr
    115                 120                 125

Gly Ile Lys Asp Val Pro Gly Asp Arg Thr Thr Ile Asp Leu Pro Asp
130                 135                 140

His Phe His Gln Tyr Ser Ile Gly Asn Leu Lys Pro Asp Thr Glu Tyr
145                 150                 155                 160

Glu Val Ser Leu Ile Cys Ala Asn Asp His Gly Phe Asp Ser Asn Pro
                165                 170                 175

Ala Lys Glu Thr Phe Thr Thr Gly Gly Gly Ser Gly Gly Gly
            180                 185                 190

Ser Gly Gly Gly Gly Ser Glu Ala His Lys Ser Glu Ile Ala His Arg
        195                 200                 205

Tyr Asn Asp Leu Gly Glu Gln His Phe Lys Gly Leu Val Leu Ile Ala
    210                 215                 220
```

```
Phe Ser Gln Tyr Leu Gln Lys Ser Ser Tyr Asp Glu His Ala Lys Leu
225                 230                 235                 240

Val Gln Glu Val Thr Asp Phe Ala Lys Thr Cys Val Ala Asp Glu Ser
                245                 250                 255

Ala Ala Asn Cys Asp Lys Ser Leu His Thr Leu Phe Gly Asp Lys Leu
            260                 265                 270

Cys Ala Ile Pro Asn Leu Arg Glu Asn Tyr Gly Glu Leu Ala Asp Cys
        275                 280                 285

Cys Thr Lys Gln Glu Pro Glu Arg Asn Glu Cys Phe Leu Gln His Lys
    290                 295                 300

Asp Asp Asn Pro Ser Leu Pro Pro Phe Glu Arg Pro Glu Ala Glu Ala
305                 310                 315                 320

Met Cys Thr Ser Phe Lys Glu Asn Pro Thr Thr Phe Met Gly His Tyr
                325                 330                 335

Leu His Glu Val Ala Arg Arg His Pro Tyr Phe Tyr Ala Pro Glu Leu
            340                 345                 350

Leu Tyr Tyr Ala Glu Gln Tyr Asn Glu Ile Leu Thr Gln Cys Cys Ala
        355                 360                 365

Glu Ala Asp Lys Glu Ser Cys Leu Thr Pro Lys Leu Asp Gly Val Lys
    370                 375                 380

Glu Lys Ala Leu Val Ser Ser Val Arg Gln Arg Met Lys Cys Ser Ser
385                 390                 395                 400

Met Gln Lys Phe Gly Glu Arg Ala Phe Lys Ala Trp Ala Val Ala Arg
                405                 410                 415

Leu Ser Gln Thr Phe Pro Asn Ala Asp Phe Ala Glu Ile Thr Lys Leu
            420                 425                 430

Ala Thr Asp Leu Thr Lys Val Asn Lys Glu Cys Cys His Gly Asp Leu
        435                 440                 445

Leu Glu Cys Ala Asp Asp Arg Ala Glu Leu Ala Lys Tyr Met Cys Glu
    450                 455                 460

Asn Gln Ala Thr Ile Ser Ser Lys Leu Gln Thr Cys Cys Asp Lys Pro
465                 470                 475                 480

Leu Leu Lys Lys Ala His Cys Leu Ser Glu Val Glu His Asp Thr Met
                485                 490                 495

Pro Ala Asp Leu Pro Ala Ile Ala Ala Asp Phe Val Glu Asp Gln Glu
            500                 505                 510

Val Cys Lys Asn Tyr Ala Glu Ala Lys Asp Val Phe Leu Gly Thr Phe
        515                 520                 525

Leu Tyr Glu Tyr Ser Arg Arg His Pro Asp Tyr Ser Val Ser Leu Leu
    530                 535                 540

Leu Arg Leu Ala Lys Lys Tyr Glu Ala Thr Leu Glu Lys Cys Cys Ala
545                 550                 555                 560

Glu Ala Asn Pro Pro Ala Cys Tyr Gly Thr Val Leu Ala Glu Phe Gln
                565                 570                 575

Pro Leu Val Glu Glu Pro Lys Asn Leu Val Lys Thr Asn Cys Asp Leu
            580                 585                 590

Tyr Glu Lys Leu Gly Glu Tyr Gly Phe Gln Asn Ala Ile Leu Val Arg
        595                 600                 605

Tyr Thr Gln Lys Ala Pro Gln Val Ser Thr Pro Thr Leu Val Glu Ala
    610                 615                 620

Ala Arg Asn Leu Gly Arg Val Gly Thr Lys Cys Cys Thr Leu Pro Glu
625                 630                 635                 640

Asp Gln Arg Leu Pro Cys Val Glu Asp Tyr Leu Ser Ala Ile Leu Asn
```

```
                    645                 650                 655

Arg Val Cys Leu Leu His Glu Lys Thr Pro Val Ser Glu His Val Thr
                660                 665                 670

Lys Cys Cys Ser Gly Ser Leu Val Glu Arg Arg Pro Cys Phe Ser Ala
                675                 680                 685

Leu Thr Val Asp Glu Thr Tyr Val Pro Lys Glu Phe Lys Ala Glu Thr
                690                 695                 700

Phe Thr Phe His Ser Asp Ile Cys Thr Leu Pro Glu Lys Glu Lys Gln
705                 710                 715                 720

Ile Lys Lys Gln Thr Ala Leu Ala Glu Leu Val Lys His Lys Pro Lys
                725                 730                 735

Ala Thr Ala Glu Gln Leu Lys Thr Val Met Asp Asp Phe Ala Gln Phe
                740                 745                 750

Leu Asp Thr Cys Cys Lys Ala Ala Asp Lys Asp Thr Cys Phe Ser Thr
                755                 760                 765

Glu Gly Pro Asn Leu Val Thr Arg Ser Lys Asp Ala Leu Ala
                770                 775                 780
```

<210> SEQ ID NO 160
<211> LENGTH: 84
<212> TYPE: PRT
<213> ORGANISM: Artificial Sequence
<220> FEATURE:
<223> OTHER INFORMATION: synthetic construct

<400> SEQUENCE: 160

```
Ile Glu Val Lys Asp Val Thr Asp Thr Thr Ala Leu Ile Thr Trp His
1               5                   10                  15

Asp Pro Ser Gly Tyr Asp Phe Trp Cys Glu Leu Thr Tyr Gly Ile Lys
                20                  25                  30

Asp Val Pro Gly Asp Arg Thr Thr Ile Asp Leu Pro Asp His Phe His
                35                  40                  45

Asn Tyr Ser Ile Gly Asn Leu Lys Pro Asp Thr Glu Tyr Glu Val Ser
        50                  55                  60

Leu Ile Cys Ala Asn Asp His Gly Phe Asp Ser Tyr Pro Ala Lys Glu
65              70                  75                  80

Thr Phe Thr Thr
```

<210> SEQ ID NO 161
<211> LENGTH: 84
<212> TYPE: PRT
<213> ORGANISM: Artificial Sequence
<220> FEATURE:
<223> OTHER INFORMATION: synthetic construct

<400> SEQUENCE: 161

```
Ile Glu Val Lys Asp Val Thr Asp Thr Thr Ala Leu Ile Thr Trp His
1               5                   10                  15

Asp Pro Ser Gly Tyr Asp Phe Trp Cys Glu Leu Thr Tyr Gly Ile Lys
                20                  25                  30

Asp Val Pro Gly Asp Arg Thr Thr Ile Asp Leu Pro Asp His Phe His
                35                  40                  45

Gln Tyr Ser Ile Gly Asn Leu Lys Pro Asp Thr Glu Tyr Glu Val Ser
        50                  55                  60

Leu Ile Cys Ala Asn Asp His Gly Phe Asp Ser Tyr Pro Ala Lys Glu
65              70                  75                  80

Thr Phe Thr Thr
```

<210> SEQ ID NO 162
<211> LENGTH: 183
<212> TYPE: PRT
<213> ORGANISM: Artificial Sequence
<220> FEATURE:
<223> OTHER INFORMATION: synthetic construct

<400> SEQUENCE: 162

```
Ser Gln Ile Glu Val Lys Asp Val Thr Asp Thr Thr Ala Leu Ile Thr
1               5                   10                  15

Trp His Asp Pro Ser Gly Tyr Asp Phe Trp Cys Glu Leu Thr Tyr Gly
            20                  25                  30

Ile Lys Asp Val Pro Gly Asp Arg Thr Thr Ile Asp Leu Pro Asp His
        35                  40                  45

Phe His Gln Tyr Ser Ile Gly Asn Leu Lys Pro Asp Thr Glu Tyr Glu
    50                  55                  60

Val Ser Leu Ile Cys Ala Asn Asp His Gly Phe Asp Ser Tyr Pro Ala
65                  70                  75                  80

Lys Glu Thr Phe Thr Thr Thr Gly Gly Gly Ser Arg Leu Asp Ala
            85                  90                  95

Pro Ser Gln Ile Glu Val Lys Asp Val Thr Asp Thr Thr Ala Leu Ile
            100                 105                 110

Thr Trp His Asp Pro Ser Gly Tyr Asp Phe Trp Cys Glu Leu Thr Tyr
        115                 120                 125

Gly Ile Lys Asp Val Pro Gly Asp Arg Thr Thr Ile Asp Leu Pro Asp
    130                 135                 140

His Phe His Gln Tyr Ser Ile Gly Asn Leu Lys Pro Asp Thr Glu Tyr
145                 150                 155                 160

Glu Val Ser Leu Ile Cys Ala Asn Asp His Gly Phe Asp Ser Tyr Pro
                165                 170                 175

Ala Lys Glu Thr Phe Thr Thr
            180
```

<210> SEQ ID NO 163
<211> LENGTH: 685
<212> TYPE: PRT
<213> ORGANISM: Artificial Sequence
<220> FEATURE:
<223> OTHER INFORMATION: synthetic construct

<400> SEQUENCE: 163

```
Ser Gln Ile Glu Val Lys Asp Val Thr Asp Thr Thr Ala Leu Ile Thr
1               5                   10                  15

Trp His Asp Pro Ser Gly Tyr Asp Phe Trp Cys Glu Leu Thr Tyr Gly
            20                  25                  30

Ile Lys Asp Val Pro Gly Asp Arg Thr Thr Ile Asp Leu Pro Asp His
        35                  40                  45

Phe His Gln Tyr Ser Ile Gly Asn Leu Lys Pro Asp Thr Glu Tyr Glu
    50                  55                  60

Val Ser Leu Ile Cys Ala Asn Asp His Gly Phe Asp Ser Tyr Pro Ala
65                  70                  75                  80

Lys Glu Thr Phe Thr Thr Gly Gly Gly Ser Gly Gly Gly Ser
            85                  90                  95

Gly Gly Gly Gly Ser Glu Ala His Lys Ser Glu Ile Ala His Arg Tyr
            100                 105                 110

Asn Asp Leu Gly Glu Gln His Phe Lys Gly Leu Val Leu Ile Ala Phe
```

```
              115                 120                 125
Ser Gln Tyr Leu Gln Lys Ser Tyr Asp Glu His Ala Lys Leu Val
    130                 135                 140
Gln Glu Val Thr Asp Phe Ala Lys Thr Cys Val Ala Asp Glu Ser Ala
145                 150                 155                 160
Ala Asn Cys Asp Lys Ser Leu His Thr Leu Phe Gly Asp Lys Leu Cys
                165                 170                 175
Ala Ile Pro Asn Leu Arg Glu Asn Tyr Gly Glu Leu Ala Asp Cys Cys
            180                 185                 190
Thr Lys Gln Glu Pro Glu Arg Asn Glu Cys Phe Leu Gln His Lys Asp
        195                 200                 205
Asp Asn Pro Ser Leu Pro Pro Phe Glu Arg Pro Glu Ala Glu Ala Met
    210                 215                 220
Cys Thr Ser Phe Lys Glu Asn Pro Thr Thr Phe Met Gly His Tyr Leu
225                 230                 235                 240
His Glu Val Ala Arg Arg His Pro Tyr Phe Tyr Ala Pro Glu Leu Leu
                245                 250                 255
Tyr Tyr Ala Glu Gln Tyr Asn Glu Ile Leu Thr Gln Cys Cys Ala Glu
            260                 265                 270
Ala Asp Lys Glu Ser Cys Leu Thr Pro Lys Leu Asp Gly Val Lys Glu
        275                 280                 285
Lys Ala Leu Val Ser Ser Val Arg Gln Arg Met Lys Cys Ser Ser Met
    290                 295                 300
Gln Lys Phe Gly Glu Arg Ala Phe Lys Ala Trp Ala Val Ala Arg Leu
305                 310                 315                 320
Ser Gln Thr Phe Pro Asn Ala Asp Phe Ala Glu Ile Thr Lys Leu Ala
                325                 330                 335
Thr Asp Leu Thr Lys Val Asn Lys Glu Cys Cys His Gly Asp Leu Leu
            340                 345                 350
Glu Cys Ala Asp Asp Arg Ala Glu Leu Ala Lys Tyr Met Cys Glu Asn
        355                 360                 365
Gln Ala Thr Ile Ser Ser Lys Leu Gln Thr Cys Cys Asp Lys Pro Leu
    370                 375                 380
Leu Lys Lys Ala His Cys Leu Ser Glu Val Glu His Asp Thr Met Pro
385                 390                 395                 400
Ala Asp Leu Pro Ala Ile Ala Ala Asp Phe Val Glu Asp Gln Glu Val
                405                 410                 415
Cys Lys Asn Tyr Ala Glu Ala Lys Asp Val Phe Leu Gly Thr Phe Leu
            420                 425                 430
Tyr Glu Tyr Ser Arg Arg His Pro Asp Tyr Ser Val Ser Leu Leu Leu
        435                 440                 445
Arg Leu Ala Lys Lys Tyr Glu Ala Thr Leu Glu Lys Cys Cys Ala Glu
    450                 455                 460
Ala Asn Pro Pro Ala Cys Tyr Gly Thr Val Leu Ala Glu Phe Gln Pro
465                 470                 475                 480
Leu Val Glu Glu Pro Lys Asn Leu Val Lys Thr Asn Cys Asp Leu Tyr
                485                 490                 495
Glu Lys Leu Gly Glu Tyr Gly Phe Gln Asn Ala Ile Leu Val Arg Tyr
            500                 505                 510
Thr Gln Lys Ala Pro Gln Val Ser Thr Pro Thr Leu Val Glu Ala Ala
        515                 520                 525
Arg Asn Leu Gly Arg Val Gly Thr Lys Cys Cys Thr Leu Pro Glu Asp
    530                 535                 540
```

```
Gln Arg Leu Pro Cys Val Glu Asp Tyr Leu Ser Ala Ile Leu Asn Arg
545                 550                 555                 560

Val Cys Leu Leu His Glu Lys Thr Pro Val Ser Glu His Val Thr Lys
                565                 570                 575

Cys Cys Ser Gly Ser Leu Val Glu Arg Arg Pro Cys Phe Ser Ala Leu
            580                 585                 590

Thr Val Asp Glu Thr Tyr Val Pro Lys Glu Phe Lys Ala Glu Thr Phe
        595                 600                 605

Thr Phe His Ser Asp Ile Cys Thr Leu Pro Glu Lys Glu Lys Gln Ile
    610                 615                 620

Lys Lys Gln Thr Ala Leu Ala Glu Leu Val Lys His Lys Pro Lys Ala
625                 630                 635                 640

Thr Ala Glu Gln Leu Lys Thr Val Met Asp Asp Phe Ala Gln Phe Leu
                645                 650                 655

Asp Thr Cys Cys Lys Ala Ala Asp Lys Asp Thr Cys Phe Ser Thr Glu
            660                 665                 670

Gly Pro Asn Leu Val Thr Arg Ser Lys Asp Ala Leu Ala
        675                 680                 685

<210> SEQ ID NO 164
<211> LENGTH: 782
<212> TYPE: PRT
<213> ORGANISM: Artificial Sequence
<220> FEATURE:
<223> OTHER INFORMATION: synthetic construct

<400> SEQUENCE: 164

Ser Gln Ile Glu Val Lys Asp Val Thr Asp Thr Thr Ala Leu Ile Thr
1                   5                   10                  15

Trp His Asp Pro Ser Gly Tyr Asp Phe Trp Cys Glu Leu Thr Tyr Gly
                20                  25                  30

Ile Lys Asp Val Pro Gly Asp Arg Thr Thr Ile Asp Leu Pro Asp His
            35                  40                  45

Phe His Gln Tyr Ser Ile Gly Asn Leu Lys Pro Asp Thr Glu Tyr Glu
        50                  55                  60

Val Ser Leu Ile Cys Ala Asn Asp His Gly Phe Asp Ser Tyr Pro Ala
65                  70                  75                  80

Lys Glu Thr Phe Thr Thr Gly Gly Gly Gly Ser Arg Leu Asp Ala
                85                  90                  95

Pro Ser Gln Ile Glu Val Lys Asp Val Thr Asp Thr Thr Ala Leu Ile
                100                 105                 110

Thr Trp His Asp Pro Ser Gly Tyr Asp Phe Trp Cys Glu Leu Thr Tyr
            115                 120                 125

Gly Ile Lys Asp Val Pro Gly Asp Arg Thr Thr Ile Asp Leu Pro Asp
        130                 135                 140

His Phe His Gln Tyr Ser Ile Gly Asn Leu Lys Pro Asp Thr Glu Tyr
145                 150                 155                 160

Glu Val Ser Leu Ile Cys Ala Asn Asp His Gly Phe Asp Ser Tyr Pro
                165                 170                 175

Ala Lys Glu Thr Phe Thr Thr Gly Gly Gly Ser Gly Gly Gly
            180                 185                 190

Ser Gly Gly Gly Gly Ser Glu Ala His Lys Ser Glu Ile Ala His Arg
        195                 200                 205

Tyr Asn Asp Leu Gly Glu Gln His Phe Lys Gly Leu Val Leu Ile Ala
210                 215                 220
```

```
Phe Ser Gln Tyr Leu Gln Lys Ser Ser Tyr Asp Glu His Ala Lys Leu
225                 230                 235                 240

Val Gln Glu Val Thr Asp Phe Ala Lys Thr Cys Val Ala Asp Glu Ser
            245                 250                 255

Ala Ala Asn Cys Asp Lys Ser Leu His Thr Leu Phe Gly Asp Lys Leu
            260                 265                 270

Cys Ala Ile Pro Asn Leu Arg Glu Asn Tyr Gly Glu Leu Ala Asp Cys
            275                 280                 285

Cys Thr Lys Gln Glu Pro Glu Arg Asn Glu Cys Phe Leu Gln His Lys
            290                 295                 300

Asp Asp Asn Pro Ser Leu Pro Pro Phe Glu Arg Pro Glu Ala Glu Ala
305                 310                 315                 320

Met Cys Thr Ser Phe Lys Glu Asn Pro Thr Thr Phe Met Gly His Tyr
            325                 330                 335

Leu His Glu Val Ala Arg Arg His Pro Tyr Phe Tyr Ala Pro Glu Leu
            340                 345                 350

Leu Tyr Tyr Ala Glu Gln Tyr Asn Glu Ile Leu Thr Gln Cys Cys Ala
            355                 360                 365

Glu Ala Asp Lys Glu Ser Cys Leu Thr Pro Lys Leu Asp Gly Val Lys
            370                 375                 380

Glu Lys Ala Leu Val Ser Ser Val Arg Gln Arg Met Lys Cys Ser Ser
385                 390                 395                 400

Met Gln Lys Phe Gly Glu Arg Ala Phe Lys Ala Trp Ala Val Ala Arg
            405                 410                 415

Leu Ser Gln Thr Phe Pro Asn Ala Asp Phe Ala Glu Ile Thr Lys Leu
            420                 425                 430

Ala Thr Asp Leu Thr Lys Val Asn Lys Glu Cys Cys His Gly Asp Leu
            435                 440                 445

Leu Glu Cys Ala Asp Asp Arg Ala Glu Leu Ala Lys Tyr Met Cys Glu
            450                 455                 460

Asn Gln Ala Thr Ile Ser Ser Lys Leu Gln Thr Cys Cys Asp Lys Pro
465                 470                 475                 480

Leu Leu Lys Lys Ala His Cys Leu Ser Glu Val Glu His Asp Thr Met
            485                 490                 495

Pro Ala Asp Leu Pro Ala Ile Ala Ala Asp Phe Val Glu Asp Gln Glu
            500                 505                 510

Val Cys Lys Asn Tyr Ala Glu Ala Lys Asp Val Phe Leu Gly Thr Phe
            515                 520                 525

Leu Tyr Glu Tyr Ser Arg Arg His Pro Asp Tyr Ser Val Ser Leu Leu
            530                 535                 540

Leu Arg Leu Ala Lys Lys Tyr Glu Ala Thr Leu Glu Lys Cys Cys Ala
545                 550                 555                 560

Glu Ala Asn Pro Pro Ala Cys Tyr Gly Thr Val Leu Ala Glu Phe Gln
            565                 570                 575

Pro Leu Val Glu Glu Pro Lys Asn Leu Val Lys Thr Asn Cys Asp Leu
            580                 585                 590

Tyr Glu Lys Leu Gly Glu Tyr Gly Phe Gln Asn Ala Ile Leu Val Arg
            595                 600                 605

Tyr Thr Gln Lys Ala Pro Gln Val Ser Thr Pro Thr Leu Val Glu Ala
            610                 615                 620

Ala Arg Asn Leu Gly Arg Val Gly Thr Lys Cys Cys Thr Leu Pro Glu
625                 630                 635                 640
```

```
Asp Gln Arg Leu Pro Cys Val Glu Asp Tyr Leu Ser Ala Ile Leu Asn
                645                 650                 655

Arg Val Cys Leu Leu His Glu Lys Thr Pro Val Ser Glu His Val Thr
            660                 665                 670

Lys Cys Cys Ser Gly Ser Leu Val Glu Arg Arg Pro Cys Phe Ser Ala
            675                 680                 685

Leu Thr Val Asp Glu Thr Tyr Val Pro Lys Glu Phe Lys Ala Glu Thr
            690                 695                 700

Phe Thr Phe His Ser Asp Ile Cys Thr Leu Pro Glu Lys Glu Lys Gln
705                 710                 715                 720

Ile Lys Lys Gln Thr Ala Leu Ala Glu Leu Val Lys His Lys Pro Lys
                725                 730                 735

Ala Thr Ala Glu Gln Leu Lys Thr Val Met Asp Asp Phe Ala Gln Phe
            740                 745                 750

Leu Asp Thr Cys Cys Lys Ala Ala Asp Lys Asp Thr Cys Phe Ser Thr
            755                 760                 765

Glu Gly Pro Asn Leu Val Thr Arg Ser Lys Asp Ala Leu Ala
            770                 775                 780

<210> SEQ ID NO 165
<211> LENGTH: 86
<212> TYPE: PRT
<213> ORGANISM: Artificial Sequence
<220> FEATURE:
<223> OTHER INFORMATION: synthetic construct

<400> SEQUENCE: 165

Ile Glu Val Lys Asp Val Thr Asp Thr Thr Ala Leu Ile Thr Trp Ser
1               5                   10                  15

Pro Gly Glu Arg Ile Trp Met Phe Thr Gly Cys Glu Leu Thr Tyr Gly
            20                  25                  30

Ile Lys Asp Val Pro Gly Asp Arg Thr Thr Ile Asp Leu Thr Glu Asp
        35                  40                  45

Glu Asn Gln Tyr Ser Ile Gly Asn Leu Lys Pro Asp Thr Glu Tyr Glu
    50                  55                  60

Val Ser Leu Ile Cys Pro Asn Tyr Glu Arg Ile Ser Asn Pro Ala Lys
65                  70                  75                  80

Glu Thr Phe Thr Thr Thr
                85

<210> SEQ ID NO 166
<211> LENGTH: 784
<212> TYPE: PRT
<213> ORGANISM: Artificial Sequence
<220> FEATURE:
<223> OTHER INFORMATION: synthetic construct

<400> SEQUENCE: 166

Ser Gln Ile Glu Val Lys Asp Val Thr Asp Thr Thr Ala Leu Ile Thr
1               5                   10                  15

Trp Ser Pro Gly Glu Arg Ile Trp Met Phe Thr Gly Cys Glu Leu Thr
            20                  25                  30

Tyr Gly Ile Lys Asp Val Pro Gly Asp Arg Thr Thr Ile Asp Leu Thr
        35                  40                  45

Glu Asp Glu Asn Gln Tyr Ser Ile Gly Asn Leu Lys Pro Asp Thr Glu
    50                  55                  60

Tyr Glu Val Ser Leu Ile Cys Pro Asn Tyr Glu Arg Ile Ser Asn Pro
65                  70                  75                  80
```

```
Ala Lys Glu Thr Phe Thr Thr Gly Gly Gly Ser Arg Leu Asp
            85              90              95

Ala Pro Ser Gln Ile Glu Val Lys Asp Val Thr Asp Thr Ala Leu
            100             105             110

Ile Thr Trp Ser Pro Gly Glu Arg Ile Trp Met Phe Thr Gly Cys Glu
            115             120             125

Leu Thr Tyr Gly Ile Lys Asp Val Pro Gly Asp Arg Thr Thr Ile Asp
            130             135             140

Leu Thr Glu Asp Glu Asn Gln Tyr Ser Ile Gly Asn Leu Lys Pro Asp
145             150             155             160

Thr Glu Tyr Glu Val Ser Leu Ile Cys Pro Asn Tyr Glu Arg Ile Ser
            165             170             175

Asn Pro Ala Lys Glu Thr Phe Thr Thr Gly Gly Gly Ser Gly Gly
            180             185             190

Gly Gly Ser Gly Gly Gly Gly Ser Glu Ala His Lys Ser Glu Ile Ala
            195             200             205

His Arg Tyr Asn Asp Leu Gly Glu Gln His Phe Lys Gly Leu Val Leu
            210             215             220

Ile Ala Phe Ser Gln Tyr Leu Gln Lys Ser Ser Tyr Asp Glu His Ala
225             230             235             240

Lys Leu Val Gln Glu Val Thr Asp Phe Ala Lys Thr Cys Val Ala Asp
            245             250             255

Glu Ser Ala Ala Asn Cys Asp Lys Ser Leu His Thr Leu Phe Gly Asp
            260             265             270

Lys Leu Cys Ala Ile Pro Asn Leu Arg Glu Asn Tyr Gly Glu Leu Ala
            275             280             285

Asp Cys Cys Thr Lys Gln Glu Pro Glu Arg Asn Glu Cys Phe Leu Gln
            290             295             300

His Lys Asp Asp Asn Pro Ser Leu Pro Pro Phe Glu Arg Pro Glu Ala
305             310             315             320

Glu Ala Met Cys Thr Ser Phe Lys Glu Asn Pro Thr Thr Phe Met Gly
            325             330             335

His Tyr Leu His Glu Val Ala Arg Arg His Pro Tyr Phe Tyr Ala Pro
            340             345             350

Glu Leu Leu Tyr Tyr Ala Glu Gln Tyr Asn Glu Ile Leu Thr Gln Cys
            355             360             365

Cys Ala Glu Ala Asp Lys Glu Ser Cys Leu Thr Pro Lys Leu Asp Gly
            370             375             380

Val Lys Glu Lys Ala Leu Val Ser Ser Val Arg Gln Arg Met Lys Cys
385             390             395             400

Ser Ser Met Gln Lys Phe Gly Glu Arg Ala Phe Lys Ala Trp Ala Val
            405             410             415

Ala Arg Leu Ser Gln Thr Phe Pro Asn Ala Asp Phe Ala Glu Ile Thr
            420             425             430

Lys Leu Ala Thr Asp Leu Thr Lys Val Asn Lys Glu Cys Cys His Gly
            435             440             445

Asp Leu Leu Glu Cys Ala Asp Asp Arg Ala Glu Leu Ala Lys Tyr Met
450             455             460

Cys Glu Asn Gln Ala Thr Ile Ser Ser Lys Leu Gln Thr Cys Cys Asp
465             470             475             480

Lys Pro Leu Leu Lys Lys Ala His Cys Leu Ser Glu Val Glu His Asp
            485             490             495
```

```
Thr Met Pro Ala Asp Leu Pro Ala Ile Ala Ala Asp Phe Val Glu Asp
            500                 505                 510

Gln Glu Val Cys Lys Asn Tyr Ala Glu Ala Lys Asp Val Phe Leu Gly
            515                 520                 525

Thr Phe Leu Tyr Glu Tyr Ser Arg Arg His Pro Asp Tyr Ser Val Ser
            530                 535                 540

Leu Leu Leu Arg Leu Ala Lys Lys Tyr Glu Ala Thr Leu Glu Lys Cys
545                 550                 555                 560

Cys Ala Glu Ala Asn Pro Pro Ala Cys Tyr Gly Thr Val Leu Ala Glu
                565                 570                 575

Phe Gln Pro Leu Val Glu Glu Pro Lys Asn Leu Val Lys Thr Asn Cys
            580                 585                 590

Asp Leu Tyr Glu Lys Leu Gly Glu Tyr Gly Phe Gln Asn Ala Ile Leu
            595                 600                 605

Val Arg Tyr Thr Gln Lys Ala Pro Gln Val Ser Thr Pro Thr Leu Val
            610                 615                 620

Glu Ala Ala Arg Asn Leu Gly Arg Val Gly Thr Lys Cys Cys Thr Leu
625                 630                 635                 640

Pro Glu Asp Gln Arg Leu Pro Cys Val Glu Asp Tyr Leu Ser Ala Ile
                645                 650                 655

Leu Asn Arg Val Cys Leu Leu His Glu Lys Thr Pro Val Ser Glu His
                660                 665                 670

Val Thr Lys Cys Cys Ser Gly Ser Leu Val Glu Arg Arg Pro Cys Phe
            675                 680                 685

Ser Ala Leu Thr Val Asp Glu Thr Tyr Val Pro Lys Glu Phe Lys Ala
            690                 695                 700

Glu Thr Phe Thr Phe His Ser Asp Ile Cys Thr Leu Pro Glu Lys Glu
705                 710                 715                 720

Lys Gln Ile Lys Lys Gln Thr Ala Leu Ala Glu Leu Val Lys His Lys
                725                 730                 735

Pro Lys Ala Thr Ala Glu Gln Leu Lys Thr Val Met Asp Asp Phe Ala
            740                 745                 750

Gln Phe Leu Asp Thr Cys Cys Lys Ala Ala Asp Lys Asp Thr Cys Phe
            755                 760                 765

Ser Thr Glu Gly Pro Asn Leu Val Thr Arg Cys Lys Asp Ala Leu Ala
            770                 775                 780

<210> SEQ ID NO 167
<211> LENGTH: 83
<212> TYPE: PRT
<213> ORGANISM: Artificial Sequence
<220> FEATURE:
<223> OTHER INFORMATION: synthetic construct

<400> SEQUENCE: 167

Ile Glu Val Lys Asp Val Thr Asp Thr Thr Ala Leu Ile Thr Trp Ser
1               5                   10                  15

Asp Asp Phe Gly Glu Tyr Val Trp Cys Glu Leu Thr Tyr Gly Ile Lys
            20                  25                  30

Asp Val Pro Gly Asp Arg Thr Thr Ile Asp Leu Trp Tyr His His Ala
        35                  40                  45

His Tyr Ser Ile Gly Asn Leu Lys Pro Asp Thr Glu Tyr Glu Val Ser
    50                  55                  60

Leu Ile Cys Arg Ser Gly Asp Met Ser Ser Asn Pro Ala Lys Glu Thr
65                  70                  75                  80
```

Phe Thr Thr

<210> SEQ ID NO 168
<211> LENGTH: 83
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (16)..(16)
<223> OTHER INFORMATION: Xaa is Ser or Leu
<220> FEATURE:
<221> NAME/KEY: MISC_FEATURE
<222> LOCATION: (18)..(18)
<223> OTHER INFORMATION: Xaa is Asp or Glu
<220> FEATURE:
<221> NAME/KEY: MISC_FEATURE
<222> LOCATION: (19)..(19)
<223> OTHER INFORMATION: Xaa is any of His, Ile, Val, Phe or Trp
<220> FEATURE:
<221> NAME/KEY: MISC_FEATURE
<222> LOCATION: (20)..(20)
<223> OTHER INFORMATION: Xaa is any of Ala, Gly, Glu or Asp
<220> FEATURE:
<221> NAME/KEY: MISC_FEATURE
<222> LOCATION: (21)..(21)
<223> OTHER INFORMATION: Xaa is any of Glu, Leu, Gln, Ser, Asp or Asn
<220> FEATURE:
<221> NAME/KEY: MISC_FEATURE
<222> LOCATION: (22)..(22)
<223> OTHER INFORMATION: Xaa is any of Phe or Tyr
<220> FEATURE:
<221> NAME/KEY: MISC_FEATURE
<222> LOCATION: (23)..(23)
<223> OTHER INFORMATION: Xaa is any of Ile, Val, His, Glu or Asp
<220> FEATURE:
<221> NAME/KEY: MISC_FEATURE
<222> LOCATION: (24)..(24)
<223> OTHER INFORMATION: Xaa is any of Gly, Trp or Val
<220> FEATURE:
<221> NAME/KEY: MISC_FEATURE
<222> LOCATION: (45)..(45)
<223> OTHER INFORMATION: Xaa is any of Trp, Phe or Tyr
<220> FEATURE:
<221> NAME/KEY: MISC_FEATURE
<222> LOCATION: (47)..(47)
<223> OTHER INFORMATION: Xaa is any of Ser, Gln, Met or His
<220> FEATURE:
<221> NAME/KEY: MISC_FEATURE
<222> LOCATION: (49)..(49)
<223> OTHER INFORMATION: Xaa is any Trp or His
<220> FEATURE:
<221> NAME/KEY: MISC_FEATURE
<222> LOCATION: (69)..(69)
<223> OTHER INFORMATION: Xaa is any of Arg or Ser

<400> SEQUENCE: 168

Ile Glu Val Lys Asp Val Thr Asp Thr Thr Ala Leu Ile Thr Trp Xaa
1               5                   10                  15

Asp Xaa Xaa Xaa Xaa Xaa Xaa Cys Glu Leu Thr Tyr Gly Ile Lys
            20                  25                  30

Asp Val Pro Gly Asp Arg Thr Thr Ile Asp Leu Trp Xaa His Xaa Ala
        35                  40                  45

Xaa Tyr Ser Ile Gly Asn Leu Lys Pro Asp Thr Glu Tyr Glu Val Ser
    50                  55                  60

Leu Ile Cys Arg Xaa Gly Asp Met Ser Ser Asn Pro Ala Lys Glu Thr
65                  70                  75                  80

Phe Thr Thr

<210> SEQ ID NO 169

```
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is any of Ser or Leu
<220> FEATURE:
<221> NAME/KEY: MISC_FEATURE
<222> LOCATION: (3)..(3)
<223> OTHER INFORMATION: Xaa is any of Asp or Glu
<220> FEATURE:
<221> NAME/KEY: MISC_FEATURE
<222> LOCATION: (4)..(4)
<223> OTHER INFORMATION: Xaa is any of His, Ile, Val, Phe or Trp
<220> FEATURE:
<221> NAME/KEY: MISC_FEATURE
<222> LOCATION: (5)..(5)
<223> OTHER INFORMATION: Xaa is any of Ala, Gly, Glu or Asp
<220> FEATURE:
<221> NAME/KEY: MISC_FEATURE
<222> LOCATION: (6)..(6)
<223> OTHER INFORMATION: Xaa is any of Glu, Leu, Gln, Ser, Asp or Asn
<220> FEATURE:
<221> NAME/KEY: MISC_FEATURE
<222> LOCATION: (7)..(7)
<223> OTHER INFORMATION: Xaa is any of Phe or Tyr
<220> FEATURE:
<221> NAME/KEY: MISC_FEATURE
<222> LOCATION: (8)..(8)
<223> OTHER INFORMATION: Xaa is any of Ile, Val, His, Glu or Asp
<220> FEATURE:
<221> NAME/KEY: MISC_FEATURE
<222> LOCATION: (9)..(9)
<223> OTHER INFORMATION: Xaa is any of Gly, Trp or Val

<400> SEQUENCE: 169

Xaa Asp Xaa Xaa Xaa Xaa Xaa Xaa Xaa
 1               5

<210> SEQ ID NO 170
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is any of Trp, Phe or Tyr
<220> FEATURE:
<221> NAME/KEY: MISC_FEATURE
<222> LOCATION: (4)..(4)
<223> OTHER INFORMATION: Xaa is any of Ser, Gln, Met or His
<220> FEATURE:
<221> NAME/KEY: MISC_FEATURE
<222> LOCATION: (6)..(6)
<223> OTHER INFORMATION: Xaa is any of Trp or His

<400> SEQUENCE: 170

Trp Xaa His Xaa Ala Xaa
 1               5

<210> SEQ ID NO 171
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is Arg or Ser
```

<400> SEQUENCE: 171

Arg Xaa Gly Asp Met Ser Ser Asn Pro Ala
1               5                   10

<210> SEQ ID NO 172
<211> LENGTH: 87
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (4)..(4)
<223> OTHER INFORMATION: Xaa is Lys or Glu
<220> FEATURE:
<221> NAME/KEY: MISC_FEATURE
<222> LOCATION: (16)..(16)
<223> OTHER INFORMATION: Xaa is Thr or Ile
<220> FEATURE:
<221> NAME/KEY: MISC_FEATURE
<222> LOCATION: (17)..(17)
<223> OTHER INFORMATION: Xaa is Asn or Ala
<220> FEATURE:
<221> NAME/KEY: MISC_FEATURE
<222> LOCATION: (20)..(20)
<223> OTHER INFORMATION: Xaa is any of Ser, Leu, Ala, Phe and Tyr
<220> FEATURE:
<221> NAME/KEY: MISC_FEATURE
<222> LOCATION: (21)..(21)
<223> OTHER INFORMATION: Xaa is any of Tyr, Ala, Gly, Val, Ile and Ser
<220> FEATURE:
<221> NAME/KEY: MISC_FEATURE
<222> LOCATION: (22)..(22)
<223> OTHER INFORMATION: Xaa is any of Tyr, Ser, Ala and His
<220> FEATURE:
<221> NAME/KEY: MISC_FEATURE
<222> LOCATION: (23)..(23)
<223> OTHER INFORMATION: Xaa is any of Asn, Asp, His and Tyr
<220> FEATURE:
<221> NAME/KEY: MISC_FEATURE
<222> LOCATION: (24)..(24)
<223> OTHER INFORMATION: Xaa is any of Leu, Phe, His and Tyr
<220> FEATURE:
<221> NAME/KEY: MISC_FEATURE
<222> LOCATION: (25)..(25)
<223> OTHER INFORMATION: Xaa is any of His, Pro, Ser, Leu and Asp
<220> FEATURE:
<221> NAME/KEY: MISC_FEATURE
<222> LOCATION: (26)..(26)
<223> OTHER INFORMATION: Xaa is any of Gly, Phe, His and Tyr
<220> FEATURE:
<221> NAME/KEY: MISC_FEATURE
<222> LOCATION: (30)..(30)
<223> OTHER INFORMATION: Xaa is Ala or Thr
<220> FEATURE:
<221> NAME/KEY: MISC_FEATURE
<222> LOCATION: (46)..(46)
<223> OTHER INFORMATION: Xaa is any of Ser, Asn, Glu, Arg and Asp
<220> FEATURE:
<221> NAME/KEY: MISC_FEATURE
<222> LOCATION: (47)..(47)
<223> OTHER INFORMATION: Xaa is any of Ser, Gln, Thr, Asn and Ala
<220> FEATURE:
<221> NAME/KEY: MISC_FEATURE
<222> LOCATION: (48)..(48)
<223> OTHER INFORMATION: Xaa is absent or is any of Pro, Val, Ile and
      Ala
<220> FEATURE:
<221> NAME/KEY: MISC_FEATURE
<222> LOCATION: (49)..(49)
<223> OTHER INFORMATION: Xaa is absent or is Ile
<220> FEATURE:
<221> NAME/KEY: MISC_FEATURE
<222> LOCATION: (63)..(63)
<223> OTHER INFORMATION: Xaa is Glu or Lys
<220> FEATURE:

<221> NAME/KEY: MISC_FEATURE
<222> LOCATION: (78)..(78)
<223> OTHER INFORMATION: Xaa is any of

<400> SEQUENCE: 172

Ile Glu Val Xaa Asp Val Thr Asp Thr Thr Ala Leu Ile Thr Trp Xaa
1               5                   10                  15

Xaa Arg Ser Xaa Xaa Xaa Xaa Xaa Xaa Cys Glu Leu Xaa Tyr Gly
            20                  25                  30

Ile Lys Asp Val Pro Gly Asp Arg Thr Thr Ile Asp Leu Xaa Xaa Xaa
            35                  40                  45

Xaa Tyr Val His Tyr Ser Ile Gly Asn Leu Lys Pro Asp Thr Xaa Tyr
        50                  55                  60

Glu Val Ser Leu Ile Cys Leu Thr Thr Asp Gly Thr Tyr Xaa Asn Pro
65                  70                  75                  80

Ala Lys Glu Thr Phe Thr Thr
                85

<210> SEQ ID NO 173
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (4)..(4)
<223> OTHER INFORMATION: Xaa is Ala or Thr

<400> SEQUENCE: 173

Cys Glu Leu Xaa Tyr Gly Ile
1               5

<210> SEQ ID NO 174
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is Lys or Glu

<400> SEQUENCE: 174

Xaa Asp Val Thr Asp Thr Thr
1               5

<210> SEQ ID NO 175
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is Thr or Ile
<220> FEATURE:
<221> NAME/KEY: MISC_FEATURE
<222> LOCATION: (2)..(2)
<223> OTHER INFORMATION: Xaa is Asn or Ala
<220> FEATURE:
<221> NAME/KEY: MISC_FEATURE
<222> LOCATION: (5)..(5)
<223> OTHER INFORMATION: Xaa is any of Ser, Leu, Ala, Phe and Tyr
<220> FEATURE:
<221> NAME/KEY: MISC_FEATURE

```
<222> LOCATION: (6)..(6)
<223> OTHER INFORMATION: Xaa is any of Tyr, Ala, Gly, Val, Ile and Ser
<220> FEATURE:
<221> NAME/KEY: MISC_FEATURE
<222> LOCATION: (7)..(7)
<223> OTHER INFORMATION: Xaa is any of Tyr, Ser, Ala and His
<220> FEATURE:
<221> NAME/KEY: MISC_FEATURE
<222> LOCATION: (8)..(8)
<223> OTHER INFORMATION: Xaa is any of Asn, Asp, His and Tyr
<220> FEATURE:
<221> NAME/KEY: MISC_FEATURE
<222> LOCATION: (9)..(9)
<223> OTHER INFORMATION: Xaa is any of Leu, Phe, His and Tyr
<220> FEATURE:
<221> NAME/KEY: MISC_FEATURE
<222> LOCATION: (10)..(10)
<223> OTHER INFORMATION: Xaa is any of His, Pro, Ser, Leu and Asp
<220> FEATURE:
<221> NAME/KEY: MISC_FEATURE
<222> LOCATION: (11)..(11)
<223> OTHER INFORMATION: Xaa is any of Gly, Phe, His and Tyr

<400> SEQUENCE: 175

Xaa Xaa Arg Ser Xaa Xaa Xaa Xaa Xaa Xaa Xaa
1               5                   10

<210> SEQ ID NO 176
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is any of Ser, Asn, Glu, Arg and Asp
<220> FEATURE:
<221> NAME/KEY: MISC_FEATURE
<222> LOCATION: (2)..(2)
<223> OTHER INFORMATION: Xaa is any of Ser, Gln, Thr, Asn and Ala
<220> FEATURE:
<221> NAME/KEY: MISC_FEATURE
<222> LOCATION: (3)..(3)
<223> OTHER INFORMATION: Xaa is not present or is any of Pro, Val, Ile
      and Ala
<220> FEATURE:
<221> NAME/KEY: MISC_FEATURE
<222> LOCATION: (4)..(4)
<223> OTHER INFORMATION: Xaa is not present or is Ile

<400> SEQUENCE: 176

Xaa Xaa Xaa Xaa Tyr Val His
1               5

<210> SEQ ID NO 177
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (8)..(8)
<223> OTHER INFORMATION: Xaa is Glu or Lys
<220> FEATURE:
<221> NAME/KEY: misc_feature
<222> LOCATION: (8)..(8)
<223> OTHER INFORMATION: Xaa can be any naturally occurring amino acid

<400> SEQUENCE: 177

Gly Asn Leu Lys Pro Asp Thr Xaa
1               5
```

<210> SEQ ID NO 178
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (8)..(8)
<223> OTHER INFORMATION: Xaa is Ser or Asn

<400> SEQUENCE: 178

Leu Thr Thr Asp Gly Thr Tyr Xaa Asn Pro Ala
1               5                   10

<210> SEQ ID NO 179
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (19)..(19)
<223> OTHER INFORMATION: N is any of G, A, T, and C
<220> FEATURE:
<221> NAME/KEY: misc_feature
<222> LOCATION: (22)..(22)
<223> OTHER INFORMATION: N is any of G, A, T, and C
<220> FEATURE:
<221> NAME/KEY: misc_feature
<222> LOCATION: (28)..(28)
<223> OTHER INFORMATION: N is any of G, A, T, and C
<220> FEATURE:
<221> NAME/KEY: misc_feature
<222> LOCATION: (34)..(34)
<223> OTHER INFORMATION: N is any of G, A, T, and C
<220> FEATURE:
<221> NAME/KEY: misc_feature
<222> LOCATION: (37)..(37)
<223> OTHER INFORMATION: N is any of G, A, T, and C
<220> FEATURE:
<221> NAME/KEY: misc_feature
<222> LOCATION: (40)..(40)
<223> OTHER INFORMATION: N is any of G, A, T, and C

<400> SEQUENCE: 179
accgcgctga ttacctggnh tnhtscgnht gstnhtnhtn htggctgtga actgacctat    60
ggcattaaa                                                            69

<210> SEQ ID NO 180
<211> LENGTH: 75
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (19)..(19)
<223> OTHER INFORMATION: N is any of G, A, T and C
<220> FEATURE:
<221> NAME/KEY: misc_feature
<222> LOCATION: (22)..(22)
<223> OTHER INFORMATION: N is any of G, A, T and C
<220> FEATURE:
<221> NAME/KEY: misc_feature
<222> LOCATION: (28)..(28)
<223> OTHER INFORMATION: N is any of G, A, T and C
<220> FEATURE:
<221> NAME/KEY: misc_feature
<222> LOCATION: (31)..(31)
<223> OTHER INFORMATION: N is any of G, A, T and C
<220> FEATURE:

<221> NAME/KEY: misc_feature
<222> LOCATION: (34)..(34)
<223> OTHER INFORMATION: N is any of G, A, T and C
<220> FEATURE:
<221> NAME/KEY: misc_feature
<222> LOCATION: (37)..(37)
<223> OTHER INFORMATION: N is any of G, A, T and C
<220> FEATURE:
<221> NAME/KEY: misc_feature
<222> LOCATION: (40)..(40)
<223> OTHER INFORMATION: N is any of G, A, T and C
<220> FEATURE:
<221> NAME/KEY: misc_feature
<222> LOCATION: (43)..(43)
<223> OTHER INFORMATION: N is any of G, A, T and C
<220> FEATURE:
<221> NAME/KEY: misc_feature
<222> LOCATION: (46)..(46)
<223> OTHER INFORMATION: N is any of G, A, T and C

<400> SEQUENCE: 180
accgcgctga ttacctggnh tnhtbstnht nhtnhtnhtn htnhtnhtgg ctgtgaactg    60
acctatggca ttaaa    75

<210> SEQ ID NO 181
<211> LENGTH: 78
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (19)..(19)
<223> OTHER INFORMATION: N is any of A, G, T and C
<220> FEATURE:
<221> NAME/KEY: misc_feature
<222> LOCATION: (28)..(28)
<223> OTHER INFORMATION: N is any of A, G, T and C
<220> FEATURE:
<221> NAME/KEY: misc_feature
<222> LOCATION: (31)..(31)
<223> OTHER INFORMATION: N is any of A, G, T and C
<220> FEATURE:
<221> NAME/KEY: misc_feature
<222> LOCATION: (34)..(34)
<223> OTHER INFORMATION: N is any of A, G, T and C
<220> FEATURE:
<221> NAME/KEY: misc_feature
<222> LOCATION: (43)..(43)
<223> OTHER INFORMATION: N is any of A, G, T and C
<220> FEATURE:
<221> NAME/KEY: misc_feature
<222> LOCATION: (49)..(49)
<223> OTHER INFORMATION: N is any of A, G, T and C

<400> SEQUENCE: 181
accgcgctga ttacctggnh tvmaccgnht nhtnhtrrcr gcnhtvttnh tggctgtgaa    60
ctgacctatg gcattaaa    78

<210> SEQ ID NO 182
<211> LENGTH: 64
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (23)..(23)
<223> OTHER INFORMATION: N is any of A, G, T and C
<220> FEATURE:
<221> NAME/KEY: misc_feature
<222> LOCATION: (26)..(26)
<223> OTHER INFORMATION: N is any of A, G, T and C
<220> FEATURE:
<221> NAME/KEY: misc_feature
<222> LOCATION: (29)..(29)
<223> OTHER INFORMATION: N is any of A, G, T and C
<220> FEATURE:
<221> NAME/KEY: misc_feature
<222> LOCATION: (32)..(32)
<223> OTHER INFORMATION: N is any of A, G, T and C
<220> FEATURE:
<221> NAME/KEY: misc_feature
<222> LOCATION: (35)..(35)
<223> OTHER INFORMATION: N is any of A, G, T and C
<220> FEATURE:
<221> NAME/KEY: misc_feature
<222> LOCATION: (38)..(38)
<223> OTHER INFORMATION: N is any of A, G, T and C

<400> SEQUENCE: 182
cgatcgcacc accatagatc tgnhtnhtnh tnhtnhtnht tatagcattg gtaacctgaa    60
accg                                                                64

<210> SEQ ID NO 183
<211> LENGTH: 73
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (25)..(25)
<223> OTHER INFORMATION: N is any of A, G, T and C
<220> FEATURE:
<221> NAME/KEY: misc_feature
<222> LOCATION: (31)..(31)
<223> OTHER INFORMATION: N is any of A, G, T and C
<220> FEATURE:
<221> NAME/KEY: misc_feature
<222> LOCATION: (34)..(34)
<223> OTHER INFORMATION: N is any of A, G, T and C
<220> FEATURE:
<221> NAME/KEY: misc_feature
<222> LOCATION: (40)..(40)
<223> OTHER INFORMATION: N is any of A, G, T and C
<220> FEATURE:
<221> NAME/KEY: misc_feature
<222> LOCATION: (43)..(43)
<223> OTHER INFORMATION: N is any of A, G, T and C
<220> FEATURE:
<221> NAME/KEY: misc_feature
<222> LOCATION: (46)..(46)
<223> OTHER INFORMATION: N is any of A, G, T and C

<400> SEQUENCE: 183
gaatatgaag tgagcctgat ttgcnhtams nhtnhtggtn htnhtnhtkc gaaagaaacc    60
tttaccaccg gtg                                                      73

<210> SEQ ID NO 184
<211> LENGTH: 76
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (25)..(25)
<223> OTHER INFORMATION: N is any of A, G, T and C
<220> FEATURE:
<221> NAME/KEY: misc_feature
<222> LOCATION: (31)..(31)
<223> OTHER INFORMATION: N is any of A, G, T and C
<220> FEATURE:
<221> NAME/KEY: misc_feature
<222> LOCATION: (34)..(34)

<223> OTHER INFORMATION: N is any of A, G, T and C
<220> FEATURE:
<221> NAME/KEY: misc_feature
<222> LOCATION: (37)..(37)
<223> OTHER INFORMATION: N is any of A, G, T and C
<220> FEATURE:
<221> NAME/KEY: misc_feature
<222> LOCATION: (40)..(40)
<223> OTHER INFORMATION: N is any of A, G, T and C
<220> FEATURE:
<221> NAME/KEY: misc_feature
<222> LOCATION: (46)..(46)
<223> OTHER INFORMATION: N is any of A, G, T and C

<400> SEQUENCE: 184
gaatatgaag tgagcctgat ttgcnhtams nhtnhtnhtn htrgcnhtcc ggcgaaagaa    60
acctttacca ccggtg                                                  76

<210> SEQ ID NO 185
<211> LENGTH: 79
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (25)..(25)
<223> OTHER INFORMATION: N is any of A, G, T and C
<220> FEATURE:
<221> NAME/KEY: misc_feature
<222> LOCATION: (31)..(31)
<223> OTHER INFORMATION: N is any of A, G, T and C
<220> FEATURE:
<221> NAME/KEY: misc_feature
<222> LOCATION: (34)..(34)
<223> OTHER INFORMATION: N is any of A, G, T and C
<220> FEATURE:
<221> NAME/KEY: misc_feature
<222> LOCATION: (40)..(40)
<223> OTHER INFORMATION: N is any of A, G, T and C
<220> FEATURE:
<221> NAME/KEY: misc_feature
<222> LOCATION: (43)..(43)
<223> OTHER INFORMATION: N is any of A, G, T and C

<400> SEQUENCE: 185
gaatatgaag tgagcctgat ttgcnhtams nhtnhtggtn htnhtagcaa cccggcgaaa    60
gaaaccttta ccaccggtg                                               79

<210> SEQ ID NO 186
<211> LENGTH: 57
<212> TYPE: DNA
<213> ORGANISM: Artificial Sequence
<220> FEATURE:
<223> OTHER INFORMATION: synthetic construct

<400> SEQUENCE: 186
cagatctatg gtggtgcgat cgcccggcac atctttaatg ccataggtca gttcaca      57

<210> SEQ ID NO 187
<211> LENGTH: 53
<212> TYPE: DNA
<213> ORGANISM: Artificial Sequence
<220> FEATURE:
<223> OTHER INFORMATION: synthetic construct

<400> SEQUENCE: 187
gcaaatcagg ctcacttcat attcggtatc cggtttcagg ttaccaatgc tat          53

```
<210> SEQ ID NO 188
<211> LENGTH: 42
<212> TYPE: DNA
<213> ORGANISM: Artificial Sequence
<220> FEATURE:
<223> OTHER INFORMATION: synthetic construct

<400> SEQUENCE: 188
cgggtcggtt ggggtaccgc caccggtggt aaaggtttct tt                           42

<210> SEQ ID NO 189
<211> LENGTH: 16
<212> TYPE: DNA
<213> ORGANISM: Artificial Sequence
<220> FEATURE:
<223> OTHER INFORMATION: synthetic construct

<400> SEQUENCE: 189
cgggtcggtt ggggta                                                        16

<210> SEQ ID NO 190
<211> LENGTH: 67
<212> TYPE: DNA
<213> ORGANISM: Artificial Sequence
<220> FEATURE:
<223> OTHER INFORMATION: synthetic construct

<400> SEQUENCE: 190
ggcccagccg gccatggccg ccattgaagt gaaagatgtg accgatacca ccgcgctgat        60
tacctgg                                                                  67

<210> SEQ ID NO 191
<211> LENGTH: 73
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (22)..(24)
<223> OTHER INFORMATION: NNN encodes for all amino acids except Cys
<220> FEATURE:
<221> NAME/KEY: misc_feature
<222> LOCATION: (25)..(27)
<223> OTHER INFORMATION: NNN encodes for Ala or Pro
<220> FEATURE:
<221> NAME/KEY: misc_feature
<222> LOCATION: (28)..(30)
<223> OTHER INFORMATION: NNN encodes for all amino acids except Cys
<220> FEATURE:
<221> NAME/KEY: misc_feature
<222> LOCATION: (31)..(33)
<223> OTHER INFORMATION: NNN encodes for Ala or Gly
<220> FEATURE:
<221> NAME/KEY: misc_feature
<222> LOCATION: (34)..(36)
<223> OTHER INFORMATION: NNN encodes for all amino acids except Cys
<220> FEATURE:
<221> NAME/KEY: misc_feature
<222> LOCATION: (37)..(39)
<223> OTHER INFORMATION: NNN encodes for all amino acids except Cys
<220> FEATURE:
<221> NAME/KEY: misc_feature
<222> LOCATION: (40)..(42)
<223> OTHER INFORMATION: NNN encodes for all amino acids except Cys

<400> SEQUENCE: 191
accgcgctga ttacctggtc tnnnnnnnnn nnnnnnnnnn nnggctgtga actgacctat        60
ggcattaaag atg                                                           73
```

```
<210> SEQ ID NO 192
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (19)..(20)
<223> OTHER INFORMATION: each N is any of A, G, T and C
<220> FEATURE:
<221> NAME/KEY: misc_feature
<222> LOCATION: (22)..(23)
<223> OTHER INFORMATION: each N is any of A, G, T and C
<220> FEATURE:
<221> NAME/KEY: misc_feature
<222> LOCATION: (28)..(29)
<223> OTHER INFORMATION: each N is any of A, G, T and C
<220> FEATURE:
<221> NAME/KEY: misc_feature
<222> LOCATION: (34)..(35)
<223> OTHER INFORMATION: each N is any of A, G, T and C
<220> FEATURE:
<221> NAME/KEY: misc_feature
<222> LOCATION: (37)..(38)
<223> OTHER INFORMATION: each N is any of A, G, T and C
<220> FEATURE:
<221> NAME/KEY: misc_feature
<222> LOCATION: (40)..(41)
<223> OTHER INFORMATION: each N is any of A, G, T and C

<400> SEQUENCE: 192
accgcgctga ttacctggnn knnksmgnnk gstnnknnkn nkggctgtga actgacctat      60
ggcattaaa                                                             69

<210> SEQ ID NO 193
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (19)..(20)
<223> OTHER INFORMATION: each N is any of A, T, C or T
<220> FEATURE:
<221> NAME/KEY: misc_feature
<222> LOCATION: (22)..(23)
<223> OTHER INFORMATION: each N is any of G, A, C and T
<220> FEATURE:
<221> NAME/KEY: misc_feature
<222> LOCATION: (25)..(26)
<223> OTHER INFORMATION: each N is any of G, A, C and T
<220> FEATURE:
<221> NAME/KEY: misc_feature
<222> LOCATION: (28)..(29)
<223> OTHER INFORMATION: each N is any of G, A, C and T
<220> FEATURE:
<221> NAME/KEY: misc_feature
<222> LOCATION: (31)..(32)
<223> OTHER INFORMATION: each N is any of G, A, C and T
<220> FEATURE:
<221> NAME/KEY: misc_feature
<222> LOCATION: (34)..(35)
<223> OTHER INFORMATION: each N is any of G, A, C and T
<220> FEATURE:
<221> NAME/KEY: misc_feature
<222> LOCATION: (37)..(37)
<223> OTHER INFORMATION: N is any of G, A, C and T
<220> FEATURE:
<221> NAME/KEY: misc_feature
<222> LOCATION: (40)..(41)
<223> OTHER INFORMATION: each N is any of G, A, C and T
<220> FEATURE:
<221> NAME/KEY: misc_feature
```

```
<222> LOCATION: (43)..(44)
<223> OTHER INFORMATION: each N is any of G, A, C and T

<400> SEQUENCE: 193
accgcgctga ttacctggnn knnknnknnk nnknnknhtn nknnktgtga actgacctat    60
ggcattaaa                                                            69

<210> SEQ ID NO 194
<211> LENGTH: 76
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (34)..(36)
<223> OTHER INFORMATION: NNN encodes for all amino acids except Cys
<220> FEATURE:
<221> NAME/KEY: misc_feature
<222> LOCATION: (37)..(39)
<223> OTHER INFORMATION: NNN encodes for all amino acids except Cys
<220> FEATURE:
<221> NAME/KEY: misc_feature
<222> LOCATION: (40)..(42)
<223> OTHER INFORMATION: NNN encodes for all amino acids except Cys
<220> FEATURE:
<221> NAME/KEY: misc_feature
<222> LOCATION: (43)..(45)
<223> OTHER INFORMATION: NNN encodes for all amino acids except Cys
<220> FEATURE:
<221> NAME/KEY: misc_feature
<222> LOCATION: (46)..(49)
<223> OTHER INFORMATION: NNN encodes for all amino acids except Cys
<220> FEATURE:
<221> NAME/KEY: misc_feature
<222> LOCATION: (50)..(51)
<223> OTHER INFORMATION: NNN encodes for all amino acids except Cys

<400> SEQUENCE: 194
gatgtgccgg gcgatcgcac caccatagat ctgnnnnnnn nnnnnnnnnn ntatagcatt    60
ggtaacctga aaccgg                                                    76

<210> SEQ ID NO 195
<211> LENGTH: 23
<212> TYPE: DNA
<213> ORGANISM: Artificial Sequence
<220> FEATURE:
<223> OTHER INFORMATION: synthetic construct

<400> SEQUENCE: 195
ccaggtaatc agcgcggtgg tat                                            23

<210> SEQ ID NO 196
<211> LENGTH: 23
<212> TYPE: DNA
<213> ORGANISM: Artificial Sequence
<220> FEATURE:
<223> OTHER INFORMATION: synthetic construct

<400> SEQUENCE: 196
cagatctatg gtggtgcgat cgc                                            23

<210> SEQ ID NO 197
<211> LENGTH: 29
<212> TYPE: DNA
<213> ORGANISM: Artificial Sequence
<220> FEATURE:
<223> OTHER INFORMATION: synthetic construct
```

<400> SEQUENCE: 197
tgtgaactga cctatggcat taaagatgt                              29

<210> SEQ ID NO 198
<211> LENGTH: 75
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (19)..(19)
<223> OTHER INFORMATION: N is any of G, A, T and C
<220> FEATURE:
<221> NAME/KEY: misc_feature
<222> LOCATION: (22)..(22)
<223> OTHER INFORMATION: N is any of G, A, T and C
<220> FEATURE:
<221> NAME/KEY: misc_feature
<222> LOCATION: (26)..(26)
<223> OTHER INFORMATION: N is any of G, A, T and C
<220> FEATURE:
<221> NAME/KEY: misc_feature
<222> LOCATION: (28)..(28)
<223> OTHER INFORMATION: N is any of G, A, T and C
<220> FEATURE:
<221> NAME/KEY: misc_feature
<222> LOCATION: (31)..(31)
<223> OTHER INFORMATION: N is any of G, A, T and C
<220> FEATURE:
<221> NAME/KEY: misc_feature
<222> LOCATION: (34)..(34)
<223> OTHER INFORMATION: N is any of G, A, T and C
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (38)..(38)
<223> OTHER INFORMATION: N is any of G, A, T and C
<220> FEATURE:
<221> NAME/KEY: misc_feature
<222> LOCATION: (40)..(40)
<223> OTHER INFORMATION: N is any of G, A, T and C
<220> FEATURE:
<221> NAME/KEY: misc_feature
<222> LOCATION: (43)..(43)
<223> OTHER INFORMATION: N is any of G, A, T and C
<220> FEATURE:
<221> NAME/KEY: misc_feature
<222> LOCATION: (46)..(46)
<223> OTHER INFORMATION: N is any of G, A, T and C

<400> SEQUENCE: 198
accgcgctga ttacctggnh tnhtvntnht nhtnhtnhtn htnhtnhtgg ctgtgaactg    60
acctatggca ttaaa                                              75

<210> SEQ ID NO 199
<211> LENGTH: 75
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (19)..(19)
<223> OTHER INFORMATION: N is any of G, A, T and C
<220> FEATURE:
<221> NAME/KEY: misc_feature
<222> LOCATION: (22)..(22)
<223> OTHER INFORMATION: N is any of G, A, T and C
<220> FEATURE:
<221> NAME/KEY: misc_feature

```
<222> LOCATION: (26)..(26)
<223> OTHER INFORMATION: N is any of G, A, T and C
<220> FEATURE:
<221> NAME/KEY: misc_feature
<222> LOCATION: (28)..(28)
<223> OTHER INFORMATION: N is any of G, A, T and C
<220> FEATURE:
<221> NAME/KEY: misc_feature
<222> LOCATION: (31)..(31)
<223> OTHER INFORMATION: N is any of G, A, T and C
<220> FEATURE:
<221> NAME/KEY: misc_feature
<222> LOCATION: (34)..(34)
<223> OTHER INFORMATION: N is any of G, A, T and C
<220> FEATURE:
<221> NAME/KEY: misc_feature
<222> LOCATION: (37)..(37)
<223> OTHER INFORMATION: N is any of G, A, T and C
<220> FEATURE:
<221> NAME/KEY: misc_feature
<222> LOCATION: (40)..(40)
<223> OTHER INFORMATION: N is any of G, A, T and C
<220> FEATURE:
<221> NAME/KEY: misc_feature
<222> LOCATION: (43)..(43)
<223> OTHER INFORMATION: N is any of G, A, T and C
<220> FEATURE:
<221> NAME/KEY: misc_feature
<222> LOCATION: (46)..(46)
<223> OTHER INFORMATION: N is any of G, A, T and C
<220> FEATURE:
<221> NAME/KEY: misc_feature
<222> LOCATION: (49)..(49)
<223> OTHER INFORMATION: N is any of G, A, T and C

<400> SEQUENCE: 199
accgcgctga ttacctggnh tnhtvntnht nhtnhtnhtn htnhtnhtnh ttgtgaactg      60
acctatggca ttaaa                                                     75

<210> SEQ ID NO 200
<211> LENGTH: 67
<212> TYPE: DNA
<213> ORGANISM: Artificial Sequence
<220> FEATURE:
<223> OTHER INFORMATION: synthetic construct

<400> SEQUENCE: 200
ggcccagccg gccatggccg ccattgaagt ggaagatgtg accgatacca ccgcgctgat      60
tacctgg                                                              67

<210> SEQ ID NO 201
<211> LENGTH: 585
<212> TYPE: PRT
<213> ORGANISM: Artificial Sequence
<220> FEATURE:
<223> OTHER INFORMATION: synthetic construct

<400> SEQUENCE: 201

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80
```

```
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Asn His
450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
```

```
Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Leu Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 202
<211> LENGTH: 683
<212> TYPE: PRT
<213> ORGANISM: Artificial Sequence
<220> FEATURE:
<223> OTHER INFORMATION: synthetic construct

<400> SEQUENCE: 202

Ser Gln Ile Glu Val Glu Asp Val Thr Asp Thr Thr Ala Leu Ile Thr
1               5                   10                  15

Trp Thr Asn Arg Ser Ser Tyr Ser Asn Leu His Gly Cys Glu Leu Ala
            20                  25                  30

Tyr Gly Ile Lys Asp Val Pro Gly Asp Arg Thr Thr Ile Asp Leu Asn
        35                  40                  45

Gln Pro Tyr Val His Tyr Ser Ile Gly Asn Leu Lys Pro Asp Thr Glu
    50                  55                  60

Tyr Glu Val Ser Leu Ile Cys Leu Thr Thr Asp Gly Thr Tyr Asn Asn
65                  70                  75                  80

Pro Ala Lys Glu Thr Phe Thr Thr Gly Gly Gly Ser Gly Gly Gly Gly
                85                  90                  95

Gly Ser Asp Ala His Lys Ser Glu Val Ala His Arg Phe Lys Asp Leu
                100                 105                 110

Gly Glu Glu Asn Phe Lys Ala Leu Val Leu Ile Ala Phe Ala Gln Tyr
            115                 120                 125

Leu Gln Gln Ser Pro Phe Glu Asp His Val Lys Leu Val Asn Glu Val
130                 135                 140

Thr Glu Phe Ala Lys Thr Cys Val Ala Asp Glu Ser Ala Glu Asn Cys
145                 150                 155                 160

Asp Lys Ser Leu His Thr Leu Phe Gly Asp Lys Leu Cys Thr Val Ala
                165                 170                 175

Thr Leu Arg Glu Thr Tyr Gly Glu Met Ala Asp Cys Cys Ala Lys Gln
            180                 185                 190

Glu Pro Glu Arg Asn Glu Cys Phe Leu Gln His Lys Asp Asp Asn Pro
        195                 200                 205

Asn Leu Pro Arg Leu Val Arg Pro Glu Val Asp Val Met Cys Thr Ala
    210                 215                 220

Phe His Asp Asn Glu Glu Thr Phe Leu Lys Lys Tyr Leu Tyr Glu Ile
225                 230                 235                 240

Ala Arg Arg His Pro Tyr Phe Tyr Ala Pro Glu Leu Leu Phe Phe Ala
                245                 250                 255

Lys Arg Tyr Lys Ala Ala Phe Thr Glu Cys Cys Gln Ala Ala Asp Lys
            260                 265                 270
```

```
Ala Ala Cys Leu Leu Pro Lys Leu Asp Glu Leu Arg Asp Glu Gly Lys
            275                 280                 285

Ala Ser Ser Ala Lys Gln Arg Leu Lys Cys Ala Ser Leu Gln Lys Phe
            290                 295                 300

Gly Glu Arg Ala Phe Lys Ala Trp Ala Val Ala Arg Leu Ser Gln Arg
305                 310                 315                 320

Phe Pro Lys Ala Glu Phe Ala Glu Val Ser Lys Leu Val Thr Asp Leu
                    325                 330                 335

Thr Lys Val His Thr Glu Cys Cys His Gly Asp Leu Leu Glu Cys Ala
                340                 345                 350

Asp Asp Arg Ala Asp Leu Ala Lys Tyr Ile Cys Glu Asn Gln Asp Ser
            355                 360                 365

Ile Ser Ser Lys Leu Lys Glu Cys Cys Glu Lys Pro Leu Leu Glu Lys
            370                 375                 380

Ser His Cys Ile Ala Glu Val Glu Asn Asp Glu Met Pro Ala Asp Leu
385                 390                 395                 400

Pro Ser Leu Ala Ala Asp Phe Val Glu Ser Lys Asp Val Cys Lys Asn
                    405                 410                 415

Tyr Ala Glu Ala Lys Asp Val Phe Leu Gly Met Phe Leu Tyr Glu Tyr
                420                 425                 430

Ala Arg Arg His Pro Asp Tyr Ser Val Val Leu Leu Arg Leu Ala
            435                 440                 445

Lys Thr Tyr Glu Thr Thr Leu Glu Lys Cys Cys Ala Ala Ala Asp Pro
            450                 455                 460

His Glu Cys Tyr Ala Lys Val Phe Asp Glu Phe Lys Pro Leu Val Glu
465                 470                 475                 480

Glu Pro Gln Asn Leu Ile Lys Gln Asn Cys Glu Leu Phe Glu Gln Leu
                    485                 490                 495

Gly Glu Tyr Lys Phe Gln Asn Ala Leu Leu Val Arg Tyr Thr Lys Lys
                500                 505                 510

Val Pro Gln Val Ser Thr Pro Thr Leu Val Glu Val Ser Arg Asn Leu
            515                 520                 525

Gly Lys Val Gly Ser Lys Cys Cys Lys His Pro Glu Ala Lys Arg Met
            530                 535                 540

Pro Cys Ala Glu Asp Tyr Leu Ser Val Val Leu Asn Gln Leu Cys Val
545                 550                 555                 560

Leu His Glu Lys Thr Pro Val Ser Asp Arg Val Thr Lys Cys Cys Thr
                    565                 570                 575

Glu Ser Leu Val Asn Arg Arg Pro Cys Phe Ser Ala Leu Glu Val Asp
                580                 585                 590

Glu Thr Tyr Val Pro Lys Glu Phe Asn Ala Glu Thr Phe Thr Phe His
                595                 600                 605

Ala Asp Ile Cys Thr Leu Ser Glu Lys Glu Arg Gln Ile Lys Lys Gln
            610                 615                 620

Thr Ala Leu Val Glu Leu Val Lys His Lys Pro Lys Ala Thr Lys Glu
625                 630                 635                 640

Gln Leu Lys Ala Val Met Asp Asp Phe Ala Ala Phe Val Glu Lys Cys
                    645                 650                 655

Cys Lys Ala Asp Asp Lys Glu Thr Cys Phe Ala Glu Glu Gly Lys Lys
                660                 665                 670

Leu Val Ala Ala Ser Gln Ala Ala Leu Gly Leu
                675                 680
```

<210> SEQ ID NO 203
<211> LENGTH: 683
<212> TYPE: PRT
<213> ORGANISM: Artificial Sequence
<220> FEATURE:
<223> OTHER INFORMATION: synthetic construct

<400> SEQUENCE: 203

```
Ser Gln Ile Glu Val Glu Asp Val Thr Asp Thr Thr Ala Leu Ile Thr
1               5                   10                  15

Trp Thr Asn Arg Ser Ser Tyr Ser Asn Leu His Gly Cys Glu Leu Thr
            20                  25                  30

Tyr Gly Ile Lys Asp Val Pro Gly Asp Arg Thr Thr Ile Asp Leu Asn
        35                  40                  45

Gln Pro Tyr Val His Tyr Ser Ile Gly Asn Leu Lys Pro Asp Thr Glu
    50                  55                  60

Tyr Glu Val Ser Leu Ile Cys Leu Thr Thr Asp Gly Thr Tyr Asn Asn
65                  70                  75                  80

Pro Ala Lys Glu Thr Phe Thr Thr Gly Gly Gly Gly Gly Gly Gly Gly
                85                  90                  95

Gly Gly Asp Ala His Lys Ser Glu Val Ala His Arg Phe Lys Asp Leu
            100                 105                 110

Gly Glu Glu Asn Phe Lys Ala Leu Val Leu Ile Ala Phe Ala Gln Tyr
        115                 120                 125

Leu Gln Gln Ser Pro Phe Glu Asp His Val Lys Leu Val Asn Glu Val
    130                 135                 140

Thr Glu Phe Ala Lys Thr Cys Val Ala Asp Glu Ser Ala Glu Asn Cys
145                 150                 155                 160

Asp Lys Ser Leu His Thr Leu Phe Gly Asp Lys Leu Cys Thr Val Ala
                165                 170                 175

Thr Leu Arg Glu Thr Tyr Gly Glu Met Ala Asp Cys Cys Ala Lys Gln
            180                 185                 190

Glu Pro Glu Arg Asn Glu Cys Phe Leu Gln His Lys Asp Asp Asn Pro
        195                 200                 205

Asn Leu Pro Arg Leu Val Arg Pro Glu Val Asp Val Met Cys Thr Ala
    210                 215                 220

Phe His Asp Asn Glu Glu Thr Phe Leu Lys Lys Tyr Leu Tyr Glu Ile
225                 230                 235                 240

Ala Arg Arg His Pro Tyr Phe Tyr Ala Pro Glu Leu Leu Phe Phe Ala
                245                 250                 255

Lys Arg Tyr Lys Ala Ala Phe Thr Glu Cys Cys Gln Ala Ala Asp Lys
            260                 265                 270

Ala Ala Cys Leu Leu Pro Lys Leu Asp Glu Leu Arg Asp Glu Gly Lys
        275                 280                 285

Ala Ser Ser Ala Lys Gln Arg Leu Lys Cys Ala Ser Leu Gln Lys Phe
    290                 295                 300

Gly Glu Arg Ala Phe Lys Ala Trp Ala Val Ala Arg Leu Ser Gln Arg
305                 310                 315                 320

Phe Pro Lys Ala Glu Phe Ala Glu Val Ser Lys Leu Val Thr Asp Leu
                325                 330                 335

Thr Lys Val His Thr Glu Cys Cys His Gly Asp Leu Leu Glu Cys Ala
            340                 345                 350

Asp Asp Arg Ala Asp Leu Ala Lys Tyr Ile Cys Glu Asn Gln Asp Ser
        355                 360                 365

Ile Ser Ser Lys Leu Lys Glu Cys Cys Glu Lys Pro Leu Leu Glu Lys
```

```
            370                 375                 380
Ser His Cys Ile Ala Glu Val Glu Asn Asp Glu Met Pro Ala Asp Leu
385                 390                 395                 400

Pro Ser Leu Ala Ala Asp Phe Val Glu Ser Lys Asp Val Cys Lys Asn
                405                 410                 415

Tyr Ala Glu Ala Lys Asp Val Phe Leu Gly Met Phe Leu Tyr Glu Tyr
            420                 425                 430

Ala Arg Arg His Pro Asp Tyr Ser Val Val Leu Leu Leu Arg Leu Ala
        435                 440                 445

Lys Thr Tyr Glu Thr Thr Leu Glu Lys Cys Cys Ala Ala Ala Asp Pro
    450                 455                 460

His Glu Cys Tyr Ala Lys Val Phe Asp Glu Phe Lys Pro Leu Val Glu
465                 470                 475                 480

Glu Pro Gln Asn Leu Ile Lys Gln Asn Cys Glu Leu Phe Glu Gln Leu
                485                 490                 495

Gly Glu Tyr Lys Phe Gln Asn Ala Leu Leu Val Arg Tyr Thr Lys Lys
            500                 505                 510

Val Pro Gln Val Ser Thr Pro Thr Leu Val Glu Val Ser Arg Asn Leu
        515                 520                 525

Gly Lys Val Gly Ser Lys Cys Cys Lys His Pro Glu Ala Lys Arg Met
    530                 535                 540

Pro Cys Ala Glu Asp Tyr Leu Ser Val Val Leu Asn Gln Leu Cys Val
545                 550                 555                 560

Leu His Glu Lys Thr Pro Val Ser Asp Arg Val Thr Lys Cys Cys Thr
                565                 570                 575

Glu Ser Leu Val Asn Arg Arg Pro Cys Phe Ser Ala Leu Glu Val Asp
            580                 585                 590

Glu Thr Tyr Val Pro Lys Glu Phe Asn Ala Glu Thr Phe Thr Phe His
        595                 600                 605

Ala Asp Ile Cys Thr Leu Ser Glu Lys Glu Arg Gln Ile Lys Lys Gln
    610                 615                 620

Thr Ala Leu Val Glu Leu Val Lys His Lys Pro Lys Ala Thr Lys Glu
625                 630                 635                 640

Gln Leu Lys Ala Val Met Asp Asp Phe Ala Ala Phe Val Glu Lys Cys
                645                 650                 655

Cys Lys Ala Asp Asp Lys Glu Thr Cys Phe Ala Glu Glu Gly Lys Lys
            660                 665                 670

Leu Val Ala Ala Ser Gln Ala Ala Leu Gly Leu
        675                 680

<210> SEQ ID NO 204
<211> LENGTH: 791
<212> TYPE: PRT
<213> ORGANISM: Artificial Sequence
<220> FEATURE:
<223> OTHER INFORMATION: synthetic construct

<400> SEQUENCE: 204

Ser Gln Ile Glu Val Glu Asp Val Thr Asp Thr Thr Ala Leu Ile Thr
1               5                   10                  15

Trp Thr Asn Arg Ser Ser Tyr Ser Asn Leu His Gly Cys Glu Leu Ala
                20                  25                  30

Tyr Gly Ile Lys Asp Val Pro Gly Asp Arg Thr Thr Ile Asp Leu Asn
            35                  40                  45

Gln Pro Tyr Val His Tyr Ser Ile Gly Asn Leu Lys Pro Asp Thr Glu
```

```
                    50                  55                  60
Tyr Glu Val Ser Leu Ile Cys Leu Thr Thr Asp Gly Thr Tyr Asn Asn
 65                  70                  75                  80

Pro Ala Lys Glu Thr Phe Thr Thr Gly Gly Gly Ser Gly Gly Gly
                     85                  90                  95

Gly Ser Gly Gly Gly Gly Ser Arg Leu Asp Ala Pro Ser Gln Ile Glu
                    100                 105                 110

Val Glu Asp Val Thr Asp Thr Thr Ala Leu Ile Thr Trp Thr Asn Arg
                    115                 120                 125

Ser Ser Tyr Ser Asn Leu His Gly Cys Glu Leu Ala Tyr Gly Ile Lys
            130                 135                 140

Asp Val Pro Gly Asp Arg Thr Thr Ile Asp Leu Asn Gln Pro Tyr Val
145                 150                 155                 160

His Tyr Ser Ile Gly Asn Leu Lys Pro Asp Thr Glu Tyr Glu Val Ser
                    165                 170                 175

Leu Ile Cys Leu Thr Thr Asp Gly Thr Tyr Asn Asn Pro Ala Lys Glu
                180                 185                 190

Thr Phe Thr Thr Gly Gly Gly Ser Gly Gly Gly Gly Ser Asp Ala
                195                 200                 205

His Lys Ser Glu Val Ala His Arg Phe Lys Asp Leu Gly Glu Glu Asn
        210                 215                 220

Phe Lys Ala Leu Val Leu Ile Ala Phe Ala Gln Tyr Leu Gln Gln Ser
225                 230                 235                 240

Pro Phe Glu Asp His Val Lys Leu Val Asn Glu Val Thr Glu Phe Ala
                245                 250                 255

Lys Thr Cys Val Ala Asp Glu Ser Ala Glu Asn Cys Asp Lys Ser Leu
                260                 265                 270

His Thr Leu Phe Gly Asp Lys Leu Cys Thr Val Ala Thr Leu Arg Glu
            275                 280                 285

Thr Tyr Gly Glu Met Ala Asp Cys Cys Ala Lys Gln Glu Pro Glu Arg
            290                 295                 300

Asn Glu Cys Phe Leu Gln His Lys Asp Asp Asn Pro Asn Leu Pro Arg
305                 310                 315                 320

Leu Val Arg Pro Glu Val Asp Val Met Cys Thr Ala Phe His Asp Asn
                325                 330                 335

Glu Glu Thr Phe Leu Lys Lys Tyr Leu Tyr Glu Ile Ala Arg Arg His
                340                 345                 350

Pro Tyr Phe Tyr Ala Pro Glu Leu Leu Phe Phe Ala Lys Arg Tyr Lys
            355                 360                 365

Ala Ala Phe Thr Glu Cys Cys Gln Ala Ala Asp Lys Ala Ala Cys Leu
        370                 375                 380

Leu Pro Lys Leu Asp Glu Leu Arg Asp Glu Gly Lys Ala Ser Ser Ala
385                 390                 395                 400

Lys Gln Arg Leu Lys Cys Ala Ser Leu Gln Lys Phe Gly Glu Arg Ala
                405                 410                 415

Phe Lys Ala Trp Ala Val Ala Arg Leu Ser Gln Arg Phe Pro Lys Ala
                420                 425                 430

Glu Phe Ala Glu Val Ser Lys Leu Val Thr Asp Leu Thr Lys Val His
            435                 440                 445

Thr Glu Cys Cys His Gly Asp Leu Leu Glu Cys Ala Asp Asp Arg Ala
        450                 455                 460

Asp Leu Ala Lys Tyr Ile Cys Glu Asn Gln Asp Ser Ile Ser Ser Lys
465                 470                 475                 480
```

Leu Lys Glu Cys Cys Glu Lys Pro Leu Leu Glu Lys Ser His Cys Ile
            485                 490                 495

Ala Glu Val Glu Asn Asp Glu Met Pro Ala Asp Leu Pro Ser Leu Ala
            500                 505                 510

Ala Asp Phe Val Glu Ser Lys Asp Val Cys Lys Asn Tyr Ala Glu Ala
            515                 520                 525

Lys Asp Val Phe Leu Gly Met Phe Leu Tyr Glu Tyr Ala Arg Arg His
            530                 535                 540

Pro Asp Tyr Ser Val Val Leu Leu Leu Arg Leu Ala Lys Thr Tyr Glu
545                 550                 555                 560

Thr Thr Leu Glu Lys Cys Cys Ala Ala Ala Asp Pro His Glu Cys Tyr
                565                 570                 575

Ala Lys Val Phe Asp Glu Phe Lys Pro Leu Val Glu Glu Pro Gln Asn
            580                 585                 590

Leu Ile Lys Gln Asn Cys Glu Leu Phe Glu Gln Leu Gly Glu Tyr Lys
            595                 600                 605

Phe Gln Asn Ala Leu Leu Val Arg Tyr Thr Lys Lys Val Pro Gln Val
            610                 615                 620

Ser Thr Pro Thr Leu Val Glu Val Ser Arg Asn Leu Gly Lys Val Gly
625                 630                 635                 640

Ser Lys Cys Cys Lys His Pro Glu Ala Lys Arg Met Pro Cys Ala Glu
                645                 650                 655

Asp Tyr Leu Ser Val Val Leu Asn Gln Leu Cys Val Leu His Glu Lys
            660                 665                 670

Thr Pro Val Ser Asp Arg Val Thr Lys Cys Cys Thr Glu Ser Leu Val
            675                 680                 685

Asn Arg Arg Pro Cys Phe Ser Ala Leu Glu Val Asp Glu Thr Tyr Val
            690                 695                 700

Pro Lys Glu Phe Asn Ala Glu Thr Phe Thr Phe His Ala Asp Ile Cys
705                 710                 715                 720

Thr Leu Ser Glu Lys Glu Arg Gln Ile Lys Lys Gln Thr Ala Leu Val
                725                 730                 735

Glu Leu Val Lys His Lys Pro Lys Ala Thr Lys Glu Gln Leu Lys Ala
            740                 745                 750

Val Met Asp Asp Phe Ala Ala Phe Val Glu Lys Cys Cys Lys Ala Asp
            755                 760                 765

Asp Lys Glu Thr Cys Phe Ala Glu Glu Gly Lys Lys Leu Val Ala Ala
            770                 775                 780

Ser Gln Ala Ala Leu Gly Leu
785                 790

```
<210> SEQ ID NO 205
<211> LENGTH: 791
<212> TYPE: PRT
<213> ORGANISM: Artificial Sequence
<220> FEATURE:
<223> OTHER INFORMATION: synthetic construct

<400> SEQUENCE: 205
```

Ser Gln Ile Glu Val Glu Asp Val Thr Asp Thr Thr Ala Leu Ile Thr
1               5                   10                  15

Trp Thr Asn Arg Ser Ser Tyr Ser Asn Leu His Gly Cys Glu Leu Thr
            20                  25                  30

Tyr Gly Ile Lys Asp Val Pro Gly Asp Arg Thr Thr Ile Asp Leu Asn
            35                  40                  45

```
Gln Pro Tyr Val His Tyr Ser Ile Gly Asn Leu Lys Pro Asp Thr Glu
     50                  55                  60

Tyr Glu Val Ser Leu Ile Cys Leu Thr Thr Asp Gly Thr Tyr Asn Asn
 65                  70                  75                  80

Pro Ala Lys Glu Thr Phe Thr Thr Gly Gly Gly Gly Gly Gly Gly Gly
                 85                  90                  95

Gly Gly Gly Gly Gly Gly Arg Leu Asp Ala Pro Ser Gln Ile Glu
            100                 105                 110

Val Glu Asp Val Thr Asp Thr Thr Ala Leu Ile Thr Trp Thr Asn Arg
            115                 120                 125

Ser Ser Tyr Ser Asn Leu His Gly Cys Glu Leu Ala Tyr Gly Ile Lys
            130                 135                 140

Asp Val Pro Gly Asp Arg Thr Thr Ile Asp Leu Asn Gln Pro Tyr Val
145                 150                 155                 160

His Tyr Ser Ile Gly Asn Leu Lys Pro Asp Thr Glu Tyr Glu Val Ser
                165                 170                 175

Leu Ile Cys Leu Thr Thr Asp Gly Thr Tyr Asn Asn Pro Ala Lys Glu
                180                 185                 190

Thr Phe Thr Thr Gly Gly Gly Gly Gly Gly Gly Gly Gly Asp Ala
        195                 200                 205

His Lys Ser Glu Val Ala His Arg Phe Lys Asp Leu Gly Glu Glu Asn
    210                 215                 220

Phe Lys Ala Leu Val Leu Ile Ala Phe Ala Gln Tyr Leu Gln Gln Ser
225                 230                 235                 240

Pro Phe Glu Asp His Val Lys Leu Val Asn Glu Val Thr Glu Phe Ala
                245                 250                 255

Lys Thr Cys Val Ala Asp Glu Ser Ala Glu Asn Cys Asp Lys Ser Leu
            260                 265                 270

His Thr Leu Phe Gly Asp Lys Leu Cys Thr Val Ala Thr Leu Arg Glu
            275                 280                 285

Thr Tyr Gly Glu Met Ala Asp Cys Cys Ala Lys Gln Glu Pro Glu Arg
    290                 295                 300

Asn Glu Cys Phe Leu Gln His Lys Asp Asp Asn Pro Asn Leu Pro Arg
305                 310                 315                 320

Leu Val Arg Pro Glu Val Asp Val Met Cys Thr Ala Phe His Asp Asn
                325                 330                 335

Glu Glu Thr Phe Leu Lys Lys Tyr Leu Tyr Glu Ile Ala Arg Arg His
            340                 345                 350

Pro Tyr Phe Tyr Ala Pro Glu Leu Leu Phe Phe Ala Lys Arg Tyr Lys
            355                 360                 365

Ala Ala Phe Thr Glu Cys Cys Gln Ala Ala Asp Lys Ala Ala Cys Leu
    370                 375                 380

Leu Pro Lys Leu Asp Glu Leu Arg Asp Glu Gly Lys Ala Ser Ser Ala
385                 390                 395                 400

Lys Gln Arg Leu Lys Cys Ala Ser Leu Gln Lys Phe Gly Glu Arg Ala
                405                 410                 415

Phe Lys Ala Trp Ala Val Ala Arg Leu Ser Gln Arg Phe Pro Lys Ala
                420                 425                 430

Glu Phe Ala Glu Val Ser Lys Leu Val Thr Asp Leu Thr Lys Val His
            435                 440                 445

Thr Glu Cys Cys His Gly Asp Leu Leu Glu Cys Ala Asp Asp Arg Ala
    450                 455                 460
```

-continued

```
Asp Leu Ala Lys Tyr Ile Cys Glu Asn Gln Asp Ser Ile Ser Ser Lys
465                 470                 475                 480

Leu Lys Glu Cys Cys Glu Lys Pro Leu Leu Glu Lys Ser His Cys Ile
            485                 490                 495

Ala Glu Val Glu Asn Asp Glu Met Pro Ala Asp Leu Pro Ser Leu Ala
        500                 505                 510

Ala Asp Phe Val Glu Ser Lys Asp Val Cys Lys Asn Tyr Ala Glu Ala
    515                 520                 525

Lys Asp Val Phe Leu Gly Met Phe Leu Tyr Glu Tyr Ala Arg Arg His
530                 535                 540

Pro Asp Tyr Ser Val Val Leu Leu Leu Arg Leu Ala Lys Thr Tyr Glu
545                 550                 555                 560

Thr Thr Leu Glu Lys Cys Cys Ala Ala Ala Asp Pro His Glu Cys Tyr
            565                 570                 575

Ala Lys Val Phe Asp Glu Phe Lys Pro Leu Val Glu Glu Pro Gln Asn
        580                 585                 590

Leu Ile Lys Gln Asn Cys Glu Leu Phe Glu Gln Leu Gly Glu Tyr Lys
    595                 600                 605

Phe Gln Asn Ala Leu Leu Val Arg Tyr Thr Lys Lys Val Pro Gln Val
610                 615                 620

Ser Thr Pro Thr Leu Val Glu Val Ser Arg Asn Leu Gly Lys Val Gly
625                 630                 635                 640

Ser Lys Cys Cys Lys His Pro Glu Ala Lys Arg Met Pro Cys Ala Glu
            645                 650                 655

Asp Tyr Leu Ser Val Val Leu Asn Gln Leu Cys Val Leu His Glu Lys
        660                 665                 670

Thr Pro Val Ser Asp Arg Val Thr Lys Cys Cys Thr Glu Ser Leu Val
    675                 680                 685

Asn Arg Arg Pro Cys Phe Ser Ala Leu Glu Val Asp Glu Thr Tyr Val
690                 695                 700

Pro Lys Glu Phe Asn Ala Glu Thr Phe Thr Phe His Ala Asp Ile Cys
705                 710                 715                 720

Thr Leu Ser Glu Lys Glu Arg Gln Ile Lys Lys Gln Thr Ala Leu Val
            725                 730                 735

Glu Leu Val Lys His Lys Pro Lys Ala Thr Lys Glu Gln Leu Lys Ala
        740                 745                 750

Val Met Asp Asp Phe Ala Ala Phe Val Glu Lys Cys Cys Lys Ala Asp
    755                 760                 765

Asp Lys Glu Thr Cys Phe Ala Glu Glu Gly Lys Lys Leu Val Ala Ala
770                 775                 780

Ser Gln Ala Ala Leu Gly Leu
785                 790
```

<210> SEQ ID NO 206
<211> LENGTH: 190
<212> TYPE: PRT
<213> ORGANISM: Artificial Sequence
<220> FEATURE:
<223> OTHER INFORMATION: synthetic construct

<400> SEQUENCE: 206

```
Ser Gln Ile Glu Val Lys Asp Val Thr Asp Thr Thr Ala Leu Ile Thr
1               5                   10                  15

Trp Ser Asp Glu Phe Gly His Tyr Asp Gly Cys Glu Leu Thr Tyr Gly
            20                  25                  30
```

-continued

Ile Lys Asp Val Pro Gly Asp Arg Thr Thr Ile Asp Leu Trp Trp His
        35                  40                  45

Ser Ala Trp Tyr Ser Ile Gly Asn Leu Lys Pro Asp Thr Glu Tyr Glu
 50                  55                  60

Val Ser Leu Ile Cys Tyr Thr Asp Gln Glu Ala Gly Asn Pro Ala Lys
 65                  70                  75                  80

Glu Thr Phe Thr Thr Gly Gly Gly Ser Gly Gly Gly Ser Gly
                 85                  90                  95

Gly Gly Gly Ser Arg Leu Asp Ala Pro Ser Gln Ile Glu Val Lys Asp
            100                 105                 110

Val Thr Asp Thr Thr Ala Leu Ile Thr Trp Ser Asp Glu Phe Gly His
            115                 120                 125

Tyr Asp Gly Cys Glu Leu Thr Tyr Gly Ile Lys Asp Val Pro Gly Asp
130                 135                 140

Arg Thr Thr Ile Asp Leu Trp Trp His Ser Ala Trp Tyr Ser Ile Gly
145                 150                 155                 160

Asn Leu Lys Pro Asp Thr Glu Tyr Glu Val Ser Leu Ile Cys Tyr Thr
                165                 170                 175

Asp Gln Glu Ala Gly Asn Pro Ala Lys Glu Thr Phe Thr Thr
            180                 185                 190

<210> SEQ ID NO 207
<211> LENGTH: 680
<212> TYPE: PRT
<213> ORGANISM: Artificial Sequence
<220> FEATURE:
<223> OTHER INFORMATION: synthetic construct

<400> SEQUENCE: 207

Ser Gln Ile Glu Val Lys Asp Val Thr Asp Thr Thr Ala Leu Ile Thr
1               5                  10                  15

Trp Ser Asp Glu Phe Gly His Tyr Asp Gly Cys Glu Leu Thr Tyr Gly
            20                  25                  30

Ile Lys Asp Val Pro Gly Asp Arg Thr Thr Ile Asp Leu Trp Trp His
        35                  40                  45

Ser Ala Trp Tyr Ser Ile Gly Asn Leu Lys Pro Asp Thr Glu Tyr Glu
 50                  55                  60

Val Ser Leu Ile Cys Tyr Thr Asp Gln Glu Ala Gly Asn Pro Ala Lys
 65                  70                  75                  80

Glu Thr Phe Thr Thr Gly Gly Gly Ser Gly Gly Gly Ser Asp
                 85                  90                  95

Ala His Lys Ser Glu Val Ala His Arg Phe Lys Asp Leu Gly Glu Glu
            100                 105                 110

Asn Phe Lys Ala Leu Val Leu Ile Ala Phe Ala Gln Tyr Leu Gln Gln
            115                 120                 125

Ser Pro Phe Glu Asp His Val Lys Leu Val Asn Glu Val Thr Glu Phe
130                 135                 140

Ala Lys Thr Cys Val Ala Asp Glu Ser Ala Glu Asn Cys Asp Lys Ser
145                 150                 155                 160

Leu His Thr Leu Phe Gly Asp Lys Leu Cys Thr Val Ala Thr Leu Arg
                165                 170                 175

Glu Thr Tyr Gly Glu Met Ala Asp Cys Cys Ala Lys Gln Glu Pro Glu
            180                 185                 190

Arg Asn Glu Cys Phe Leu Gln His Lys Asp Asp Asn Pro Asn Leu Pro
            195                 200                 205

```
Arg Leu Val Arg Pro Glu Val Asp Val Met Cys Thr Ala Phe His Asp
    210             215                 220

Asn Glu Glu Thr Phe Leu Lys Lys Tyr Leu Tyr Glu Ile Ala Arg Arg
225             230                 235                 240

His Pro Tyr Phe Tyr Ala Pro Glu Leu Leu Phe Phe Ala Lys Arg Tyr
            245                 250                 255

Lys Ala Ala Phe Thr Glu Cys Cys Gln Ala Ala Asp Lys Ala Ala Cys
            260                 265                 270

Leu Leu Pro Lys Leu Asp Glu Leu Arg Asp Glu Gly Lys Ala Ser Ser
            275                 280                 285

Ala Lys Gln Arg Leu Lys Cys Ala Ser Leu Gln Lys Phe Gly Glu Arg
290             295                 300

Ala Phe Lys Ala Trp Ala Val Ala Arg Leu Ser Gln Arg Phe Pro Lys
305             310                 315                 320

Ala Glu Phe Ala Glu Val Ser Lys Leu Val Thr Asp Leu Thr Lys Val
            325                 330                 335

His Thr Glu Cys Cys His Gly Asp Leu Leu Glu Cys Ala Asp Asp Arg
            340                 345                 350

Ala Asp Leu Ala Lys Tyr Ile Cys Glu Asn Gln Asp Ser Ile Ser Ser
            355                 360                 365

Lys Leu Lys Glu Cys Cys Glu Lys Pro Leu Leu Glu Lys Ser His Cys
370             375                 380

Ile Ala Glu Val Glu Asn Asp Glu Met Pro Ala Asp Leu Pro Ser Leu
385             390                 395                 400

Ala Ala Asp Phe Val Glu Ser Lys Asp Val Cys Lys Asn Tyr Ala Glu
            405                 410                 415

Ala Lys Asp Val Phe Leu Gly Met Phe Leu Tyr Glu Tyr Ala Arg Arg
            420                 425                 430

His Pro Asp Tyr Ser Val Val Leu Leu Leu Arg Leu Ala Lys Thr Tyr
            435                 440                 445

Glu Thr Thr Leu Glu Lys Cys Cys Ala Ala Ala Asp Pro His Glu Cys
    450                 455                 460

Tyr Ala Lys Val Phe Asp Glu Phe Lys Pro Leu Val Glu Glu Pro Gln
465             470                 475                 480

Asn Leu Ile Lys Gln Asn Cys Glu Leu Phe Glu Gln Leu Gly Glu Tyr
            485                 490                 495

Lys Phe Gln Asn Ala Leu Leu Val Arg Tyr Thr Lys Lys Val Pro Gln
            500                 505                 510

Val Ser Thr Pro Thr Leu Val Glu Val Ser Arg Asn Leu Gly Lys Val
            515                 520                 525

Gly Ser Lys Cys Cys Lys His Pro Glu Ala Lys Arg Met Pro Cys Ala
530             535                 540

Glu Asp Tyr Leu Ser Val Val Leu Asn Gln Leu Cys Val Leu His Glu
545             550                 555                 560

Lys Thr Pro Val Ser Asp Arg Val Thr Lys Cys Cys Thr Glu Ser Leu
            565                 570                 575

Val Asn Arg Arg Pro Cys Phe Ser Ala Leu Glu Val Asp Glu Thr Tyr
            580                 585                 590

Val Pro Lys Glu Phe Asn Ala Glu Thr Phe Thr Phe His Ala Asp Ile
            595                 600                 605

Cys Thr Leu Ser Glu Lys Glu Arg Gln Ile Lys Lys Gln Thr Ala Leu
610             615                 620

Val Glu Leu Val Lys His Lys Pro Lys Ala Thr Lys Glu Gln Leu Lys
```

```
            625                 630                 635                 640
Ala Val Met Asp Asp Phe Ala Ala Phe Val Glu Lys Cys Cys Lys Ala
                    645                 650                 655

Asp Asp Lys Glu Thr Cys Phe Ala Glu Gly Lys Lys Leu Val Ala
                660                 665                 670

Ala Ser Gln Ala Ala Leu Gly Leu
            675                 680

<210> SEQ ID NO 208
<211> LENGTH: 785
<212> TYPE: PRT
<213> ORGANISM: Artificial Sequence
<220> FEATURE:
<223> OTHER INFORMATION: synthetic construct

<400> SEQUENCE: 208

Ser Gln Ile Glu Val Lys Asp Val Thr Asp Thr Thr Ala Leu Ile Thr
1               5                   10                  15

Trp Ser Asp Glu Phe Gly His Tyr Asp Gly Cys Glu Leu Thr Tyr Gly
            20                  25                  30

Ile Lys Asp Val Pro Gly Asp Arg Thr Thr Ile Asp Leu Trp Trp His
        35                  40                  45

Ser Ala Trp Tyr Ser Ile Gly Asn Leu Lys Pro Asp Thr Glu Tyr Glu
    50                  55                  60

Val Ser Leu Ile Cys Tyr Thr Asp Gln Glu Ala Gly Asn Pro Ala Lys
65                  70                  75                  80

Glu Thr Phe Thr Thr Gly Gly Gly Ser Gly Gly Gly Ser Gly
                85                  90                  95

Gly Gly Gly Ser Arg Leu Asp Ala Pro Ser Gln Ile Glu Val Lys Asp
            100                 105                 110

Val Thr Asp Thr Thr Ala Leu Ile Thr Trp Ser Asp Glu Phe Gly His
        115                 120                 125

Tyr Asp Gly Cys Glu Leu Thr Tyr Gly Ile Lys Asp Val Pro Gly Asp
    130                 135                 140

Arg Thr Thr Ile Asp Leu Trp Trp His Ser Ala Trp Tyr Ser Ile Gly
145                 150                 155                 160

Asn Leu Lys Pro Asp Thr Glu Tyr Glu Val Ser Leu Ile Cys Tyr Thr
                165                 170                 175

Asp Gln Glu Ala Gly Asn Pro Ala Lys Glu Thr Phe Thr Thr Gly Gly
            180                 185                 190

Gly Gly Ser Gly Gly Gly Gly Ser Asp Ala His Lys Ser Glu Val Ala
        195                 200                 205

His Arg Phe Lys Asp Leu Gly Glu Glu Asn Phe Lys Ala Leu Val Leu
    210                 215                 220

Ile Ala Phe Ala Gln Tyr Leu Gln Gln Ser Pro Phe Glu Asp His Val
225                 230                 235                 240

Lys Leu Val Asn Glu Val Thr Glu Phe Ala Lys Thr Cys Val Ala Asp
                245                 250                 255

Glu Ser Ala Glu Asn Cys Asp Lys Ser Leu His Thr Leu Phe Gly Asp
            260                 265                 270

Lys Leu Cys Thr Val Ala Thr Leu Arg Glu Thr Tyr Gly Glu Met Ala
        275                 280                 285

Asp Cys Cys Ala Lys Gln Glu Pro Glu Arg Asn Glu Cys Phe Leu Gln
    290                 295                 300

His Lys Asp Asp Asn Pro Asn Leu Pro Arg Leu Val Arg Pro Glu Val
```

```
                305                 310                 315                 320
Asp Val Met Cys Thr Ala Phe His Asp Asn Glu Glu Thr Phe Leu Lys
                    325                 330                 335

Lys Tyr Leu Tyr Glu Ile Ala Arg Arg His Pro Tyr Phe Tyr Ala Pro
                    340                 345                 350

Glu Leu Leu Phe Phe Ala Lys Arg Tyr Lys Ala Ala Phe Thr Glu Cys
                    355                 360                 365

Cys Gln Ala Ala Asp Lys Ala Ala Cys Leu Leu Pro Lys Leu Asp Glu
                    370                 375                 380

Leu Arg Asp Glu Gly Lys Ala Ser Ser Ala Lys Gln Arg Leu Lys Cys
385                 390                 395                 400

Ala Ser Leu Gln Lys Phe Gly Glu Arg Ala Phe Lys Ala Trp Ala Val
                    405                 410                 415

Ala Arg Leu Ser Gln Arg Phe Pro Lys Ala Glu Phe Ala Glu Val Ser
                    420                 425                 430

Lys Leu Val Thr Asp Leu Thr Lys Val His Thr Glu Cys Cys His Gly
                    435                 440                 445

Asp Leu Leu Glu Cys Ala Asp Asp Arg Ala Asp Leu Ala Lys Tyr Ile
                    450                 455                 460

Cys Glu Asn Gln Asp Ser Ile Ser Ser Lys Leu Lys Glu Cys Cys Glu
465                 470                 475                 480

Lys Pro Leu Leu Glu Lys Ser His Cys Ile Ala Glu Val Glu Asn Asp
                    485                 490                 495

Glu Met Pro Ala Asp Leu Pro Ser Leu Ala Ala Asp Phe Val Glu Ser
                    500                 505                 510

Lys Asp Val Cys Lys Asn Tyr Ala Glu Ala Lys Asp Val Phe Leu Gly
                    515                 520                 525

Met Phe Leu Tyr Glu Tyr Ala Arg Arg His Pro Asp Tyr Ser Val Val
                    530                 535                 540

Leu Leu Leu Arg Leu Ala Lys Thr Tyr Glu Thr Thr Leu Glu Lys Cys
545                 550                 555                 560

Cys Ala Ala Ala Asp Pro His Glu Cys Tyr Ala Lys Val Phe Asp Glu
                    565                 570                 575

Phe Lys Pro Leu Val Glu Glu Pro Gln Asn Leu Ile Lys Gln Asn Cys
                    580                 585                 590

Glu Leu Phe Glu Gln Leu Gly Glu Tyr Lys Phe Gln Asn Ala Leu Leu
                    595                 600                 605

Val Arg Tyr Thr Lys Lys Val Pro Gln Val Ser Thr Pro Thr Leu Val
                    610                 615                 620

Glu Val Ser Arg Asn Leu Gly Lys Val Gly Ser Lys Cys Cys Lys His
625                 630                 635                 640

Pro Glu Ala Lys Arg Met Pro Cys Ala Glu Asp Tyr Leu Ser Val Val
                    645                 650                 655

Leu Asn Gln Leu Cys Val Leu His Glu Lys Thr Pro Val Ser Asp Arg
                    660                 665                 670

Val Thr Lys Cys Cys Thr Glu Ser Leu Val Asn Arg Arg Pro Cys Phe
                    675                 680                 685

Ser Ala Leu Glu Val Asp Glu Thr Tyr Val Pro Lys Glu Phe Asn Ala
                    690                 695                 700

Glu Thr Phe Thr Phe His Ala Asp Ile Cys Thr Leu Ser Glu Lys Glu
705                 710                 715                 720

Arg Gln Ile Lys Lys Gln Thr Ala Leu Val Glu Leu Val Lys His Lys
                    725                 730                 735
```

```
Pro Lys Ala Thr Lys Glu Gln Leu Lys Ala Val Met Asp Asp Phe Ala
            740                 745                 750

Ala Phe Val Glu Lys Cys Cys Lys Ala Asp Asp Lys Glu Thr Cys Phe
            755                 760                 765

Ala Glu Glu Gly Lys Lys Leu Val Ala Ala Ser Gln Ala Ala Leu Gly
            770                 775                 780

Leu
785

<210> SEQ ID NO 209
<211> LENGTH: 190
<212> TYPE: PRT
<213> ORGANISM: Artificial Sequence
<220> FEATURE:
<223> OTHER INFORMATION: synthetic construct

<400> SEQUENCE: 209

Ser Gln Ile Glu Val Lys Asp Val Thr Asp Thr Thr Ala Leu Ile Thr
1               5                   10                  15

Trp Ser Asp Asp Phe Gly Glu Tyr Val Trp Cys Glu Leu Thr Tyr Gly
            20                  25                  30

Ile Lys Asp Val Pro Gly Asp Arg Thr Thr Ile Asp Leu Trp Tyr His
            35                  40                  45

His Ala His Tyr Ser Ile Gly Asn Leu Lys Pro Asp Thr Glu Tyr Glu
        50                  55                  60

Val Ser Leu Ile Cys Arg Ser Gly Asp Met Ser Ser Asn Pro Ala Lys
65                  70                  75                  80

Glu Thr Phe Thr Thr Gly Gly Gly Gly Ser Gly Gly Gly Gly Ser Gly
            85                  90                  95

Gly Gly Gly Ser Arg Leu Asp Ala Pro Ser Gln Ile Glu Val Lys Asp
            100                 105                 110

Val Thr Asp Thr Thr Ala Leu Ile Thr Trp Ser Asp Asp Phe Gly Glu
            115                 120                 125

Tyr Val Trp Cys Glu Leu Thr Tyr Gly Ile Lys Asp Val Pro Gly Asp
            130                 135                 140

Arg Thr Thr Ile Asp Leu Trp Tyr His His Ala His Tyr Ser Ile Gly
145                 150                 155                 160

Asn Leu Lys Pro Asp Thr Glu Tyr Glu Val Ser Leu Ile Cys Arg Ser
            165                 170                 175

Gly Asp Met Ser Ser Asn Pro Ala Lys Glu Thr Phe Thr Thr
            180                 185                 190

<210> SEQ ID NO 210
<211> LENGTH: 26
<212> TYPE: PRT
<213> ORGANISM: Artificial Sequence
<220> FEATURE:
<223> OTHER INFORMATION: synthetic construct

<400> SEQUENCE: 210

Met Thr Asn Ile Thr Lys Arg Ser Leu Val Ala Ala Gly Val Leu Ala
1               5                   10                  15

Ala Leu Met Ala Gly Asn Val Ala Met Ala
            20                  25
```